US012648997B2

(12) United States Patent
Sprogøe et al.

(10) Patent No.: US 12,648,997 B2
(45) Date of Patent: Jun. 9, 2026

(54) TREATMENT OF INFECTIONS

(71) Applicant: Ascendis Pharma A/S, Hellerup (DK)

(72) Inventors: Kennett Sprogøe, Hellerup (DK); Sebastian Stark, Heidelberg (DE); Tobias Voigt, Heidelberg (DE); Lars Holten-Andersen, Hellerup (DK); Nicola Bisek, Heidelberg (DE)

(73) Assignee: ASCENDIS PHARMA A/S, Hellerup (DK)

( * ) Notice: Subject to any disclaimer, the term of this patent is extended or adjusted under 35 U.S.C. 154(b) by 1331 days.

(21) Appl. No.: 17/280,774

(22) PCT Filed: Sep. 25, 2019

(86) PCT No.: PCT/EP2019/075877
§ 371 (c)(1),
(2) Date: Mar. 26, 2021

(87) PCT Pub. No.: WO2020/064844
PCT Pub. Date: Apr. 2, 2020

(65) Prior Publication Data

US 2021/0330798 A1 Oct. 28, 2021

(30) Foreign Application Priority Data

Sep. 26, 2018 (EP) .................................... 18196857
Sep. 26, 2018 (EP) .................................... 18196858
Sep. 26, 2018 (EP) .................................... 18196860

(51) Int. Cl.

| | |
|---|---|
| ***A61K 47/00*** | (2006.01) |
| ***A61K 9/00*** | (2006.01) |
| ***A61K 9/46*** | (2006.01) |
| ***A61K 31/06*** | (2006.01) |
| ***A61K 31/74*** | (2006.01) |
| ***A61K 31/765*** | (2006.01) |
| ***A61K 38/12*** | (2006.01) |
| ***A61K 47/60*** | (2017.01) |
| ***A61K 47/64*** | (2017.01) |
| ***A61K 47/69*** | (2017.01) |

(52) U.S. Cl.
CPC ............ *A61K 47/60* (2017.08); *A61K 9/0007* (2013.01); *A61K 9/0019* (2013.01); *A61K 9/0024* (2013.01); *A61K 31/06* (2013.01); *A61K 31/74* (2013.01); *A61K 31/765* (2013.01); *A61K 38/12* (2013.01); *A61K 47/645* (2017.08); *A61K 47/6903* (2017.08)

(58) Field of Classification Search
CPC ...... A61K 47/60; A61K 9/0024; A61K 38/12; A61K 47/645; A61K 47/6903; A61P 19/02; A61P 31/04
See application file for complete search history.

(56) References Cited

U.S. PATENT DOCUMENTS

| | | | | |
|---|---|---|---|---|
| 7,585,837 | B2 | 9/2009 | Shechter et al. | |
| 8,618,124 | B2 | 12/2013 | Greenwald et al. | |
| 8,754,190 | B2 | 6/2014 | Ashley et al. | |
| 8,946,405 | B2 | 2/2015 | Ashley et al. | |
| 2013/0030359 | A1* | 1/2013 | Vetter ................ | A61K 47/6903 604/82 |
| 2015/0290337 | A1* | 10/2015 | Vetter .................. | A61K 39/395 424/85.2 |

FOREIGN PATENT DOCUMENTS

| | | | |
|---|---|---|---|
| EP | 1534334 | B1 | 6/2014 |
| WO | WO-2002089789 | A1 | 11/2002 |
| WO | WO-2005099768 | A2 | 10/2005 |
| WO | WO-2006136586 | A2 | 12/2006 |
| WO | WO-2008034122 | A2 | 3/2008 |
| WO | WO-2009009712 | A1 | 1/2009 |
| WO | WO-2009095479 | A2 | 8/2009 |
| WO | WO-2009143412 | A2 | 11/2009 |
| WO | WO-2010086421 | A1 | 8/2010 |
| WO | WO-2010145821 | A1 | 12/2010 |
| WO | WO-2011012722 | A1 | 2/2011 |
| WO | WO-2011082368 | A2 | 7/2011 |

(Continued)

OTHER PUBLICATIONS

Antony et al., "Efficacy of Single-stage Revision with Aggressive Debridement Using Intra-articular Antibiotics in the Treatment of Infected Joint Prosthesis," Infect Dis (Auckl). (2015) 8:17-23.
Bertazzoni Minelli et al., "Different microbial biofilm formation on polymethylmethacrylate (PMMA) bone cement loaded with gentamicin and vancomycin," Anaerobe. (2011) 17(6):380-3.
Bistolfi et al., "Antibiotic-loaded cement in orthopedic surgery: a review," ISRN Orthop. (2011) 2011:290851.
Bjarnsholt et al., "Applying insights from biofilm biology to drug development—can a new approach be developed?," Nat Rev Drug Discov. (2013) 12(10):791-808.
Casadidio et al., "Daptomycin-loaded biodegradable thermosensitive hydrogels enhance drug stability and foster bactericidal activity against *Staphylococcus aureus*," Eur J Pharm Biopharm. (2018) 130:260-271.

(Continued)

*Primary Examiner* — Jeanette M Lieb
(74) *Attorney, Agent, or Firm* — Raphael Bellum PLLC

(57) ABSTRACT

The present invention relates among other aspects to a conjugate or a pharmaceutically acceptable salt thereof or a pharmaceutical composition comprising said conjugate or its pharmaceutically acceptable salt for use in a method of preventing or treating an infection, wherein said conjugate is water-insoluble and comprises a polymeric moiety —Z to which a plurality of moieties $-L^2-X^{0D}-L^1-D$ are covalently conjugated, wherein each -D is independently an antibiotic moiety; each $-L^1-$ is independently a linker moiety to which -D is covalently and reversibly conjugated; each $—X^{0D}—$ is independently absent or a linkage and each $-L^2-$ is independently either a chemical bond or a spacer moiety.

11 Claims, No Drawings

(56) References Cited

FOREIGN PATENT DOCUMENTS

| | | | |
|---|---|---|---|
| WO | WO-2011089214 | A1 | 7/2011 |
| WO | WO-2011089215 | A1 | 7/2011 |
| WO | WO-2011089216 | A1 | 7/2011 |
| WO | WO-2013024052 | A1 | 2/2013 |
| WO | WO-2013024053 | A1 | 2/2013 |
| WO | WO-2013036857 | A1 | 3/2013 |
| WO | WO-2013053856 | A1 | 4/2013 |
| WO | WO-2013160340 | A1 | 10/2013 |
| WO | WO-2015059623 | A1 | 4/2015 |
| WO | WO-2016020373 | A1 | 2/2016 |
| WO | WO-2017044983 | A1 | 3/2017 |
| WO | WO-2018187740 | A1 | 10/2018 |
| WO | WO-2019135715 | A1 | 7/2019 |
| WO | WO/2020/064844 | | 4/2020 |

OTHER PUBLICATIONS

Ceri et al., "The Calgary Biofilm Device: new technology for rapid determination of antibiotic susceptibilities of bacterial biofilms," J Clin Microbiol. (1999) 37(6):1771-6.
Gude et al., "An accurate method for the quantitation of Fmoc-derivatized solid phase supports," Letters in Peptide Science. (2002) 9(4):203-206.
Hinarejos et al., "Use of antibiotic-loaded cement in total knee arthroplasty," World J Orthop. (2015) 6(11):877-85.
Joseph et al., "Use of antibiotic-impregnated cement in total joint arthroplasty," J Am Acad Orthop Surg. (2003) 11(1):38-47.
Molnár-perl et al., "HPLC of amines as o-phthalaldehyde derivatives," Quantitation of Amino Acids and Amines by Chromatography: Methods and Protocols (vol. 70) (Journal of Chromatography Library, vol. 70). (2005) pp. 405-444.
Patti et al., "Antibiotic-loaded acrylic bone cement in the revision of septic arthroplasty: where's the evidence?," Orthopedics. (2011) 34(3):210.
Runner et al., "Renal failure after placement of an articulating, antibiotic impregnated polymethylmethacryate hip spacer," Arthroplast Today. (2017) 4(1):51-57.
Smyth et al., "Reactions of N-ethylmaleimide with peptides and amino acids," Biochem J. (1964) 91(3):589-95.
Wang et al., "Dual-Functional Dextran-PEG Hydrogel as an Antimicrobial Biomedical Material,"Macromol Biosci. (2018) 18(2).
Salkind, et al., "Antibiotic Prophylaxis to Prevent Surgical Site Infections," Am Fam Physician. 2011;83(5):585-590.

* cited by examiner

TREATMENT OF INFECTIONS

CROSS-REFERENCE TO RELATED APPLICATIONS

The present application is a § 371 National Stage of PCT International Application No. PCT/EP2019/075877, filed Sep. 25, 2019, which claims the benefit of EP patent application Ser. No. 18/196,857.9, filed on Sep. 26, 2018; EP patent application Ser. No. 18/196,858.7, filed on Sep. 26, 2018; and EP patent application Ser. No. 18/196,860.3, filed on Sep. 26, 2018. The entirety of each application is incorporated herein by reference thereto.

The present invention relates among other aspects to a conjugate or a pharmaceutically acceptable salt thereof or a pharmaceutical composition comprising said conjugate or its pharmaceutically acceptable salt for use in a method of preventing or treating an infection, wherein said conjugate is water-insoluble and comprises a polymeric moiety —Z to which a plurality of moieties -$L^2$-$X^{0D}$-$L^1$-D are covalently conjugated, wherein each -D is independently an antibiotic moiety; each -$L^1$- is independently a linker moiety to which -D is covalently and reversibly conjugated; each —$X^{0D}$— is independently absent or a linkage and each -$L^2$- is independently either a chemical bond or a spacer moiety.

The growing threat of untreatable infections caused by multi-drug resistant (MDR) pathogens is considered amongst the most significant challenges to public health systems worldwide. As bacteria and fungi are found to becoming less susceptible to the treatment with antibiotic compounds, the risk of severe and life-threatening chronic infections increases and challenges today's standard of care that suffers from a relative gap in therapeutic innovations.

Recently, new studies have revealed the ability of relevant pathogens to aggregate as coherent clusters of bacterial cells embedded in a matrix of proteins and mucus, a so-called biofilm. It has been shown that bacterial biofilms can form preferably on foreign surfaces, such as implants and (necrotic) tissue, or can be embedded in host material. Biofilms exhibit an extreme resistance to antibiotics, and a high capacity to evade the host defense. The eradication of mature biofilm requires magnitudes higher antibiotic drug levels with concentrations 500 to 1000× above the minimal inhibitory concentration (MIC) for planktonic bacteria. However, often the required bactericidal concentration to defeat biofilm cannot reliably be achieved in all tissues when the drug is given by intravenous (IV) or oral route. The relative toxicity of antibiotic compounds, their short half-life and potentially low vascularization at the site of infection require a new therapeutic strategy to ensure successful antimicrobial treatment (Bjarnsholt T. et al., Nature Reviews Drug Discovery 2013:791-808).

Given the huge impact on patient morbidity and mortality, and the significant health-economic burden of chronic infections, it is a surprising fact that more effective treatment options aiming at biofilm eradication have not yet been developed.

For example, the shortcomings of the current anti-infectives therapy can be observed with the treatment of prosthetic joint infections (PJI) following a total or partial joint replacement surgery (arthroplasty). PJI of the hip and knee result in significant morbidity and mortality when they do occur. Current management consists of a combination of either single- or two-stage exchange of the prosthesis and/or exchange of polymer components with IV antibiotics (4-6 weeks) and intraoperative debridement of the joint prior to reimplantation. However, failure rate, morbidity, and expense associated with current management are high, especially if the infection involves resistant pathogens and/or osteomyelitis. PJI represent a high economic burden with US$ >5 billion annual cost and a predicted increase in the incidence rate (Anthony et al., Infectious Diseases: Research and Treatment 2015:8 17-23).

Several attempts of localized anti-infective treatments are known in the field, however, surprisingly little progress has been made to improve the rate of prosthetic infections or treat the infected joints. Most commonly used preparations consist of poly(methyl methacrylate) (PMM) cements that contain 5-10% (m/m) of antibiotic compound or combinations of antibiotic compounds in the powder mix. Often, cements are used for the fixation of the implant to the bone during arthroplasty. During two-stage revision surgery, cements are inserted as a spacer, before re-implantation of the secondary orthopedic device. When applied during the surgical procedure, they transiently release certain quantities of the antibiotic ingredient (Joseph et al., Journal of the American Academy of Orthopedic Surgeons 2003:11(1) 38-47).

However, antibiotic cement mixtures exhibit significant shortcomings that may explain why a real breakthrough in the clinical management of biofilm related infections has not yet been achieved. For example, little reliability of antibiotic elution has been reported, with release rates in the range of hours or many months making the treatment success somewhat unpredictable (Patti et al., Orthopedics 211:34(3) 210-218). Upon elution, changes in the mechanical properties of cements were observed causing substantial risk of implant loosening and the need for revision surgery. A prolonged elution of sub-therapeutic doses of the antibiotic compound are reported to promote bacterial drug resistance (Hinarejos et al., World Journal of Orthopedics 2015:6(11) 877-885). Given the relative chemical instability of antibiotic compounds, such as vancomycin, daptomycin, gentamicin, tobramycin and others, exposure to high temperature as occurring during preparation of cement mixtures or physiological conditions quickly degrades commonly used antibiotic compounds and thus substantially impacting their efficacy (Bistolfi et al., ISRN Orthopedics Volume 2011 1-8 (2011)). As the cements represent permanent foreign surfaces, they exhibit an intrinsic risk for the formation of novel biofilms and thereby delaying cure of the infections or worsening of symptoms (Bertazzoni et al., Anaerobe 2011: 17(6) 380-383). Furthermore, as low amount of antibiotics below bactericidal levels are released at later time points, the risk of formation of antibiotic resistant biofilm strains exists, which potentially can worsen the therapeutic outcome. Recently, antibiotic impregnated PMM cement spacers have been associated with renal failure and allergic reactions (Runner et al., Arthroplasty Today 2017:4(1) 51-57). Amongst the most relevant downsides of commonly used cements is their non-degradability, requiring surgical procedure for removal and the risk of providing a surface for biofilm formation.

Currently, there is no product approved or on the market that offers better therapeutic success by overcoming the insufficiencies described above.

In summary, there is a need for a more efficacious treatment of infections.

It is an object of the present invention to at least partially overcome the above-described shortcomings.

This object is achieved with a conjugate or a pharmaceutically acceptable salt thereof or a pharmaceutical composition comprising said conjugate or its pharmaceutically acceptable salt for use in a method of preventing or treating an infection, wherein said conjugate is water-insoluble and comprises a polymeric moiety —Z to which a plurality of moieties $-L^2-X^{0D}-L^1-D$ are covalently conjugated, wherein each -D is independently an antibiotic moiety;

each $-L^1-$ is independently a linker moiety to which -D is covalently and reversibly conjugated;

each $—X^{0D}—$ is independently absent or a linkage; and each $-L^2-$ is independently absent or a spacer moiety.

This object is also achieved with a water-insoluble conjugate or a pharmaceutically acceptable salt thereof or a pharmaceutical composition comprising said conjugate or its pharmaceutically acceptable salt comprising a plurality of antibiotic moieties -D covalently and reversibly bound to a polymeric moiety, wherein the antibiotic moieties are released from the polymeric moiety and wherein a single intra-articular injection provides a concentration of said antibiotic in the intra-articular compartment of at least 1 μg antibiotic/ml synovial fluid for at least 3 days.

This object is also achieved with a sustained-release compound or a pharmaceutically acceptable salt thereof or a pharmaceutical composition comprising said compound or its pharmaceutically acceptable salt comprising a plurality of antibiotic moieties -D or antibiotic molecules D-H or D-OH, wherein the antibiotic moieties or molecules are released from said sustained-release compound and provide a concentration in the intra-articular compartment of said antibiotic that is at least 1.1-fold above the minimal biofilm eradicating concentration of the respective antibiotic for at least 3 days after a single intra-articular injection.

The present inventors were able to identify the concentration of antibiotics required to eradicate biofilms (minimal biofilm eradication concentration, MBEC) formed by pathogens that lead to infections, in particular to infections in body compartments, such as for example in joints and in particular to joint infections related to surgical implants. Surprisingly, the longer the exposure to antibiotics the lower the concentration required to eradicate the biofilm of a given pathogen. This unexpected observation was made when biofilm was exposed to constant daptomycin, a cyclic lipopeptide antibiotic, over one, three and five days. The concentrations of daptomycin required to fully eradicate biofilm are representative of drug levels that can be achieved following release from the conjugates of the present invention. To our knowledge, this is the first time that data demonstrate that the MBEC of, for example, daptomycin is much lower when biofilm is exposed to a given antibiotic for multiple days. It was thus concluded that continuous release of an antibiotic is advantageous to the eradication of a biofilm and therefore to the treatment of joint infections as compared to one or more bolus injections of the respective antibiotic.

Within the present invention the terms are used having the meaning as follows.

As used herein, the term “antibiotic” refers to an antimicrobial drug for the prevention or treatment of bacterial infections, which either kills or inhibits growth of bacteria. The term also refers to drugs having antiprotozoal and antifungal activity.

As used herein, the term “biofilm” refers to a plurality of microorganisms, such as microorganisms selected from the group consisting of bacteria, archaea, protozoa, fungi and algae, such as to a plurality of bacteria, embedded within an extracellular matrix that is composed of extracellular polymeric substances, such as polysaccharides, proteins and DNA, and said extracellular matrix may comprise material from the surrounding environment, such as blood components. Biofilms may form on living and non-living surfaces and may comprise one or more species of microorganism. It is known that during the ageing process of a biofilm it becomes increasingly difficult to eradicate it, because not only do individual cells form tighter bonds with the surface, but the extracellular matrix also provides a protective environment that restricts access of the antibiotics to the microorganisms.

As used herein the terms “compartment” and “body compartment” are used synonymously and refer to any particular space in the body comprising a diffusion barrier impeding the exchange of solutes with the surrounding tissue. Such space may also be artificially introduced by, for example, an implant. This space may be fluid, solid or may contain a gas phase or may be any combination thereof. It is understood that said solutes may comprise pharmacologically active compounds. The terms “compartment” and “body compartment” also refer to body structures that are separated by membranes, sheaths, linings, fascia and other connective tissue, bones, cartilage, or any combination thereof.

As used herein, the term “water-insoluble” refers to a compound, such as a conjugate of the present invention, of which less than 1 g can be dissolved in one liter of water at 20° C. to form a homogeneous solution. Accordingly, the term “water-soluble” refers to a compound of which 1 g or more can be dissolved in one liter of water at 20° C. to form a homogeneous solution.

As used herein, the term “sustained release” refers to the property of a compound, such as the conjugates of the present invention, to release a drug, such as one or more antibiotic, with a release half-life of at least 1 day.

It is understood that the conjugates of the present invention are prodrugs.

As used herein the term “prodrug” refers to a drug moiety reversibly and covalently connected to a specialized protective group through a reversible prodrug linker moiety which is a linker moiety comprising a reversible linkage with the drug moiety and wherein the specialized protective group alters or eliminates undesirable properties in the parent molecule. This also includes the enhancement of desirable properties in the drug and the suppression of undesirable properties. The specialized non-toxic protective group may also be referred to as “carrier”. A prodrug releases the reversibly and covalently bound drug moiety in the form of its corresponding drug. In other words, a prodrug is a conjugate comprising a drug moiety, which is covalently and reversibly conjugated to a carrier moiety via a reversible linker moiety, which covalent and reversible conjugation of the carrier to the reversible linker moiety is either directly or through a spacer. The reversible linker may also be referred to as “reversible prodrug linker”. Such conjugate may release the formerly conjugated drug moiety in the form of a free drug, in which case the reversible linker or reversible prodrug linker is a traceless linker.

As used herein, the term “free form” of a drug means the drug in its unmodified, pharmacologically active form.

As used herein the term “spacer” refers to a moiety that connects at least two other moieties with each other.

As used herein, the term “reversible”, “reversibly”, “degradable” or “degradably” with regard to the attachment of a first moiety to a second moiety means that the linkage that connects said first and second moiety is cleavable under physiological conditions, which physiological conditions are aqueous buffer at pH 7.4 and 37° C., with a half-life ranging from one day to three month, such as from one day to two months, such as from one day to one month. Such cleavage is non-enzymatically. Accordingly, the term "stable" with regard to the attachment of a first moiety to a second moiety means that the linkage that connects said first and second moiety exhibits a half-life of more than three months under physiological conditions.

As used herein, the term "reagent" means a chemical compound, which comprises at least one functional group for reaction with the functional group of another chemical compound or drug. It is understood that a drug comprising a functional group is also a reagent.

As used herein, the term "moiety" means a part of a molecule, which lacks one or more atom(s) compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a drug moiety, such as an antibiotic moiety, is released from a reversible linkage as a drug, such as an antibiotic drug.

It is understood that if the chemical structure of a group of atoms is provided and if this group of atoms is attached to two moieties or is interrupting a moiety, said sequence or chemical structure can be attached to the two moieties in either orientation, unless explicitly stated otherwise. For example, a moiety "—C(O)N($R^1$)—" can be attached to two moieties or interrupting a moiety either as "—C(O)N($R^1$)—" or as "—N($R^1$)C(O)—". Similarly, a moiety

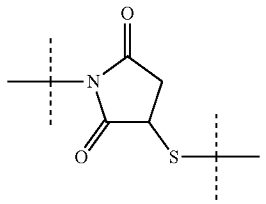

can be attached to two moieties or can interrupt a moiety either as

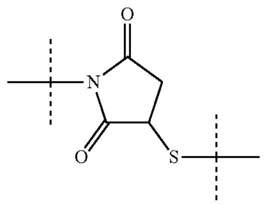

or as

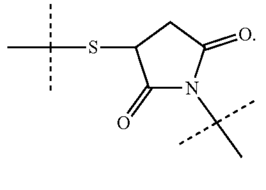

The term "substituted" as used herein means that one or more —H atom(s) of a molecule or moiety are replaced by a different atom or a group of atoms, which are referred to as "substituent".

As used herein, the term "substituent" in certain embodiments refers to a moiety selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

—R$^{x1}$, —R$^{x1a}$, —R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more —R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$), —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more —R$^{x2}$, which are the same or different;

each —R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), OC(O)N(R$^{x4}$R$^{x4a}$), and C$_{1-6}$ alkyl; wherein C$_{1-6}$ alkyl is optionally substituted with one or more halogen, which are the same or different;

each —R$^{x3}$, —R$^{x3a}$, —R$^{x4}$, —R$^{x4a}$, —R$^{x4b}$ is independently selected from the group consisting of —H and C$_{1-6}$ alkyl; wherein C$_{1-6}$ alkyl is optionally substituted with one or more halogen, which are the same or different.

In certain embodiments a maximum of 6-H atoms of an optionally substituted molecule are independently replaced by a substituent, e.g. 5-H atoms are independently replaced by a substituent, 4-H atoms are independently replaced by a substituent, 3-H atoms are independently replaced by a substituent, 2-H atoms are independently replaced by a substituent, or 1-H atom is replaced by a substituent.

As used herein the term "crosslinker" refers to a moiety that is a connection between different elements of a hydrogel, such as between two or more backbone moieties or between two or more hyaluronic acid strands.

As used herein, the term "hydrogel" means a hydrophilic or amphiphilic polymeric network composed of homopolymers or copolymers, which is insoluble due to the presence of hydrophobic interactions, hydrogen bonds, ionic interactions and/or covalent chemical crosslinks. The crosslinks provide the network structure and physical integrity.

As used herein the term "about" in combination with a numerical value is used to indicate a range ranging from and including the numerical value plus and minus no more than 25% of said numerical value, such as no more than plus and minus 20% of said numerical value or such as no more than plus and minus 10% of said numerical value. For example, the phrase “about 200” is used to mean a range ranging from and including 200+/−25%, i.e. ranging from and including 150 to 250; such as 200+/−20%, i.e. ranging from and including 160 to 240; such as ranging from and including 200+/−10%, i.e. ranging from and including 180 to 220. It is understood that a percentage given as “about 50%” does not mean “50%+/−25%”, i.e. ranging from and including 25 to 75%, but “about 50%” means ranging from and including 37.5 to 62.5%, i.e. plus and minus 25% of the numerical value which is 50.

As used herein, the term “polymer” means a molecule comprising repeating structural units, i.e. the monomers, connected by chemical bonds in a linear, circular, branched, crosslinked or dendrimeric way or a combination thereof, which may be of synthetic or biological origin or a combination of both. The monomers may be identical, in which case the polymer is a homopolymer, or may be different, in which case the polymer is a heteropolymer. A heteropolymer may also be referred to as a “copolymer” and includes, for example, alternating copolymers in which monomers of different types alternate, periodic copolymers, in which monomers of different types are arranged in a repeating sequence; statistical copolymers, in which monomers of different types are arranged randomly; block copolymers, in which blocks of different homopolymers consisting of only one type of monomers are linked by a covalent bond; and gradient copolymers, in which the composition of different monomers changes gradually along a polymer chain. It is understood that a polymer may also comprise one or more other moieties, such as, for example, one or more functional groups. The term “polymer” also relates to a peptide or protein, even though the side chains of individual amino acid residues may be different. It is understood that for covalently crosslinked polymers, such as hydrogels, no meaningful molecular weight ranges can be provided.

As used herein, the term “polymeric” refers to a reagent or a moiety comprising one or more polymers or polymer moieties. A polymeric reagent or moiety may optionally also comprise one or more other moieties, which in certain embodiments are selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

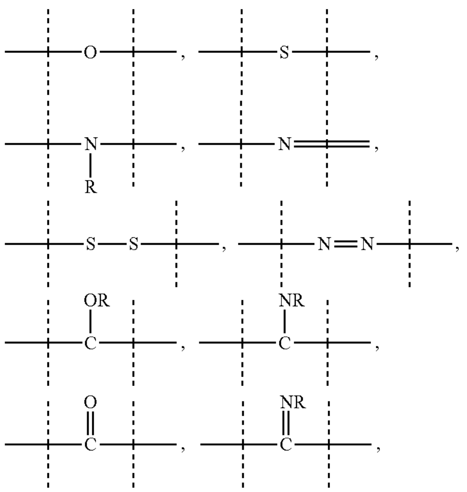

-continued

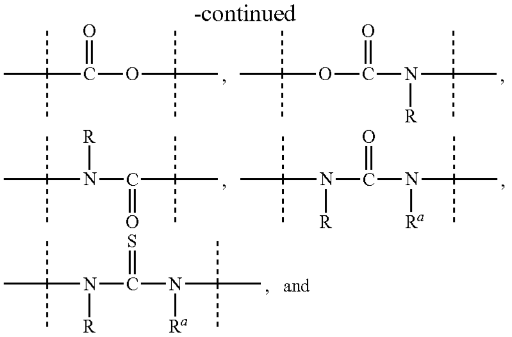

, and

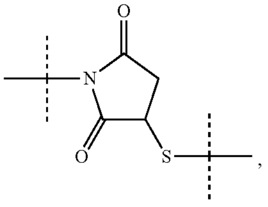

wherein dashed lines indicate attachment to the remainder of the moiety or reagent, and —R and —$R^a$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl; and which moieties and linkages are optionally further substituted.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising “x” monomer units any integer given for “x” therefore corresponds to the arithmetic mean number of monomers. Any range of integers given for “x” provides the range of integers in which the arithmetic mean numbers of monomers lies. An integer for “x” given as “about x” means that the arithmetic mean numbers of monomers lies in a range of integers of x+/−25%, such as x+/−20% or such as x+/−10%.

As used herein, the term “number average molecular weight” means the ordinary arithmetic mean of the molecular weights of the individual polymers.

As used herein, the term “PEG-based” in relation to a moiety or reagent means that said moiety or reagent comprises PEG. Such PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60 (w/w) PEG, such as at least 70% (w/w) PEG, such as at least 80% (w/w) PEG, such as at least 90% (w/w) PEG, or such as at least 95% (w/w) PEG. The remaining weight percentage of the PEG-based moiety or reagent may be other moieties, such as those selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group consisting of

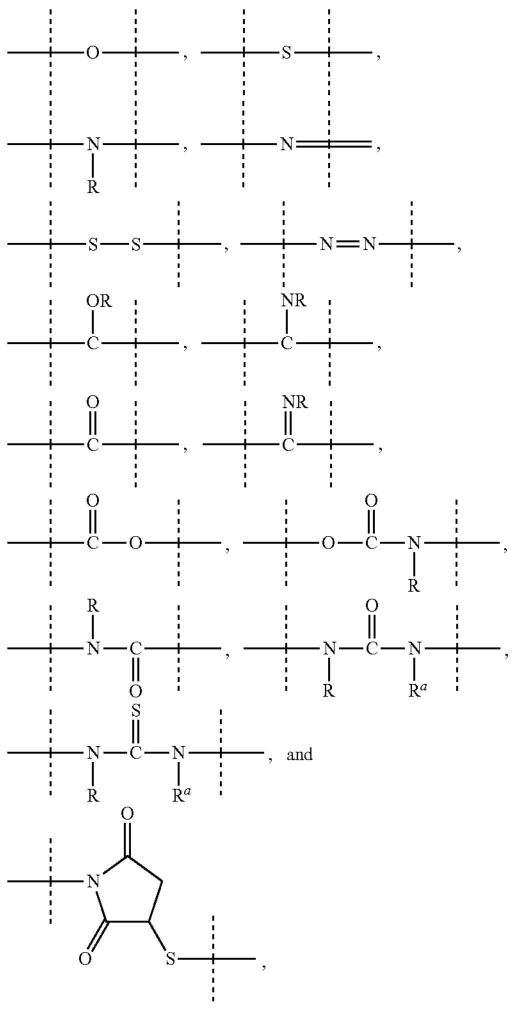

wherein dashed lines indicate attachment to the remainder of the moiety or reagent, and —R and —$R^a$ are independently of each other selected from the group consisting of —H, and $C_{1-6}$ alkyl; and which moieties and linkages are optionally further substituted.

The terms "poly(alkylene glycol)-based", "poly(propylene glycol)-based" and "hyaluronic acid-based" are used accordingly.

The term "interrupted" means that a moiety is inserted between two carbon atoms or—if the insertion is at one of the moiety's ends—between a carbon or heteroatom and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are $—CH_2—$, $—CH_2—CH_2—$, $—CH(CH_3)—$, $—CH_2—CH_2—CH_2—$, $—CH(C_2H_5)—$, $—C(CH_3)_2—$. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are $—CH_2—$, $—CH_2—CH_2—$, $—CH(CH_3)—$, $—CH_2—CH_2—CH_2—$, $—CH(C_2H_5)—$ and $—C(CH_3)_2—$. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are $—CH{=}CH_2$, $—CH{=}CH—CH_3$, $—CH_2—CH{=}CH_2$, $—CH{=}CHCH_2—CH_3$ and $—CH{=}CH—CH{=}CH_2$. When two moieties of a molecule are linked by the $C_{2-6}$ alkenyl group, then an example for such $C_{2-6}$ alkenyl is $—CH{=}CH—$. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the terms "$C_{2-10}$ alkenyl", "$C_{2-20}$ alkenyl" or "$C_{2-50}$ alkenyl" alone or in combination mean a straight-chain or branched hydrocarbon moiety comprising at least one carbon-carbon double bond having 2 to 10, 2 to 20 or 2 to 50 carbon atoms, respectively. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means a straight-chain or branched hydrocarbon moiety comprising at least one carbon-carbon triple bond having 2 to 6 carbon atoms. If present at the end of a molecule, examples are $—C{\equiv}CH$, $—CH_2—C{\equiv}CH$, $CH_2—CH_2—C{\equiv}CH$ and $CH_2—C{\equiv}C—CH_3$. When two moieties of a molecule are linked by the alkynyl group, then an example is $—C{\equiv}C—$. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkenyl or $C_{2-50}$ alkynyl may optionally be interrupted by one or more moieties which may be selected from the group consisting of

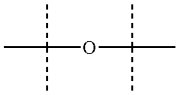, 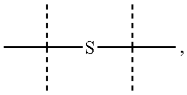,

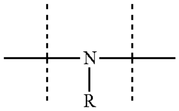, 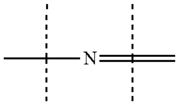,

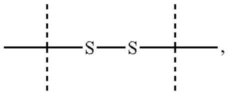, 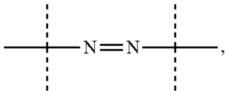,

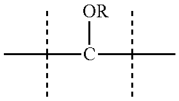, 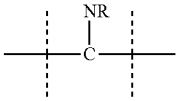,

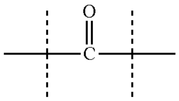, 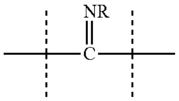,

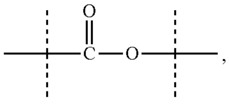, 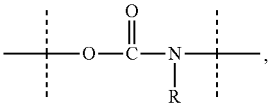,

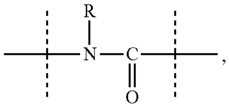, 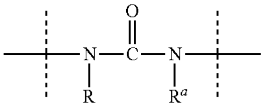,

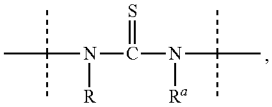, and

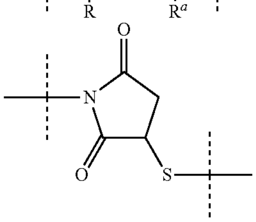, wherein dashed lines indicate attachment to the remainder of the moiety or reagent; and —R and —$R^a$ are independently of each other selected from the group consisting of —H and $C_{1-6}$ alkyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). In one embodiment a 8- to 30-membered carbopolycyclyl means a cyclic moiety of two, three, four or five rings. In another embodiment a 8- to 30-membered carbopolycyclyl means a cyclic moiety of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —$S(O_2)$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent.

Similarly, the term "8- to 30-membered heteropolycyclyl" or "8- to 30-membered heteropolycycle" means a heterocyclic moiety of more than two rings with 8 to 30 ring atoms, such as of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

It is understood that the phrase "the pair $R^x/R^y$ is joined together with the atom to which they are attached to form a $C_{3-10}$ cycloalkyl or a 3- to 10-membered heterocyclyl" in relation with a moiety of the structure

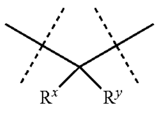

means that $R^x$ and $R^y$ form the following structure:

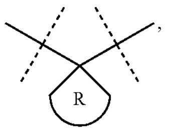

wherein R is $C_{3-10}$ cycloalkyl or 3- to 10-membered heterocyclyl.

It is also understood that the phrase "the pair $R^x/R^y$ is joint together with the atoms to which they are attached to form a ring A" in relation with a moiety of the structure

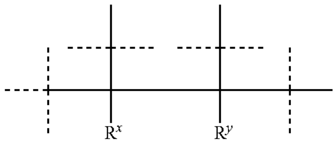

means that $R^x$ and $R^y$ form the following structure:

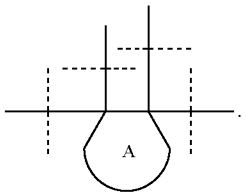

As used herein, "halogen" means fluoro, chloro, bromo or iodo. In certain embodiments halogen is fluoro or chloro.

As used herein the term "alkali metal ion" refers to $Na^+$, $K^+$, $Li^+$, $Rb^+$ and $Cs^+$. In certain embodiments "alkali metal ion" refers to $Na^+$, $K^+$ and $Li^+$.

As used herein the term "alkaline earth metal ion" refers to $Mg^{2+}$, $Ca^{2+}$, $Sr^{2+}$ and $Ba^{2+}$. In certain embodiments an alkaline earth metal ion is $Mg^{2+}$ or $Ca^{2+}$.

As used herein, the term "functional group" means a group of atoms which can react with other groups of atoms. Exemplary functional groups are carboxylic acid, primary amine, secondary amine, tertiary amine, maleimide, thiol, sulfonic acid, carbonate, carbamate, hydroxyl, aldehyde, ketone, hydrazine, isocyanate, isothiocyanate, phosphoric acid, phosphonic acid, haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the conjugates of the present invention comprise one or more acidic or basic groups, the invention also comprises their corresponding pharmaceutically or toxicologically acceptable salts, in particular their pharmaceutically utilizable salts. Thus, the conjugates of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine, amino acids, and quarternary ammonium salts, like tetrabutylammonium or cetyl trimethylammonium. Conjugates of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, trifluoroacetic acid, and other acids known to the person skilled in the art. For the person skilled in the art further methods are known for converting the basic group into a cation like the alkylation of an amine group resulting in a positively-charge ammonium group and an appropriate counterion of the salt. If the conjugates of the present invention simultaneously comprise acidic and basic groups, the invention also includes, in addition to the salt forms mentioned, inner salts or betaines (zwitterions). The respective salts can be obtained by customary methods, which are known to the person skilled in the art like, for example by contacting these prodrugs with an organic or inorganic acid or base in a solvent or dispersant, or by anion exchange or cation exchange with other salts. The present invention also includes all salts of the conjugates of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does not cause harm when administered to a patient and in certain embodiments means approved by a regulatory agency, such as the EMA (Europe) and/or the FDA (US) and/or any other national regulatory agency for use in animals, such as for use in humans.

As used herein, the term "excipient" refers to a diluent, adjuvant, or vehicle with which the therapeutic, such as a drug or prodrug, is administered. Such pharmaceutical excipient may be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, hyaluronic acid, propylene glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or may contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or drug moiety, together with a suitable amount of excipient so as to provide the form for proper administration to the patient. The formulation should suit the mode of administration.

The term "peptide" as used herein refers to a chain of at least 2 and up to and including 50 amino acid monomer moieties, which may also be referred to as "amino acid residues", linked by peptide (amide) linkages. The amino acid monomers may be selected from the group consisting of proteinogenic amino acids and non-proteinogenic amino acids and may be D- or L-amino acids. The term "peptide" also includes peptidomimetics, such as peptoids, beta-peptides, cyclic peptides and depsipeptides and covers such peptidomimetic chains with up to and including 50 monomer moieties.

As used herein, the term "protein" refers to a chain of more than 50 amino acid monomer moieties, which may also be referred to as "amino acid residues", linked by peptide linkages, in which preferably no more than 12000 amino acid monomers are linked by peptide linkages, such as no more than 10000 amino acid monomer moieties, no more than 8000 amino acid monomer moieties, no more than 5000 amino acid monomer moieties or no more than 2000 amino acid monomer moieties.

As used herein the term "micelle" means an aggregate of amphiphilic molecules dispersed in a liquid colloid. In aqueous solution a typical micelle forms an aggregate with the hydrophilic moiety of the surfactant molecules facing the surrounding solvent and the hydrophobic moiety of the surfactant molecule facing inwards, also called "normal-phase micelle". "Invers micelles" have the hydrophilic moiety facing inwards and the hydrophobic moiety facing the surrounding solvent.

As used herein the term "liposome" refers to a vesicle, preferably a spherical vesicle, having at least one lipid bilayer. Preferably, liposomes comprise phospholipids, even more preferably phosphatidylcholine. The term "liposome" refers to various structures and sizes, such as, for example, to multilamellar liposome vesicles (MLV) having more than one concentric lipid bilayer with an average diameter of 100 to 1000 nm, small unilamellar liposome vesicles (SUV) having one lipid bilayer and an average diameter of 25 to 100 nm, large unilamellar liposome vesicles (LUV) having one lipid bilayer and an average diameter of about 1000 μm and giant unilamellar vesicles (GUV) having one lipid bilayer and an average diameter of 1 to 100 μm. The term "liposome" also includes elastic vesicles such as transferosomes and ethosomes, for example.

As used herein the term "aquasome" refers to spherical nanoparticles having a diameter of 60 to 300 nm that comprise at least three layers of self-assembled structure, namely a solid phase nanocrystalline core coated with an oligomeric film to which drug molecules are adsorbed with or without modification of the drug.

As used herein the term "ethosome" refers to lipid vesicles comprising phospholipids and ethanol and/or isopropanol in relatively high concentration and water, having a size ranging from tens of nanometers to micrometers.

As used herein the term "LeciPlex" refers to positively charged phospholipid-based vesicular system which comprises soy PC, a cationic agent, and a bio-compatible solvent like PEG 300, PEG 400, diethylene glycol monoethyl ether, tetrahydrofurfuryl alcohol polyethylene glycol ether or 2-pyrrolidone or N-methyl-2-pyrrolidone.

As used herein the term "niosome" refers to unilamellar or multilamellar vesicles comprising non-ionic surfactants.

As used herein the term "pharmacosome" refers to ultrafine vesicular, micellar or hexagonal aggregates from lipids covalently bound to biologically active moieties.

As used herein the term "proniosome" refers to dry formulations of surfactant-coated carrier which on rehydration and mild agitation gives niosomes.

As used herein the term "polymersome" refers to an artificial spherical vesicle comprising a membrane formed from amphiphilic synthetic block copolymers and may optionally comprise an aqueous solution in its core. A polymersome has a diameter ranging from 50 nm to 5 μm and larger. The term also includes syntosomes, which are polymersomes engineered to comprise channels that allow certain chemicals to pass through the membrane into or out of the vesicle.

As used herein the term "sphingosome" refers to a concentric, bilayered vesicle in which an aqueous volume is entirely enclosed by a membranous lipid bilayer mainly composed of natural or synthetic sphingolipid.

As used herein the term "transferosome" refers to ultraflexible lipid vesicles comprising an aqueous core that are formed from a mixture of common polar and suitable edge-activated lipids which facilitate the formation of highly curved bilayers which render the transferosome highly deformable.

As used herein the term "ufasome" refers to a vesicle comprising unsaturated fatty acids.

In general, the terms "comprise" or "comprising" also encompasses "consist of" or "consisting of".

In a first aspect the present invention relates to a conjugate or a pharmaceutically acceptable salt thereof or a pharmaceutical composition comprising said conjugate or its pharmaceutically acceptable salt for use in a method of preventing or treating an infection, wherein said conjugate is water-insoluble and comprises a polymeric moiety —Z to which a plurality of moieties $-L^2-X^{0D}-L^1-D$ are covalently conjugated, wherein each -D is independently an antibiotic moiety;

each $-L^1-$ is independently a linker moiety to which -D is covalently and reversibly conjugated;

each $—X^{0D}—$ is independently absent or a linkage; and each $-L^2-$ is independently absent or a spacer moiety.

The present invention also relates to the conjugates of the first embodiment per se.

In a second aspect the present invention relates to a water-insoluble conjugate or a pharmaceutically acceptable salt thereof or a pharmaceutical composition comprising said conjugate or its pharmaceutically acceptable salt comprising a plurality of antibiotic moieties -D covalently and reversibly bound to a polymeric moiety, wherein the antibiotic moieties are released from the polymeric moiety and wherein a single intra-articular injection provides a concentration of said antibiotic in the intra-articular compartment of at least 1 μg antibiotic/ml synovial fluid for at least 3 days.

In the third aspect the present invention relates to a sustained-release compound or a pharmaceutically acceptable salt thereof or a pharmaceutical composition comprising said compound or its pharmaceutically acceptable salt comprising a plurality of antibiotic moieties -D or antibiotic molecules D-H or D-OH, wherein the antibiotic moieties or molecules are released from said sustained-release compound and provide a concentration in the intra-articular compartment of said antibiotic that is at least 1.1-fold above the minimal biofilm eradicating concentration of the respective antibiotic for at least 3 days after a single intra-articular injection.

In certain embodiments the sustained-release compound of the third aspect of the present invention is water-soluble.

In certain embodiments such water-soluble sustained-release compound of the third embodiment comprises $C_{8-24}$ alkyl moiety or a polymeric moiety to which the plurality of antibiotic moieties are covalently and reversibly connected. If the water-soluble sustained release compound of the third embodiment comprises a polymeric moiety it is preferably selected from the group consisting of 2-methacryloyl-oxyethyl phosphoyl cholins, poly(acrylic acids), poly(acrylates), poly(acrylamides), poly(alkyloxy) polymers, poly (amides), poly(amidoamines), poly(amino acids), poly (anhydrides), poly(aspartamides), poly(butyric acids), poly (glycolic acids), polybutylene terephthalates, poly (caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly (hydroxypropyloxazolines), poly(iminocarbonates), poly (lactic acids), poly(lactic-co-glycolic acids), poly (methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments such polymeric moiety is PEG. In certain embodiments such polymeric moiety is hyaluronic acid.

In certain embodiments the sustained-release compound of the third aspect is water-insoluble. In such case the sustained-release compound is preferably selected from the group consisting of crystals, nanoparticles, microparticles, nanospheres and microspheres.

In certain embodiments the plurality of antibiotic moieties in the compounds of the third aspect is covalently conjugated to or embedded into a carrier. In certain embodiments the plurality of antibiotic moieties is reversibly and covalently conjugated to the carrier. In certain embodiments the carrier is water-insoluble. In certain embodiments such water-insoluble carrier degrades into soluble degradation products after no more than 4 months after administration to the infected joint, such as after no more than 3 months, such as after no more than 2 months. This degradability reduces the risk that the polymeric carrier provides a new artificial surface for biofilm formation.

In certain embodiments the sustained-release compound of the third aspect is a crystal comprising the plurality of antibiotic moieties.

In certain embodiments the sustained-release compound of the third aspect is a nanoparticle comprising the plurality of antibiotic moieties.

In certain embodiments the sustained-release compound of the third aspect is a microparticle comprising the plurality of antibiotic moieties.

In certain embodiments the sustained-release compound of the third aspect is a nanosphere comprising the plurality of antibiotic moieties.

In certain embodiments the sustained-release compound of the third aspect is a microsphere comprising the plurality of antibiotic moieties.

In certain embodiments the sustained-release compound of the third aspect is a vesicle comprising the plurality of antibiotic moieties. Such vesicle may be a micelle, liposome or polymersome.

In certain embodiments the sustained-release compound of the third aspect is a micelle comprising the plurality of antibiotic moieties.

In certain embodiments the sustained-release compound of the third aspect is a liposome comprising the plurality of antibiotic moieties. Such liposome may be selected from the group consisting of aquasomes; non-ionic surfactant vesicles, such as niosomes and proniosomes; cationic liposomes, such as LeciPlex; transfersomes; ethosomes; ufasomes; sphingosomes; and pharmacosomes.

In certain embodiments the sustained-release compound of the third aspect is a polymersome comprising the plurality of antibiotic moieties.

The antibiotic moieties -D or antibiotic molecules D-H or D-OH of the third aspect of the present invention are as described elsewhere herein.

In certain embodiments the sustained-release compound of the third aspect comprises the plurality of antibiotic moieties non-covalently embedded in a water-insoluble polymer. In certain embodiments such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly (ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments the sustained-release compound of the third aspect comprises the plurality of antibiotic moieties non-covalently embedded in poly(lactic-co-glycolic acid) (PLGA).

In certain embodiments the sustained-release compound of the third aspect comprises the plurality of antibiotic moieties covalently and reversibly conjugated to a polymer.

The conjugates of the first and second aspect and the compounds of the third aspect of the present invention release one or more types of antibiotic over an extended period of time, i.e. they are sustained-release conjugates. In certain embodiments the release occurs with a release half-life ranging between 1 day and 1 month. In certain embodiments the release occurs with a release half-life ranging between 1 day and 20 days. In certain embodiments the release occurs with a release half-life between 1 day and 15 days. In certain embodiments the release half-life may also range from 2 to 20 days or from 4 to 15 days. Such continuous release of an antibiotic is advantageous for the eradication of biofilms and thus the treatment of infections, such as infections in body compartments, such as for example joint infections, compared to one or more bolus injections of the respective antibiotic, as discussed above.

In certain embodiments the water-insoluble conjugate of the second aspect and the sustained-release compound of the third aspect is a conjugate comprising a polymeric moiety —Z to which a plurality of moieties $-L^2-X^{0D}-L^1-D$ are covalently conjugated, wherein each -D is independently an antibiotic moiety;

each $-L^1-$ is independently a linker moiety to which -D is covalently and reversibly conjugated;

each $—X^{0D}—$ is independently absent or a linkage; and each $-L^2-$ is independently either a chemical bond or a spacer moiety.

In certain embodiments a single injection into the intra-articular compartment of at least one conjugate of the first or second aspect or of the compound of the third aspect of the present invention provides a concentration of at least 1 μg antibiotic/ml synovial fluid for at least 3 days, such as for 3 days, 4 days or 5 days.

It is understood that an initial release of antibiotic from the conjugate of the first, second or third aspect of the present invention is required after administration to reach an antibiotic concentration in the intra-articular compartment of at least 1 μg antibiotic per ml of synovial fluid, i.e. the antibiotic concentration in the intra-articular compartment will not immediately after intra-articular injection be at least 1 μg/ml. In certain embodiments the stated antibiotic concentrations may be achieved 15 hours after administration. In certain embodiments the stated antibiotic concentrations may be achieved 18 hours after administration. In certain embodiments the stated antibiotic concentrations may be achieved 21 hours after administration. In certain embodiments the stated antibiotic concentrations may be achieved 24 hours after administration. In certain embodiments the stated antibiotic concentrations may be achieved 36 hours after administration.

In certain embodiments a single injection into the intra-articular compartment of at least one conjugate of the first or second aspect or of the compound of the third aspect provides a concentration of at least 5 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 25 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 50 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 75 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 100 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 150 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 200 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 250 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 300 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 400 μg antibiotic/ml synovial fluid for at least 3 days, such as for 3 days, 4 days or 5 days.

In certain embodiments a single injection into the intra-articular compartment of at least one conjugate of the first or second aspect or of the compound of the third aspect provides a concentration of at least 500 μg antibiotic/ml synovial fluid for at least 3 days, such as for 3 days, 4 days or 5 days.

It is understood that if a conjugate or compound provides a certain antibiotic concentration in the intra-articular compartment for a certain period of time, such as for 3 days, 4 days or 5 days, that this is the minimal time period for which said concentration is provided and that this concentration may also be provided for a longer period of time.

In certain embodiments the antibiotic molecules released from a conjugate of the first or second aspect or from a compound of the third aspect after a single intra-articular injection provide a concentration of said antibiotic in the intra-articular compartment that is at least 1.1-fold above the minimal biofilm eradicating concentration of the respective antibiotic for at least 3 days, such as for at least 4 days, at least 5 days, at least 6 days or at least 7 days.

In certain embodiments the antibiotic molecules released from a conjugate of the first or second aspect or from a compound of the third aspect after a single intra-articular injection provide a concentration of said antibiotic in the intra-articular compartment that is at least 1.2-fold above the minimal biofilm eradicating concentration of the respective antibiotic for at least 3 days, such as for at least 4 days, at least 5 days, at least 6 days or at least 7 days.

In certain embodiments the antibiotic molecules released from a conjugate of the first or second aspect or from a compound of the third aspect after a single intra-articular injection provide a concentration of said antibiotic in the intra-articular compartment that is at least 1.3-fold above the minimal biofilm eradicating concentration of the respective antibiotic for at least 3 days, such as for at least 4 days, at least 5 days, at least 6 days or at least 7 days.

In certain embodiments the antibiotic molecules released from a conjugate of the first or second aspect or from a compound of the third aspect after a single intra-articular injection provide a concentration of said antibiotic in the intra-articular compartment that is at least 1.4-fold above the minimal biofilm eradicating concentration of the respective antibiotic for at least 3 days, such as for at least 4 days, at least 5 days, at least 6 days or at least 7 days.

In certain embodiments the antibiotic molecules released from a conjugate of the first or second aspect or from a compound of the third aspect after a single intra-articular injection provide a concentration of said antibiotic in the intra-articular compartment that is at least 1.5-fold above the minimal biofilm eradicating concentration of the respective antibiotic for at least 3 days, such as for at least 4 days, at least 5 days, at least 6 days or at least 7 days.

In certain embodiments the antibiotic molecules released from a conjugate of the first or second aspect or from a compound of the third aspect a single intra-articular injection provide a concentration of said antibiotic in the intra-articular compartment that is at least 1.6-fold above the minimal biofilm eradicating concentration of the respective antibiotic for at least 3 days, such as for at least 4 days, at least 5 days, at least 6 days or at least 7 days.

In certain embodiments the antibiotic molecules released from a conjugate of the first or second aspect or from a compound of the third aspect after a single intra-articular injection provide a concentration of said antibiotic in the intra-articular compartment that is at least 1.7-fold above the minimal biofilm eradicating concentration of the respective antibiotic for at least 3 days, such as for at least 4 days, at least 5 days, at least 6 days or at least 7 days.

The following sections describe embodiments of -D, $-L^1-$, $-L^2-$, $—X^{0D}—$ and —Z of the first, second and third aspect.

In certain embodiments each -D is independently selected from the group consisting of aminoglycosides, tetracycline antibiotics, amphenicols, pleuromutilins, macrolid antibiotics, lincosamides, steroid antibiotics, antifolate antibiotics, sulfonamides, topoisomerase inhibitors, quinolones, fluoroquinolones, nitroimidazole antibiotics, nitrofuran antibiotics, rifamycins, glycopeptides, penicillins, cephalosporins, monobactams, beta-lactamase inhibitors, polymyxin antibiotics, lipopeptide antibiotics, oxazolidinon, antimicrobial peptides, antimicrobial proteins, porphyrins, azole antifungals, polyenes, antiprotozoal drugs, fosfomycin, cycloserine, and bacitracin.

In certain embodiments -D is an aminoglycoside, such as an aminoglycoside selected from the group consisting of streptomycin, dihydrostreptomycin, neomycin, paromomycin, amikacin, kanamycin, tobramycin, spectinomycin, hygromycin b, gentamicin, plazomicin, verdamicin, netilmicin, astromicin and sisomicin. In certain embodiments -D is amikacin. In certain embodiments -D is kanamycin. In certain embodiments -D is tobramycin. In certain embodiments -D is gentamicin. In another embodiment -D is plazomicin.

In certain embodiments -D is a tetracycline antibiotic, such as a tetracycline antibiotic selected from the group consisting of doxycycline, chloretetracycline, tetracycline, metacycline, minocycline, oxytetracycline and glycocyclines, such as a glycocyclines selected from the group consisting of tigecycline, omadacycline and sarecycline. In certain embodiments -D tetracycline. In certain embodiments -D is minocycline. In certain embodiments -D is oxytetracycline. In certain embodiments -D is tigecycline. In certain embodiments -D is omadacycline. In another embodiment -D is sarecycline.

In certain embodiments -D is an amphenicol, such as an amphenicol selected from the group consisting of chloramphenicol, thiamphenicol, azidamfenicol and florfenicol.

In certain embodiments -D is a pleuromutilin, such as a pleuromutilin selected from the group consisting of azamulin, lefamulin, tiamulin and valnemulin.

In certain embodiments -D is a macrolid antibiotic, such as a macrolid antibiotic selected from the group consisting of azithromycin, boromycin, clarithromycin, oleandomycin, erythromycin, roxithromycin, spiramycin, telithromycin and tylosine.

In certain embodiments -D is a lincosamide, such as a lincosamide selected from the group consisting of clindamycin and lincomycin. In certain embodiments -D is clindamycin.

In certain embodiments -D is a steroid antibiotic, such as fusidic acid.

In certain embodiments -D is an antifolate antibiotic, such as an antifolate antibiotic selected from the group consisting of trimethoprim and iclaprim.

In certain embodiments -D is a sulfonamide, such as a sulfonamide selected from the group consisting of sufathiazole, sulfamethoxazole, sulfadiazine and sulfamerazine.

In certain embodiments -D is a topoisomerase inhibitor, such as a topoisomerase inhibitor selected from the group consisting of flumequine, nalidixic acid, oxolinic acid and pipemidic acid. In certain embodiments -D is nalidixic acid.

In certain embodiments -D is a quinolone or fluroquinolone, such as a quinolone or fluroquinolone selected from the group consisting of nemonoxacin, ciprofloxacin, ofloxacin, norfloxacin, pefloxacin, levofloxacin, sparfloxacin, moxifloxacin, gatifloxacin, difloxacin, enrofloxacin, marbofloxacin, delafloxacin and nemonovobiocin. In certain embodiments -D is ciprofloxacin. In certain embodiments -D is levofloxacin. In certain embodiments -D is delafloxacin.

In certain embodiments -D is a nitroimidazole antibiotic, such as metronidazole.

In certain embodiments -D is a nitrofuran antibiotic, such as a nitrofuran antibiotic selected from the group consisting of nitrofurantoin and furazolidone.

In certain embodiments -D is a rifamycin, such as rifampicin.

In certain embodiments -D is a glycopeptide, such as a glycoprotein selected from the group consisting of vancomycin, oritavancin, telavancin, dalbavancin and teicoplanin. In certain embodiments -D is vancomycin. In certain embodiments -D is oritavancin. In certain embodiments -D is telavancin. In another embodiment -D is dalbavancin.

In certain embodiments -D is a penicillin, such as a penicillin selected from the group consisting of penams, penems and carbapenems. In certain embodiments such penams are selected from the group consisting of amoxicillin, ampicillin, carbenicillin, ticarcillin, temocillin, azlocillin, piperacillin, mezlocillin, mecillinam, benzylpenicillin, cloxacillin, dicloxacillin, flucloxacillin, oxacillin, methicillin and nafcillin. In certain embodiments such penems and carbapenes are selected from the group consisting of faropenem, ertapenem, doripenem, thiopenem, sulopenem, imipenem and meropenem. In certain embodiments -D is imipenem. In another embodiment -D is meropenem.

In certain embodiments -D is a cephalosporin, such as a cephalosporin selected from the group consisting of cefazolin, cefadroxil, cefalexin, cefradine, cefaclor, cefamandole, cefminox, cefotiam, cefprozil, cefuroxime, cefoxitin, cefotetan, cefmetazole, cefixime, ceftriaxone, ceftazidime, cefoperazone, cefpodoxime, cefdinir, cefditoren, cefotaxime, cefsulodin, cefteram, ceftibuten, ceftizoxime, cefepime, cefozopran, cefpirome, ceftaroline and ceftobiprole. In certain embodiments -D is cefazolin. In certain embodiments -D is cephalexin. In certain embodiments -D is ceftaroline. In certain embodiments -D is ceftobiprole. Cepholosporins are also known as cephamycins.

In certain embodiments -D is a monobactam, such as aztreonam.

In certain embodiments -D is a beta-lactamase inhibitor, such as a beta-lactamase inhibitor selected from the group consisting of sulbactam, tazobactam, clavulanic acid and cefdinir.

In certain embodiments -D is a polymycin antibiotic, such as a polymcin antibiotic selected from the group consisting of colistin and polymyxin B. In certain embodiments -D is colistin.

In certain embodiments -D is polymyxin B.

In certain embodiments -D is a lipopeptide antibiotic, such as a lipopeptide antibiotic selected from the group consisting of daptomycin, arylomycins and gramicidin. In certain embodiments -D is daptomycin. Daptomycin has the following chemical structure

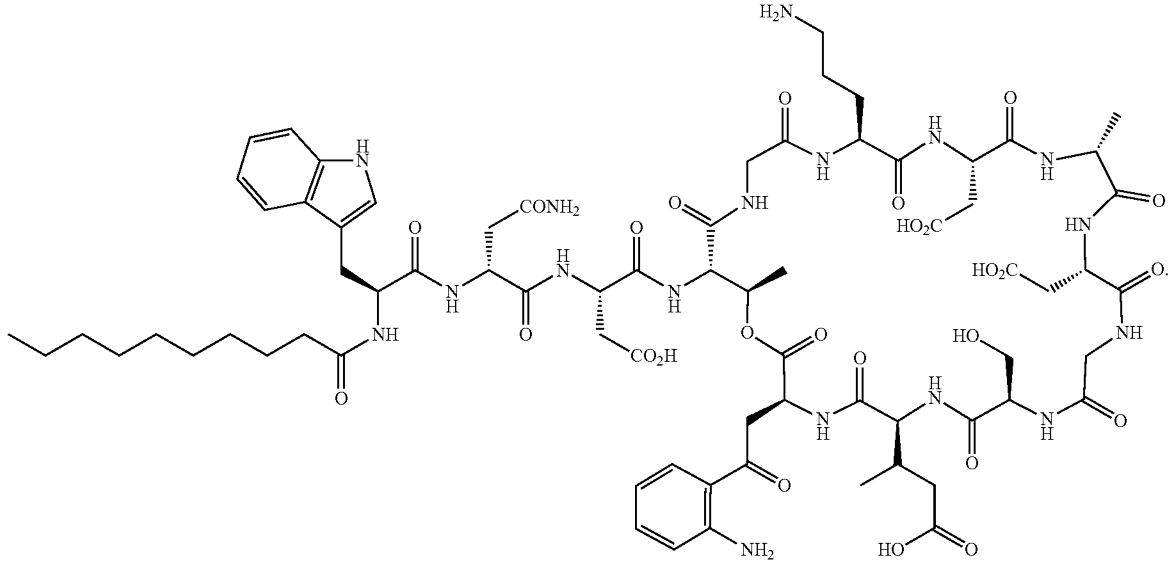 [SMILES: CCCCCCCCCC(=O)N[C@@H](Cc1c[nH]c2ccccc12)C(=O)N[C@H](CC(N)=O)C(=O)N[C@@H](CC(=O)O)C(=O)N[C@@H]1C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H](C(C)CC(=O)O)C(=O)N[C@@H](CC(=O)c2ccccc2N)C(=O)O[C@@H]1C]

In certain embodiments -D is an oxazolidinon, such as an oxazolidinon selected from the group consisting of linezolid, tedizolid, esperezolid, posizolid, radezolid, sutezolid and cadazolid. In certain embodiments -D is tedizolid.

In certain embodiments -D is an antimicrobial peptide, such as an antimicrobial peptide selected from the group consisting of cationic amphipathic peptides (CAP) and host defense proteins (HDP). In certain embodiments such CAP is selected from the group consisting of omiganan pentahydrochloride and novispirin g-10. In certain embodiments such HDP is brilacidin.

In certain embodiments -D is an antimicrobial protein, such as lysins.

In certain embodiments -D is a porphyrin, such as exeporfinium chloride.

In certain embodiments -D is an azole antifungal, such as an azole antifungal selected from the group consisting of fluconazole, isavuconazonium sulfate, posaconazole, itraconazole, voriconazole, albaconazole and miconazole. In certain embodiments -D is fluconazole. In certain embodiments -D is voriconazole. In certain embodiments -D is albaconazole.

In certain embodiments -D is a polyene, such as a polyene selected from the group consisting of amphotericin, echinocandins, flucytosine, tavaborole and triterpinoids. In certain embodiments an echinocandin is selected from the group consisting of caspofungin, micafungin, anidulafungin, cilofungin and rezafungin. In certain embodiments -D is amphotericin. In certain embodiments -D is caspofungin. In certain embodiments -D is micafungin. In certain embodiments -D is anidulafungin. In certain embodiments -D is cilofungin. In certain embodiments -D is rezafungin.

In certain embodiments -D is an antiprotozoal drug moiety, such as an antiprotozoal drug moiety selected from the list comprising eflornithine, furazolidone, melarsoprol, nifursemizone, ornidazole, pentamidine, pyrimethamine, quinapyramine, tinidazole, chlorproguanil, proguanil, atovaquone, dehydroemetine, diloxanide, eflornithine, halofantrine, lumefantrine, mepacrine, miltefosine, nitazoxanide, tizoxanide, pyronaridine, suramin, amodiaquine, chloroquine, hydroxychloroquine, primaquine, pamaquine, tafenoquine, mefloquine, artemether, artemisinin, artemotil, artesunate and dihydroartemisinin.

In certain embodiments all moieties -D of a conjugate are identical. In certain embodiments the conjugate comprises more than one type of -D, i.e. two or more different types of -D, such as two different types of -D, three different types of -D, four different types of -D or five different types of -D. If the conjugate comprises more than one type of -D one preferred combination is a combination of a beta-lactamase inhibitor and an antibiotic selected from the group consisting of penicillins, cephalosporins and monobactam antibiotics. Accordingly, in certain embodiments the conjugates of the present invention may comprise a beta-lactamase inhibitor and a penicillin. In certain embodiments the conjugates of the present invention may comprise a beta-lactamase inhibitor and a cephalosporin. In certain embodiments the conjugates of the present invention may comprise a beta-lactamase inhibitor and a monobactam antibiotic. If the conjugates of the present comprise more than one type of -D, all -D may be connected to the same type of $-L^1-$ or may be connected to different types of $-L^1-$, i.e. a first type of -D may be connected to a first type of $-L^1-$, a second type of -D may be connected to a second type of $-L^1-$ and so on. Using different types of $-L^1-$ may in certain embodiments allow different release kinetics for different types of -D, such as for example a faster release for a first type of -D, a medium release for a second type of -D and a slow release for a third type of -D. Accordingly, in certain embodiments the conjugates of the present invention comprise one type of $-L^1-$. In certain embodiments the conjugates of the present invention comprise two types of $-L^1-$. In certain embodiments the conjugates of the present invention comprise three types of $-L^1-$. In certain embodiments the conjugates of the present invention comprise four types of $-L^1-$.

In certain embodiments the conjugates of the present invention comprise one type of -D and one type of $-L^1-$. In certain embodiments the conjugates of the present invention comprise two types of -D and two types of $-L^1-$. In certain embodiments the conjugates of the present invention comprise three types of -D and three types of $-L^1-$. In certain embodiments the conjugates of the present invention comprise four types of -D and four types of $-L^1-$.

The moiety $-L^1-$ is conjugated to -D via a functional group of -D, which functional group is in certain embodiments selected from the group consisting of carboxylic acid, primary amine, secondary amine, thiol, sulfonic acid, carbonate, carbamate, hydroxyl, aldehyde, ketone, hydrazine, isothiocyanate, phosphoric acid, phosphonic acid, acryloyl, hydroxylamine, sulfate, vinyl sulfone, vinyl ketone, diazoalkane, guanidine, aziridine, amide, imide, imine, urea, amidine, guanidine, sulfonamide, phosphonamide, phorphoramide, hydrazide and selenol. In certain embodiments $-L^1-$ is conjugated to -D via a functional group of -D selected from the group consisting of carboxylic acid, primary amine, secondary amine, thiol, sulfonic acid, carbonate, carbamate, hydroxyl, aldehyde, ketone, hydrazine, isothiocyanate, phosphoric acid, phosphonic acid, acryloyl, hydroxylamine, sulfate, vinyl sulfone, vinyl ketone, diazoalkane, guanidine, amidine and aziridine. In certain embodiments $-L^1-$ is conjugated to -D via a functional group of -D selected from the group consisting of hydroxyl, primary amine, secondary amine, amidine and carboxylic acid.

In certain embodiments $-L^1-$ is conjugated to -D via a hydroxyl group of -D.

In certain embodiments $-L^1-$ is conjugated to -D via a primary amine group of -D.

In certain embodiments $-L^1-$ is conjugated to -D via a secondary amine group of -D.

In certain embodiments $-L^1-$ is conjugated to -D via a carboxylic acid group of -D.

In certain embodiments $-L^1-$ is conjugated to -D via an amidine group of -D.

The moiety $-L^1-$ can be connected to -D through any type of linkage, provided that it is reversible. In certain embodiments $-L^1-$ is connected to -D through a linkage selected from the group consisting of amide, ester, carbamate, acetal, aminal, imine, oxime, hydrazone, disulfide, acylguanidine, acylamidine, carbonate, phosphate, sulfate, urea, hydrazide, thioester, thiophosphate, thiosulfate, sulfonamide, sulfoamidine, sulfaguanidine, phosphoramide, phosphoamidine, phosphoguanidine, phosphonamide, phosphonamidine, phosphonguanidine, phosphonate, borate and imide. In certain embodiments $-L^1-$ is connected to -D through a linkage selected from the group consisting of amide, ester, carbonate, carbamate, acetal, aminal, imine, oxime, hydrazone, disulfide, acylamidine and acylguanidine.

In certain embodiments $-L^1-$ is connected to -D through a linkage selected from the group consisting of amide, ester, caronate, acylamide and carbamate. It is understood that some of these linkages may not be reversible per se, but that in the present invention neighboring groups present in $-L^1-$ render these linkages reversible.

In certain embodiments $-L^1-$ is connected to -D through an ester linkage.

In certain embodiments $-L^1-$ is connected to -D through a carbonate linkage.

In certain embodiments $-L^1-$ is connected to -D through an acylamidine linkage.

In certain embodiments $-L^1-$ is connected to -D through a carbamate linkage.

In certain embodiments $-L^1-$ is connected to -D through an amide linkage.

If -D is daptomycin, $-L^1-$ is in certain embodiments connected via the primary amine of the ornithine side chain. In certain embodiments such daptomycin is connected to $-L^1-$ via the primary amine of the ornithine side chain via an amide linkage.

The moiety $-L^1-$ is a linker moiety from which -D is released in its free form, i.e. in the form of D-H or D-OH. Such moieties are also known as "prodrug linkers" or "reversible prodrug linkers" and are known in the art, such as for example the reversible linker moieties disclosed in WO 2005/099768 A2, WO 2006/136586 A2, WO 2011/089216 A1, WO 2013/024053 A1, WO 2011/012722 A1, WO 2011/089214 A1, WO 2011/089215 A1, WO 2013/024052 A1 and WO 2013/160340 A1, which are incorporated by reference herewith.

In certain embodiments the moiety $-L^1-$ is as disclosed in WO 2009/095479 A2. Accordingly, in certain embodiments the moiety $-L^1-$ is of formula (I):

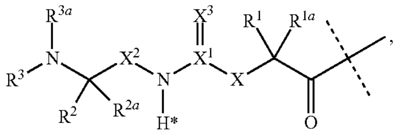

(I)

wherein the dashed line indicates the attachment to a nitrogen, hydroxyl or thiol of -D;

—X— is selected from the group consisting of —C($R^4R^{4a}$)—, —N($R^4$)—, —O—, —C($R^4R^{4a}$)—C($R^5R^{5a}$)—, —C($R^5R^{5a}$)—C($R^4R^{4a}$)—, —C($R^4R^{4a}$)—N($R^6$)—, —N($R^6$)—C($R^4R^{4a}$)—, —C($R^4R^{4a}$)—O—, —O—C($R^4R^{4a}$)—, and —C($R^7R^{7a}$)—, $X^1$ is selected from the group consisting of C and S(O);

—$X^2$— is selected from the group consisting of —C($R^8R^{8a}$)— and —C($R^8R^{8a}$)—C($R^9R^{9a}$)—, =$X^3$ is selected from the group consisting of =O, =S, and =N—CN;

—$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$ and —$R^{9a}$ are independently selected from the group consisting of —H and $C_{1-6}$ alkyl;

—$R^3$ and —$R^{3a}$ are independently selected from the group consisting of —H and $C_{1-6}$ alkyl, provided that in case one or both of —$R^3$ and —$R^{3a}$ are other than —H they are connected to N to which they are attached through an $sp^3$-hybridized carbon atom;

—$R^7$ is selected from the group consisting of —N($R^{10}R^{10a}$) and —$NR^{10}$—(C=O)—$R^{11}$;

—$R^{7a}$, —$R^1$, —$R^{10a}$ and —$R^{11}$ are independently selected from the group consisting of —H and $C_{1-6}$ alkyl;

alternatively, one or more of the pairs —$R^{1a}$/—$R^{4a}$, —$R^{1a}$/—$R^{5a}$, —$R^{1a}$/—$R^{7a}$, —$R^{4a}$/—$R^{5a}$ and —$R^{8a}$/—$R^{9a}$ form a chemical bond;

alternatively, one or more of the pairs —$R^1$/—$R^{1a}$, —$R^2$/—$R^{2a}$, —$R^4$/—$R^{4a}$, —$R^5$/—$R^{5a}$, —$R^8$/—$R^{8a}$ and —$R^9$/—$R^{9a}$ are joined together with the atom to which they are attached to form a $C_{3-10}$ cycloalkyl or 3- to 10-membered heterocyclyl;

alternatively, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^1$/—$R^9$ and —$R^2$/—$R^3$ are joined together with the atoms to which they are attached to form a ring A;

alternatively, $R^3$/$R^{3a}$ are joined together with the nitrogen atom to which they are attached to form a 3- to 10-membered heterocycle;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein -$L^1$- is substituted with —$X^{0D}$-$L^2$- and wherein -$L^1$- is optionally further substituted, provided that the hydrogen marked with the asterisk in formula (I) is not replaced by —$X^{0D}$-$L^2$- or a substituent.

The optional further substituents of -$L^1$- of formula (I) are as described above.

In certain embodiments -$L^1$- of formula (I) is substituted with one moiety —$X^{0D}$-$L^2$-.

In certain embodiments -$L^1$- of formula (I) is not further substituted.

It is understood that if —$R^3$/—$R^{3a}$ of formula (I) are joined together with the nitrogen atom to which they are attached to form a 3- to 10-membered heterocycle, only such 3- to 10-membered heterocycles may be formed in which the atoms directly attached to the nitrogen are $sp^3$-hybridized carbon atoms. In other words, such 3- to 10-membered heterocycle formed by —$R^3$/—$R^{3a}$ together with the nitrogen atom to which they are attached has the following structure:

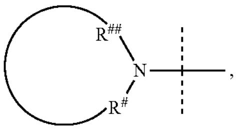

wherein the dashed line indicates attachment to the rest of -$L^1$-;

the ring comprises 3 to 10 atoms comprising at least one nitrogen; and $R^\#$ and $R^{\#\#}$ represent an $sp^3$-hydridized carbon atom.

It is also understood that the 3- to 10-membered heterocycle may be further substituted.

Exemplary embodiments of suitable 3- to 10-membered heterocycles formed by —$R^3$/—$R^{3a}$ of formula (I) together with the nitrogen atom to which they are attached are the following:

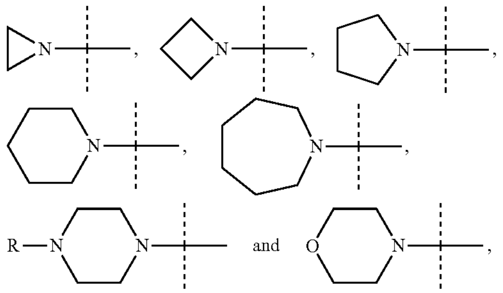

wherein dashed lines indicate attachment to the rest of the molecule; and

—R is selected from the group consisting of —H and $C_{1-6}$ alkyl.

-$L^1$- of formula (I) may optionally be further substituted. In general, any substituent may be used as far as the cleavage principle is not affected, i.e. the hydrogen marked with the asterisk in formula (I) is not replaced and the nitrogen of the moiety

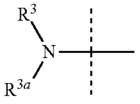

of formula (I) remains part of a primary, secondary or tertiary amine, i.e. —$R^3$ and —$R^{3a}$ are independently of each other —H or are connected to —N< through an $sp^3$-hybridized carbon atom.

In certain embodiments —$R^1$ of formula (I) is —H, which —H is substituted with —$X^{0D}$-$L^2$-. In certain embodiments —$R^{1a}$ of formula (I) is —H, which —H is substituted with —$X^{0D}$-$L^2$-. In certain embodiments —$R^2$ of formula (I) is —H, which —H is substituted with —$X^{0D}$-$L^2$-. In certain embodiments —$R^{2a}$ of formula (I) is —H, which —H is substituted with —$X^{0D}$-$L^2$-. In certain embodiments —$R^3$ of formula (I) is —H, which —H is substituted with —$X^{0D}$-$L^2$-. In certain embodiments —$R^{3a}$ of formula (I) is —H, which —H is substituted with —$X^{0D}$-$L^2$-. In certain embodiments —$R^4$ of formula (I) is —H, which —H is substituted with —$X^{0D}$-$L^2$-. In certain embodiments —$R^5$ of formula (I) is —H, which —H is substituted with —$X^{0D}$-$L^2$-. In certain embodiments —$R^{4a}$ of formula (I) is —H, which —H is substituted with —$X^{0D}$-$L^2$-. In certain embodiments —$R^6$ of formula (I) is —H, which —H is substituted with —$X^{0D}$-$L^2$-. In certain embodiments —$R^5$ of formula (I) is —H, which —H is substituted with —$X^{0D}$-$L^2$-. In certain embodiments —$R^{7a}$ of formula (I) is —H, which —H is substituted with —$X^{0D}$-$L^2$-. In certain embodiments —$R^8$ of formula (I) is —H, which —H is substituted with —$X^{0D}$-$L^2$-. In certain embodiments —$R^{8a}$ of formula (I) is —H, which —H is substituted with —$X^{0D}$-$L^2$-. In certain embodiments —$R^9$ of formula (I) is —H, which —H is substituted with —$X^{0D}$-$L^2$-. In certain embodiments —$R^{9a}$ of formula (I) is —H, which —H is substituted with —$X^{0D}$-$L^2$-. In certain embodiments —$R^{10}$ of formula (I) is —H, which —H is substituted with —$X^{0D}$-$L^2$-. In certain embodiments —$R^{11}$ of formula (I) is —H, which —H is substituted with —$X^{0D}$-$L^2$-.

In certain embodiments —X— of formula (I) is selected from the group consisting of —$C(R^4R^{4a})$—, —$N(R^4)$— and —$C(R^7R^{7a})$—.

In certain embodiments —X— of formula (I) is —$C(R^4R^{4a})$—.

In certain embodiments —X— of formula (I) is —$N(R^4)$—.

In certain embodiments —X— of formula (I) is —$C(R^7R^{7a})$—.

In certain embodiments —$R^7$ of formula (I) is —$NR^{10}$—(C═O)—$R^{11}$.

In certain embodiments —$R^{7a}$ of formula (I) is selected from —H, methyl and ethyl.

In certain embodiments —$R^{7a}$ of formula (I) is —H.

In certain embodiments —$R^{10}$ of formula (I) is selected from —H, methyl and ethyl.

In certain embodiments —$R^{10}$ of formula (I) is methyl. In certain embodiments —$R^{10}$ is —H.

In certain embodiments —$R^{11}$ of formula (I) is selected from —H, methyl and ethyl. In certain embodiments —$R^{11}$ is —H.

In certain embodiments —$R^{11}$ of formula (I) is substituted with —$X^{0D}$-$L^2$-.

In certain embodiments $X^1$ of formula (I) is C.

In certain embodiments ═$X^3$ of formula (I) is ═O.

In certain embodiments —$X^2$— of formula (I) is —$C(R^8R^{8a})$—.

In certain embodiments —$R^8$ and —$R^{8a}$ of formula (I) are independently selected from the group consisting of —H, methyl and ethyl. In certain embodiments at least one of —$R^8$ and —$R^{8a}$ of formula (I) is —H. In certain embodiments both —$R^8$ and —$R^{8a}$ of formula (I) are —H.

In certain embodiments —$R^1$ and —$R^{1a}$ of formula (I) are independently selected from the group consisting of —H, methyl and ethyl. In certain embodiments at least one of —$R^1$ and —$R^{1a}$ of formula (I) is —H. In certain embodiments both —$R^1$ and —$R^{1a}$ of formula (I) are —H.

In certain embodiments —$R^2$ and —$R^{2a}$ of formula (I) are independently selected from the group consisting of —H, methyl and ethyl. In certain embodiments at least one of —$R^2$ and —$R^{2a}$ of formula (I) is —H. In certain embodiments both —$R^2$ and —$R^{2a}$ of formula (I) are H.

In certain embodiments —$R^3$ and —$R^{3a}$ of formula (I) are independently selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of —$R^3$ and —$R^{3a}$ of formula (I) is methyl. In certain embodiments both —$R^3$ and —$R^{3a}$ of formula (I) are methyl.

In certain embodiments -D is connected to -$L^1$- through a nitrogen by forming an amide bond. It is understood that the carbonyl to the left of the dashed line and the nitrogen of -D form the amide bond.

In certain embodiments the nitrogen that connects -D to -$L^1$- by forming an amide bond is provided by a primary or secondary amine of -D.

In certain embodiments the moiety -$L^1$- is of formula (Ia):

(Ia)

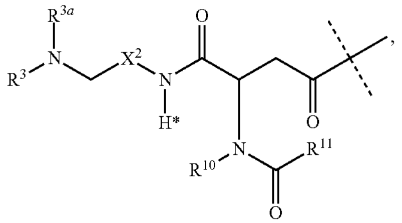

wherein the dashed line indicates the attachment to a nitrogen of -D by forming an amide bond;

—$R^3$, —$R^{3a}$, —$R^{10}$, —$R^{11}$ and —$X^2$— are used as defined in formula (I); and wherein -$L^1$- is substituted with —$X^{0D}$-$L^2$- and wherein -$L^1$- is optionally further substituted, provided that the hydrogen marked with the asterisk in formula (Ia) is not replaced by —$X^{0D}$-$L^2$- or a substituent.

The optional further substituents of -$L^1$- of formula (Ia) are as described above.

In certain embodiments -$L^1$- of formula (Ia) is substituted with one moiety —$X^{0D}$-$L^2$-.

In certain embodiments the moiety -$L^1$- of formula (Ia) is not further substituted.

In certain embodiments —$X^2$— of formula (Ia) is —$C(R^8R^{8a})$—.

In certain embodiments —$R^8$ and —$R^{8a}$ of formula (Ia) are independently selected from the group consisting of —H, methyl and ethyl. In certain embodiments at least one of —$R^8$ and —$R^{8a}$ of formula (Ia) is —H. In certain embodiments both —$R^8$ and —$R^{8a}$ of formula (Ia) are —H.

In certain embodiments —$R^3$ and —$R^{3a}$ of formula (Ia) are independently selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of —$R^3$ and —$R^{3a}$ of formula (Ia) is methyl. In certain embodiments both —$R^3$ and —$R^{3a}$ of formula (Ia) are methyl.

In certain embodiments —$R^{10}$ of formula (Ia) is selected from —H, methyl and ethyl. In certain embodiments —$R^{10}$ of formula (Ia) is methyl.

In certain embodiments —$R^{11}$ of formula (Ia) is selected from —H, methyl and ethyl. In certain embodiments —$R^{11}$ of formula (Ia) is —H.

In certain embodiments $—R^{11}$ of formula (Ia) is substituted with $—X^{0D}$-$L^2$-.

In certain embodiments the moiety -$L^1$- is of formula (Ib):

(Ib)

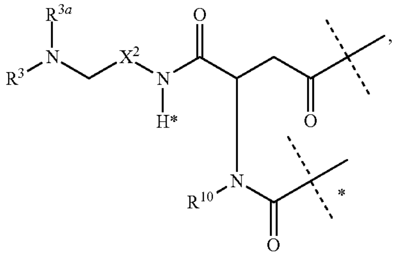

wherein wherein the dashed line indicates the attachment to a nitrogen of -D by forming an amide bond;

the dashed line marked with the asterisk indicates attachment to $—X^{0D}$-$L^2$-;

$—R^3$, $—R^{3a}$, $—R^{10}$ and $—X^2—$ are used as defined in formula (I); and wherein -$L^1$- is optionally further substituted, provided that the hydrogen marked with the asterisk in formula (Ib) is not replaced by a substituent.

The optional further substituents of -$L^1$- of formula (Ib) are as described above.

In certain embodiments the moiety -$L^1$- of formula (Ib) is not further substituted.

In certain embodiments $—X^2—$ of formula (Ib) is $—C(R^8R^{8a})—$.

In certain embodiments $—R^8$ and $—R^{8a}$ of formula (Ib) are independently selected from the group consisting of —H, methyl and ethyl. In certain embodiments at least one of $—R^8$ and $—R^{8a}$ of formula (Ib) is —H. In certain embodiments both $—R^8$ and $—R^{8a}$ of formula (Ib) are —H.

In certain embodiments $—R^3$ and $—R^{3a}$ of formula (Ib) are independently selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. In certain embodiments at least one of $—R^3$ and $—R^{3a}$ of formula (Ib) is methyl. In certain embodiments both $—R^3$ and $—R^{3a}$ of formula (Ib) are methyl.

In certain embodiments $—R^{10}$ of formula (Ib) is selected from —H, methyl and ethyl. In certain embodiments $—R^{10}$ of formula (Ib) is methyl.

In certain embodiments the moiety -$L^1$- is of formula (Ic):

(Ic)

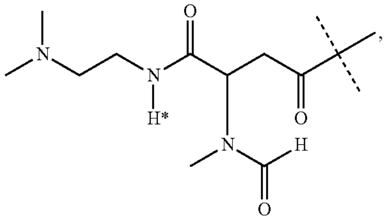

wherein the dashed line indicates the attachment to a nitrogen of -D by forming an amide bond; and wherein -$L^1$- is substituted with $—X^{0D}$-$L^2$- and wherein -$L^1$- is optionally further substituted, provided that the hydrogen marked with the asterisk in formula (Ic) is not replaced by $—X^{0D}$-$L^2$- or a substituent.

The optional further substituents of -$L^1$- of formula (Ic) are as described above.

In certain embodiments -$L^1$- of formula (Ic) is substituted with one moiety $—X^{0D}$-$L^2$-.

In certain embodiments the moiety -$L^1$- of formula (Ic) is not further substituted.

-D is connected to -$L^1$- of formula (Ic) through a nitrogen of -D by forming an amide bond. In certain embodiments said nitrogen is provided by a primary or secondary amine of -D.

In certain embodiments the moiety -$L^1$- is of formula (Id):

(Id)

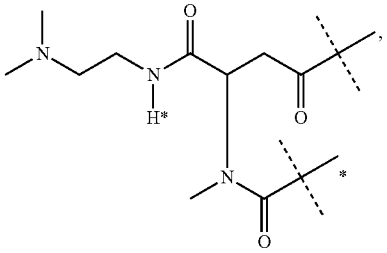

wherein wherein the dashed line indicates the attachment to a nitrogen of -D by forming an amide bond;

the dashed line marked with the asterisk indicates attachment to $—X^{0D}$-$L^2$-; and wherein -$L^1$- is optionally further substituted, provided that the hydrogen marked with the asterisk in formula (Id) is not replaced by a substituent.

In certain embodiments the moiety -$L^1$- of formula (Id) is not further substituted.

-D is connected to -$L^1$- of formula (Id) through a nitrogen of -D by forming an amide bond. In certain embodiments said nitrogen is provided by a primary or secondary amine of -D.

In certain embodiments the moiety -$L^1$- is of formula (Ie)

(Ie)

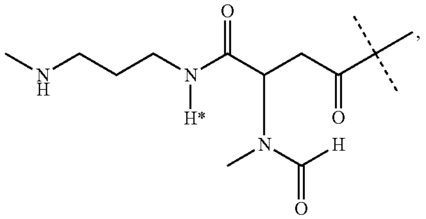

wherein the dashed line indicates the attachment to a nitrogen of -D by forming an amide bond; and wherein -$L^1$- is substituted with $—X^{0D}$-$L^2$- and wherein -$L^1$- is optionally further substituted, provided that the hydrogen marked with the asterisk in formula (Ie) is not replaced by $—X^{0D}$-$L^2$- or a substituent.

The optional further substituents of -$L^1$- of formula (Ie) are as described above.

In certain embodiments -$L^1$- of formula (Ie) is substituted with one moiety $—X^{0D}$-$L^2$-.

In certain embodiments the moiety -$L^1$- of formula (Ie) is not further substituted.

-D is connected to -$L^1$- of formula (Ie) through a nitrogen of -D by forming an amide bond. In certain embodiments said nitrogen is provided by a primary or secondary amine of -D.

In certain embodiments the moiety -$L^1$- is of formula (If):

(If)

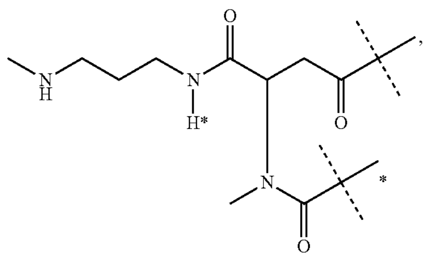

wherein the dashed line indicates the attachment to a nitrogen of -D by forming an amide bond;

the dashed line marked with the asterisk indicates attachment to —$X^{0D}$-$L^2$-; and wherein -$L^1$- is optionally further substituted, provided that the hydrogen marked with the asterisk in formula (If) is not replaced by a substituent.

In certain embodiments the moiety -$L^1$- of formula (If) is not further substituted.

-D is connected to -$L^1$- of formula (If) through a nitrogen of -D by forming an amide bond. In certain embodiments said nitrogen is provided by a primary or secondary amine of -D.

Another moiety -$L^1$- is disclosed in WO 2016/020373 A1. Accordingly, in certain embodiments the moiety -$L^1$- is of formula (II):

(II)

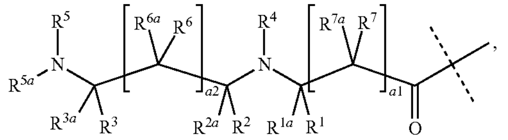

wherein the dashed line indicates attachment to a primary or secondary amine or hydroxyl of -D by forming an amide or ester linkage, respectively;

—$R^1$, —$R^{1a}$, —$R^2$, —$R^{2a}$, —$R^3$ and —$R^{3a}$ are independently of each other selected from the group consisting of —H, —C($R^8R^{8a}R^{8b}$), —C(=O)$R^8$, —C≡N, —C(=N$R^8$)$R^{8a}$, —C$R^8$(=C$R^{8a}R^{8b}$), —C≡C$R^8$ and -T;

—$R^4$, —$R^5$ and —$R^{5a}$ are independently of each other selected from the group consisting of —H, —C($R^9R^{9a}R^{9b}$) and -T;

a1 and a2 are independently of each other 0 or 1;

each —$R^6$, —$R^{6a}$, —$R^7$, —$R^{7a}$, —$R^8$, —$R^{8a}$, —$R^{8b}$, —$R^9$, —$R^{9a}$, —$R^{9b}$ are independently of each other selected from the group consisting of —H, halogen, —CN, —COO$R^{10}$, —O$R^{10}$, —C(O)$R^{10}$, —C(O)N($R^{10}R^{10a}$), —$S(O)_2$N($R^{10}R^{10a}$), —S(O)N($R^{10}R^{10a}$), —$S(O)_2R^{10}$, —S(O)$R^{10}$, —N($R^{10}$)$S(O)_2$N($R^{10a}R^{10b}$), —S$R^{10}$, —N($R^{10}R^{10a}$), —$NO_2$, —OC(O)$R^{10}$, —N($R^{10}$)C(O)$R^{10a}$, —N($R^{10}$)$S(O)_2R^{10a}$, —N($R^{10}$)S(O)$R^{10a}$, —N($R^{10}$)C(O)O$R^{10a}$, —N($R^{10}$)C(O)N($R^{10a}R^{10b}$), —OC(O)N($R^{10}R^{10a}$), -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —$S(O)_2$N($R^{12}$)—, —S(O)N($R^{12}$)—, —$S(O)_2$—, —S(O)—, —N($R^{12}$)$S(O)_2$N($R^{12a}$)—, —S—, —N($R^{12}$)—, —OC(O$R^{12}$)($R^{12a}$)—, —N($R^{12}$)C(O)N($R^{12a}$)—, and —OC(O)N($R^{12}$)—;

each —$R^{10}$, —$R^{10a}$, —$R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^1$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{12}$)—, —$S(O)_2$N($R^{12}$)—, —S(O)N($R^{12}$)—, —$S(O)_2$—, —S(O)—, —N($R^{12}$)$S(O)_2$N($R^{12a}$)—, —S—, —N($R^{12}$)—, —OC(O$R^{12}$)($R^{12a}$)—, —N($R^{12}$)C(O)N($R^{12a}$)—, and —OC(O)N($R^{12}$)—;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more —$R^{11}$, which are the same or different;

each —$R^{11}$ is independently of each other selected from halogen, —CN, oxo (=O), —COO$R^{13}$, —O$R^{13}$, —C(O)$R^{13}$, —C(O)N($R^{13}R^{13a}$), —$S(O)_2$N($R^{13}R^{13a}$), —S(O)N($R^{13}R^{13a}$), —$S(O)_2R^{13}$, —S(O)$R^{13}$, —N($R^{13}$)$S(O)_2$N($R^{13a}R^{13b}$), —S$R^{13}$, —N($R^{13}R^{13a}$), —$NO_2$, —OC(O)$R^{13}$, —N($R^{13}$)C(O)$R^{13a}$, —N($R^{13}$)$S(O)_2R^{13a}$, —N($R^{13}$)S(O)$R^{13a}$, —N($R^{13}$)C(O)O$R^{13a}$, —N($R^{13}$)C(O)N($R^{13a}R^{13b}$), —OC(O)N($R^{13}R^{13a}$), and $C_{1-6}$ alkyl; wherein $C_{1-6}$ alkyl is optionally substituted with one or more halogen, which are the same or different;

each —$R^{12}$, —$R^{12a}$, —$R^{13}$, —$R^{13a}$, —$R^{13b}$ is independently selected from the group consisting of —H, and $C_{1-6}$ alkyl; wherein $C_{1-6}$ alkyl is optionally substituted with one or more halogen, which are the same or different;

optionally, one or more of the pairs —$R^1$/—$R^{1a}$, —$R^2$/—$R^{2a}$, —$R^3$/—$R^{3a}$, —$R^6$/—$R^{6a}$, —$R^7$/—$R^{7a}$ are joined together with the atom to which they are attached to form a $C_{3-10}$ cycloalkyl or a 3- to 10-membered heterocyclyl;

optionally, one or more of the pairs —$R^1$/—$R^2$, —$R^1$/—$R^3$, —$R^1$/—$R^4$, —$R^1$/—$R^5$, —$R^1$/—$R^6$, —$R^1$/—$R^7$, —$R^2$/—$R^3$, —$R^2$/—$R^4$, —$R^2$/—$R^5$, —$R^2$/—$R^6$, —$R^2$/—$R^7$, —$R^3$/—$R^4$, —$R^3$/—$R^5$, —$R^3$/—$R^6$, —$R^3$/—$R^7$, —$R^4$/—$R^5$, —$R^4$/—$R^6$, —$R^4$/—$R^7$, —$R^5$/—$R^6$, —$R^5$/—$R^7$, —$R^6$/—$R^7$ are joint together with the atoms to which they are attached to form a ring A;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein $-L^1-$ is substituted with $—X^{0D}-L^2-$ and wherein $-L^1-$ is optionally further substituted.

The optional further substituents of $-L^1-$ of formula (II) are as described above.

In certain embodiments $-L^1-$ of formula (II) is substituted with one moiety $—X^{0D}-L^2-$.

In certain embodiments $-L^1-$ of formula (II) is not further substituted.

Additional embodiments for $-L^1-$ are disclosed in EP1536334B1, WO2009/009712A1, WO2008/034122A1, WO2009/143412A2, WO2011/082368A2, and U.S. Pat. No. 8,618,124B2, which are herewith incorporated by reference in their entirety.

Further embodiments for $-L^1-$ are disclosed in U.S. Pat. No. 8,946,405B2 and U.S. Pat. No. 8,754,190B2, which are herewith incorporated by reference in their entirety. Accordingly, in certain embodiments $-L^1-$ is of formula (III):

(III)

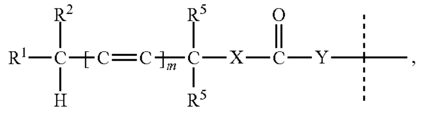

wherein the dashed line indicates attachment to -D through a functional group of -D selected from the group consisting of —OH, —SH and $—NH_2$;

m is 0 or 1;

at least one or both of $—R^1$ and $—R^2$ is/are independently of each other selected from the group consisting of —CN, $—NO_2$, optionally substituted aryl, optionally substituted heteroaryl, optionally substituted alkenyl, optionally substituted alkynyl, $—C(O)R^3$, $—S(O)R^3$, $—S(O)_2R^3$, and $—SR^4$, one and only one of $—R^1$ and $—R^2$ is selected from the group consisting of —H, optionally substituted alkyl, optionally substituted arylalkyl, and optionally substituted heteroarylalkyl;

$—R^3$ is selected from the group consisting of —H, optionally substituted alkyl, optionally substituted aryl, optionally substituted arylalkyl, optionally substituted heteroaryl, optionally substituted heteroarylalkyl, $—OR^9$ and $—N(R^9)_2$;

$—R^4$ is selected from the group consisting of optionally substituted alkyl, optionally substituted aryl, optionally substituted arylalkyl, optionally substituted heteroaryl, and optionally substituted heteroarylalkyl;

each $—R^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;

$—R^9$ is selected from the group consisting of —H and optionally substituted alkyl;

—Y— is absent and —X— is —O— or —S—; or

—Y— is $—N(Q)CH_2—$ and —X— is —O—;

Q is selected from the group consisting of optionally substituted alkyl, optionally substituted aryl, optionally substituted arylalkyl, optionally substituted heteroaryl and optionally substituted heteroarylalkyl;

optionally, $—R^1$ and $—R^2$ may be joined to form a 3 to 8-membered ring; and optionally, both $—R^9$ together with the nitrogen to which they are attached form a heterocyclic ring; and wherein $-L^1-$ is substituted with $—X^{0D}-L^2-$ and wherein $-L^1-$ is optionally further substituted.

Only in the context of formula (III) the terms used have the following meaning:

The term "alkyl" as used herein includes linear, branched or cyclic saturated hydrocarbon groups of 1 to 8 carbon atoms, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted.

Optional substituents on any group, including the above, include halo, nitro, cyano, —OR, —SR, $—NR_2$, —OCOR, —NRCOR, —COOR, $—CONR_2$, —SOR, $—SO_2R$, $—SONR_2$, $—SO_2N\ R_2$, wherein each R is independently alkyl, alkenyl, alkynyl, aryl or heteroaryl, or two R groups taken together with the atoms to which they are attached form a ring.

In certain embodiments $-L^1-$ of formula (III) is substituted with one moiety $—X^{0D}-L^2-$.

Another embodiment for $-L^1-$ is disclosed in WO2013/036857A1, which is herewith incorporated by reference in its entirety. Accordingly, in certain embodiments $-L^1-$ is of formula (IV):

(IV)

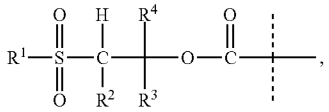

wherein the dashed line indicates attachment to -D through an amine functional group of -D;

—$R^1$ is selected from the group consisting of optionally substituted $C_1$-$C_6$ linear, branched, or cyclic alkyl; optionally substituted aryl; optionally substituted heteroaryl; alkoxy; and —$NR^5{}_2$;

—$R^2$ is selected from the group consisting of —H; optionally substituted $C_1$-$C_6$ alkyl; optionally substituted aryl; and optionally substituted heteroaryl;

—$R^3$ is selected from the group consisting of —H; optionally substituted $C_1$-$C_6$ alkyl; optionally substituted aryl; and optionally substituted heteroaryl;

—$R^4$ is selected from the group consisting of —H; optionally substituted $C_1$-$C_6$ alkyl; optionally substituted aryl; and optionally substituted heteroaryl;

each —$R^5$ is independently of each other selected from the group consisting of —H; optionally substituted $C_1$-$C_6$ alkyl; optionally substituted aryl; and optionally substituted heteroaryl; or when taken together two —$R^5$ can be cycloalkyl or cycloheteroalkyl; and wherein -$L^1$- is substituted with —$X^{0D}$-$L^2$- and wherein -$L^1$- is optionally further substituted.

Only in the context of formula (IV) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

In one embodiment -$L^1$- of formula (IV) is substituted with one moiety —$X^{0D}$-$L^2$-.

A further embodiment for -$L^1$- is disclosed in U.S. Pat. No. 7,585,837B2, which is herewith incorporated by reference in its entirety. Accordingly, in certain embodiments -$L^1$- is of formula (V):

(V)

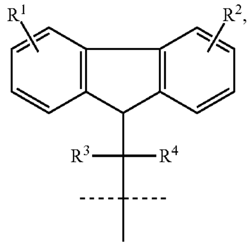

wherein the dashed line indicates attachment to -D through an amine functional group of -D;

$R^1$ and $R^2$ are independently selected from the group consisting of hydrogen, alkyl, alkoxy, alkoxyalkyl, aryl, alkaryl, aralkyl, halogen, nitro, —$SO_3H$, —$SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl; and wherein -$L^1$- is substituted with —$X^{0D}$-$L^2$- and wherein -$L^1$- is optionally further substituted.

Suitable substituents for formulas (V) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (V) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

In certain embodiments -$L^1$- of formula (V) is substituted with one moiety —$X^{0D}$-$L^2$-.

In certain embodiments -$L^1$- of formula (V) is not further substituted.

In certain embodiments -$L^1$- is as disclosed in WO2002/089789A1, which is herewith incorporated by reference in its entirety. Accordingly, in certain embodiments -$L^1$- is of formula (VI):

(VI)

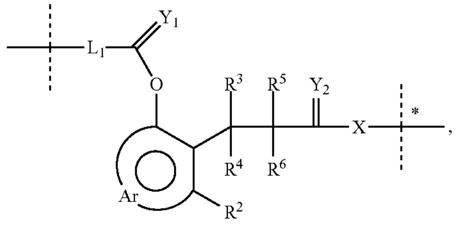

wherein the dashed line indicates attachment to -D through an amine functional group of -D;

$L_1$ is a bifunctional linking group, $Y_1$ and $Y_2$ are independently O, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VI) forms a multisubstituted aromatic hydrocarbon or a multisubstituted heterocyclic group;

X is a chemical bond or a moiety that is actively transported into a target cell, a hydrophobic moiety, or a combination thereof, y is 0 or 1; and wherein $-L^1-$ is substituted with $—X^{0D}-L^2-$ and wherein $-L^1-$ is optionally further substituted.

Only in the context of formula (VI) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moieties such as methoxy; and phenoxy includes moieties such as 3-nitrophenoxy. Halo-shall be understood to include fluoro, chloro, iodo and bromo.

In certain embodiments $-L^1-$ of formula (VI) is substituted with one moiety $—X^{0D}-L^2-$.

In certain embodiments $-L^1-$ of formula (VI) is not further substituted.

In certain embodiments $-L^1-$ comprises a substructure of formula (VII)

(VII)

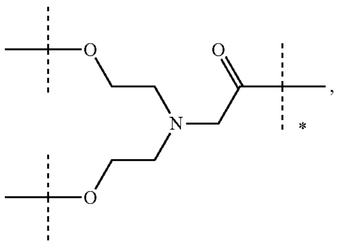

wherein the dashed line marked with the asterisk indicates attachment to a nitrogen of -D by forming an amide bond;

the unmarked dashed lines indicate attachment to the remainder of $-L^1-$; and wherein $-L^1-$ is substituted with $—X^{0D}-L^2-$ and wherein $-L^1-$ is optionally further substituted.

The optional further substituents of $-L^1-$ of formula (VII) are as described above.

In certain embodiments $-L^1-$ of formula (VII) is substituted with one moiety $—X^{0D}-L^2-$.

In certain embodiments $-L^1-$ of formula (VII) is not further substituted.

In certain embodiments $-L^1-$ comprises a substructure of formula (VIII)

(VIII)

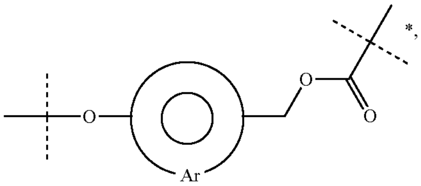

wherein the dashed line marked with the asterisk indicates attachment to a nitrogen of -D by forming a carbamate bond;

the unmarked dashed lines indicate attachment to the remainder of $-L^1-$; and wherein $-L^1-$ is substituted with $—X^{0D}-L^2-$ and wherein $-L^1-$ is optionally further substituted.

The optional further substituents of $-L^1-$ of formula (VIII) are as described above.

In certain embodiments $-L^1-$ of formula (VIII) is substituted with one moiety $—X^{0D}-L^2-$.

In certain embodiments $-L^1-$ of formula (VIII) is not further substituted.

It is understood that a moiety $-L^2-X^{0D}-L^1-D$ is connected to Z through covalent attachment of $-L^1-$ to —Z.

It is also understood that the phrase "$-L^1-$ is substituted with $—X^{0D}-L^2-$" means that $-L^2-$ is attached to $-L^1-$ via $—X^{0D}—$, which is either absent or a linkage, and that the moiety $—X^{0D}-L^2-$ is not attached to $-L^1-$ via $-L^2-$.

In certain embodiments all moieties $—X^{0D}—$ are identical. In certain embodiments a conjugate of the present invention comprises more than one type of $—X^{0D}—$, such as two, three or four different types of $—X^{0D}—$.

In certain embodiments $—X^{0D}—$ is a stable linkage, i.e $-L^1-$ and $—X^{0D}-L^2-$ are connected through a stable linkage.

In certain embodiments $—X^{0D}—$ is absent, in which case the moiety $-L^2-X^{0D}-L^1-$ is a moiety $-L^2-L^1-$, wherein the bond between $-L^2-$ and $-L^1-$ is a stable bond.

In the conjugates of the present invention $-L^2-$ is absent or a spacer moiety. In certain embodiments $-L^2-$ does not comprise a reversible linkage, i.e. all linkages in $-L^2-$ are stable linkages. $-L^1-$ is connected to $-L^2-$ via a stable linkage. $-L^2-$ is connected to —Z via a stable linkage.

In certain embodiments $-L^2-$ is absent.

In certain embodiments $-L^2-$ is a spacer moiety.

In certain embodiments $-L^2-$ is a spacer moiety selected from the group consisting of -T-, —C(O)O—, —O—, —C(O)—, $—C(O)N(R^{y1})—$, $—S(O)_2N(R^{y1})—$, $—S(O)N(R^{y1})—$, $—S(O)_2—$, —S(O)—, $—N(R^{y1})S(O)_2N(R^{y1a})—$, —S—, $—N(R^{y1})—$, $—OC(OR^{y1})(R^{y1a})—$, $—N(R^{y1})C(O)N(R^{y1a})—$, $—OC(O)N(R^{y1})—$, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $—R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —$S(O)_2N(R^{y4})$—, —S(O)N($R^{y4}$)—, —$S(O)_2$—, —S(O)—, —$N(R^{y4})S(O)_2N(R^{y4a})$—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (═O), —$COOR^{y5}$, —$OR^{y5}$, —C(O)$R^{y5}$, —C(O)N($R^{y5}R^{y5a}$), —$S(O)_2N(R^{y5}R^{y5a})$, —S(O)N($R^{y5}R^{y5a}$), —$S(O)_2R^{y5}$, —S(O)$R^{y5}$, —$N(R^{y5})S(O)_2N(R^{y5a}R^{y})$, —$SR^{y5}$, —N($R^{y5}R^{y5a}$), —$NO_2$, —OC(O)$R^{y5}$, —N($R^{y5}$)C(O)$R^{y5a}$, —$N(R^{y5})S(O)_2R^{y5a}$, —N($R^{y5}$)S(O)$R^{y5a}$, —N($R^{y5}$)C(O)$OR^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different.

In certain embodiments -$L^2$- is a spacer moiety selected from -T-, —C(O)O—, —O—, —C(O)—, —C(O)N($R^{y1}$)—, —$S(O)_2N(R^{y1})$—, —S(O)N($R^{y1}$)—, —$S(O)_2$—, —S(O)—, —$N(R^{y1})S(O)_2N(R^{y1a})$—, —S—, —N($R^{y1}$)—, —OC($OR^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —$N(R^{y3})S(O)_2N(R^{y3a})$—, —S—, —N($R^{y3}$)—, —OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —$S(O)_2$(Re)—, —S(O)N($R^{y4}$)—, —$S(O)_2$—, —S(O)—, —$N(R^{y4})S(O)_2N(R^{y4a})$—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (═O), —$COOR^{y5}$, —$OR^{y5}$, —C(O)$R^{y5}$, —C(O)N($R^{y5}R^{y5a}$), —$S(O)_2N(R^{y5}R^{y5a})$, —S(O)N($R^{y5}R^{y5a}$), —$S(O)_2R^{y5}$, —S(O)$R^{y5}$, —$N(R^{y5})S(O)_2N(R^{y5a}R^{y5b})$, —$SR^{y5}$, —N($R^{y5}R^{y5a}$), —$NO_2$, —OC(O)$R^5$, —N($R^{y5}$) C(O)$R^{y5a}$, —$N(R^{y5})S(O)_2R^{y5a}$, —N($R^{y5}$)S(O)$R^{y5a}$, —N($R^{y5}$)C(O)$OR^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

In certain embodiments -$L^2$- is a spacer moiety selected from the group consisting of -T-, —C(O)O—, —O—, —C(O)—, —C(O)N($R^{y1}$)—, —$S(O)_2N(R^{y1})$—, —S(O)N($R^{y1}$)—, —$S(O)_2$—, —S(O)—, —$N(R^{y1})S(O)_2N(R^{y1a})$—, —S—, —N($R^{y1}$)—, —OC($OR^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —$N(R^{y3})S(O)_2N(R^{y3a})$—, —S—, —N($R^{y3}$)—, —OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen, and $C_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

In certain embodiments -$L^2$- is a $C_{1-20}$ alkyl chain, which is optionally interrupted by one or more groups independently selected from —O—, -T- and —C(O)N($R^{y1}$)—; and which $C_{1-20}$ alkyl chain is optionally substituted with one or more groups independently selected from —OH, -T and —C(O)N($R^{y6}R^{y6a}$); wherein —$R^{y1}$, —$R^{y6}$, —$R^{y6a}$ are independently selected from the group consisting of H and $C_{1-4}$ alkyl and wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

In certain embodiments -$L^2$- has a molecular weight ranging from 14 g/mol to 750 g/mol.

In certain embodiments -$L^2$- comprises a moiety selected from

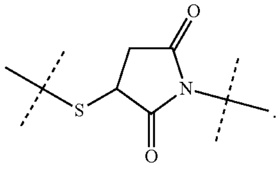
.

In certain embodiments $-L^2-$ has a chain lengths of 1 to 20 atoms.

As used herein the term "chain length" with regard to the moiety $-L^2-$ refers to the number of atoms of $-L^2-$ present in the shortest connection between $—X^{0D}-L^1-$ and —Z.

In certain embodiments $-L^2-$ is of formula (i)

(i)

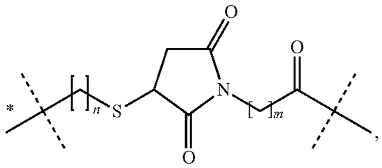
, wherein the dashed line marked with the asterisk indicates attachment to $-L^1-$;

the unmarked dashed line indicates attachment to —Z;

n is selected from the group consisting of 0, 1, 2, 3, 4, 5, 6, 7, 8, 9, 10, 11, 12, 13, 14, 15, 16, 17 and 18;

m is selected from the group consisting of 0, 1, 2, 3, 4, 5, 6, 7, 8, 9, 10, 11, 12, 13, 14, 15, 16, 17 and 18; and wherein the moiety of formula (i) is optionally further substituted.

In certain embodiments n of formula (i) is selected from the group consisting of 3, 4, 5, 6, 7, 8, and 9. In certain embodiments n of formula (i) is 3, 4, 5, 6, or 7. In certain embodiments n of formula (i) is 3. In certain embodiments n of formula (i) is 4. In certain embodiments n of formula (i) is 5. In certain embodiments n of formula (i) is 6.

In certain embodiments m of formula (i) is selected from the group consisting of 1, 2, 3, 4, 5, 6 or 7. In certain embodiments m of formula (i) is 1, 2, 3, 4 or 5. In certain embodiments m of formula (i) is 1. In certain embodiments m of formula (i) is 2. In certain embodiments m of formula (i) is 3. In certain embodiments m of formula (i) is 4.

In certain embodiments the moiety $-L^2-X^{0D}-L^1-$ is selected from the group consisting of (Ia-i)

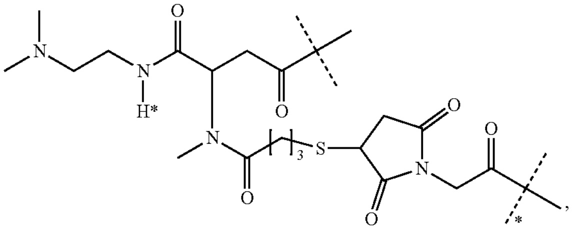
,

-continued (Ia-ii)

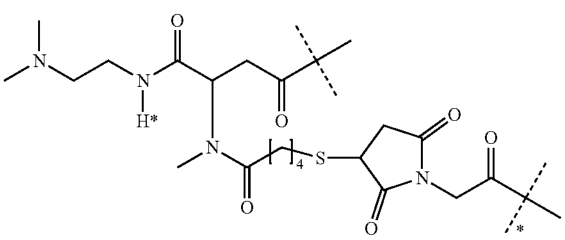

(Ia-iii)

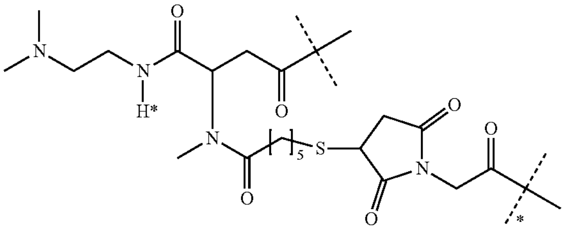

(Ia-iv)

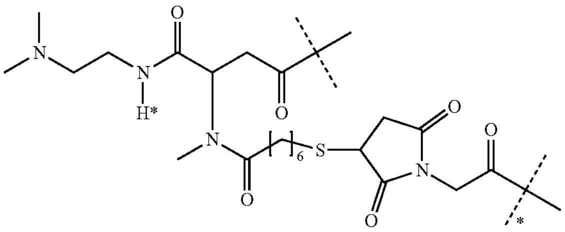

(Ib-i)

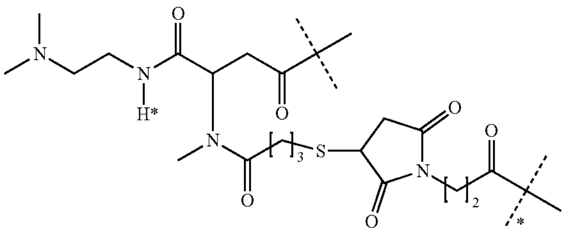
, (Ib-ii)

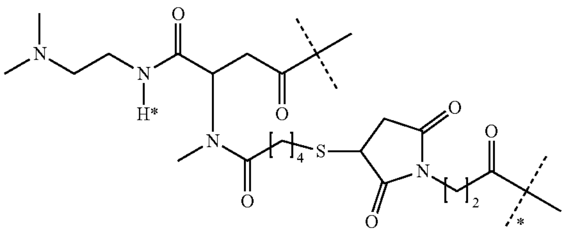
, (Ib-iii)

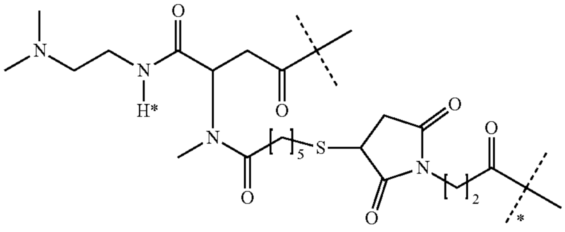
,

-continued (Ib-iv)

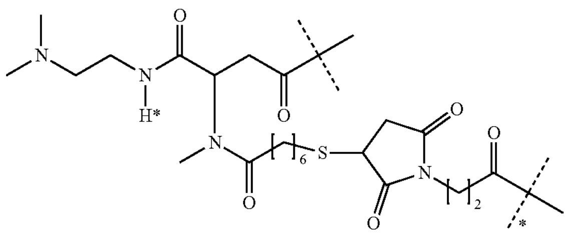, (Ic-i)

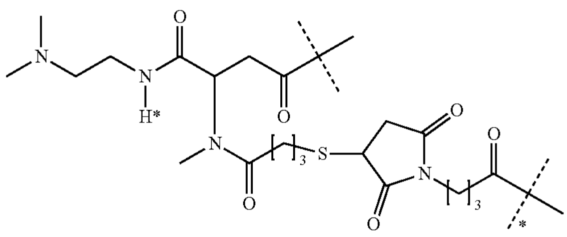, (Ic-ii)

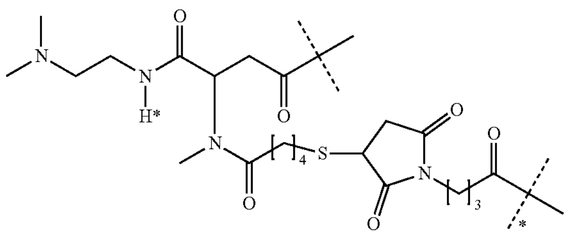, (Ic-iii)

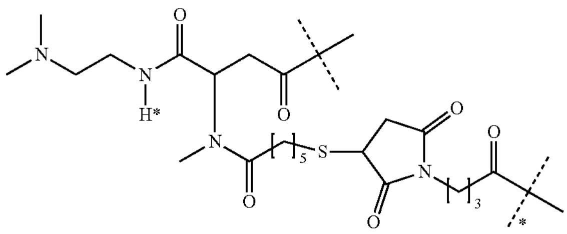, (Ic-iv)

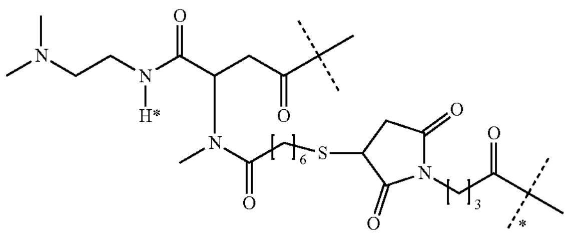, (Id-i)

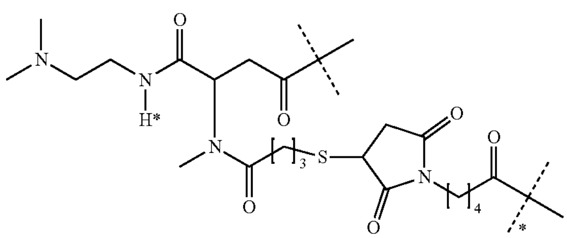,

-continued (Id-ii)

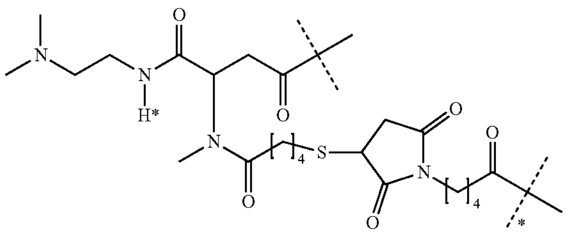, (Id-iii)

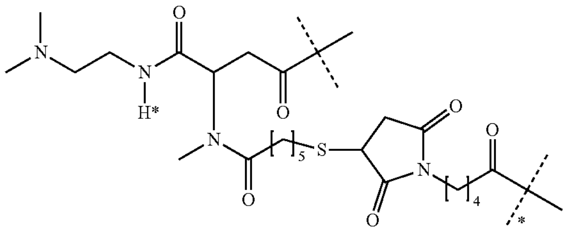, (Id-iv)

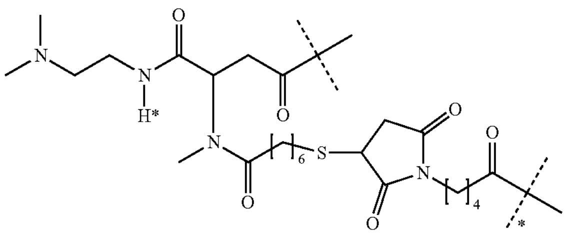;

wherein the unmarked dashed line indicates the attachment to a nitrogen of -D by forming an amide bond; and the dashed line marked with the asterisk indicates attachment to —Z.

In certain embodiments the moiety $-L^2-X^{0D}-L^1-$ is of formula (IIa-i). In certain embodiments the moiety $-L^2-X^{0D}-L^1-$ is of formula (IIa-ii). In certain embodiments the moiety $-L^2-X^{0D}-L^1-$ is of formula (IIa-iii). In certain embodiments the moiety $-L^2-X^{0D}-L^1-$ is of formula (IIa-iv). In certain embodiments the moiety $-L^2-X^{0D}-L^1-$ is of formula (IIb-i). In certain embodiments the moiety $-L^2-X^{0D}-L^1-$ is of formula (IIb-ii). In certain embodiments the moiety $-L^2-X^{0D}-L^1-$ is of formula (IIb-iii). In certain embodiments the moiety $-L^2$-XD $-L^1-$ is of formula (IIb-iv). In certain embodiments the moiety $-L^2-X^{0D}-L^1-$ is of formula (IIc-i). In certain embodiments the moiety $-L^2-X^{0D}-L^1-$ is of formula (IIc-ii). In certain embodiments the moiety $-L^2-X^{0D}-L^1-$ is of formula (IIc-iii). In certain embodiments the moiety $-L^2-X^{0D}-L^1-$ is of formula (IIc-iv). In certain embodiments the moiety $-L^2-X^{0D}-L^1-$ is of formula (IId-i). In certain embodiments the moiety $-L^2-X^{0D}-L^1-$ is of formula (IId-ii). In certain embodiments the moiety $-L^2-X^{0D}-L^1-$ is of formula (IId-iii). In certain embodiments the moiety $-L^2-X^{0D}-L^1-$ is of formula (IId-iv).

In certain embodiments —Z is degradable.

It was surprisingly found that it is highly advantageous to use a degradable moiety —Z that degrades into soluble degradation products after no more than 4 months after administration to the infected joint, such as after no more than 3 months, such as after no more than 2 months. This degradability of —Z reduces the risk that the polymeric matrix provides a new artificial surface for biofilm formation.

In certain embodiments —Z is a hydrogel. In certain embodiments such hydrogel is a hydrophilic or amphiphilic polymeric network composed of homopolymers or copolymers, which is water-insoluble due to the presence of covalent chemical crosslinks.

It was surprisingly found that when —Z is a hydrogel, such hydrogel provides a protective environment for the antibiotic moieties that prevents their hydrolysis. This effect is particularly useful for antibiotic moieties comprising for example a lactone moiety, such as daptomycin, erythromycin, clarithromycin, azithromycin, boromycin, oleandomycin, roxithromycin, spiramycin, telithromycin, arylomycins, tylosine and linezolid, because lactone hydrolysis tends to lead to a loss of activity which reduces overall treatment efficacy.

In certain embodiments the conjugate of the first or second aspect or the compound of the third aspect is a pre-synthesized conjugate or compound, i.e. the conjugate or compound is synthesized in vitro and is not formed in vivo after administration to a patient. This is in contrast to hydrogel conjugates that are formed in vivo upon administration to a patient, such as by in vivo polymerization.

In certain embodiments such hydrogel comprises a polymer selected from the group consisting of 2-methacryloyloxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(alkylene glycols), such as poly(ethylene glycols) and poly(propylene glycol), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In certain embodiments —Z is a poly(alkylene glycol)-based or hyaluronic acid-based hydrogel.

In certain embodiments —Z is a poly(propylene glycol)-based hydrogel.

In certain embodiments —Z is a PEG-based hydrogel.

In certain embodiments such PEG-based hydrogel comprise a plurality of backbone moieties that are crosslinked via crosslinker moieties —$CL^P$-. Optionally, there is a spacer moiety —$SP^1$— between a backbone moiety and a crosslinker moiety. In certain embodiments such spacer —$SP^1$— is defined as described above for -$L^2$-.

In certain embodiments a backbone moiety has a molecular weight ranging from 1 kDa to 20 kDa.

In certain embodiments a backbone moiety is of formula (pA)

$$B^*\text{-}(A\text{-}Hyp)_x \qquad (pA),$$

wherein
- B* is a branching core,
- A is a PEG-based polymer,
- Hyp is a branched moiety,
- x is an integer of from 3 to 16;
- and wherein each backbone moiety is connected to one or more crosslinker moieties and to one or more moieties -$L^2$-, which crosslinker moieties and moieties -$L^2$- are connected to Hyp, either directly or through a spacer moiety.

In certain embodiments B* of formula (pA) is selected from the group consisting of polyalcohol moieties and polyamine moieties. In certain embodiments B* of formula (pA) is a polyalcohol moiety. In certain embodiments B* of formula (pA) is a polyamine moiety.

In certain embodiments the polyalcohol moieties for B* of formula (pA) are selected from the group consisting of a pentaerythritol moiety, tripentaerythritol moiety, hexaglycerine moiety, sucrose moiety, sorbitol moiety, fructose moiety, mannitol moiety and glucose moiety. In certain embodiments B* of formula (pA) is a pentaerythritol moiety, i.e. a moiety of formula

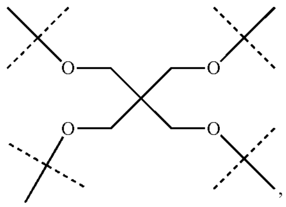

wherein dashed lines indicate attachment to -A-.

In certain embodiments the polyamine moieties for B* of formula (pA) is selected from the group consisting of an ornithine moiety, diaminobutyric acid moiety, trilysine moiety, tetralysine moiety, pentalysine moiety, hexalysine moiety, heptalysine moiety, octalysine moiety, nonalysine moiety, decalysine moiety, undecalysine moiety, dodecalysine moiety, tridecalysine moiety, tetradecalysine moiety and pentadecalysine moiety. In certain embodiments B* of formula (pA) is selected from the group consisting of an ornithine moiety, diaminobutyric acid moiety and a trilysine moiety.

A backbone moiety of formula (pA) may consist of the same or different PEG-based moieties -A- and each moiety -A- may be chosen independently. In certain embodiments all moieties -A- present in a backbone moiety of formula (pA) have the same structure. It is understood that the phrase “have the same structure” with regard to polymeric moieties, such as with regard to the PEG-based polymer -A-, means that the number of monomers of the polymer, such as the number of ethylene glycol monomers, may vary due to the polydisperse nature of polymers. In certain embodiments the number of monomer units does not vary by more than a factor of 2 between all moieties -A- of a hydrogel.

In certain embodiments each -A- of formula (pA) has a molecular weight ranging from 0.3 kDa to 40 kDa; e.g. from 0.4 to 30 kDa, from 0.4 to 25 kDa, from 0.4 to 20 kDa, from 0.4 to 15 kDa, from 0.4 to 10 kDa or from 0.4 to 5 kDa. In certain embodiments each -A- has a molecular weight from 0.4 to 5 kDa. In certain embodiments -A- has a molecular weight of about 0.5 kDa. In certain embodiments -A- has a molecular weight of about 1 kDa. In certain embodiments -A- has a molecular weight of about 2 kDa. In certain embodiments -A- has a molecular weight of about 3 kDa. In certain embodiments -A- has a molecular weight of about 5 kDa.

In certain embodiments -A- of formula (pA) is of formula (pB-i)

$$—(CH_2)_{n1}(OCH_2CH_2)_nX— \quad \text{(pB-i)},$$

wherein n1 is 1 or 2;

n is an integer ranging from 3 to 250, such as from 5 to 200, such as from 8 to 150 or from 10 to 100; and X is a chemical bond or a linkage covalently linking A and Hyp.

In certain embodiments -A- of formula (pA) is of formula (pB-ii)

$$—(CH_2)_{n1}(OCH_2CH_2)_n—(CH_2)_{n2}X— \quad \text{(pB-ii)},$$

wherein n1 is 1 or 2;

n is an integer ranging from 3 to 250, such as from 5 to 200, such as from 8 to 150 or from 10 to 100;

n2 is 0 or 1; and

X is a chemical bond or a linkage covalently linking A and Hyp.

In certain embodiments -A- of formula (pA) is of formula (pB-i')

(pB-i')

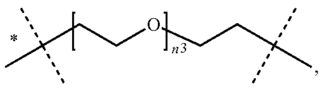

, wherein the dashed line marked with the asterisk indicates attachment to B*, the unmarked dashed line indicates attachment to -Hyp; and n3 is an integer ranging from 10 to 50.

In certain embodiments n3 of formula (pB-i') is 25. In certain embodiments n3 of formula (pB-i') is 26. In certain embodiments n3 of formula (pB-i') is 27. In certain embodiments n3 of formula (pB-i') is 28. In certain embodiments n3 of formula (pB-i') is 29. In certain embodiments n3 of formula (pB-i') is 30.

In certain embodiments a moiety $B^*-(A)_4$ is of formula (pB-a)

(pB-a)

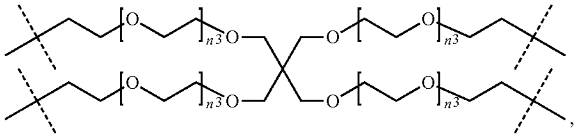

, wherein dashed lines indicate attachment to Hyp; and each n3 is independently an integer selected from 10 to 50.

In certain embodiments n3 of formula (pB-a) is 25. In certain embodiments n3 of formula (pB-a) is 26. In certain embodiments n3 of formula (pB-a) is 27. In certain embodiments n3 of formula (B-a) is 28. In certain embodiments n3 of formula (pB-a) is 29. In certain embodiments n3 of formula (pB-a) is 30.

A backbone moiety of formula (pA) may consist of the same or different dendritic moieties -Hyp and that each -Hyp can be chosen independently. In certain embodiments all moieties -Hyp present in a backbone moiety of formula (pA) have the same structure.

In certain embodiments each -Hyp of formula (pA) has a molecular weight ranging from 0.3 kDa to 5 kDa.

In certain embodiments -Hyb is be selected from the group consisting of a moiety of formula (pHyp-i)

(pHyp-i)

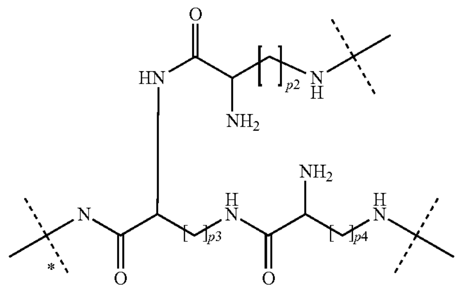

, wherein the dashed line marked with the asterisk indicates attachment to -A-, the unmarked dashed lines indicate attachment to a spacer moiety $—SP^1—$, a crosslinker moiety $—CL^P$- or to $-L^2$-; and p2, p3 and p4 are identical or different and each is independently of the others an integer from 1 to 5;

a moiety of formula (pHyp-ii)

(pHyp-ii)

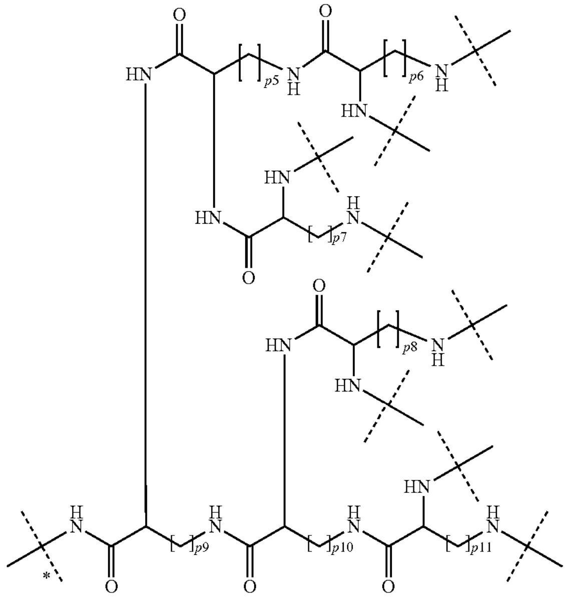

, wherein the dashed line marked with the asterisk indicates attachment to -A-, the unmarked dashed lines indicate attachment to a spacer moiety —$SP^1$—, a crosslinker moiety —$CL^P$- or to -$L^2$-; and p5 to p11 are identical or different and each is independently of the others an integer from 1 to 5;

a moiety of formula (pHyp-iii)

(pHyp-iii)

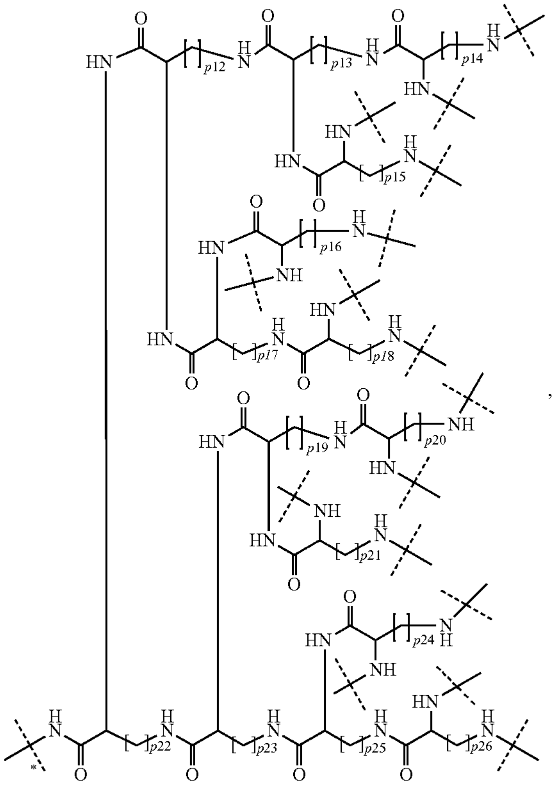

, wherein the dashed line marked with the asterisk indicates attachment to -A-, the unmarked dashed lines indicate attachment to a spacer moiety —$SP^1$—, a crosslinker moiety —$CL^P$- or to -$L^2$-; and p12 to p26 are identical or different and each is independently of the others an integer from 1 to 5; and a moiety of formula (pHyp-iv)

(pHyp-iv)

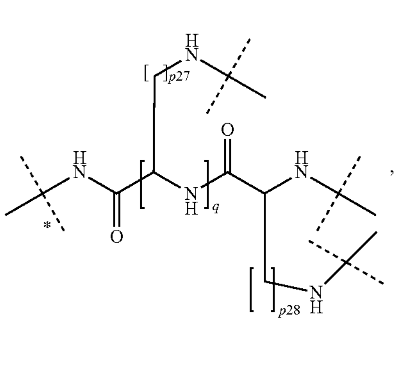

, wherein the dashed line marked with the asterisk indicates attachment to -A-, the unmarked dashed lines indicate attachment to a spacer moiety —$SP^1$—, a crosslinker moiety —$CL^P$- or to -$L^2$-;

p27 and p28 are identical or different and each is independently of the other an integer from 1 to 5; and q is an integer from 1 to 8;

wherein the moieties (pHyp-i) to (pHyp-iv) may at each chiral center be in either R- or S-configuration.

In certain embodiments all chiral centers of a moiety (pHyp-i), (pHyp-ii), (pHyp-iii) or (pHyp-iv) are in the same configuration. In certain embodiments all chiral centers of a moiety (pHyp-i), (pHyp-ii), (pHyp-iii) or (pHyp-iv) are in R-configuration. In certain embodiments all chiral centers of a moiety (pHyp-i), (pHyp-ii), (pHyp-iii) or (pHyp-iv) are in S-configuration.

In certain embodiments p2, p3 and p4 of formula (pHyp-i) are identical. In certain embodiments p2, p3 and p4 of formula (pHyp-i) are 1. In certain embodiments p2, p3 and p4 of formula (pHyp-i) are 2. In certain embodiments p2, p3 and p4 of formula (pHyp-i) are 3. In certain embodiments p2, p3 and p4 of formula (pHyp-i) are 4. In certain embodiments p2, p3 and p4 of formula (pHyp-i) are 5.

In certain embodiments p5 to p11 of formula (pHyp-ii) are identical. In certain embodiments p5 to p11 of formula (pHyp-ii) are 1. In certain embodiments p5 to p11 of formula (pHyp-ii) are 2. In certain embodiments p5 to p11 of formula (pHyp-ii) are 3. In certain embodiments p5 to p11 of formula (pHyp-ii) are 4. In certain embodiments p5 to p11 of formula (pHyp-ii) are 5.

In certain embodiments p12 to p26 of formula (pHyp-iii) are identical. In certain embodiments p12 to p26 of formula (pHyp-iii) are 1. In certain embodiments p12 to p26 of formula (pHyp-iii) are 2. In certain embodiments p12 to p26 of formula (pHyp-iii) are 3. In certain embodiments p12 to p26 of formula (pHyp-iii) are 4. In certain embodiments p12 to p26 of formula (pHyp-iii) are 5.

In certain embodiments q of formula (pHyp-iv) is 1. In certain embodiments of formula (pHyp-iv) is 2. In certain embodiments q of formula (pHyp-iv) is 3. In certain embodiments q of formula (pHyp-iv) is 4. In certain embodiments q of formula (pHyp-iv) is 5. In certain embodiments q of formula (pHyp-iv) is 6. In certain embodiments q of formula (pHyp-iv) is 7. In certain embodiments q of formula (pHyp-iv) is 8. In certain embodiments q of formula (pHyp-iv) is 2 or 6.

In certain embodiments p27 and p28 of formula (pHyp-iv) are 4.

In certain embodiments -Hyp of formula (pA) comprises a branched polypeptide moiety.

In certain embodiments -Hyp of formula (pA) comprises a lysine moiety. In certain embodiments each -Hyp of formula (pA) is independently selected from the group consisting of a trilysine moiety, tetralysine moiety, pentalysine moiety, hexalysine moiety, heptalysine moiety, octalysine moiety, nonalysine moiety, decalysine moiety, undecalysine moiety, dodecalysine moiety, tridecalysine moiety, tetradecalysine moiety, pentadecalysine moiety, hexadecalysine moiety, heptadecalysine moiety, octadecalysine moiety and nonadecalysine moiety.

In certain embodiments -Hyp comprises 3 lysine moieties. In certain embodiments -Hyb comprises 7 lysine moieties. In certain embodiments -Hyb comprises 15 lysine moieties. In certain embodiments -Hyp comprises heptalysinyl.

In certain embodiments x of formula (pA) is 3. In certain embodiments x of formula (pA) is 4. In certain embodiments x of formula (pA) is 4. In certain embodiments x of formula (pA) is 5.

In certain embodiments x of formula (pA) is 6. In certain embodiments x of formula (pA) is 4. In certain embodiments x of formula (pA) is 7. In certain embodiments x of formula (pA) is 8.

In certain embodiments the backbone moiety is of formula (pC)

—$Y^1$— is of formula

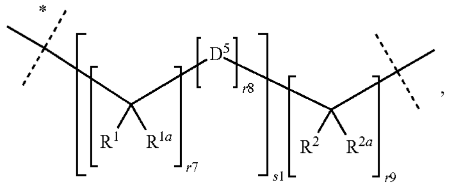

(pC)

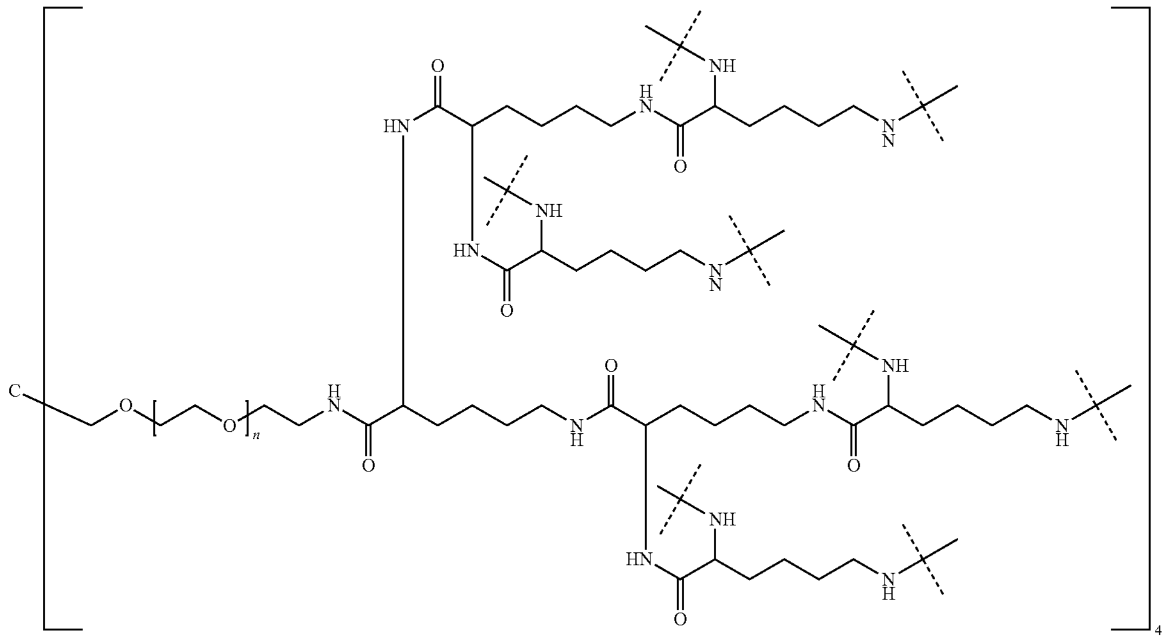

wherein dashed lines indicate attachment to a spacer moiety —$SP^1$—, a crosslinker moiety —$CL^P$- or to -$L^2$-; and n ranges from 10 to 40.

In certain embodiments n of formula (pB) is about 28.

In certain embodiments there is no spacer moiety —$SP^1$— between a backbone moiety and a crosslinker moiety —$CL^P$-, i.e. —$CL^P$- is directly linked to -Hyp.

The crosslinker —$CL^P$- of the PEG-based hydrogel is in certain embodiments poly(alkylene glycol) (PAG)-based. In certain embodiments the crosslinker is poly(propylene glycol)-based. In certain embodiments the crosslinker —$CL^P$- is PEG-based.

In certain embodiments such PAG-based crosslinker moiety —$CL^P$- is of formula (pD)

wherein the dashed line marked with the asterisk indicates attachment to -$D^1$- and the unmarked dashed line indicates attachment to -$D^2$-;

—$Y^2$— is of formula

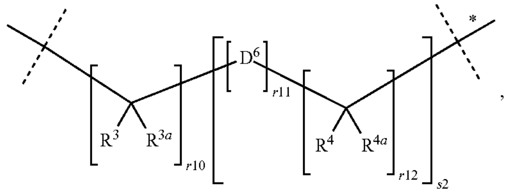

(pD)

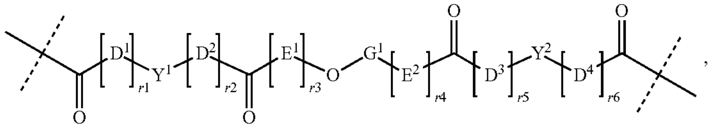

wherein dashed lines indicate attachment to a backbone moiety or to a spacer moiety —$SP^1$—;

wherein the dashed line marked with the asterisk indicates attachment to -$D^4$- and the unmarked dashed line indicates attachment to -$D^3$-;

$-E^1-$ is of formula

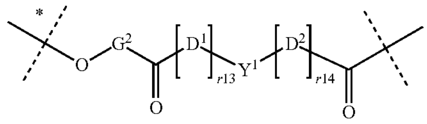
, wherein the dashed line marked with the asterisk indicates attachment to —(C═O)— and the unmarked dashed line indicates attachment to —O—;

$-E^2-$ is of formula

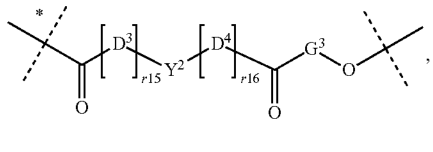
, wherein the dashed line marked with the asterisk indicates attachment to $-G^1-$ and the unmarked dashed line indicates attachment to —(C═O)—;

$-G^1-$ is of formula

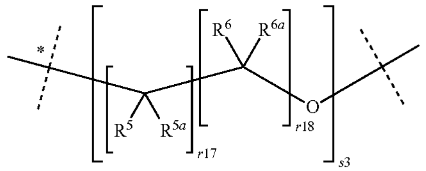
, wherein the dashed line marked with the asterisk indicates attachment to —O— and the unmarked dashed line indicates attachment to $-E^2-$;

$-G^2-$ is of formula

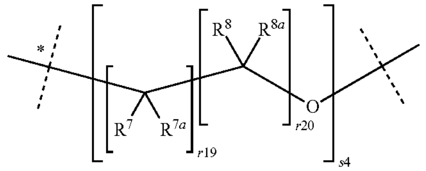
, wherein the dashed line marked with the asterisk indicates attachment to —O— and the unmarked dashed line indicates attachment to —(C═O)—;

$-G^3-$ is of formula

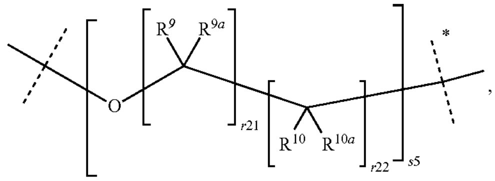
, wherein the dashed line marked with the asterisk indicates attachment to —O— and the unmarked dashed line indicates attachment to —(C═O)—;

$-D^1-$, $-D^2-$, $-D^3-$, $-D^4-$, $-D^5-$ and $-D^6-$ are identical or different and each is independently of the others selected from the group comprising —O—, $NR^{11}$—, —$NR^{12}R^{12a}$—, —(S═O)—, —$(S(O)_2)$—, —C(O)—, —$P(O)R^{13}$—, —$P(O)(OR^{13})$ and —$CR^{14}R^{14a}$—;

—$R^1$, —$R^{1a}$, —$R^2$, —$R^{2a}$, —$R^3$, —$R^{3a}$, —$R^4$, —$R^{4a}$, —$R^5$, —$R^{5a}$, —$R^6$, —$R^{6a}$, —$R^7$, —$R^{7a}$, —$R^8$, —$R^{8a}$, —$R^9$, —$R^{9a}$, —$R^{10}$, —$R^{10a}$, —$R^{11}$, —$R^{12}$, —$R^{12a}$, —$R^{13}$, —$R^{14}$ and —$R^{14a}$ are identical or different and each is independently of the others selected from the group consisting of —H and $C_{1-6}$ alkyl;

optionally, one or more of the pairs —$R^1$/—$R^{1a}$, —$R^2$/—$R^{2a}$, —$R^3$/—$R^{3a}$, —$R^4$/—$R^{4a}$, —$R^1$/—$R^2$, —$R^3$/—$R^4$, —$R^{1a}$/—$R^{2a}$, —$R^{3a}$/—$R^{4a}$, —$R^{12}$/—$R^{12a}$, and —$R^{14}$/—$R^{14a}$ form a chemical bond or are joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;

A is selected from the group consisting of phenyl, naphthyl, indenyl, indanyl and tetralinyl;

r1, r2, r5, r6, r13, r14, r15 and r16 are independently 0 or 1;

r3, r4, r7, r8, r9, r10, r11, r12 are independently 0, 1, 2, 3, or 4;

r17, r18, r19, r20, r21 and r22 are independently 1, 2, 3, 4, 5, 6, 7, 8, 9 or 10;

s1, s2, s4, s5 are independently 1, 2, 3, 4, 5 or 6; and s3 ranges from 1 to 900.

In certain embodiments s3 of formula (pD) ranges from 1 to 500. In certain embodiments s3 of formula (pD) ranges from 1 to 200.

In certain embodiments r1 of formula (pD) is 0. In certain embodiments r1 of formula (pD) is 1. In certain embodiments r2 of formula (pD) is 0. In certain embodiments r2 of formula (pD) is 1. In certain embodiments r5 of formula (pD) is 0. In certain embodiments r5 of formula (pD) is 1.

In certain embodiments r1, r2, r5 and r6 of formula (pD) are 0.

In certain embodiments r6 of formula (pD) is 0. In certain embodiments r6 of formula (pD) is 1. In certain embodiments r13 of formula (pD) is 0. In certain embodiments r13 of formula (pD) is 1. In certain embodiments r14 of formula (pD) is 0. In certain embodiments r14 of formula (pD) is 1. In certain embodiments r15 of formula (pD) is 0. In certain embodiments r15 of formula (pD) is 1. In certain embodiments r16 of formula (pD) is 0. In certain embodiments r16 of formula (pD) is 1.

In certain embodiments r3 of formula (pD) is 1. In certain embodiments r3 of formula (pD) is 2. In certain embodiments r4 of formula (pD) is 1. In certain embodiments r4 of formula (pD) is 2. In certain embodiments r3 and r4 of formula (pD) are both 1. In certain embodiments r3 and r4 of formula (pD) are both 2. In certain embodiments r3 and r4 of formula (pD) are both 3.

In certain embodiments r7 of formula (pD) is 0. In certain embodiments r7 of formula (pD) is 1. In certain embodiments r7 of formula (pD) is 2. In certain embodiments r8 of formula (pD) is 0. In certain embodiments r8 of formula (pD) is 1. In certain embodiments r8 of formula (pD) is 2. In certain embodiments r9 of formula (pD) is 0. In certain embodiments r9 of formula (pD) is 1. In certain embodiments r9 of formula (pD) is 2. In certain embodiments r10 of formula (pD) is 0. In certain embodiments r10 of formula (pD) is 1. In certain embodiments r10 of formula (pD) is 2. In certain embodiments r11 of formula (pD) is 0. In certain embodiments r11 of formula (pD) is 1. In certain embodiments r11 of formula (pD) is 2. In certain embodiments r12 of formula (pD) is 0. In certain embodiments r12 of formula (pD) is 1. In certain embodiments r12 of formula (pD) is 2.

In certain embodiments r17 of formula (pD) is 1. In certain embodiments r18 of formula (pD) is 1. In certain embodiments r19 of formula (pD) is 1. In certain embodiments r20 of formula (pD) is 1. In certain embodiments r21 of formula (pD) is 1. In certain embodiments r22 of formula (pD) is 1.

In certain embodiments s1 of formula (pD) is 1. In certain embodiments s1 of formula (pD) is 2. In certain embodiments s2 of formula (pD) is 1. In certain embodiments s2 of formula (pD) is 2. In certain embodiments s4 of formula (pD) is 1. In certain embodiments s4 of formula (pD) is 2. In certain embodiments s5 of formula (pD) is 1. In certain embodiments s5 of formula (pD) is 2.

In certain embodiments s3 of formula (pD) ranges from 5 to 500. In certain embodiments s3 of formula (pD) ranges from 10 to 250. In certain embodiments s3 of formula (pD) ranges from 12 to 150. In certain embodiments s3 of formula (pD) ranges from 15 to 100. In certain embodiments s3 of formula (pD) ranges from 18 to 75. In certain embodiments s3 of formula (pD) ranges from 20 to 50.

In certain embodiments —$R^1$ of formula (pD) is —H. In certain embodiments —$R^1$ of formula (pD) is methyl. In certain embodiments —$R^1$ of formula (pD) is ethyl. In certain embodiments —$R^{1a}$ of formula (pD) is —H. In certain embodiments —$R^{1a}$ of formula (pD) is methyl. In certain embodiments —$R^{1a}$ of formula (pD) is ethyl. In certain embodiments —$R^2$ of formula (pD) is —H. In certain embodiments —$R^2$ of formula (pD) is methyl. In certain embodiments —$R^2$ of formula (pD) is ethyl. In certain embodiments —$R^{2a}$ of formula (pD) is —H. In certain embodiments —$R^{2a}$ of formula (pD) is methyl. In certain embodiments —$R^{2a}$ of formula (pD) is ethyl. In certain embodiments —$R^3$ of formula (pD) is —H. In certain embodiments —$R^3$ of formula (pD) is methyl. In certain embodiments —$R^3$ of formula (pD) is ethyl. In certain embodiments —$R^{3a}$ of formula (pD) is —H. In certain embodiments —$R^{3a}$ of formula (pD) is methyl. In certain embodiments —$R^{3a}$ of formula (pD) is ethyl. In certain embodiments —$R^4$ of formula (pD) is —H. In certain embodiments —$R^4$ of formula (pD) is methyl. In certain embodiments —$R^4$ of formula (pD) is methyl. In certain embodiments —$R^{4a}$ of formula (pD) is —H. In certain embodiments —$R^{4a}$ of formula (pD) is methyl. In certain embodiments —$R^{4a}$ of formula (pD) is ethyl. In certain embodiments —$R^5$ of formula (pD) is —H. In certain embodiments —$R^5$ of formula (pD) is methyl. In certain embodiments —$R^5$ of formula (pD) is ethyl. In certain embodiments —$R^{5a}$ of formula (pD) is —H. In certain embodiments —$R^{5a}$ of formula (pD) is methyl. In certain embodiments —$R^{5a}$ of formula (pD) is ethyl. In certain embodiments —$R^6$ of formula (pD) is —H. In certain embodiments —$R^6$ of formula (pD) is methyl. In certain embodiments —$R^6$ of formula (pD) is ethyl. In certain embodiments —$R^{6a}$ of formula (pD) is —H. In certain embodiments —$R^{6a}$ of formula (pD) is methyl. In certain embodiments —$R^{6a}$ of formula (pD) is ethyl. In certain embodiments —$R^7$ of formula (pD) is —H. In certain embodiments —$R^7$ of formula (pD) is methyl. In certain embodiments —$R^7$ of formula (pD) is ethyl. In certain embodiments —$R^{7a}$ of formula (pD) is —H. In certain embodiments —$R^{7a}$ of formula (pD) is methyl. In certain embodiments —$R^{7a}$ of formula (A) is ethyl. In certain embodiments —$R^8$ of formula (pD) is —H. In certain embodiments —$R^8$ of formula (pD) is methyl. In certain embodiments —$R^8$ of formula (pD) is ethyl. In certain embodiments —$R^{8a}$ of formula (pD) is —H. In certain embodiments —$R^{8a}$ of formula (pD) is methyl. In certain embodiments —$R^{8a}$ of formula (pD) is ethyl. In certain embodiments —$R^9$ of formula (pD) is —H. In certain embodiments —$R^9$ of formula (pD) is methyl. In certain embodiments —$R^9$ of formula (pD) is ethyl. In certain embodiments —$R^{9a}$ of formula (pD) is —H. In certain embodiments —$R^{9a}$ of formula (pD) is methyl. In certain embodiments —$R^{9a}$ of formula (pD) is ethyl. In certain embodiments —$R^{10}$ of formula (pD) is —H. In certain embodiments —$R^{10}$ of formula (pD) is methyl. In certain embodiments —$R^{10}$ of formula (pD) is ethyl. In certain embodiments —$R^{10a}$ of formula (pD) is —H. In certain embodiments —$R^{11a}$ of formula (pD) is methyl. In certain embodiments —$R^{10a}$ of formula (pD) is ethyl. In certain embodiments —$R^{11}$ of formula (pD) is —H. In certain embodiments —$R^{11}$ of formula (pD) is methyl. In certain embodiments —$R^{11}$ of formula (pD) is ethyl. In certain embodiments —$R^{12}$ of formula (pD) is —H. In certain embodiments —$R^{12}$ of formula (pD) is methyl. In certain embodiments —$R^{12}$ of formula (pD) is ethyl. In certain embodiments —$R^{12a}$ of formula (pD) is —H. In certain embodiments —$R^{12a}$ of formula (pD) is methyl. In certain embodiments —$R^{12a}$ of formula (pD) is ethyl. In certain embodiments —$R^{13}$ of formula (pD) is —H. In certain embodiments —$R^{13}$ of formula (pD) is methyl. In certain embodiments —$R^{13}$ of formula (pD) is ethyl. In certain embodiments —$R^{14}$ of formula (pD) is —H. In certain embodiments —$R^{14}$ of formula (pD) is methyl. In certain embodiments —$R^{14}$ of formula (pD) is ethyl. In certain embodiments —$R^{14a}$ of formula (pD) is —H. In certain embodiments —$R^{14a}$ of formula (pD) is methyl. In certain embodiments —$R^{14a}$ of formula (pD) is ethyl.

In certain embodiments -$D^1$- of formula (pD) is —O—. In certain embodiments -$D^1$- of formula (pD) is —$NR^{11}$—. In certain embodiments -$D^1$- of formula (pD) is —$N^+R^{12}R^{12a}$—. In certain embodiments -$D^1$- of formula (pD) is —S—. In certain embodiments -$D^1$- of formula (pD) is —(S═O). In certain embodiments -$D^1$- of formula (pD) is —$(S(O)_2)$—. In certain embodiments -$D^1$- of formula (pD) is —C(O)—. In certain embodiments -$D^1$- of formula (pD) is —$P(O)R^{13}$—. In certain embodiments -$D^1$- of formula (pD) is —$P(O)(OR^{13})$—. In certain embodiments -$D^1$- of formula (pD) is —$CR^{14}R^{14a}$—.

In certain embodiments -$D^2$- of formula (pD) is —O—. In certain embodiments -$D^2$- of formula (pD) is —$NR^{11}$—. In certain embodiments -$D^2$- of formula (pD) is —$N^+R^{12}R^{12a}$—. In certain embodiments -$D^2$- of formula (pD) is —S—. In certain embodiments -$D^2$- of formula (pD) is —(S═O). In certain embodiments -$D^2$- of formula (pD) is —$(S(O)_2)$—. In certain embodiments -$D^2$- of formula (pD) is —C(O)—. In certain embodiments -$D^2$- of formula (pD) is —$P(O)R^{13}$—. In certain embodiments -$D^2$- of formula (pD) is —$P(O)(OR^{13})$—. In certain embodiments -$D^2$- of formula (pD) is —$CR^{14}R^{14a}$—.

In certain embodiments -$D^3$- of formula (pD) is —O—. In certain embodiments -$D^3$- of formula (pD) is —$NR^{11}$—. In certain embodiments -$D^3$- of formula (pD) is —$N^+R^{12}R^{12a}$—. In certain embodiments -$D^3$- of formula (pD) is —S—. In certain embodiments -$D^3$- of formula (pD) is —(S═O). In certain embodiments -$D^3$- of formula (pD) is —$(S(O)_2)$—. In certain embodiments -$D^3$- of formula (pD) is —C(O)—. In certain embodiments -$D^3$- of formula (pD) is —$P(O)R^{13}$—. In certain embodiments -$D^3$- of formula (pD) is —$P(O)(OR^{13})$—. In certain embodiments -$D^3$- of formula (pD) is —$CR^{14}R^{14a}$—.

In certain embodiments $-D^4-$ of formula (pD) is —O—. In certain embodiments $-D^4-$ of formula (pD) is $—NR^{11}—$. In certain embodiments $-D^4-$ of formula (pD) is $—N^+R^{12}R^{12a}—$. In certain embodiments $-D^4-$ of formula (pD) is —S—. In certain embodiments $-D^4-$ of formula (pD) is —(S═O). In certain embodiments $-D^4-$ of formula (pD) is $—(S(O)_2)—$. In certain embodiments $-D^4-$ of formula (pD) is —C(O)—. In certain embodiments $-D^4-$ of formula (pD) is $—P(O)R^{13}—$. In certain embodiments $-D^4-$ of formula (pD) is $—P(O)(OR^{13})—$. In certain embodiments $-D^4-$ of formula (pD) is $—CR^{14}R^{14a}—$.

In certain embodiments $-D^5-$ of formula (pD) is —O—. In certain embodiments $-D^5-$ of formula (pD) is $—NR^{11}—$. In certain embodiments $-D^5-$ of formula (pD) is $—N^+R^{12}R^{12a}—$. In certain embodiments $-D^5-$ of formula (pD) is —S—. In certain embodiments $-D^5-$ of formula (pD) is —(S═O)—. In certain embodiments $-D^5-$ of formula (pD) is $—(S(O)_2)—$. In certain embodiments $-D^5-$ of formula (pD) is —C(O)—. In certain embodiments $-D^5-$ of formula (pD) is $—P(O)R^{13}—$. In certain embodiments $-D^5-$ of formula (pD) is $—P(O)(OR^{13})—$. In certain embodiments $-D^5-$ of formula (pD) is $—CR^{14}R^{14a}—$.

In certain embodiments $-D^6-$ of formula (pD) is —O—. In certain embodiments $-D^6-$ of formula (pD) is $—NR^{11}—$. In certain embodiments $-D^6-$ of formula (pD) is $—N^+R^{12}R^{12a}—$. In certain embodiments $-D^6-$ of formula (pD) is —S—. In certain embodiments $-D^6-$ of formula (pD) is —(S═O). In certain embodiments $-D^6-$ of formula (pD) is $—(S(O)_2)—$. In certain embodiments $-D^6-$ of formula (pD) is —C(O)—. In certain embodiments $-D^6-$ of formula (pD) is $—P(O)R^{13}—$. In certain embodiments $-D^6-$ of formula (pD) is $—P(O)(OR^{13})—$. In certain embodiments $-D^6-$ of formula (pD) is $—CR^{14}R^{14a}—$.

In one embodiment $—CL^P-$ is of formula (pE)

In certain embodiments d of formula (pE) ranges from 3 to 200. In certain embodiments d of formula (pE) ranges from 4 to 150. In certain embodiments d of formula (pE) ranges from 5 to 100. In certain embodiments d of formula (pE) ranges from 10 to 50. In certain embodiments d of formula (pE) ranges from 15 to 30. In certain embodiments d of formula (pE) is about 23.

In certain embodiments $—R^{b1}$ and $—R^{b1a}$ of formula (pE) are —H. In certain embodiments $—R^{b2}$ and $—R^{b2a}$ of formula (pE) are —H. In certain embodiments $—R^{b3}$ and $—R^{b3a}$ of formula (pE) are —H. In certain embodiments $—R^{b4}$ and $—R^{b4a}$ of formula (pE) are —H. In certain embodiments $—R^{b5}$ and $—R^{b5a}$ of formula (pE) are —H. In certain embodiments $—R^{b6}$ and $—R^{b6a}$ of formula (pE) are —H.

In certain embodiments $—R^{b1}$, $—R^{b1a}$, $—R^{b2}$, $—R^{b2a}$, $—R^{b3}$, $—R^{b3a}$, $—R^{b4}$, $—R^{b4a}$, $—R^{b5}$, $—R^{b5a}$, $—R^{b6}$ and $—R^{b6}$ of formula (pE) are all —H.

In certain embodiments c1 of formula (pE) is 1. In certain embodiments c1 of formula (pE) is 2. In certain embodiments c1 of formula (pE) is 3. In certain embodiments c1 of formula (pE) is 4. In certain embodiments c1 of formula (pE) is 5. In certain embodiments c1 of formula (pE) is 6.

In certain embodiments c2 of formula (pE) is 1. In certain embodiments c2 of formula (pE) is 2. In certain embodiments c2 of formula (pE) is 3. In certain embodiments c2 of formula (pE) is 4. In certain embodiments c2 of formula (pE) is 5. In certain embodiments c2 of formula (pE) is 6.

In certain embodiments c3 of formula (pE) is 1. In certain embodiments c3 of formula (pE) is 2. In certain embodiments c3 of formula (pE) is 3. In certain embodiments c3 of formula (pE) is 4. In certain embodiments c3 of formula (pE) is 5. In certain embodiments c3 of formula (pE) is 6.

(pE)

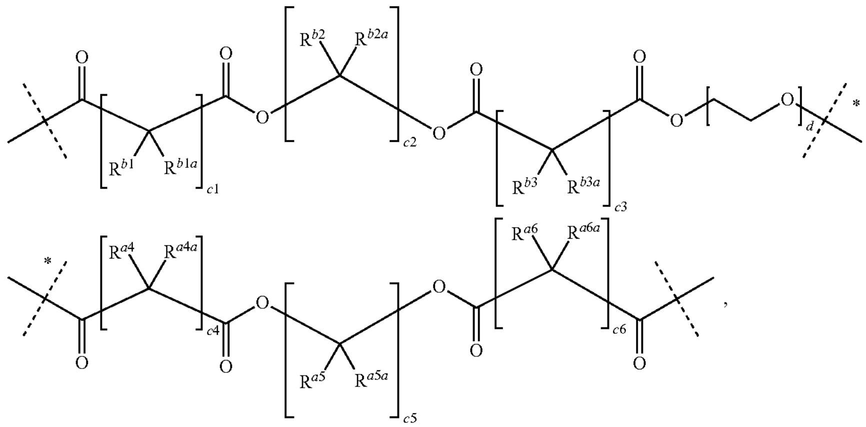

wherein dashed lines marked with an asterisk indicate the connection point between the upper and the lower substructure, unmarked dashed lines indicate attachment to a backbone moiety or to a spacer moiety $—SP^1—$;

$—R^{b1}$, $—R^{b1a}$, $—R^{b2}$, $—R^{b2a}$, $—R^{b3}$, $—R^{b3a}$, $—R^{b4}$, $—R^{b4a}$, $—R^{b5}$, $—R^{b5a}$, $—R^{b6}$ and $—R^{b6a}$ are independently selected from the group consisting of —H and $C_{1-6}$ alkyl;

c1, c2, c3, c4, c5 and c6 are independently selected from the group consisting of 1, 2, 3, 4, 5 and 6;

d is an integer ranging from 2 to 250.

In certain embodiments c4 of formula (pE) is 1. In certain embodiments c4 of formula (pE) is 2. In certain embodiments c4 of formula (pE) is 3. In certain embodiments c4 of formula (pE) is 4. In certain embodiments c4 of formula (pE) is 5. In certain embodiments c4 of formula (pE) is 6.

In certain embodiments c5 of formula (pE) is 1. In certain embodiments c5 of formula (pE) is 2. In certain embodiments c5 of formula (pE) is 3. In certain embodiments c5 of formula (pE) is 4. In certain embodiments c5 of formula (pE) is 5. In certain embodiments c5 of formula (pE) is 6.

In certain embodiments c6 of formula (pE) is 1. In certain embodiments c6 of formula (pE) is 2. In certain embodiments c6 of formula (pE) is 3. In certain embodiments c6 of formula (pE) is 4. In certain embodiments c6 of formula (pE) is 5. In certain embodiments c6 of formula (pE) is 6.

In certain embodiments a crosslinker moiety —$CL^P$- is of formula (pE-i)

(pE-i)

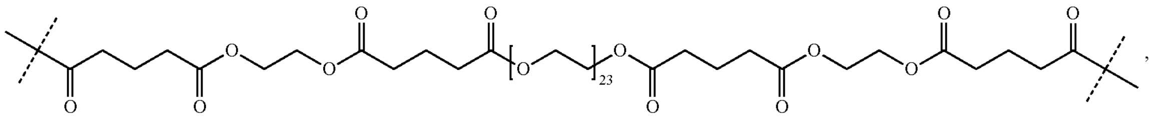

wherein dashed lines indicate attachment to a backbone moiety or to a spacer moiety —$SP^1$—.

In certain embodiments a crosslinker moiety —$CL^P$- is selected from the group consisting of (pE-i2)

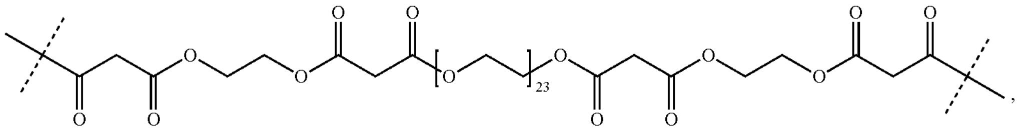

(pE-i3)

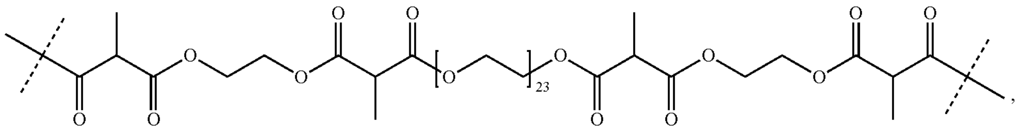

(pE-i4)

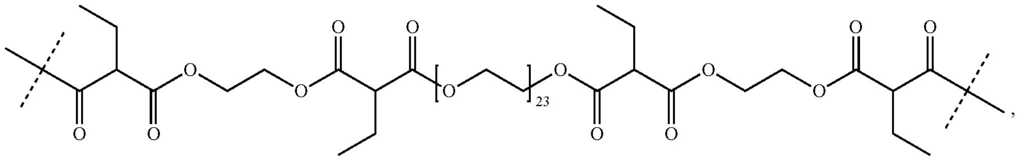

(pE-i5)

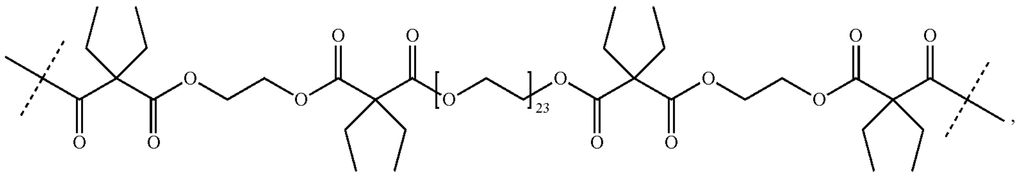

(pE-i6)

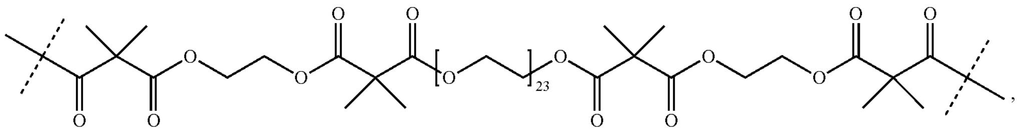

(pE-i7)

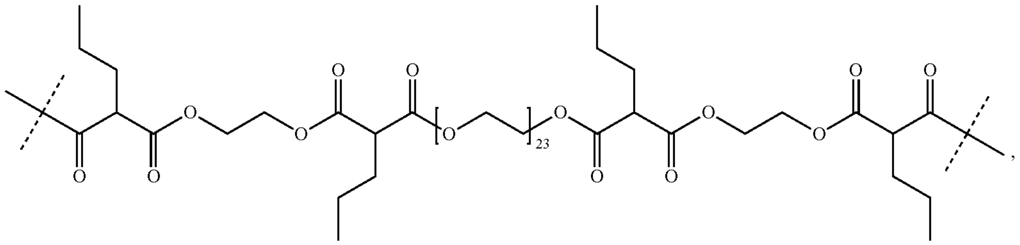

-continued
(pE-i8)
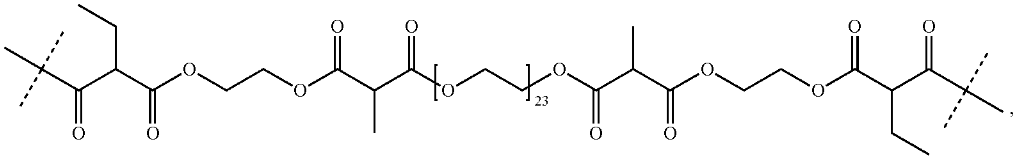
(pE-i9)
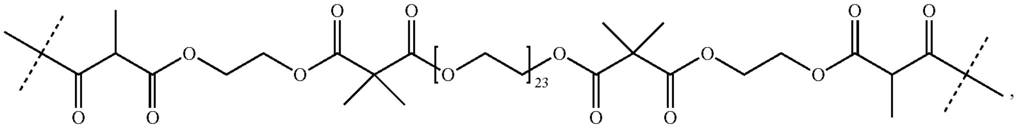
(pE-i10)
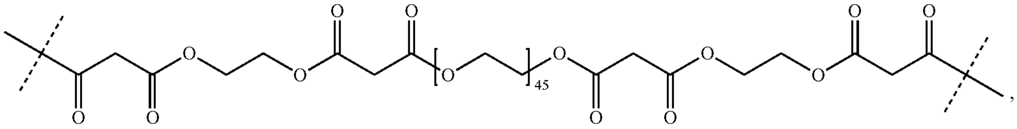
(pE-i11)
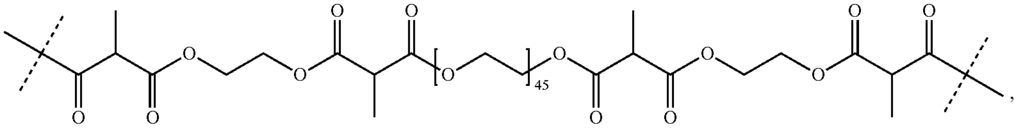
(pE-i12)
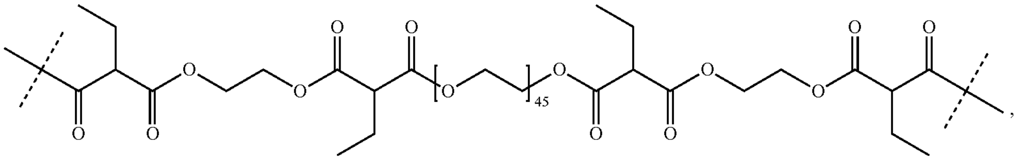
(pE-i13)
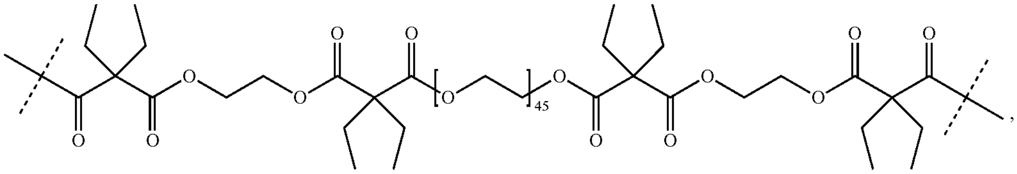
(pE-i14)
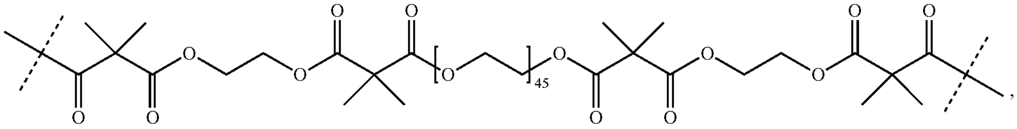
(pE-i15)
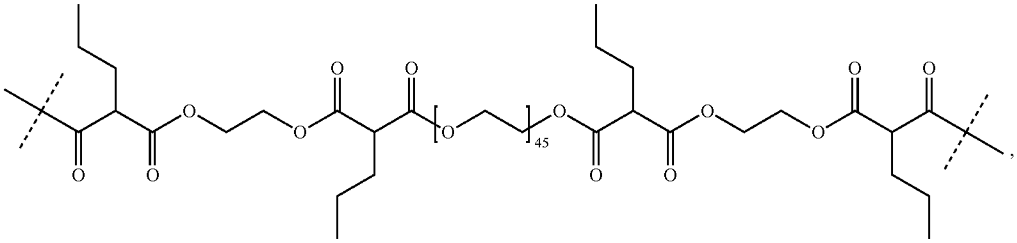
(pE-i16)
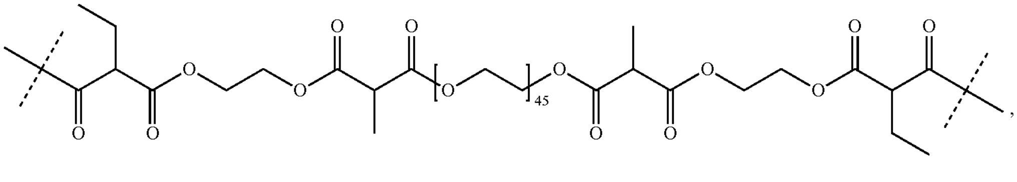

-continued
(pE-i17)
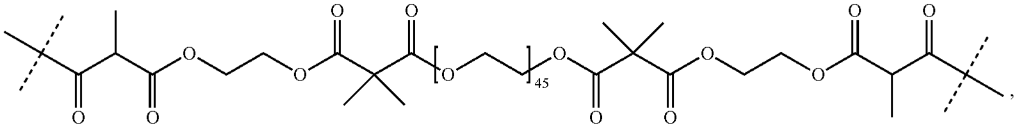
(pE-i18)
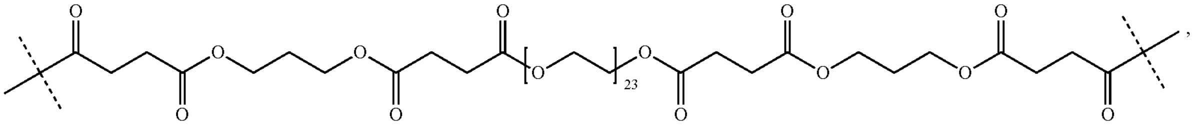
(pE-i19)
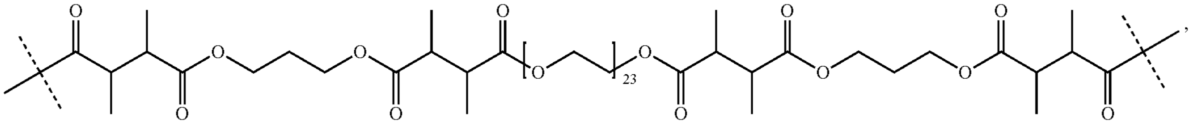
(pE-i20)
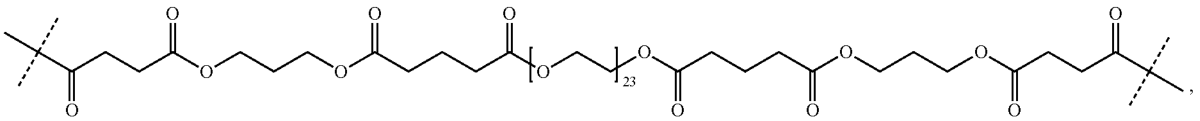
(pE-i21)
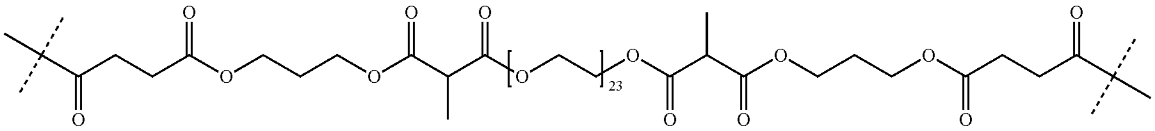
(pE-i22)
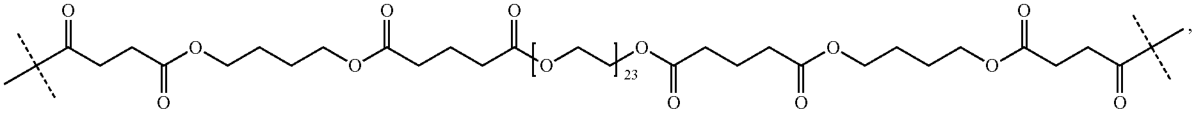
(pE-i23)
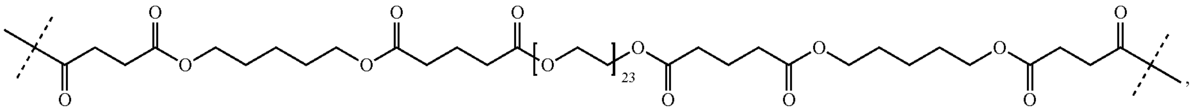
(pE-i24)
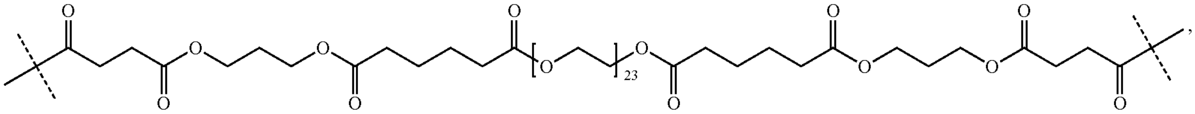
(pE-i25)
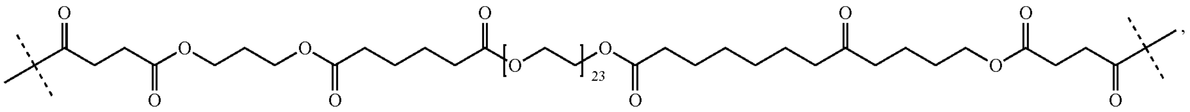
(pE-i26)
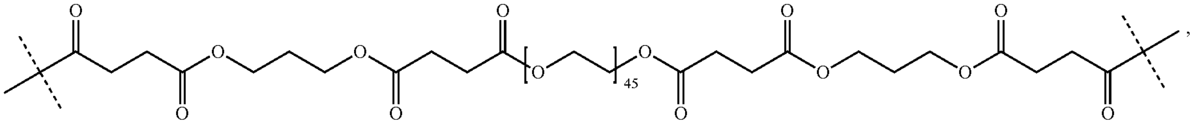

-continued
(pE-i27)
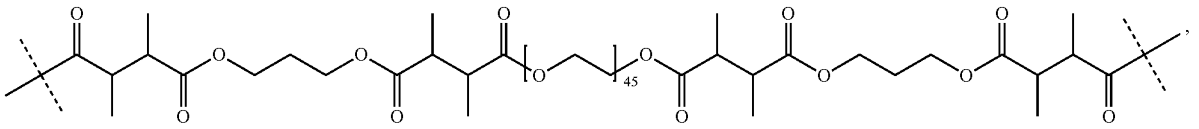
(pE-i28)
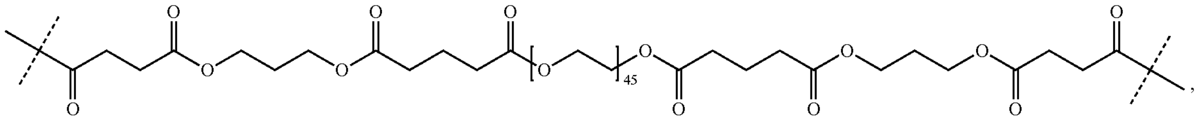
(pE-i29)
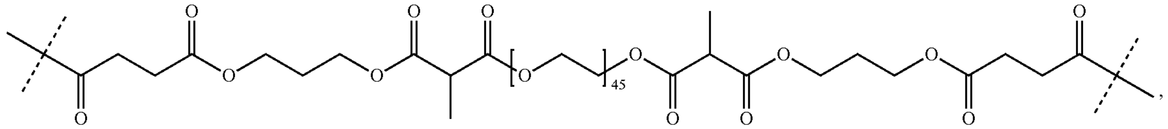
(pE-i30)
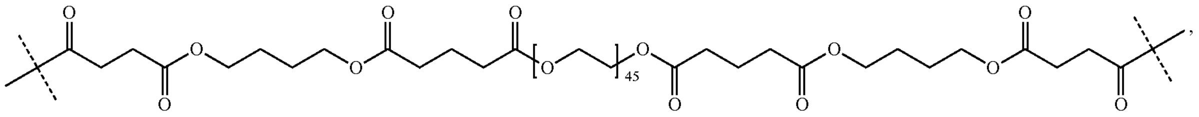
(pE-i31)
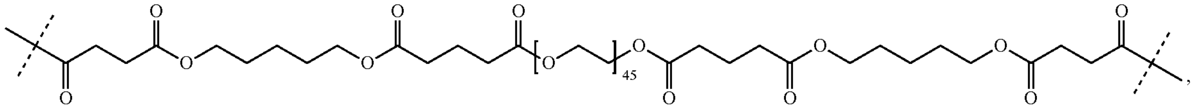
(pE-i32)
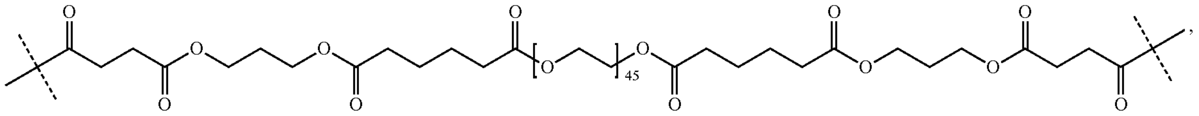
(pE-i33)
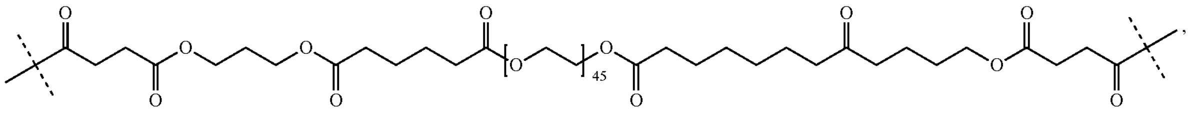
(pE-i34)
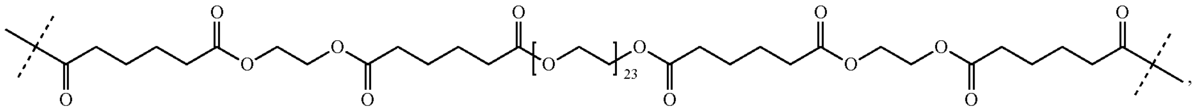
(pE-i35)
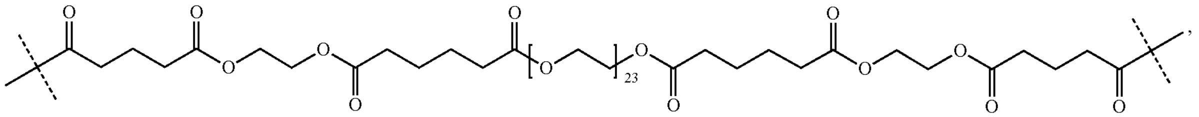
(pE-i36)
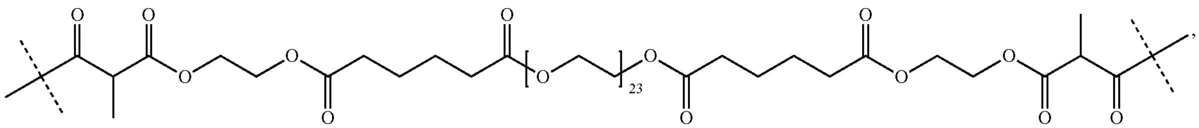

-continued
(pE-i37)
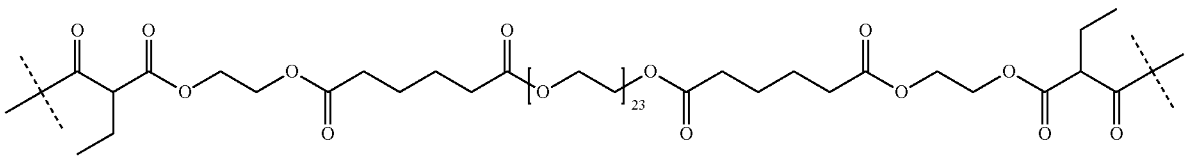
,
(pE-i38)
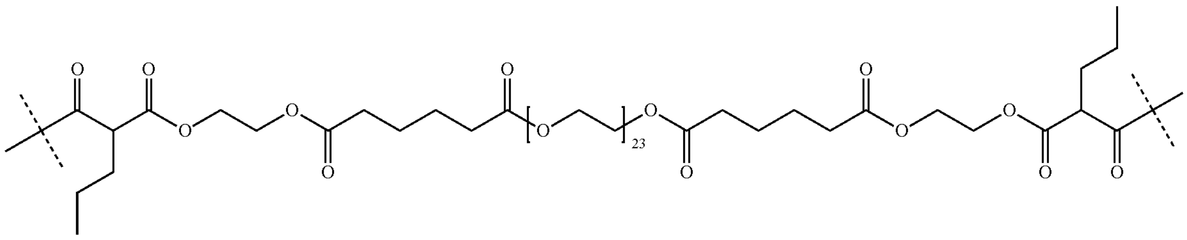
,
(pE-i39)
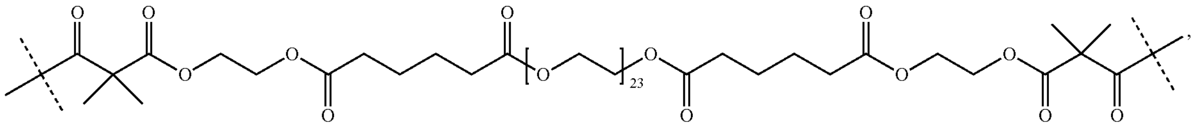
,
(pE-i40)
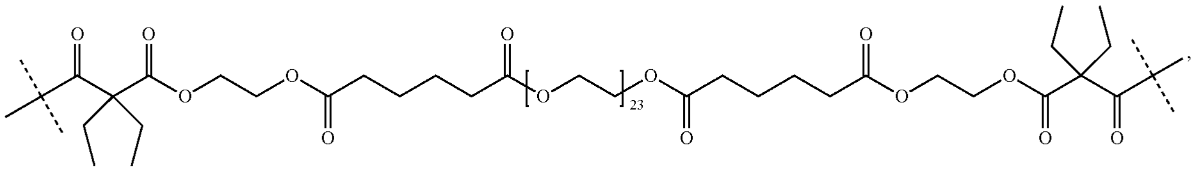
,
(pE-i41)
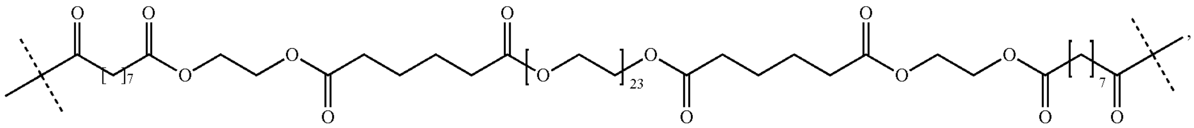
,
(pE-i42)
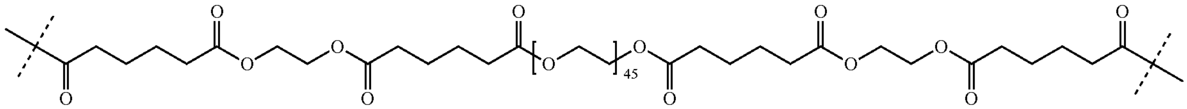
,
(pE-i43)
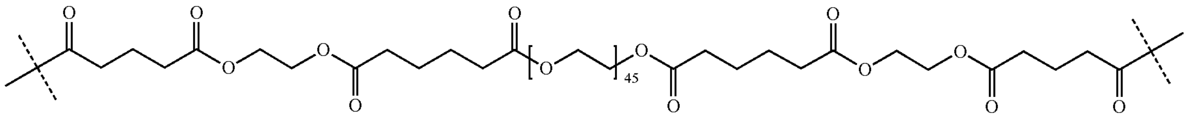
,
(pE-i44)
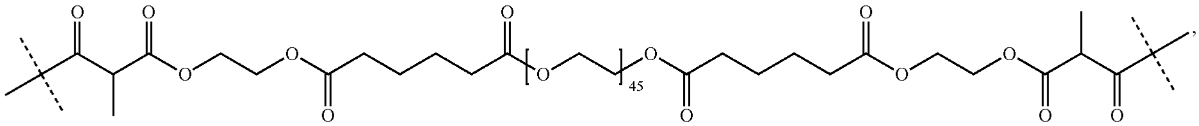
,
(pE-i45)
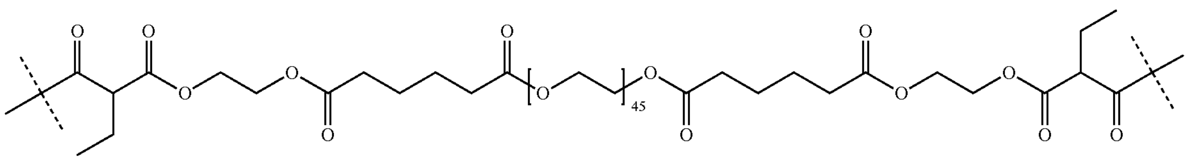
, -continued
(pE-i46)
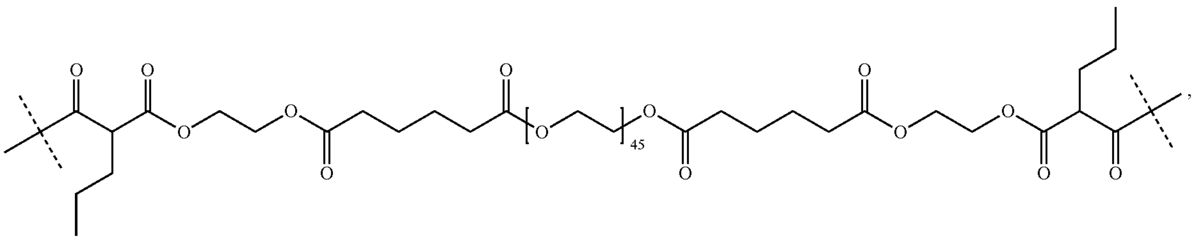
(pE-i47)
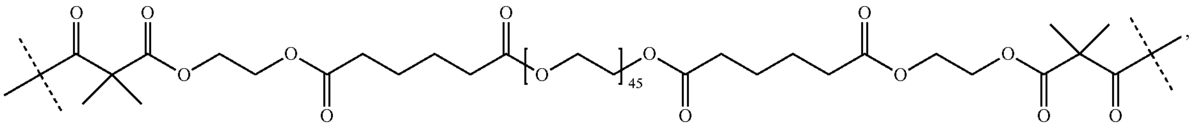
(pE-i48)
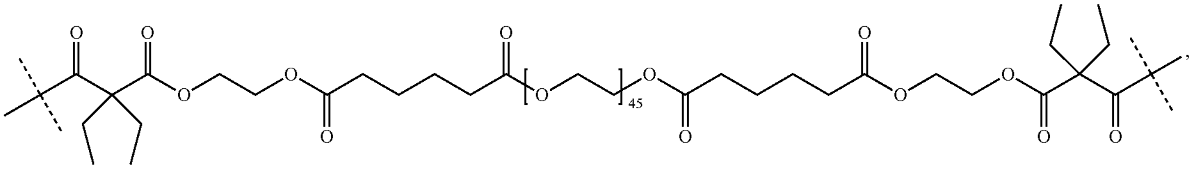
(pE-i49)
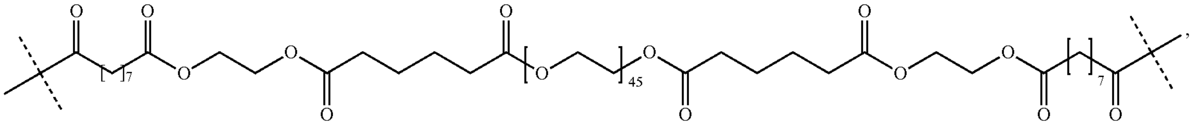
(pE-i50)
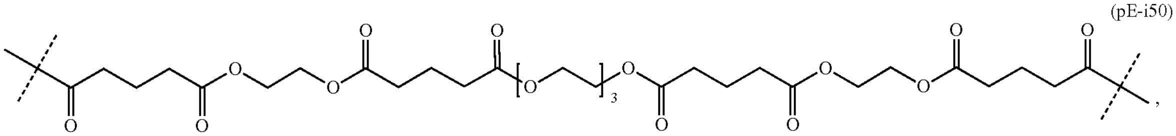
(pE-i51)
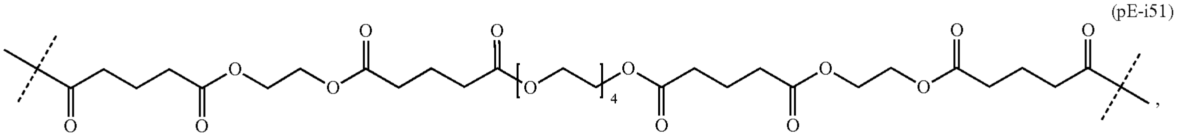
(pE-i52)
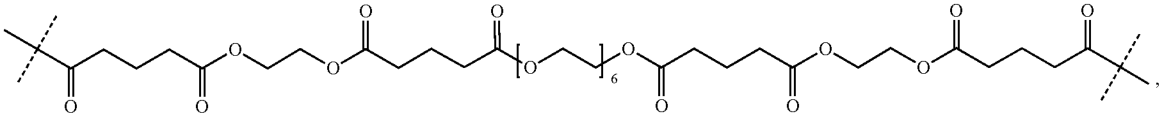
(pE-i53)
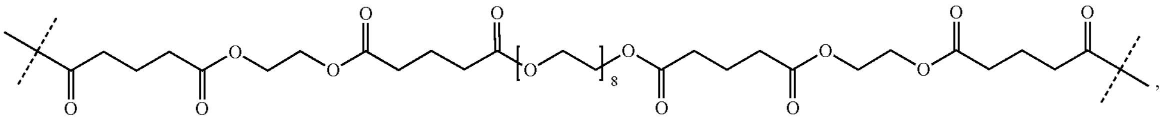
(pE-i54)
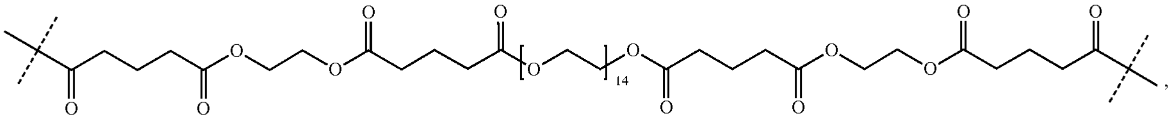
(pE-i55)
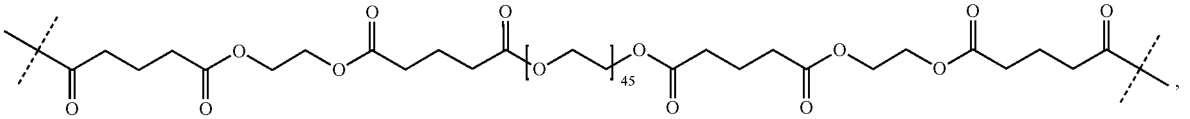

-continued
(pE-i56)
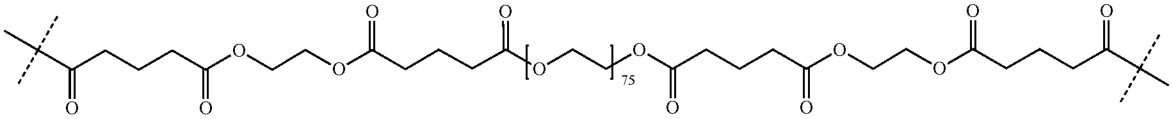,
(pE-i57)
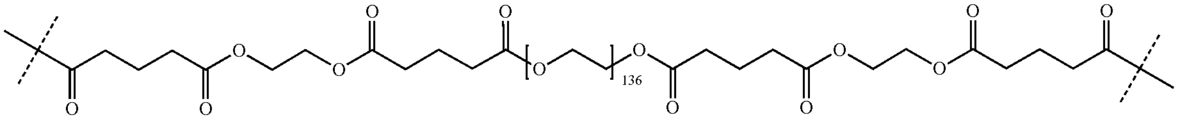,
(pE-i58)
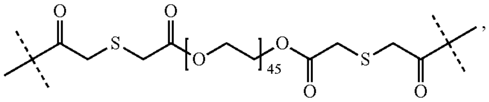,
(pE-i59)
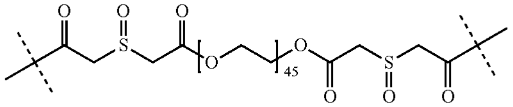,
(pE-60)
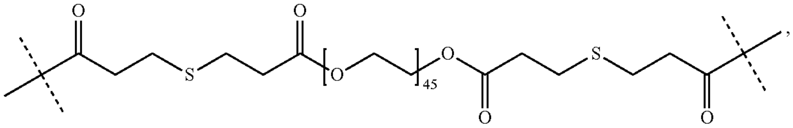,
(pE-61)
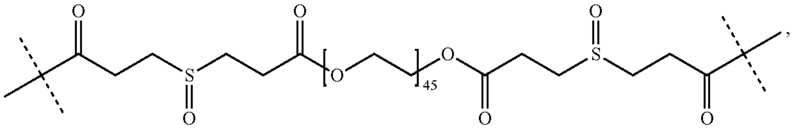,
(pE-62)
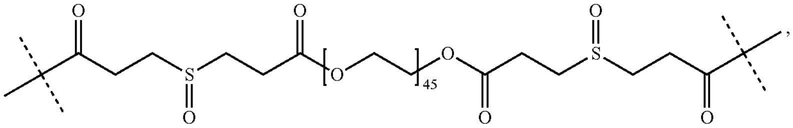,
(pE-63)
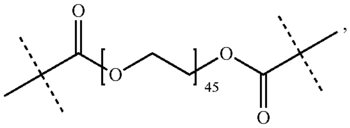,
(pE-64)
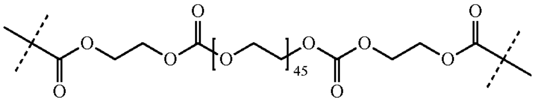,
(pE-65)
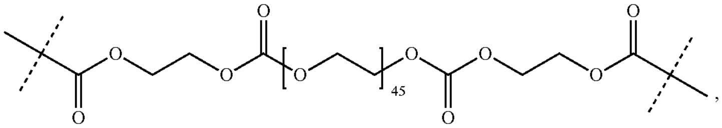,
(pE-66)
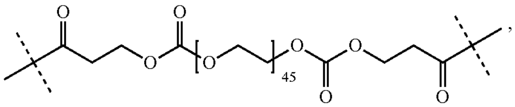,
(pE-67)
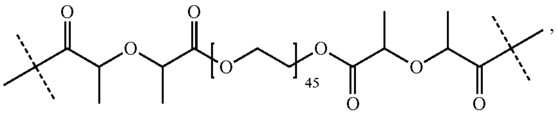,
(pE-68)
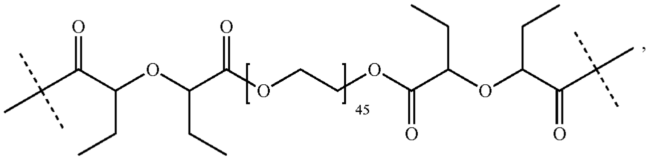,
(pE-69)
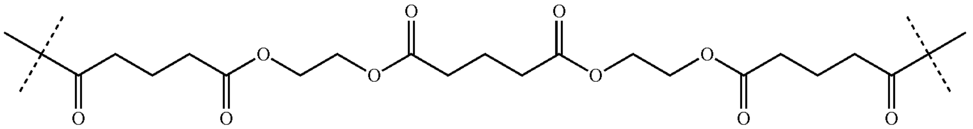, and -continued (pE-70)

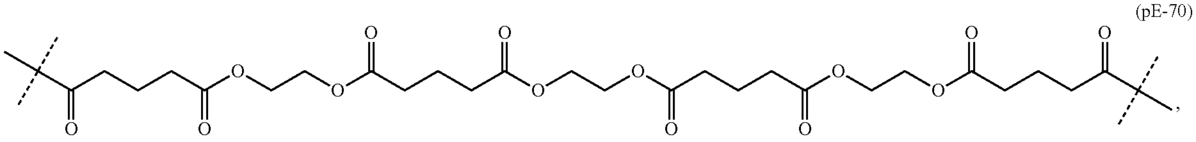

wherein dashed lines indicate attachment to a backbone moiety or to a spacer moiety —SP—.

In certain embodiments a crosslinker moiety —CL- is of formula (pE-i2). In certain embodiments a crosslinker moiety —CL- is of formula (pE-i3). In certain embodiments a crosslinker moiety —CL- is of formula (pE-i4). In certain embodiments a crosslinker moiety —CL- is of formula (pE-i5). In certain embodiments a crosslinker moiety —CL- is of formula (pE-i6). In certain embodiments a crosslinker moiety —CL- is of formula (pE-i7). In certain embodiments a crosslinker moiety —CL- is of formula (pE-i8). In certain embodiments a crosslinker moiety —CL- is of formula (pE-i9). In certain embodiments a crosslinker moiety —CL- is of formula (pE-i10). In certain embodiments a crosslinker moiety —CL- is of formula (pE-i11). In certain embodiments a crosslinker moiety —CL- is of formula (pE-i12). In certain embodiments a crosslinker moiety —CL- is of formula (pE-i13). In certain embodiments a crosslinker moiety —CL- is of formula (pE-i14). In certain embodiments a crosslinker moiety —CL- is of formula (pE-i15). In certain embodiments a crosslinker moiety —CL- is of formula (pE-i16). In certain embodiments a crosslinker moiety —CL- is of formula (pE-i17). In certain embodiments a crosslinker moiety —CL- is of formula (pE-i18). In certain embodiments a crosslinker moiety —CL- is of formula (pE-i19). In certain embodiments a crosslinker moiety —CL- is of formula (pE-i20). In certain embodiments a crosslinker moiety —CL- is of formula (pE-i21). In certain embodiments a crosslinker moiety —CL- is of formula (pE-i22). In certain embodiments a crosslinker moiety —CL- is of formula (pE-i23). In certain embodiments a crosslinker moiety —CL- is of formula (pE-i24). In certain embodiments a crosslinker moiety —CL- is of formula (pE-i25). In certain embodiments a crosslinker moiety —CL- is of formula (pE-i26). In certain embodiments a crosslinker moiety —CL- is of formula (pE-i27). In certain embodiments a crosslinker moiety —CL- is of formula (pE-i28). In certain embodiments a crosslinker moiety —CL- is of formula (pE-i29). In certain embodiments a crosslinker moiety —CL- is of formula (pE-i30). In certain embodiments a crosslinker moiety —CL- is of formula (pE-i31). In certain embodiments a crosslinker moiety —CL- is of formula (pE-i32). In certain embodiments a crosslinker moiety —CL- is of formula (pE-i33). In certain embodiments a crosslinker moiety —CL- is of formula (pE-i34). In certain embodiments a crosslinker moiety —CL- is of formula (pE-i35). In certain embodiments a crosslinker moiety —CL- is of formula (pE-i36). In certain embodiments a crosslinker moiety —CL- is of formula (pE-i37). In certain embodiments a crosslinker moiety —CL- is of formula (pE-i38). In certain embodiments a crosslinker moiety —CL- is of formula (pE-i39). In certain embodiments a crosslinker moiety —CL- is of formula (pE-i40). In certain embodiments a crosslinker moiety —CL- is of formula (pE-i41). In certain embodiments a crosslinker moiety —CL- is of formula (pE-i42). In certain embodiments a crosslinker moiety —CL- is of formula (pE-i43). In certain embodiments a crosslinker moiety —CL- is of formula (pE-i44). In certain embodiments a crosslinker moiety —CL- is of formula (pE-i45). In certain embodiments a crosslinker moiety —CL- is of formula (pE-i46). In certain embodiments a crosslinker moiety —CL- is of formula (pE-i47). In certain embodiments a crosslinker moiety —CL- is of formula (pE-i48). In certain embodiments a crosslinker moiety —CL- is of formula (pE-i49). In certain embodiments a crosslinker moiety —CL- is of formula (pE-i50). In certain embodiments a crosslinker moiety —CL- is of formula (pE-i51). In certain embodiments a crosslinker moiety —CL- is of formula (pE-i52). In certain embodiments a crosslinker moiety —CL- is of formula (pE-i53). In certain embodiments a crosslinker moiety —CL- is of formula (pE-i54). In certain embodiments a crosslinker moiety —CL- is of formula (pE-i55). In certain embodiments a crosslinker moiety —CL- is of formula (pE-i56). In certain embodiments a crosslinker moiety —CL- is of formula (pE-i57). In certain embodiments a crosslinker moiety —CL- is of formula (pE-i58). In certain embodiments a crosslinker moiety —CL- is of formula (pE-i59). In certain embodiments a crosslinker moiety —CL- is of formula (pE-i60). In certain embodiments a crosslinker moiety —CL- is of formula (pE-i61). In certain embodiments a crosslinker moiety —CL- is of formula (pE-i62). In certain embodiments a crosslinker moiety —CL- is of formula (pE-i63). In certain embodiments a crosslinker moiety —CL- is of formula (pE-i64). In certain embodiments a crosslinker moiety —CL- is of formula (pE-i65). In certain embodiments a crosslinker moiety —CL- is of formula (pE-i66). In certain embodiments a crosslinker moiety —CL- is of formula (pE-i67). In certain embodiments a crosslinker moiety —CL- is of formula (pE-i68). In certain embodiments a crosslinker moiety —CL- is of formula (pE-i69). In certain embodiments a crosslinker moiety —CL- is of formula (pE-i70).

In certain embodiments a backbone moiety has a molecular weight ranging from 1 kDa to 20 kDa, such as from 1 to 18 kDa, from 2 to 15 kDa, from 4 to 13 kDa or from 5 to 12 kDa.

In certain embodiments a backbone moiety comprises at least one polymeric moiety. In certain embodiments a backbone moiety comprises a multi-arm polymer, such as a polymer having 3 to 8 polymeric arms, such as having three polymeric arms, four polymeric arms, five polymeric arms, six polymeric arms, seven polymeric arms or eight polymeric arms. In certain embodiments a backbone moiety comprises 3 to 6 polymeric arms.

In certain embodiments such polymeric arm comprises a polymer selected from the group consisting of the group consisting of 2-methacryloyl-oxyethyl phosphoyl cholins, poly(acrylic acids), poly(acrylates), poly(acrylamides), poly (alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly (ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, alginate, mannans, pectins, rhamnogalacturonans, starches, hydroxyalkyl starches, hydroxyethyl starches and other carbohydrate-based polymers, xylans, and copolymers thereof.

In certain embodiments such polymeric arm is a PEG-based polymer. In certain embodiments such polymeric moiety is a hyaluronic acid-based polymer.

In certain embodiments —Z is a hyaluronic acid-based hydrogel.

If —Z is a hyaluronic acid-based hydrogel, a conjugate of the present invention is in certain embodiments a conjugate comprising crosslinked hyaluronic acid strands to which a plurality of drug moieties are covalently and reversibly conjugated, wherein the conjugate comprises a plurality of connected units selected from the group consisting of $Z^1$

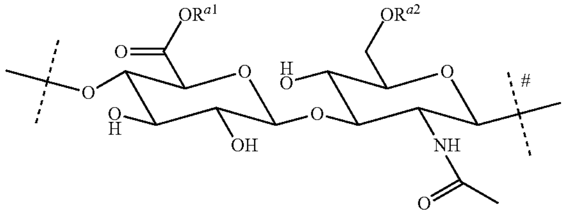

, $Z^2$

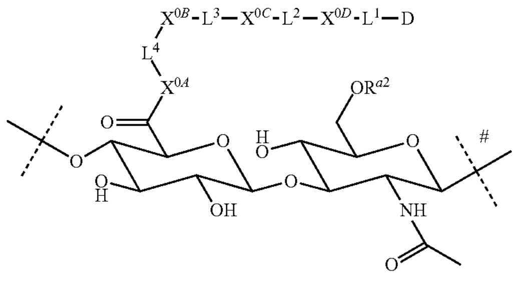

and

-continued $Z^3$

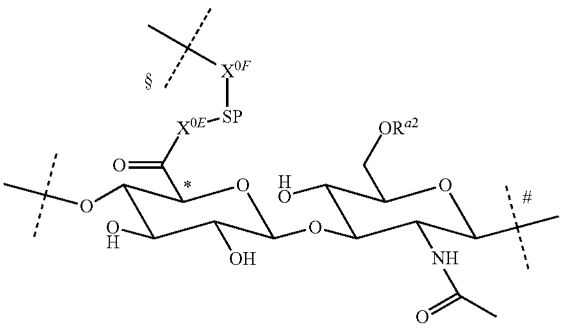

, wherein an unmarked dashed line indicates a point of attachment to an adjacent unit at a dashed line marked with # or to a hydrogen;

a dashed line marked with # indicates a point of attachment to an adjacent unit at an unmarked dashed line or to a hydroxyl;

a dashed line marked with § indicates a point of connection between at least two units $Z^3$ via a moiety —CL-;

each -D is independently an antibiotic moiety;

each $-L^1-$ is independently a linker moiety to which -D is covalently and reversibly conjugated;

each $-L^2-$, $-L^3-$ and $-L^4-$ is independently either absent or a spacer moiety;

each —CL- is independently a moiety connecting at least two units $Z^3$ and wherein there is at least one degradable bond in the direct connection between any two carbon atoms marked with the * connected by a moiety —CL-;

each —SP— is independently absent or a spacer moiety;

each —Rai is independently selected from the group consisting of —H, $C_{1-4}$ alkyl, an ammonium ion, a tetrabutylammonium ion, a cetyl methylammonium ion, an alkali metal ion and an alkaline earth metal ion;

each $—R^{a2}$ is independently selected from the group consisting of —H and $C_{1-10}$ alkyl;

each $—X^{0A}—$, $—X^{0B}—$, $—X^{0C}—$, $—X^{0D}—$, $—X^{0E}—$ and $—X^{0F}—$ is independently either absent or a linkage;

optionally $—X^{0A}—$ and/or $—X^{0B}—$ form together with $-L^4-$ or parts of $-L^4-$ one or more ring structure selected from the group consisting of 4- to 7-membered heterocyclyl, 8- to 11-membered heterobicyclyl and adamantyl;

optionally $—X^{0B}—$ and/or $—X^{0C}—$ form together with $-L^3-$ or parts of $-L^3-$ one or more ring structure selected from the group consisting of 4- to 7-membered heterocyclyl, 8- to 11-membered heterobicyclyl and adamantyl;

optionally, $—X^{0C}—$ and/or $—X^{0D}—$ form together with $-L^2-$ or parts of $-L^2-$ one or more ring structure selected from the group consisting of 4- to 7-membered heterocyclyl, 8- to 11-membered heterobicyclyl and adamantyl;

optionally $—X^{0E}—$ and/or $—X^{0F}—$ form together with —SP— or parts of —SP— one or more ring structure selected from the group consisting of 4- to 7-membered heterocyclyl, 8- to 11-membered heterobicyclyl and adamantyl;

wherein all units $Z^1$ present in the conjugate may be the same or different;

all units $Z^2$ present in the conjugate may be the same or different;

all units $Z^3$ present in the conjugate may be the same or different;

at least one unit $Z^3$ is present per hyaluronic acid strand which is connected to at least one unit $Z^3$ on a different hyaluronic acid strand; and the conjugate comprises at least one moiety $-L^1-D$.

The presence of at least one degradable bond between the carbon atom marked with the * of a first moiety $Z^3$ and the direct connection to the carbon atom marked with the * of a second moiety $Z^3$ ensures that after cleavage of all such degradable bonds present in the conjugates of the present invention the hyaluronic acid strands present in said conjugate are no longer crosslinked, which allows clearance of the hyaluronic acid network It is understood that in case a degradable bond is located in a ring structure present in the direct connection of the carbon atom marked with the * of a first moiety $Z^3$ and the carbon atom marked with the * of a second moiety $Z^3$ such degradable bond is not sufficient to allow complete cleavage and accordingly one or more additional degradable bonds are present in the direct connection of the carbon atom marked with the * of a first moiety $Z^3$ and the carbon atom marked with the * of a second moiety $Z^3$.

It is understood that the phrase "a dashed line marked with § indicates a point of connection between at least two units $Z^3$ via a moiety —CL-" refers to the following structure

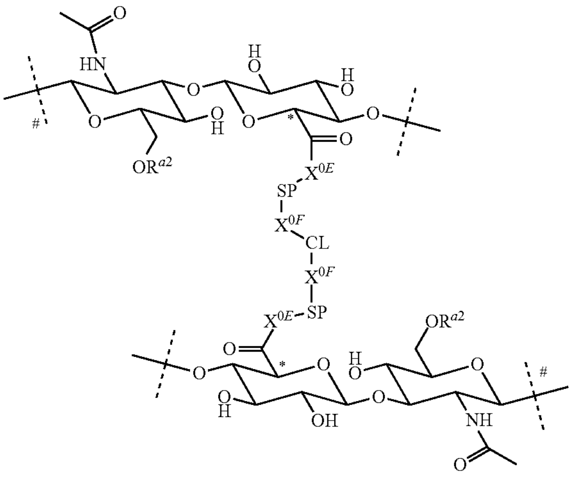

if —CL- is for example connected to two units $Z^3$, which two moieties $Z^3$ are connected at the position indicated with § via a moiety —CL-.

It is understood that the phrase "$—X^{0E}—$ and/or $—X^{0F}—$ form together with —SP— or parts of —SP— one or more ring structure selected from the group consisting of 4- to 7-membered heterocyclyl, 8- to 11-membered heterobicyclyl and adamantyl" refers to for example structures as shown below:

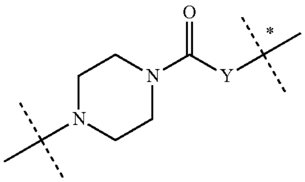

,

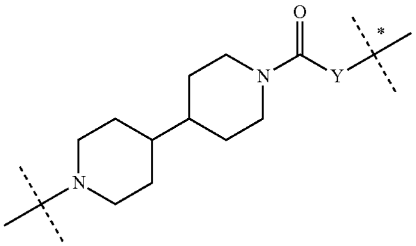

,

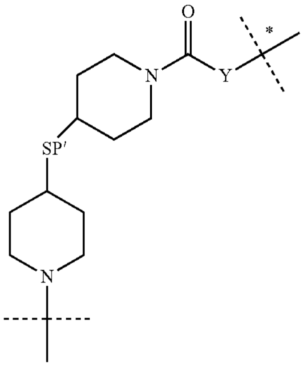

,

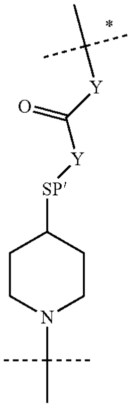

,

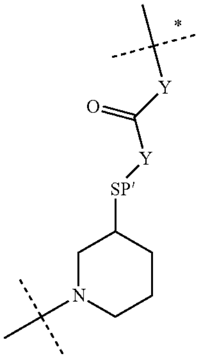

,

-continued

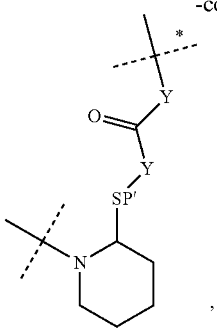

,

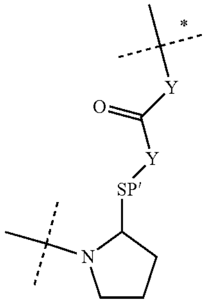

and

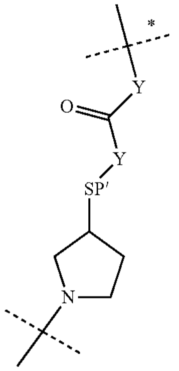

;

wherein the dashed line marked with the asterisk indicates attachment to —CL-;

the unmarked dashed line indicates attachment to the remainder of $Z^3$, i.e. to the carbonyl of the hyaluronic acid moiety;

—SP'— refers to the remainder of —SP—;

each —Y— is independently absent or is selected from the group consisting of —O—, —NR— and —S—; and each —R is independently selected from the group consisting of is independently selected from the group consisting of —H and $C_{1-6}$ alkyl; wherein $C_{1-6}$ alkyl is optionally substituted with one or more halogen, which are the same or different.

This applies analogously to other variables.

It is understood that no three-dimensionally crosslinked hydrogel can be formed if all hyaluronic acid strands of the present conjugate comprise only one unit $Z^3$, which is connected to only one unit $Z^3$ on a different hyaluronic acid strand. However, if a first unit $Z^3$ is connected to more than one unit $Z^3$ on a different strand, i.e. if —CL- is branched, such first unit $Z^3$ may be crosslinked to two or more other units $Z^3$ on two or more different hyaluronic acid strands. Accordingly, the number of units $Z^3$ per hyaluronic acid strand required for a crosslinked hyaluronic acid hydrogel depends on the degree of branching of —CL-. In certain embodiments at least 30% of all hyaluronic acid strands present in the conjugate are connected to at least two other hyaluronic acid strands. It is understood that it is sufficient if the remaining hyaluronic acid strands are connected to only one other hyaluronic acid strand.

It is understood that a moiety $Z^1$ is an unmodified disaccharide of hyaluronic acid, a moiety $Z^2$ is a disaccharide unit reversibly conjugated to a drug moiety and a moiety $Z^3$ is a disaccharide unit that is crosslinked via a moiety —CL-.

The conjugate of the present invention may also comprise units selected from the group consisting of $Z^4$

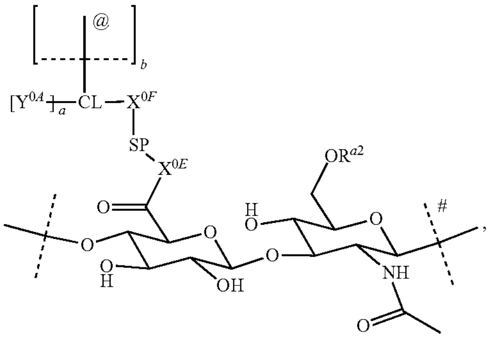

$Z^5$

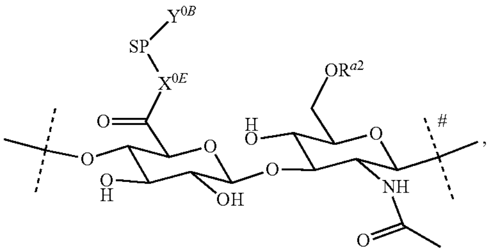

$Z^6$

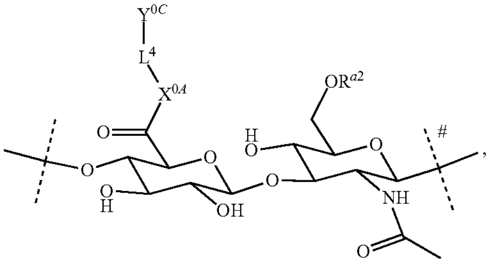

$Z^7$

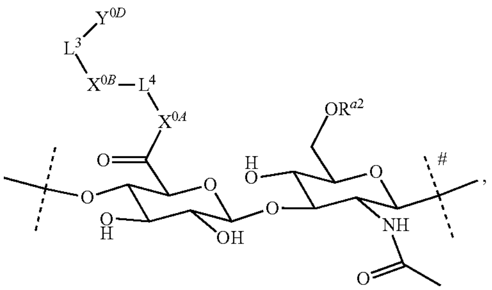

-continued $Z^8$

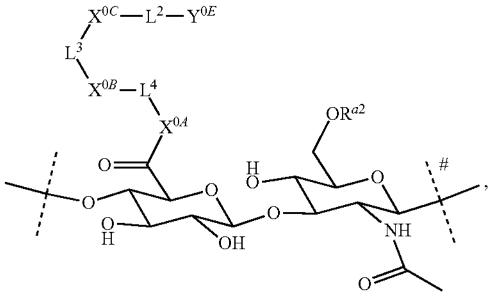

$Z^9$

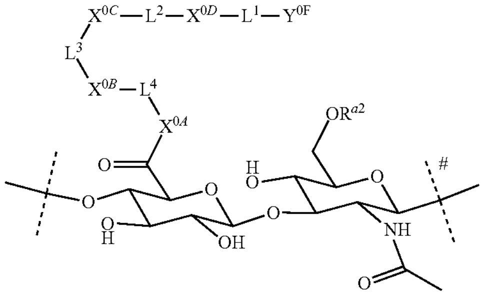

and $Z^{10}$

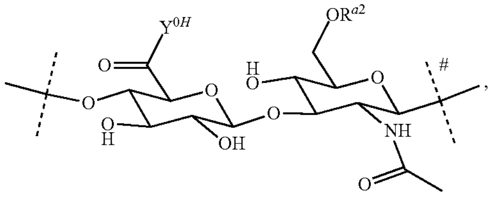

wherein an unmarked dashed line indicates a point of attachment to an adjacent unit $Z^1$, $Z^2$, $Z^3$, $Z^4$, $Z^5$, $Z^6$, $Z^7$, $Z^8$, $Z^9$ and $Z^{10}$ at a dashed line marked with # or to a hydrogen;

a dashed line marked with # indicates a point of attachment to an adjacent unit $Z^1$, $Z^2$ $Z^3$, $Z^4$, $Z^5$, $Z^6$, $Z^7$, $Z^8$, $Z^9$ and $Z^{10}$ at an unmarked dashed line or to a hydroxyl;

a dashed line marked with @ indicates attachment to a moiety $—X^{0F}—$ of a moiety $Z^3$;

a indicates the number of unreacted ends of —CL- and is a positive integer;

b indicates the number of ends of —CL- connected to a moiety $—X^{0F}$, of a moiety $Z^3$ and is 0 or a positive integer;

$-L^1-$, $-L^2-$, $-L^3-$, $-L^4-$, —SP—, —CL-, $—X^{0A}—$, $—X^{0B}—$, $—X^{0C}—$, $—X^{0D}—$, $—X^{0E}—$, $—X^{0F}—$ and $—R^{a2}$ are used as defined for $Z^1$, $Z^2$ and $Z^3$;

each $—Y^{0A}$, $—Y^{0B}$, $—Y^{0C}$, $—Y^{0D}$, $—Y^{0E}$, $—Y^{0F}$ and $—Y^{0H}$ is independently a functional group; optionally, $—Y^{0A}$ and/or $—X^{0F}—$ forms together with —CL- or parts of —CL- one or more ring structure selected from the group consisting of 4- to 7-membered heterocyclyl, 8- to 11-membered heterobicyclyl and adamantyl;

optionally, $—Y^{0B}$ and/or $—X^{0E}—$ forms together with —SP— or parts of —SP— one or more ring structure selected from the group consisting of 4- to 7-membered heterocyclyl, 8- to 11-membered heterobicyclyl and adamantyl optionally, $—Y^{0C}$ and/or $—X^{0A}—$ forms together with $-L^4-$ or parts of $-L^4-$ one or more ring structure selected from the group consisting of 4- to 7-membered heterocyclyl, 8- to 11-membered heterobicyclyl and adamantyl;

optionally, $—Y^{0D}$ and/or $—X^{0B}—$ forms together with $-L^3-$ or parts of $-L^3-$ one or more ring structure selected from the group consisting of 4- to 7-membered heterocyclyl, 8- to 11-membered heterobicyclyl and adamantyl; and optionally, $—Y^{0E}$ and/or $—X^{0C}—$ forms together with $-L^2-$ or parts of $-L^2-$ one or more ring structure selected from the group consisting of 4- to 7-membered heterocyclyl, 8- to 11-membered heterobicyclyl and adamantyl.

Units $Z^4$, $Z^5$, $Z^6$, $Z^7$, $Z^8$, $Z^9$ and $Z^{10}$ represent partly reacted or unreacted units. For example, a unit $Z^4$ represents a unit in which at least end of —CL- was not conjugated to a unit $Z^3$.

Depending on the order in which the elements of the conjugate of the present invention are assembled, different such partly reacted or unreacted units may be present. It is understood that the presence of such moieties cannot be avoided. In certain embodiments the sum of units $Z^4$, $Z^5$, $Z^6$, $Z^7$, $Z^8$, $Z^9$ and $Z^{10}$ is no more than 25% of the total number of units $Z^2$ $Z^3$, $Z^4$, $Z^5$, $Z^6$, $Z^7$, $Z^8$, $Z^9$ and $Z^{10}$ present in the conjugate, such as no more than 10%, such as no more than 15% or such as no more than 10%.

In certain embodiments variable a of $Z^4$ is selected from the group consisting of 1, 2, 3, 4, 5, 6, 7, 8, 9, 10, 11, 12, 13, 14, 15, 16, 17, 18 and 19. In certain embodiments variable a of $Z^4$ is a positive integer ranging from 20 to 200.

In certain embodiments b of $Z^4$ is selected from the group consisting of 0, 1, 2, 3, 4, 5, 6, 7, 8, 9, 10, 11, 12, 13, 14, 15, 16, 17, 18 and 19. In certain embodiments b of $Z^4$ is a positive integer ranging from 20 to 200.

It is further understood that in addition to units $Z^1$, $Z^2$, $Z^3$, $Z^4$, $Z^5$, $Z^6$, $Z^7$, $Z^8$, $Z^9$ and $Z^{10}$ a conjugate may also comprise units that are the result of cleavage of the reversible bond between -D and $-L^1-$ or of one or more of the degradable bonds present in the direct connection between any two carbon atoms marked with the * connected by a moiety —CL-, i.e. units resulting from degradation of the conjugate.

In certain embodiments each strand present in the conjugates of the present invention comprises at least 20 units, such as from 20 to 2500 units, from 25 to 2200 units, from 50 to 2000 units, from 75 to 100 units, from 75 to 100 units, from 80 to 560 units, from 100 to 250 units, from 200 to 800 units, from 20 to 1000, from 60 to 1000, from 60 to 400 or from 200 to 600 units.

In certain embodiments the moieties —CL- present in the conjugates of the present invention have different structures. In certain embodiments the moieties —CL- present in the conjugates of the present invention have the same structure.

In general, any moiety that connects at least two other moieties is suitable for use as a moiety —CL-, which may also be referred to as a "crosslinker moiety".

The at least two units $Z^3$ that are connected via a moiety —CL- may either be located on the same hyaluronic acid strand or on different hyaluronic acid strands.

The moiety —CL- may be linear or branched. In certain embodiments —CL- is linear. In certain embodiments —CL- is branched.

In certain embodiments —CL- connects two units $Z^3$. In certain embodiments —CL- connects three units $Z^3$. In certain embodiments —CL- connects four unis $Z^3$. In certain embodiments —CL- connects five units $Z^3$. In certain embodiments —CL- connects six units $Z^3$.

In certain embodiments —CL- connects seven units $Z^3$. In certain embodiments —CL- connects eight units $Z^3$. In certain embodiments —CL- connects nine units $Z^3$.

If —CL- connects two units $Z^3$—CL- may be linear or branched. If —CL- connects more than two units $Z^3$—CL- is branched.

A branched moiety —CL- comprises at least one branching point from which at least three branches extend, which branches may also be referred to as "arms". Such branching point may be selected from the group consisting of

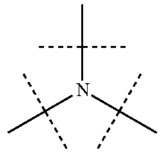
,
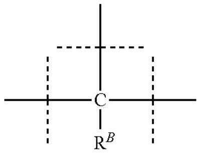
and
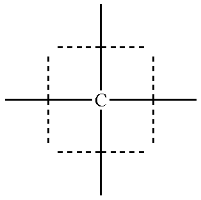
, wherein dashed lines indicate attachment to an arm; and —$R^B$ is selected from the group consisting of —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more —$R^{B1}$, which are the same or different, and wherein $C_{1-6}$ alkyl, $C_{2-6}$ alkenyl and $C_{2-6}$ alkynyl are optionally interrupted with —C(O)O—, —O—, —C(O)—, —C(O)N($R^{B2}$)—, —$S(O)_2N$($R^{B2}$)—, —S(O)N($R^{B2}$)—, —$S(O)_2$—, —S(O)—, —N($R^{B2}$)$S(O)_2N$($R^{B2a}$)—, —S—, —N($R^{B2}$)—, —OC($OR^{B2}$)($R^{B2a}$)—, —N($R^{B2}$)C(O)N($R^{B2a}$)—, and —OC(O)N($R^{B2}$)—; wherein —$R^{B1}$, —$R^{B2}$ and —$R^{B2a}$ are selected from —H, $C_{1-6}$ alkyl, $C_{2-6}$ alkenyl and $C_{2-6}$ alkynyl.

In certain embodiments —$R^B$ is selected from the group consisting of —H, methyl and ethyl.

A branched moiety —CL- may comprise a plurality of branching points, such as 1, 2, 3, 4, 5, 6, 7 or more branching points, which may be the same or different.

If a moiety —CL- connects three units $Z^3$, such moiety —CL- comprises at least one branching point from which at least three arms extend.

If a moiety —CL- connects four units $Z^3$, such moiety —CL- may comprise one branching point from which four arms extend. However, alternative geometries are possible, such as at least two branching points from which at least three arms each extend. The larger the number of connected units $Z^3$, the larger the number of possible geometries is.

In a first embodiment at least 70%, such as at least 75%, such as at least 80%, such as at least 85%, such as at least 90% or such as at least 95% of the number of hyaluronic acid strands of the conjugate of the present invention comprise at least one moiety $Z^2$ and at least one moiety $Z^3$. In such embodiment units $Z^2$ and $Z^3$ can be found in essentially all hyaluronic acid strands present in the conjugates of the present invention.

Accordingly, a conjugate of this first embodiment comprises crosslinked hyaluronic acid strands to which a plurality of drug moieties are covalently and reversibly conjugated, wherein the conjugate comprises a plurality of connected units selected from the group consisting of $Z^1$

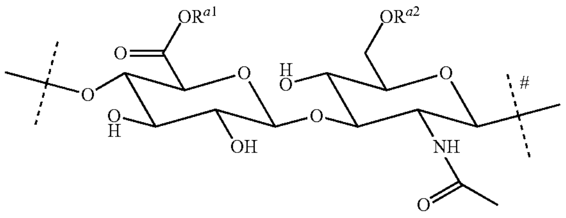
, $Z^2$

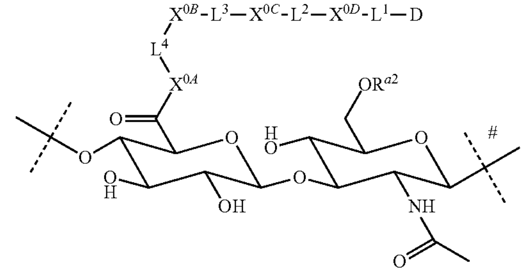
and $Z^3$

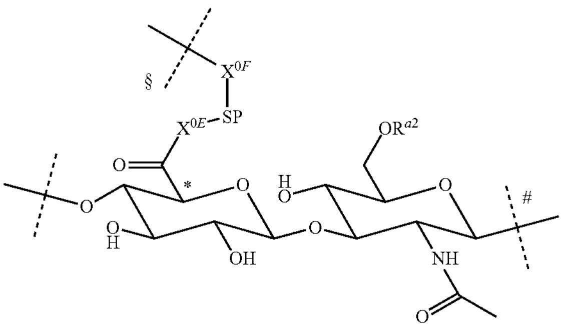
, wherein an unmarked dashed line indicates a point of attachment to an adjacent unit at a dashed line marked with # or to a hydrogen;

a dashed line marked with # indicates a point of attachment to an adjacent unit at an unmarked dashed line or to a hydroxyl;

a dashed line marked with § indicates a point of connection between at least two units $Z^3$ via a moiety —CL-;

D, -$L^1$-, -$L^2$-, -$L^3$-, -$L^4$-, —SP—, —CL-, —$X^{0A}$—, —$X^{0B}$—, —$X^{0C}$—, —$X^{0D}$—, —$X^{0E}$—, —$X^{0F}$—, —$R^{a1}$ and —$R^{a2}$ are used as defined for $Z^1$, $Z^2$ and $Z^3$;

wherein all units $Z^1$ present in the conjugate may be the same or different;

all units $Z^2$ present in the conjugate may be the same or different;

all units $Z^3$ present in the conjugate may be the same or different;

the number of $Z^1$ units ranges from 1% to 98% of the total number of units present in the conjugate;

the number of $Z^2$ units ranges from 1% to 98% of the total number of units present in the conjugate, provided at least one unit $Z^2$ is present in the conjugate;

the number of $Z^3$ units ranges from 1% to 97% of the total number of units present in the conjugate, provided that at least one unit $Z^3$ is present per strand; and wherein at least 70% of all hyaluronic acid strands comprise at least one moiety $Z^2$ and at least one moiety $Z^3$.

The conjugate according to this first embodiment may also comprise units selected from the group consisting of $Z^4$, $Z^5$, $Z^6$, $Z^7$, $Z^8$, $Z^9$ and $Z^{10}$ as described above.

In a conjugate according to this first embodiment the number of units $Z^2$ ranges from 1 to 70% of all units present in the conjugate, such as from 2 to 15%, from 2 to 10%, from 16 to 39, from 40 to 65%, or from 50 to 60% of all units present in the conjugate.

In a conjugate according to this first embodiment the number of units $Z^3$ ranges from 1 to 30% of all units present in the conjugate, such as from 2 to 5%, from 5 to 20%, from 10 to 18%, or from 14 to 18% of all units present in the conjugate.

In a conjugate according to this first embodiment the number of units $Z^1$ ranges from 10 to 97% of all units present in the conjugate, such as from 20 to 40%, such as from 25 to 35%, such as from 41 to 95%, such as from 45 to 90%, such as from 50 to 70% of all units present in the conjugate.

Each degradable bond present in the direct connection between any two carbon atoms marked with the * connected by a moiety —CL- may be different or all such degradable bonds present in the conjugate may be the same.

Each direct connection between two carbon atoms marked with the * connected by a moiety —CL- may have the same or a different number of degradable bonds.

In certain embodiments the number of degradable bonds present in the conjugate of the present invention between all combinations of two carbon atoms marked with the * connected by a moiety —CL- is the same and all such degradable bonds have the same structure.

In the first embodiment the at least one degradable bond present in the direct connection between any two carbon atoms marked with the * connected by a moiety —CL- may be selected from the group consisting of ester, carbonate, sulfate, phosphate bonds, carbamate and amide bonds. It is understood that carbamates and amides are not reversible per se, and that in this context neighboring groups render these bonds reversible. In certain embodiments there is one degradable bond selected from the group consisting of ester, carbonate, sulfate, phosphate bonds, carbamate and amide bonds in the direct connection between any two carbon atoms marked with the * connected by a moiety —CL-. In certain embodiments there are two degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are three degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are four degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are five degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. In certain embodiments there are six degradable bonds selected from the group consisting of ester, carbonate, sulfate, phosphate bonds, carbamate and amide bonds in the direct connection between any two carbon atoms marked with the * connected by a moiety —CL-, which degradable bonds may be the same or different. It is understood that if more than two units $Z^3$ are connected by —CL- there are more than two carbons marked with * that are connected and thus there is more than one shortest connection with at least one degradable bond present. Each shortest connection may have the same or different number of degradable bonds.

In certain embodiments the at least one degradable bond, such as one, two, three, four, five, six degradable bonds, are located within —CL-.

In certain embodiments the at least one degradable bond present in the direct connection between any two carbon atoms marked with * connected by a moiety —CL- is one ester bond.

In other embodiments the at least one degradable bond are two ester bonds. In other embodiments the at least one degradable bond are three ester bonds. In other embodiments the at least one degradable bond are four ester bonds. In other embodiments the at least one degradable bond are five ester bonds. In other embodiments the at least one degradable bond are six ester bonds.

In certain embodiments the at least one degradable bond present in the direct connection between any two carbon atoms marked with * connected by a moiety —CL- is one carbonate bond. In other embodiments the at least one degradable bond are two carbonate bonds. In other embodiments the at least one degradable bond are three carbonate bonds. In other embodiments the at least one degradable bond are four carbonate bonds. In other embodiments the at least one degradable bond are five carbonate bonds. In other embodiments the at least one degradable bond are six carbonate bonds.

In certain embodiments the at least one degradable bond present in the direct connection between any two carbon atoms marked with * connected by a moiety —CL- is one phosphate bond. In other embodiments the at least one degradable bond are two phosphate bonds. In other embodiments the at least one degradable bond are three phosphate bonds. In other embodiments the at least one degradable bond are four phosphate bonds. In other embodiments the at least one degradable bond are five phosphate bonds. In other embodiments the at least one degradable bond are six phosphate bonds.

In certain embodiments the at least one degradable bond present in the direct connection between any two carbon atoms marked with * connected by a moiety —CL- is one sulfate bond. In other embodiments the at least one degradable bond are two sulfate bonds. In other embodiments the at least one degradable bond are three sulfate bonds. In other embodiments the at least one degradable bond are four sulfate bonds. In other embodiments the at least one degradable bond are five sulfate bonds. In other embodiments the at least one degradable bond are six sulfate bonds.

In certain embodiments the at least one degradable bond present in the direct connection between any two carbon atoms marked with * connected by a moiety —CL- is one carbamate bond. In other embodiments the at least one degradable bond are two carbamate bonds. In other embodiments the at least one degradable bond are three carbamate bonds. In other embodiments the at least one degradable bond are four carbamate bonds. In other embodiments the at least one degradable bond are five carbamate bonds. In other embodiments the at least one degradable bond are six carbamate bonds.

In certain embodiments the at least one degradable bond present in the direct connection between any two carbon atoms marked with * connected by a moiety —CL- is one amide bond. In other embodiments the at least one degradable bond are two amide bonds. In other embodiments the at least one degradable bond are three amide bonds. In other embodiments the at least one degradable bond are four amide bonds. In other embodiments the at least one degradable bond are five amide bonds. In other embodiments the at least one degradable bond are six amide bonds.

It was found that a high degree of derivatization of the disaccharide units of hyaluronic acid, meaning that the number of units $Z^1$ is less than 80% of all units present in the conjugate, interferes with degradation of the hydrogel by certain hyaluronidases. This has the effect that less degradation by hyaluronidases occurs and that chemical cleavage of the degradable bonds becomes more relevant. This renders degradation of the conjugate more predictable. The reason for this is that the level of enzymes, such as hyaluronidases, exhibits inter-patient variability and may vary between different administration sites, whereas chemical cleavage predominantly depends on temperature and pH which are more stable parameters and thus chemical cleavage tends to be more predictable.

In some embodiments —CL- is $C_{1-50}$ alkyl, which is optionally interrupted by one or more atoms or groups selected from the group consisting of -T-, —C(O)O—, —O—, —C(O)—, —C(O)N($R^{c1}$)—, —$S(O)_2$—, —S(O)—, —S—, —N($R^{c1}$)—, —OC(O$R^{c1}$)($R^{c1a}$)— and —OC(O)N($R^{c1}$)—;

wherein -T- is selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; and —$R^{c1}$ and —$R^{c1a}$ are selected from the group consisting of —H and $C_{1-6}$ alkyl.

In certain embodiments such moiety —CL- comprises at least one (such as one, two, three, four, five or six) degradable bond, such as a degradable bond selected from the group consisting of ester, carbonate, sulfate, phosphate bonds, carbamate and amide bonds.

In certain embodiments —CL- is a moiety of formula (A)

(A)

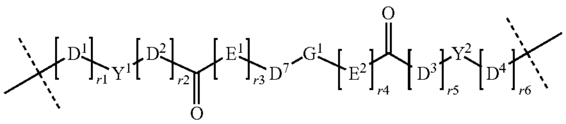, wherein

—$Y^1$— is of formula

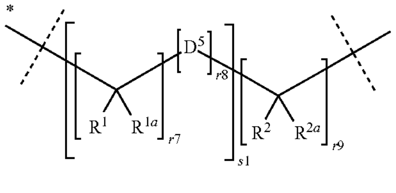, wherein the dashed line marked with the asterisk indicates attachment to -$D^1$- and the unmarked dashed line indicates attachment to -$D^2$-;

—$Y^2$— is of formula

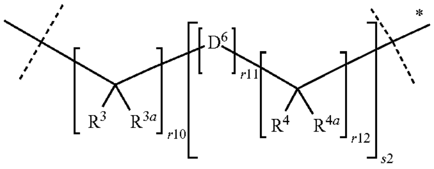, wherein the dashed line marked with the asterisk indicates attachment to -$D^4$- and the unmarked dashed line indicates attachment to -$D^3$-;

-$E^1$- is of formula

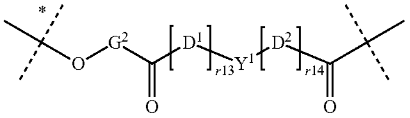, wherein the dashed line marked with the asterisk indicates attachment to —(C═O)— and the unmarked dashed line indicates attachment to —O—;

-$E^2$- is of formula

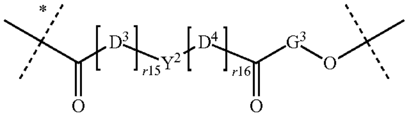, wherein the dashed line marked with the asterisk indicates attachment to -$G^1$- and the unmarked dashed line indicates attachment to —(C═O)—;

-$G^1$- is of formula

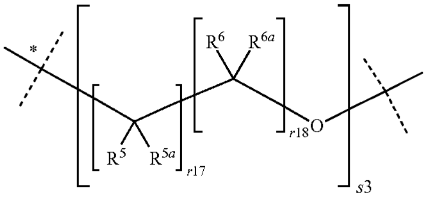, wherein the dashed line marked with the asterisk indicates attachment to —O— and the unmarked dashed line indicates attachment to -$E^2$-;

-$G^2$- is of formula

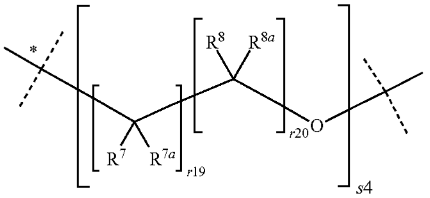, wherein the dashed line marked with the asterisk indicates attachment to —O— and the unmarked dashed line indicates attachment to —(C=O)—;

-$G^3$- is of formula (C-vii),

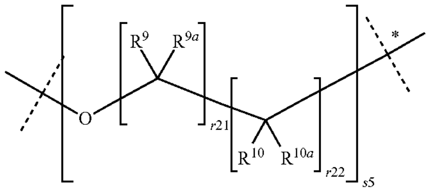

wherein the dashed line marked with the asterisk indicates attachment to —O— and the unmarked dashed line indicates attachment to —(C=O)—;

-$D^1$-, -$D^2$-, -$D^3$-, -$D^4$-, -$D^5$-, -$D^6$- and -$D^7$- are identical or different and each is independently of the others selected from the group comprising —O—, —$NR^{11}$—, —$N^+R^{12}R^{12a}$—, —S—, —(S=O)—, —$(S(O)_2)$, —C(O)—, —$P(O)R^{13}$ and —$CR^{14}R^{14a}$—.

—$R^1$, —$R^{1a}$, —$R^2$, —$R^{2a}$, —$R^3$, —$R^{3a}$, —$R^4$, —$R^{4a}$, —$R^5$, —$R^{5a}$, —$R^6$, —$R^{6a}$, —$R^7$, —$R^{7a}$, —$R^8$, —$R^{8a}$, —$R^9$, —$R^{9a}$, —$R^{10}$, —$R^{10a}$, —$R^{11}$, —$R^{12}$, —$R^{12a}$, —$R^{13}$, —$R^{14}$ and —$R^{14a}$ are identical or different and each is independently of the others selected from the group comprising —H and $C_{1-6}$ alkyl;

optionally, one or more of the pairs —$R^1$/—$R^{1a}$, —$R^2$/—$R^{2a}$, —$R^3$/—$R^{3a}$, —$R^4$/—$R^{4a}$, —$R^1$/—$R^2$, —$R^3$/—$R^4$, —$R^{1a}$/—$R^{2a}$, —$R^{3a}$/—$R^{4a}$, —$R^{12}$/—$R^{12a}$, and —$R^{14}$/—$R^{14a}$ form a chemical bond or are joined together with the atom to which they are attached to form a $C_{3-8}$ cycloalkyl or to form a ring A or are joined together with the atom to which they are attached to form a 4- to 7-membered heterocyclyl or 8- to 11-membered heterobicyclyl or adamantyl;

A is selected from the group consisting of phenyl, naphthyl, indenyl, indanyl and tetralinyl;

r1, r2, r5, r6, r13, r14, r15 and r16 are independently 0 or 1;

r3, r4, r7, r8, r9, r10, r11, r12 are independently 0, 1, 2, 3, or 4;

r17, r18, r19, r20, r21 and r22 are independently 1, 2, 3, 4, 5, 6, 7, 8, 9 or 10; and s1, s2, s4, s5 are independently 1, 2, 3, 4, 5 or 6.

s3 ranges from 1 to 200, preferably from 1 to 100 and more preferably from 1 to 50

In certain embodiments r1 of formula (A) is 0. In certain embodiments r1 of formula (A) is 1. In certain embodiments r2 of formula (A) is 0. In certain embodiments r2 of formula (A) is 1. In certain embodiments r5 of formula (A) is 0. In certain embodiments r5 of formula (A) is 1. In certain embodiments r6 of formula (A) is 0. In certain embodiments r6 of formula (A) is 1. In certain embodiments r13 of formula (A) is 0. In certain embodiments r13 of formula (A) is 1. In certain embodiments r14 of formula (A) is 0. In certain embodiments r14 of formula (A) is 1. In certain embodiments r15 of formula (A) is 0. In certain embodiments r15 of formula (A) is 1. In certain embodiments r16 of formula (A) is 0. In certain embodiments r16 of formula (A) is 1.

In certain embodiments r3 of formula (A) is 0. In certain embodiments r3 of formula (A) is 1. In certain embodiments r3 of formula (A) is 2. In certain embodiments r3 of formula (A) is 3. In certain embodiments r3 of formula (A) is 4. In certain embodiments r4 of formula (A) is 0. In certain embodiments r4 of formula (A) is 1. In certain embodiments r4 of formula (A) is 2. In certain embodiments r4 of formula (A) is 3. In certain embodiments r4 of formula (A) is 4. In certain embodiments r3 of formula (A) and r4 of formula (A) are both 0.

In certain embodiments r7 of formula (A) is 0. In certain embodiments r7 of formula (A) is 1. In certain embodiments r7 of formula (A) is 2. In certain embodiments r7 of formula (A) is 3. In certain embodiments r7 of formula (A) is 4. In certain embodiments r8 of formula (A) is 0. In certain embodiments r8 of formula (A) is 1. In certain embodiments r8 of formula (A) of formula (A) is 2. In certain embodiments r8 of formula (A) of formula (A) is 3. In certain embodiments r8 of formula (A) of formula (A) is 4. In certain embodiments r9 of formula (A) is 0. In certain embodiments r9 of formula (A) is 1. In certain embodiments r9 of formula (A) is 2. In certain embodiments r9 of formula (A) is 3. In certain embodiments r9 of formula (A) is 4. In certain embodiments r10 of formula (A) is 0. In certain embodiments r10 of formula (A) is 1. In certain embodiments r10 of formula (A) is 2. In certain embodiments r10 of formula (A) is 3. In certain embodiments r10 of formula (A) is 4. In certain embodiments r11 of formula (A) is 0. In certain embodiments r11 of formula (A) is 1. In certain embodiments r 11 of formula (A) is 2. In certain embodiments r11 of formula (A) is 3. In certain embodiments r1 of formula (A) is 4. In certain embodiments r12 of formula (A) is 0. In certain embodiments r12 of formula (A) is 1. In certain embodiments r12 of formula (A) is 2. In certain embodiments r12 of formula (A) is 3. In certain embodiments r12 of formula (A) is 4.

In certain embodiments r17 of formula (A) is 1. In certain embodiments r17 of formula (A) is 2. In certain embodiments r17 of formula (A) is 3. In certain embodiments r18 of formula (A) is 1. In certain embodiments r18 of formula (A) is 2. In certain embodiments r18 of formula (A) is 3. In certain embodiments r19 of formula (A) is 1. In certain embodiments r19 of formula (A) is 2. In certain embodiments r19 of formula (A) is 3. In certain embodiments r20 of formula (A) is 1. In certain embodiments r20 of formula (A) is 2. In certain embodiments r20 of formula (A) is 3. In certain embodiments r21 of formula (A) is 1. In certain embodiments r21 of formula (A) is 2. In certain embodiments r21 of formula (A) is 3. In certain embodiments r22 of formula (A) is 1. In certain embodiments r22 of formula (A) is 2. In certain embodiments r22 of formula (A) is 3.

In certain embodiments s1 of formula (A) is 1. In certain embodiments s1 of formula (A) is 2. In certain embodiments s1 of formula (A) is 3. In certain embodiments s2 of formula (A) is 1. In certain embodiments s2 of formula (A) is 2. In certain embodiments s2 of formula (A) is 3. In certain embodiments s4 of formula (A) is 1. In certain embodiments s4 of formula (A) is 2. In certain embodiments s4 of formula (A) is 3.

In certain embodiments s3 of formula (A) ranges from 1 to 100. In certain embodiments s3 of formula (A) ranges from 1 to 75. In certain embodiments s3 of formula (A) ranges from 2 to 50. In certain embodiments s3 of formula (A) ranges from 2 to 40. In certain embodiments s3 of formula (A) ranges from 3 to 30. In certain embodiments s3 of formula (A) ranges from 3 to 20. In certain embodiments s3 of formula (A) ranges from 3 to 10. In certain embodiments s3 of formula (A) is about 2. In certain embodiments s3 of formula (A) is about 3. In certain embodiments s3 of formula (A) is about 4. In certain embodiments s3 of formula (A) is about 5. In certain embodiments s3 of formula (A) is about 6. In certain embodiments s3 of formula (A) is about 7. In certain embodiments s3 of formula (A) is about 8. In certain embodiments s3 of formula (A) is about 9. In certain embodiments s3 of formula (A) is about 10. In certain embodiments s3 of formula (A) is 2. In certain embodiments s3 of formula (A) is 3. In certain embodiments s3 of formula (A) is 4. In certain embodiments s3 of formula (A) is 5. In certain embodiments s3 of formula (A) is 6. In certain embodiments s3 of formula (A) is 7. In certain embodiments s3 of formula (A) is 8. In certain embodiments s3 of formula (A) is 9. In certain embodiments s3 of formula (A) is 10. In certain embodiments s3 of formula (A) is 20. In certain embodiments s3 of formula (A) is 25.

In certain embodiments —$R^1$ of formula (A) is —H. In certain embodiments —$R^1$ of formula (A) is methyl. In certain embodiments —$R^1$ of formula (A) is ethyl. In certain embodiments —$R^{1a}$ of formula (A) is —H. In certain embodiments —$R^{1a}$ of formula (A) is methyl. In certain embodiments —$R^{1a}$ of formula (A) is ethyl. In certain embodiments —$R^2$ of formula (A) is —H. In certain embodiments —$R^2$ of formula (A) is methyl. In certain embodiments —$R^2$ of formula (A) is ethyl. In certain embodiments —$R^{2a}$ of formula (A) is —H. In certain embodiments —$R^{2a}$ of formula (A) is methyl. In certain embodiments —$R^{2a}$ of formula (A) is ethyl. In certain embodiments —$R^3$ of formula (A) is —H. In certain embodiments —$R^3$ of formula (A) is methyl. In certain embodiments —$R^3$ of formula (A) is ethyl. In certain embodiments —$R^{3a}$ of formula (A) is —H. In certain embodiments —$R^{3a}$ of formula (A) is methyl. In certain embodiments —$R^{3a}$ of formula (A) is ethyl. In certain embodiments —$R^4$ of formula (A) is —H. In certain embodiments —$R^4$ of formula (A) is methyl. In certain embodiments —$R^4$ of formula (A) is methyl. In certain embodiments —$R^{4a}$ of formula (A) is —H. In certain embodiments —$R^{4a}$ of formula (A) is methyl. In certain embodiments —$R^{4a}$ of formula (A) is ethyl. In certain embodiments —$R^5$ of formula (A) is —H. In certain embodiments —$R^5$ of formula (A) is methyl. In certain embodiments —$R^5$ of formula (A) is ethyl. In certain embodiments —$R^{5a}$ of formula (A) is —H. In certain embodiments —$R^{5a}$ of formula (A) is methyl. In certain embodiments —$R^{5a}$ of formula (A) is ethyl. In certain embodiments —$R^6$ of formula (A) is —H. In certain embodiments —$R^6$ of formula (A) is methyl. In certain embodiments —$R^6$ of formula (A) is ethyl. In certain embodiments —$R^{6a}$ of formula (A) is —H. In certain embodiments —$R^{6a}$ of formula (A) is methyl. In certain embodiments —$R^{6a}$ of formula (A) is ethyl. In certain embodiments —$R^7$ of formula (A) is —H. In certain embodiments —$R^7$ of formula (A) is methyl. In certain embodiments —$R^7$ of formula (A) is ethyl. In certain embodiments —$R^8$ of formula (A) is —H. In certain embodiments —$R^8$ of formula (A) is methyl. In certain embodiments —$R^8$ of formula (A) is ethyl. In certain embodiments —$R^{8a}$ of formula (A) is —H. In certain embodiments —$R^{8a}$ of formula (A) is methyl. In certain embodiments —$R^{8a}$ of formula (A) is ethyl. In certain embodiments —$R^9$ of formula (A) is —H. In certain embodiments —$R^9$ of formula (A is methyl. In certain embodiments —$R^9$ of formula (A) is ethyl. In certain embodiments —$R^{9a}$ of formula (A) is —H. In certain embodiments —$R^{9a}$ of formula (A) is methyl. In certain embodiments —$R^{9a}$ of formula (A) is ethyl. In certain embodiments —$R^{9a}$ of formula (A) is —H. In certain embodiments —$R^{9a}$ of formula (A) is methyl. In certain embodiments —$R^{9a}$ of formula (A) is ethyl. In certain embodiments —$R^{10}$ of formula (A) is —H. In certain embodiments —$R^{10}$ of formula (A) is methyl. In certain embodiments —$R^{10}$ of formula (A) is ethyl. In certain embodiments —$R^{10a}$ of formula (A) is —H. In certain embodiments —$R^{11a}$ of formula (A) is methyl. In certain embodiments —$R^{10a}$ of formula (A) is ethyl. In certain embodiments —$R^{11}$ of formula (A) is —H. In certain embodiments —$R^{11}$ of formula (A) is methyl. In certain embodiments —$R^{11}$ of formula (A) is ethyl. In certain embodiments —$R^{12}$ of formula (A) is —H. In certain embodiments —$R^{12}$ of formula (A) is methyl. In certain embodiments —$R^{12}$ of formula (A) is ethyl. In certain embodiments —$R^{12a}$ of formula (A) is —H. In certain embodiments —$R^{12a}$ of formula (A) is methyl. In certain embodiments —$R^{12a}$ of formula (A) is ethyl. In certain embodiments —$R^{13}$ of formula (A) is —H. In certain embodiments —$R^{13}$ of formula (A) is methyl. In certain embodiments —$R^{13}$ of formula (A) is ethyl In certain embodiments —$R^{14}$ of formula (A) is —H. In certain embodiments —$R^{14}$ of formula (A) is methyl. In certain embodiments —$R^{14}$ of formula (A) is ethyl. In certain embodiments —$R^{14a}$ of formula (A) is —H. In certain embodiments —$R^{14a}$ of formula (A) is methyl. In certain embodiments —$R^{14a}$ of formula (A) is ethyl.

In certain embodiments -$D^1$- of formula (A) is —O—. In certain embodiments -$D^1$- of formula (A) is —$NR^{11}$—. In certain embodiments -$D^1$- of formula (A) is —$N^+R^{12}R^{12a}$—. In certain embodiments -$D^1$- of formula (A) is —S—. In certain embodiments -$D^1$- of formula (A) is —(S═O). In certain embodiments -$D^1$- of formula (A) is —$(S(O)_2)$—. In certain embodiments -$D^1$- of formula (A) is —C(O)—. In certain embodiments -$D^1$- of formula (A) is —$P(O)R^{13}$—. In certain embodiments -$D^1$- of formula (A) is —$P(O)(OR^{13})$—. In certain embodiments -$D^1$- of formula (A) is —$CR^{14}R^{14a}$—.

In certain embodiments -$D^2$- of formula (A) is —O—. In certain embodiments -$D^2$- of formula (A) is —$NR^{11}$—. In certain embodiments -$D^2$- of formula (A) is —$N^+R^{12}R^{12a}$—. In certain embodiments -$D^2$- of formula (A) is —S—. In certain embodiments -$D^2$- of formula (A) is —(S═O). In certain embodiments -$D^2$- of formula (A) is —$(S(O)_2)$—. In certain embodiments -$D^2$- of formula (A) is —C(O)—. In certain embodiments -$D^2$- of formula (A) is —$P(O)R^{13}$—. In certain embodiments -$D^2$- of formula (A) is —P((O)OR)—. In certain embodiments -$D^2$- of formula (A) is —$CR^{14}R^{14a}$—.

In certain embodiments -$D^3$- of formula (A) is —O—. In certain embodiments -$D^3$- of formula (A) is —$NR^{11}$—. In certain embodiments -$D^3$- of formula (A) is —$N^+R^{12}R^{12a}$—. In certain embodiments -$D^3$- of formula (A) is —S—. In certain embodiments -$D^3$- of formula (A) is —(S═O). In certain embodiments -$D^3$- of formula (A) is —$(S(O)_2)$—. In certain embodiments -$D^3$- of formula (A) is —C(O)—. In certain embodiments -$D^3$- of formula (A) is —$P(O)R^{13}$—. In certain embodiments -$D^3$- of formula (A) is —$P(O)(OR^{13})$—. In certain embodiments -$D^3$- of formula (A) is —$CR^{14}R^{14a}$—.

In certain embodiments -$D^4$- of formula (A) is —O—. In certain embodiments -$D^4$- of formula (A) is —$NR^{11}$—. In certain embodiments -$D^4$- of formula (A) is —$N^+R^{12}R^{12a}$—. In certain embodiments -$D^4$- of formula (A) is —S—. In certain embodiments -$D^4$- of formula (A) is —(S═O). In certain embodiments -$D^4$- of formula (A) is —$(S(O)_2)$—. In certain embodiments -$D^4$- of formula (A) is —C(O)—. In certain embodiments -$D^4$- of formula (A) is —P(O)$R^{13}$—. In certain embodiments -$D^4$- of formula (A) is —P(O)($OR^{13}$)—. In certain embodiments -$D^4$- of formula (A) is —$CR^{14}R^{14a}$—.

In certain embodiments -$D^5$- of formula (A) is —O—. In certain embodiments -$D^5$- of formula (A) is —$NR^{11}$—. In certain embodiments -$D^5$- of formula (A) is —$N^+R^{12}R^{12a}$—. In certain embodiments -$D^5$- of formula (A) is —S—. In certain embodiments -$D^5$- of formula (A) is —(S═O)—. In certain embodiments -$D^5$- of formula (A) is —($S(O)_2$)—. In certain embodiments -$D^5$- of formula (A) is —C(O)—. In certain embodiments -$D^5$- of formula (A) is —P(O)$R^{13}$—. In certain embodiments -$D^5$- of formula (A) is —P(O)($OR^{13}$)—. In certain embodiments -$D^5$- of formula (A) is —$CR^{14}R^{14a}$—.

In certain embodiments -$D^6$- of formula (A) is —O—. In certain embodiments -$D^6$- of formula (A) is —$NR^{11}$—. In certain embodiments -$D^6$- of formula (A) is —$N^+R^{12}R^{12a}$—. In certain embodiments -$D^6$- of formula (A) is —S—. In certain embodiments -$D^6$- of formula (A) is —(S═O). In certain embodiments -$D^6$- of formula (A) is —($S(O)_2$)—. In certain embodiments -$D^6$- of formula (A) is —C(O)—. In certain embodiments -$D^6$- of formula (A) is —P(O)$R^{13}$—. In certain embodiments -$D^6$- of formula (A) is —P(O)($OR^{13}$)—. In certain embodiments -$D^6$- of formula (A) is —$CR^{14}R^{14a}$—.

In certain embodiments -$D^7$- of formula (A) is —O—. In certain embodiments -$D^7$- of formula (A) is —$NR^{11}$—. In certain embodiments -$D^7$- of formula (A) is —$N^+R^{12}R^{12a}$—. In certain embodiments -$D^7$- of formula (A) is —S—. In certain embodiments -$D^7$- of formula (A) is —(S═O). In certain embodiments -$D^7$- of formula (A) is —($S(O)_2$)—. In certain embodiments -$D^7$- of formula (A) is —C(O)—. In certain embodiments -$D^7$- of formula (A) is —P(O)$R^{13}$—. In certain embodiments -$D^7$- of formula (A) is —P(O)($OR^{13}$)—. In certain embodiments -$D^7$- of formula (A) is —$CR^{14}R^{14a}$—.

In certain embodiments —$CL^P$- is of formula (B)

(B)

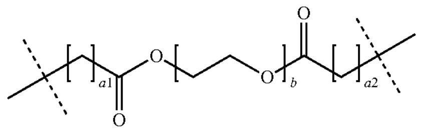

, wherein a1 and a2 are independently selected from the group consisting of a1 and a2 are independently selected from the group consisting of 1, 2, 3, 4, 5, 6, 7, 8, 9, 10, 11, 12, 13 and 14; and b is an integer ranging from 1 to 50.

In certain embodiments a1 and a2 of formula (B) are different. In certain embodiments a1 and a2 of formula (B) are the same.

In certain embodiments a1 of formula (B) is 1. In certain embodiments a1 of formula (B) is 2. In certain embodiments a1 of formula (B) is 3. In certain embodiments a1 of formula (B) is 4. In certain embodiments a1 of formula (B) is 5. In certain embodiments a1 of formula (B) is 6. In certain embodiments a1 of formula (B) is 7. In certain embodiments a1 of formula (B) is 8. In certain embodiments a1 of formula (B) is 9. In certain embodiments a1 of formula (B) is 10.

In certain embodiments a2 of formula (B) is 1. In certain embodiments a2 of formula (B) is 2. In certain embodiments a2 of formula (B) is 3. In certain embodiments a2 of formula (B) is 4. In certain embodiments a2 of formula (B) is 5. In certain embodiments a2 of formula (B) is 6. In certain embodiments a2 of formula (B) is 7. In certain embodiments a2 of formula (B) is 8.

In certain embodiments a2 of formula (B) is 9. In certain embodiments a2 of formula (B) is 10.

In certain embodiments a1 and a2 of formula (B) are both 1. In certain embodiments a1 and a2 of formula (B) are both 2. In certain embodiments a1 and a2 of formula (B) are both 3. In certain embodiments a1 and a2 of formula (B) are both 4. In certain embodiments a1 and a2 of formula (B) are both 5. In certain embodiments a1 and a2 of formula (B) are both 6. In certain embodiments a1 and a2 of formula (B) are both 7. In certain embodiments a1 and a2 of formula (B) are both 8. In certain embodiments a1 and a2 of formula (B) are both 9. In certain embodiments a1 and a2 of formula (B) are both 10.

In certain embodiments a1 and a2 of formula (B) are both 1 and b of formula (B) is 3. In certain embodiments a1 and a2 of formula (B) are both 1 and b of formula (B) is 4. In certain embodiments a1 and a2 of formula (B) are both 1 and b of formula (B) is 5. In certain embodiments a1 and a2 of formula (B) are both 1 and b of formula (B) is 6. In certain embodiments a1 and a2 of formula (B) are both 1 and b of formula (B) is 7. In certain embodiments a1 and a2 of formula (B) are both 1 and b of formula (B) is 8. In certain embodiments a1 and a2 of formula (B) are both 1 and b of formula (B) is 9. In certain embodiments a1 and a2 of formula (B) are both 1 and b of formula (B) is 10. In certain embodiments a1 and a2 of formula (B) are both 1 and b of formula (B) is 20. In certain embodiments a1 and a2 of formula (B) are both 1 and b of formula (B) is 25.

In certain embodiments a1 and a2 of formula (B) are both 2 and b of formula (B) is 3. In certain embodiments a1 and a2 of formula (B) are both 2 and b of formula (B) is 4. In certain embodiments a1 and a2 of formula (B) are both 2 and b of formula (B) is 5. In certain embodiments a1 and a2 of formula (B) are both 2 and b of formula (B) is 6. In certain embodiments a1 and a2 of formula (B) are both 2 and b of formula (B) is 7. In certain embodiments a1 and a2 of formula (B) are both 2 and b of formula (B) is 8. In certain embodiments a1 and a2 of formula (B) are both 2 and b of formula (B) is 9. In certain embodiments a1 and a2 of formula (B) are both 2 and b of formula (B) is 10. In certain embodiments a1 and a2 of formula (B) are both 2 and b of formula (B) is 20. In certain embodiments a1 and a2 of formula (B) are both 2 and b of formula (B) is 25.

In certain embodiments a1 and a2 of formula (B) are both 3 and b of formula (B) is 3. In certain embodiments a1 and a2 of formula (B) are both 3 and b of formula (B) is 4. In certain embodiments a1 and a2 of formula (B) are both 3 and b of formula (B) is 5. In certain embodiments a1 and a2 of formula (B) are both 3 and b of formula (B) is 6. In certain embodiments a1 and a2 of formula (B) are both 3 and b of formula (B) is 7. In certain embodiments a1 and a2 of formula (B) are both 3 and b of formula (B) is 8. In certain embodiments a1 and a2 of formula (B) are both 3 and b of formula (B) is 9. In certain embodiments a1 and a2 of formula (B) are both 3 and b of formula (B) is 10. In certain embodiments a1 and a2 of formula (B) are both 3 and b of formula (B) is 20. In certain embodiments a1 and a2 of formula (B) are both 3 and b of formula (B) is 25.

In certain embodiments a1 and a2 of formula (B) are both 4 and b of formula (B) is 3. In certain embodiments a1 and a2 of formula (B) are both 4 and b of formula (B) is 4. In certain embodiments a1 and a2 of formula (B) are both 4 and b of formula (B) is 5. In certain embodiments a1 and a2 of formula (B) are both 4 and b of formula (B) is 6. In certain embodiments a1 and a2 of formula (B) are both 4 and b of formula (B) is 7. In certain embodiments a1 and a2 of formula (B) are both 4 and b of formula (B) is 8. In certain embodiments a1 and a2 of formula (B) are both 4 and b of formula (B) is 9. In certain embodiments a1 and a2 of formula (B) are both 4 and b of formula (B) is 10. In certain embodiments a1 and a2 of formula (B) are both 4 and b of formula (B) is 20. In certain embodiments a1 and a2 of formula (B) are both 4 and b of formula (B) is 25.

In certain embodiments a1 and a2 of formula (B) are both 5 and b of formula (B) is 3. In certain embodiments a1 and a2 of formula (B) are both 5 and b of formula (B) is 4. In certain embodiments a1 and a2 of formula (B) are both 5 and b of formula (B) is 5. In certain embodiments a1 and a2 of formula (B) are both 5 and b of formula (B) is 6. In certain embodiments a1 and a2 of formula (B) are both 5 and b of formula (B) is 7. In certain embodiments a1 and a2 of formula (B) are both 5 and b of formula (B) is 8. In certain embodiments a1 and a2 of formula (B) are both 5 and b of formula (B) is 9. In certain embodiments a1 and a2 of formula (B) are both 5 and b of formula (B) is 10. In certain embodiments a1 and a2 of formula (B) are both 5 and b of formula (B) is 20. In certain embodiments a1 and a2 of formula (B) are both 5 and b of formula (B) is 25.

In certain embodiments a1 and a2 of formula (B) are both 6 and b of formula (B) is 3. In certain embodiments a1 and a2 of formula (B) are both 6 and b of formula (B) is 4. In certain embodiments a1 and a2 of formula (B) are both 6 and b of formula (B) is 5. In certain embodiments a1 and a2 of formula (B) are both 6 and b of formula (B) is 6. In certain embodiments a1 and a2 of formula (B) are both 6 and b of formula (B) is 7. In certain embodiments a1 and a2 of formula (B) are both 6 and b of formula (B) is 8. In certain embodiments a1 and a2 of formula (B) are both 6 and b of formula (B) is 9. In certain embodiments a1 and a2 of formula (B) are both 6 and b of formula (B) is 10. In certain embodiments a1 and a2 of formula (B) are both 6 and b of formula (B) is 20. In certain embodiments a1 and a2 of formula (B) are both 6 and b of formula (B) is 25.

In certain embodiments a1 and a2 of formula (B) are both 7 and b of formula (B) is 3. In certain embodiments a1 and a2 of formula (B) are both 7 and b of formula (B) is 4. In certain embodiments a1 and a2 of formula (B) are both 7 and b of formula (B) is 5. In certain embodiments a1 and a2 of formula (B) are both 7 and b of formula (B) is 6. In certain embodiments a1 and a2 of formula (B) are both 7 and b of formula (B) is 7. In certain embodiments a1 and a2 of formula (B) are both 7 and b of formula (B) is 8. In certain embodiments a1 and a2 of formula (B) are both 7 and b of formula (B) is 9. In certain embodiments a1 and a2 of formula (B) are both 7 and b of formula (B) is 10. In certain embodiments a1 and a2 of formula (B) are both 7 and b of formula (B) is 20. In certain embodiments a1 and a2 of formula (B) are both 7 and b of formula (B) is 25.

In certain embodiments a1 and a2 of formula (B) are both 8 and b of formula (B) is 3. In certain embodiments a1 and a2 of formula (B) are both 8 and b of formula (B) is 4. In certain embodiments a1 and a2 of formula (B) are both 8 and b of formula (B) is 5. In certain embodiments a1 and a2 of formula (B) are both 8 and b of formula (B) is 6. In certain embodiments a1 and a2 of formula (B) are both 8 and b of formula (B) is 7. In certain embodiments a1 and a2 of formula (B) are both 8 and b of formula (B) is 8. In certain embodiments a1 and a2 of formula (B) are both 8 and b of formula (B) is 9. In certain embodiments a1 and a2 of formula (B) are both 8 and b of formula (B) is 10. In certain embodiments a1 and a2 of formula (B) are both 8 and b of formula (B) is 20. In certain embodiments a1 and a2 of formula (B) are both 8 and b of formula (B) is 25.

In certain embodiments a1 and a2 of formula (B) are both 9 and b of formula (B) is 3. In certain embodiments a1 and a2 of formula (B) are both 9 and b of formula (B) is 4. In certain embodiments a1 and a2 of formula (B) are both 9 and b of formula (B) is 5. In certain embodiments a1 and a2 of formula (B) are both 9 and b of formula (B) is 6. In certain embodiments a1 and a2 of formula (B) are both 9 and b of formula (B) is 7. In certain embodiments a1 and a2 of formula (B) are both 9 and b of formula (B) is 8. In certain embodiments a1 and a2 of formula (B) are both 9 and b of formula (B) is 9. In certain embodiments a1 and a2 of formula (B) are both 9 and b of formula (B) is 10. In certain embodiments a1 and a2 of formula (B) are both 9 and b of formula (B) is 20. In certain embodiments a1 and a2 of formula (B) are both 9 and b of formula (B) is 25.

In certain embodiments a1 and a2 of formula (B) are both 10 and b of formula (B) is 3. In certain embodiments a1 and a2 of formula (B) are both 10 and b of formula (B) is 4. In certain embodiments a1 and a2 of formula (B) are both 10 and b of formula (B) is 5. In certain embodiments a1 and a2 of formula (B) are both 10 and b of formula (B) is 6. In certain embodiments a1 and a2 of formula (B) are both 10 and b of formula (B) is 7. In certain embodiments a1 and a2 of formula (B) are both 10 and b of formula (B) is 8. In certain embodiments a1 and a2 of formula (B) are both 10 and b of formula (B) is 9. In certain embodiments a1 and a2 of formula (B) are both 10 and b of formula (B) is 10. In certain embodiments a1 and a2 of formula (B) are both 10 and b of formula (B) is 20. In certain embodiments a1 and a2 of formula (B) are both 10 and b of formula (B) is 25.

In certain embodiments b of formula (B) ranges from 1 to 500. In certain embodiments b of formula (B) ranges from 2 to 250. In certain embodiments b of formula (B) ranges from 3 to 100. In certain embodiments b of formula (B) ranges from 3 to 50. In certain embodiments b of formula (B) ranges from 3 to 25. In certain embodiments b of formula (B) is 2. In certain embodiments b of formula (B) is 3. In certain embodiments b of formula (B) is 4. In certain embodiments b of formula (B) is 5. In certain embodiments b of formula (B) is 6. In certain embodiments b of formula (B) is 7. In certain embodiments b of formula (B) is 8. In certain embodiments b of formula (B) is 9. In certain embodiments b of formula (B) is 10. In certain embodiments b of formula (B) is 20. In certain embodiments b of formula (B) is 25.

In certain embodiments —CL- is of formula (B-i)

(B-i)

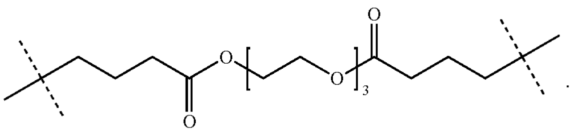

In certain embodiments —$CL^P$- is of formula (C)

(C)

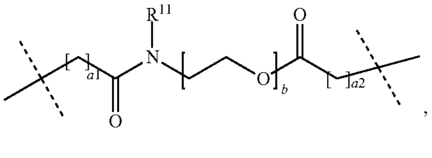

wherein a1 and a2 are independently selected from the group consisting of 1, 2, 3, 4, 5, 6, 7, 8, 9, 10, 11, 12, 13 and 14;

b is an integer ranging from 1 to 50; and

—$R^{11}$ is selected from the group comprising —H and $C_{1-6}$ alkyl.

In certain embodiments a1 and a2 of formula (C) are different. In certain embodiments a1 and a2 of formula (B) are the same.

In certain embodiments a1 of formula (C) is 1. In certain embodiments a1 of formula (C) is 2. In certain embodiments a1 of formula (C) is 3. In certain embodiments a1 of formula (C) is 4. In certain embodiments a1 of formula (C) is 5. In certain embodiments a1 of formula (C) is 6. In certain embodiments a1 of formula (C) is 7. In certain embodiments a1 of formula (C) is 8. In certain embodiments a1 of formula (C) is 9. In certain embodiments a1 of formula (C) is 10.

In certain embodiments a2 of formula (C) is 1. In certain embodiments a2 of formula (C) is 2. In certain embodiments a2 of formula (C) is 3. In certain embodiments a2 of formula (C) is 4. In certain embodiments a2 of formula (C) is 5. In certain embodiments a2 of formula (C) is 6. In certain embodiments a2 of formula (C) is 7. In certain embodiments a2 of formula (C) is 8. In certain embodiments a2 of formula (C) is 9. In certain embodiments a2 of formula (C) is 10.

In certain embodiments a1 and a2 of formula (C) are both 1. In certain embodiments a1 and a2 of formula (C) are both 2. In certain embodiments a1 and a2 of formula (C) are both 3. In certain embodiments a1 and a2 of formula (C) are both 4. In certain embodiments a1 and a2 of formula (C) are both 5. In certain embodiments a1 and a2 of formula (C) are both 6. In certain embodiments a1 and a2 of formula (C) are both 7. In certain embodiments a1 and a2 of formula (C) are both 8. In certain embodiments a1 and a2 of formula (C) are both 9. In certain embodiments a1 and a2 of formula (C) are both 10.

In certain embodiments a1 and a2 of formula (C) are both 1 and b of formula (C) is 3. In certain embodiments a1 and a2 of formula (C) are both 1 and b of formula (C) is 4. In certain embodiments a1 and a2 of formula (C) are both 1 and b of formula (C) is 5. In certain embodiments a1 and a2 of formula (C) are both 1 and b of formula (C) is 6. In certain embodiments a1 and a2 of formula (C) are both 1 and b of formula (C) is 7. In certain embodiments a1 and a2 of formula (C) are both 1 and b of formula (C) is 8. In certain embodiments a1 and a2 of formula (C) are both 1 and b of formula (C) is 9. In certain embodiments a1 and a2 of formula (C) are both 1 and b of formula (C) is 10. In certain embodiments a1 and a2 of formula (C) are both 1 and b of formula (C) is 20. In certain embodiments a1 and a2 of formula (C) are both 1 and b of formula (C) is 25.

In certain embodiments a1 and a2 of formula (C) are both 2 and b of formula (C) is 3. In certain embodiments a1 and a2 of formula (C) are both 2 and b of formula (C) is 4. In certain embodiments a1 and a2 of formula (C) are both 2 and b of formula (C) is 5. In certain embodiments a1 and a2 of formula (C) are both 2 and b of formula (C) is 6. In certain embodiments a1 and a2 of formula (C) are both 2 and b of formula (C) is 7. In certain embodiments a1 and a2 of formula (C) are both 2 and b of formula (C) is 8. In certain embodiments a1 and a2 of formula (C) are both 2 and b of formula (C) is 9. In certain embodiments a1 and a2 of formula (C) are both 2 and b of formula (C) is 10. In certain embodiments a1 and a2 of formula (C) are both 2 and b of formula (C) is 20. In certain embodiments a1 and a2 of formula (C) are both 2 and b of formula (C) is 25.

In certain embodiments a1 and a2 of formula (C) are both 3 and b of formula (C) is 3. In certain embodiments a1 and a2 of formula (C) are both 3 and b of formula (C) is 4. In certain embodiments a1 and a2 of formula (C) are both 3 and b of formula (C) is 5. In certain embodiments a1 and a2 of formula (C) are both 3 and b of formula (C) is 6. In certain embodiments a1 and a2 of formula (C) are both 3 and b of formula (C) is 7. In certain embodiments a1 and a2 of formula (C) are both 3 and b of formula (C) is 8. In certain embodiments a1 and a2 of formula (C) are both 3 and b of formula (C) is 9. In certain embodiments a1 and a2 of formula (C) are both 3 and b of formula (C) is 10. In certain embodiments a1 and a2 of formula (C) are both 3 and b of formula (C) is 20. In certain embodiments a1 and a2 of formula (C) are both 3 and b of formula (C) is 25.

In certain embodiments a1 and a2 of formula (C) are both 4 and b of formula (C) is 3. In certain embodiments a1 and a2 of formula (C) are both 4 and b of formula (C) is 4. In certain embodiments a1 and a2 of formula (C) are both 4 and b of formula (C) is 5. In certain embodiments a1 and a2 of formula (C) are both 4 and b of formula (C) is 6. In certain embodiments a1 and a2 of formula (C) are both 4 and b of formula (C) is 7. In certain embodiments a1 and a2 of formula (C) are both 4 and b of formula (C) is 8. In certain embodiments a1 and a2 of formula (C) are both 4 and b of formula (C) is 9. In certain embodiments a1 and a2 of formula (C) are both 4 and b of formula (C) is 10. In certain embodiments a1 and a2 of formula (C) are both 4 and b of formula (C) is 20. In certain embodiments a1 and a2 of formula (C) are both 4 and b of formula (C) is 25.

In certain embodiments a1 and a2 of formula (C) are both 5 and b of formula (C) is 3. In certain embodiments a1 and a2 of formula (C) are both 5 and b of formula (C) is 4. In certain embodiments a1 and a2 of formula (C) are both 5 and b of formula (C) is 5. In certain embodiments a1 and a2 of formula (C) are both 5 and b of formula (C) is 6. In certain embodiments a1 and a2 of formula (C) are both 5 and b of formula (C) is 7. In certain embodiments a1 and a2 of formula (C) are both 5 and b of formula (C) is 8. In certain embodiments a1 and a2 of formula (C) are both 5 and b of formula (C) is 9. In certain embodiments a1 and a2 of formula (C) are both 5 and b of formula (C) is 10. In certain embodiments a1 and a2 of formula (C) are both 5 and b of formula (C) is 20. In certain embodiments a1 and a2 of formula (C) are both 5 and b of formula (C) is 25.

In certain embodiments a1 and a2 of formula (C) are both 6 and b of formula (C) is 3. In certain embodiments a1 and a2 of formula (C) are both 6 and b of formula (C) is 4. In certain embodiments a1 and a2 of formula (C) are both 6 and b of formula (C) is 5. In certain embodiments a1 and a2 of formula (C) are both 6 and b of formula (C) is 6. In certain embodiments a1 and a2 of formula (C) are both 6 and b of formula (C) is 7. In certain embodiments a1 and a2 of formula (C) are both 6 and b of formula (C) is 8. In certain embodiments a1 and a2 of formula (C) are both 6 and b of formula (C) is 9. In certain embodiments a1 and a2 of formula (C) are both 6 and b of formula (C) is 10. In certain embodiments a1 and a2 of formula (C) are both 6 and b of formula (C) is 20. In certain embodiments a1 and a2 of formula (C) are both 6 and b of formula (C) is 25.

In certain embodiments a1 and a2 of formula (C) are both 7 and b of formula (C) is 3. In certain embodiments a1 and a2 of formula (C) are both 7 and b of formula (C) is 4. In certain embodiments a1 and a2 of formula (C) are both 7 and b of formula (C) is 5. In certain embodiments a1 and a2 of formula (C) are both 7 and b of formula (C) is 6. In certain embodiments a1 and a2 of formula (C) are both 7 and b of formula (C) is 7. In certain embodiments a1 and a2 of formula (C) are both 7 and b of formula (C) is 8. In certain embodiments a1 and a2 of formula (C) are both 7 and b of formula (C) is 9. In certain embodiments a1 and a2 of formula (C) are both 7 and b of formula (C) is 10. In certain embodiments a1 and a2 of formula (C) are both 7 and b of formula (C) is 20. In certain embodiments a1 and a2 of formula (C) are both 7 and b of formula (C) is 25.

In certain embodiments a1 and a2 of formula (C) are both 8 and b of formula (C) is 3. In certain embodiments a1 and a2 of formula (C) are both 8 and b of formula (C) is 4. In certain embodiments a1 and a2 of formula (C) are both 8 and b of formula (C) is 5. In certain embodiments a1 and a2 of formula (C) are both 8 and b of formula (C) is 6. In certain embodiments a1 and a2 of formula (C) are both 8 and b of formula (C) is 7. In certain embodiments a1 and a2 of formula (C) are both 8 and b of formula (C) is 8. In certain embodiments a1 and a2 of formula (C) are both 8 and b of formula (C) is 9. In certain embodiments a1 and a2 of formula (C) are both 8 and b of formula (C) is 10. In certain embodiments a1 and a2 of formula (C) are both 8 and b of formula (C) is 20. In certain embodiments a1 and a2 of formula (C) are both 8 and b of formula (C) is 25.

In certain embodiments a1 and a2 of formula (C) are both 9 and b of formula (C) is 3. In certain embodiments a1 and a2 of formula (C) are both 9 and b of formula (C) is 4. In certain embodiments a1 and a2 of formula (C) are both 9 and b of formula (C) is 5. In certain embodiments a1 and a2 of formula (C) are both 9 and b of formula (C) is 6. In certain embodiments a1 and a2 of formula (C) are both 9 and b of formula (C) is 7. In certain embodiments a1 and a2 of formula (C) are both 9 and b of formula (C) is 8. In certain embodiments a1 and a2 of formula (C) are both 9 and b of formula (C) is 9. In certain embodiments a1 and a2 of formula (C) are both 9 and b of formula (C) is 10. In certain embodiments a1 and a2 of formula (C) are both 9 and b of formula (C) is 20. In certain embodiments a1 and a2 of formula (C) are both 9 and b of formula (C) is 25.

In certain embodiments a1 and a2 of formula (C) are both 10 and b of formula (C) is 3. In certain embodiments a1 and a2 of formula (C) are both 10 and b of formula (C) is 4. In certain embodiments a1 and a2 of formula (C) are both 10 and b of formula (C) is 5. In certain embodiments a1 and a2 of formula (C) are both 10 and b of formula (C) is 6. In certain embodiments a1 and a2 of formula (C) are both 10 and b of formula (C) is 7. In certain embodiments a1 and a2 of formula (C) are both 10 and b of formula (C) is 8. In certain embodiments a1 and a2 of formula (C) are both 10 and b of formula (C) is 9. In certain embodiments a1 and a2 of formula (C) are both 10 and b of formula (C) is 10. In certain embodiments a1 and a2 of formula (C) are both 10 and b of formula (C) is 20. In certain embodiments a1 and a2 of formula (C) are both 10 and b of formula (C) is 25.

In certain embodiments b of formula (C) ranges from 1 to 500. In certain embodiments b of formula (C) ranges from 2 to 250. In certain embodiments b of formula (C) ranges from 3 to 100. In certain embodiments b of formula (C) ranges from 3 to 50. In certain embodiments b of formula (C) ranges from 3 to 25. In certain embodiments b of formula (C) is 2. In certain embodiments b of formula (C) is 3. In certain embodiments b of formula (C) is 4. In certain embodiments b of formula (C) is 5. In certain embodiments b of formula (C) is 6. In certain embodiments b of formula (C) is 7. In certain embodiments b of formula (C) is 8. In certain embodiments b of formula (C) is 9. In certain embodiments b of formula (C) is 10. In certain embodiments b of formula (C) is 20. In certain embodiments b of formula (C) is 25.

In certain embodiments —$R^{11}$ of formula (C) is —H. In certain embodiments —$R^{11}$ of formula (C) is methyl. In certain embodiments —$R^{11}$ of formula (C) is ethyl. In certain embodiments —$R^{11}$ of formula (C) is n-propyl. In certain embodiments —$R^{11}$ of formula (C) is isopropyl. In certain embodiments —$R^{11}$ of formula (C) is n-butyl. In certain embodiments —$R^{11}$ of formula (C) is isobutyl. In certain embodiments —$R^{11}$ of formula (C) is sec-butyl. In certain embodiments —$R^{11}$ of formula (C) is tert-butyl. In certain embodiments —$R^{11}$ of formula (C) is n-pentyl. In certain embodiments —$R^{11}$ of formula (C) is 2-methylbutyl. In certain embodiments —$R^{11}$ of formula (C) is 2,2-dimethylpropyl. In certain embodiments —$R^{11}$ of formula (C) is n-hexyl. In certain embodiments —$R^{11}$ of formula (C) is 2-methylpentyl. In certain embodiments —$R^{11}$ of formula (C) is 3-methylpentyl. In certain embodiments —$R^{11}$ of formula (C) is 2,2-dimethylbutyl. In certain embodiments —$R^{11}$ of formula (C) is 2,3-dimethylbutyl. In certain embodiments —$R^{11}$ of formula (C) is 3,3-dimethylpropyl.

In certain embodiments —CL- is of formula (C-i)

(C-i)

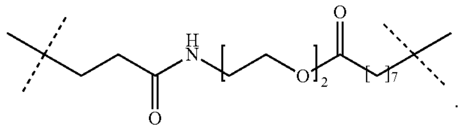

Specific embodiments for —$R^{a1}$, —$R^{a2}$, -$L^1$-, -$L^2$-, -$L^3$-, -$L^4$-, —SP—, —$X^{0A}$—, —$X^{0B}$—, —$X^{0C}$—, —$X^{0D}$—, —$X^{0E}$—, —$X^{0F}$— and -D of the first embodiment are as described elsewhere herein.

In certain embodiments —CL- is of formula (D)

(D)

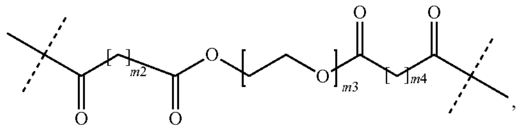

wherein the dashed lines indicate attachment to a moiety —$X^{0F}$—; and m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D) is an integer selected from the group consisting of 2, 3, 4, 5, 6, 7, 8, 9 and 10. In certain embodiments m2 of formula (D) is an integer selected from the group consisting of 3, 4, 5, 6 and 7. In certain embodiments m2 of formula (D) is 3. In certain embodiments m2 of formula (D) is 4. In certain embodiments m2 of formula (D) is 5. In certain embodiments m2 of formula (D) is 6. In certain embodiments m2 of formula (D) is 7. In certain embodiments m3 of formula (D) is an integer selected from the group consisting of 1, 2, 3, 4, 5, 6, 7, 8, 9 and 10. In certain embodiments m3 of formula (D) is an integer selected from the group consisting of 1, 2, 3, 4, and 5. In certain embodiments m3 of formula (D) is 1. In certain embodiments m3 of formula (D) is 2. In certain embodiments m3 of formula (D) is 3. In certain embodiments m3 of formula (D) is 4. In certain embodiments m4 of formula (D) is an integer selected from the group consisting of 2, 3, 4, 5, 6, 7, 8, 9 and 10. In certain embodiments m4 of formula (D) is an integer selected from the group consisting of 3, 4, 5, 6 and 7. In certain embodiments m4 of formula (D) is 3. In certain embodiments m4 of formula (D) is 4. In certain embodiments m4 of formula (D) is 5. In certain embodiments m4 of formula (D) is 6. In certain embodiments m4 of formula (D) is 7.

In certain embodiments a moiety —$X^{0E}$—SP—$X^{0F}$—$CL^{P}$-$X^{0F}$—SP—$X^{0E}$— has the structure of formula (D-i)

(D-i)

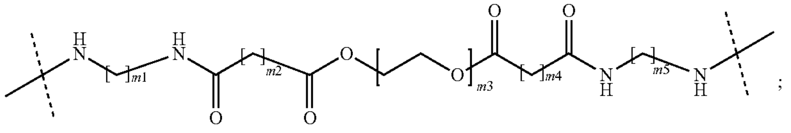

wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-i) is an integer selected from the group consisting of 2, 3, 4, 5, and 6. In certain embodiments m1 of formula (D-i) is 3. In certain embodiments m2 of formula (D-i) is an integer selected from the group consisting of 2, 3, 4, 5, 6, 7, 8, 9 and 10. In certain embodiments m2 of formula (D-i) is an integer selected from the group consisting of 3, 4, 5, 6 and 7. In certain embodiments m2 of formula (D-i) is 3. In certain embodiments m2 of formula (D-i) is 4. In certain embodiments m2 of formula (D-i) is 5. In certain embodiments m2 of formula (D-i) is 6. In certain embodiments m2 of formula (D-i) is 7. In certain embodiments m3 of formula (D-i) is an integer selected from the group consisting of 1, 2, 3, 4, 5, 6, 7, 8, 9 and 10. In certain embodiments m3 of formula (D-i) is an integer selected from the group consisting of 1, 2, 3, 4, and 5. In certain embodiments m3 of formula (D-i) is 1. In certain embodiments m3 of formula (D-i) is 2. In certain embodiments m3 of formula (D-i) is 3. In certain embodiments m3 of formula (D-i) is 4. In certain embodiments m4 of formula (D-i) is an integer selected from the group consisting of 2, 3, 4, 5, 6, 7, 8, 9 and 10. In certain embodiments m4 of formula (D-i) is an integer selected from the group consisting of 3, 4, 5, 6 and 7. In certain embodiments m4 of formula (D-i) is 3. In certain embodiments m4 of formula (D-i) is 4. In certain embodiments m4 of formula (D-i) is 5. In certain embodiments m4 of formula (D-i) is 6. In certain embodiments m4 of formula (D-i) is 7. In certain embodiments m5 of formula (D-i) is an integer selected from the group consisting of 2, 3, 4, 5 and 6. In certain embodiments m5 of formula (D-1) is 3.

In certain embodiments —CL- is of formula (D-ii)

(D-ii)

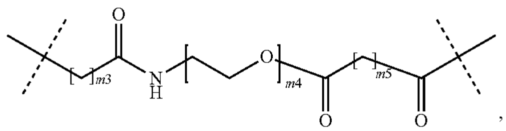

wherein dashed lines indicate attachment to a moiety —$X^{0F}$—;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-ii) is an integer selected from the group consisting of 1, 2, 3, 4 and 5. In certain embodiments m3 of formula (D-ii) is 2. In certain embodiments m4 of formula (D-ii) is an integer selected from the group consisting of 1, 2, 3, 4, 5, 6, 7, 8, 9 and 10. In certain embodiments m4 of formula (D-ii) is 1. In certain embodiments m4 of formula (D-ii) is 2. In certain embodiments m4 of formula (D-ii) is 3. In certain embodiments m4 of formula (D-ii) is 4. In certain embodiments m5 of formula (D-ii) is an integer selected from 2, 3, 4, 5, 6, 7, 8, 9 and 10. In certain embodiments m5 of formula (D-ii) is 3. In certain embodiments m5 of formula (D-ii) is 4. In certain embodiments m5 of formula (D-ii) is 5. In certain embodiments m5 of formula (D-ii) is 6. In certain embodiments m5 of formula (D-ii) is 7.

In certain embodiments a moiety —$X^{0E}$—SP—$X^{0F}$—CL-$X^{0F}$—SP—$X^{0E}$— has the structure of formula (D-iii)

(D-iii)

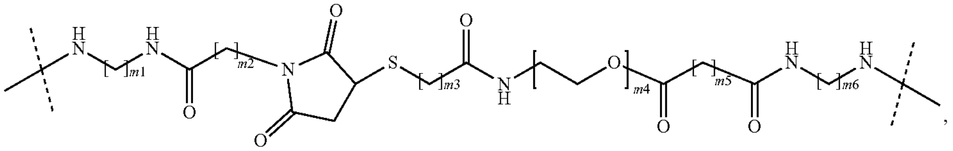

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-iii) is an integer selected from the group consisting of 2, 3, 4, 5 and 6. In certain embodiments m1 of formula (D-iii) is 3. In certain embodiments m2 is an integer selected from the group consisting of 1, 2, 3, 4 and 5. In certain embodiments m2 of formula (D-iii) is 2. In certain embodiments m3 of formula (D-iii) is an integer selected from the group consisting of 1, 2, 3, 4 and 5. In certain embodiments m3 of formula (D-iii) is 2. In certain embodiments m4 of formula (D-iii) is an integer selected from the group consisting of 1, 2, 3, 4, 5, 6, 7, 8, 9 and 10. In certain embodiments m4 of formula (D-iii) is 1. In certain embodiments m4 of formula (D-iii) is 2. In certain embodiments m4 of formula (D-iii) is 3. In certain embodiments m4 of formula (D-iii) is 4. In certain embodiments m5 of formula (D-iii) is an integer selected from 2, 3, 4, 5, 6, 7, 8, 9 and 10. In certain embodiments m5 of formula (D-iii) is 3. In certain embodiments m5 of formula (D-iii) is 4. In certain embodiments m5 of formula (D-iii) is 5. In certain embodiments m5 of formula (D-iii) is 6. In certain embodiments m5 of formula (D-iii) is 7. In certain embodiments m6 of formula (D-iii) is an integer selected from the group consisting of 2, 3, 4, 5 and 6. In certain embodiments m6 of formula (D-iiii) is 3.

In certain embodiments —$CL^P$- is of formula (D-iv):

(D-iv)

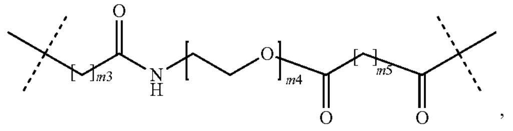

wherein dashed lines indicate attachment to a moiety —$X^{0F}$—;

dashed lines indicate attachment to the carbonyl of the hyaluronic acid; and m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-iv) is an integer selected from the group consisting of 1, 2, 3, 4 and 5. In certain embodiments m3 of formula (D-iv) is 2. In certain embodiments m4 of formula (D-iv) is an integer selected from the group consisting of 1, 2, 3, 4, 5, 6, 7, 8, 9 and 10. In certain embodiments m4 of formula (D-iv) is 1. In certain embodiments m4 of formula (D-iv) is 2. In certain embodiments m4 of formula (D-iv) is 3. In certain embodiments m4 of formula (D-iv) is 4. In certain embodiments m5 of formula (D-iv) is an integer selected from 2, 3, 4, 5, 6, 7, 8, 9 and 10. In certain embodiments m5 of formula (D-iv) is 3. In certain embodiments m5 of formula (D-iv) is 4. In certain embodiments m5 of formula (D-iv) is 5. In certain embodiments m5 of formula (D-iv) is 6. In certain embodiments m5 of formula (D-iv) is 7.

In certain embodiments a moiety —$X^{0E}$—SP—$X^{0F}$—CL-$X^{0F}$—SP—$X^{0E}$— has the structure of formula (D-v)

(D-v)

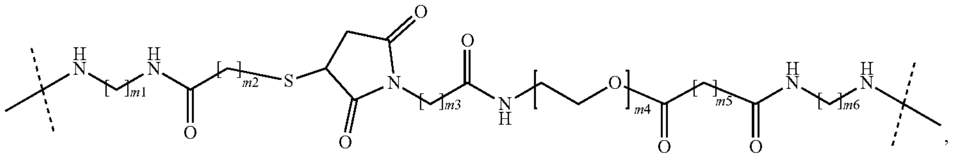

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-v) is an integer selected from the group consisting of 2, 3, 4, 5 and 6. In certain embodiments m1 of formula (D-v) is 3. In certain embodiments m2 is an integer selected from the group consisting of 1, 2, 3, 4 and 5. In certain embodiments m2 of formula (D-v) is 2. In certain embodiments m3 of formula (D-v) is an integer selected from the group consisting of 1, 2, 3, 4 and 5. In certain embodiments m3 of formula (D-v) is 2. In certain embodiments m4 of formula (D-v) is an integer selected from the group consisting of 1, 2, 3, 4, 5, 6, 7, 8, 9 and 10. In certain embodiments m4 of formula (D-v) is 1. In certain embodiments m4 of formula (D-v) is 2. In certain embodiments m4 of formula (D-v) is 3. In certain embodiments m4 of formula (D-v) is 4. In certain embodiments m5 of formula (D-v) is an integer selected from 2, 3, 4, 5, 6, 7, 8, 9 and 10. In certain embodiments m5 of formula (D-v) is 3. In certain embodiments m5 of formula (D-v) is 4. In certain embodiments m5 of formula (D-v) is 5. In certain embodiments m5 of formula (D-v) is 6. In certain embodiments m5 of formula (D-v) is 7. In certain embodiments m6 of formula (D-v) is an integer selected from the group consisting of 2, 3, 4, 5 and 6. In certain embodiments m6 of formula (D-v) is 3.

In certain embodiments —$CL^P$- is of formula (D-vi)

(D-vi)

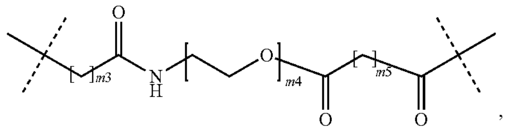

wherein dashed lines indicate attachment to a moiety —$X^{0F}$—;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-vi) is an integer selected from the group consisting of 1, 2, 3, 4 and 5. In certain embodiments m3 of formula (D-vi) is 1. In certain embodiments m3 of formula (D-vi) is 2. In certain embodiments m4 of formula (D-vi) is an integer selected from the group consisting of 1, 2, 3, 4, 5, 6, 7, 8, 9 and 10. In certain embodiments m4 of formula (D-vi) is 1. In certain embodiments m4 of formula (D-vi) is 2. In certain embodiments m4 of formula (D-vi) is 3. In certain embodiments m4 of formula (D-vi) is 4. In certain embodiments m5 of formula (D-vi) is an integer selected from 2, 3, 4, 5, 6, 7, 8, 9 and 10. In certain embodiments m5 of formula (D-vi) is 3. In certain embodiments m5 of formula (D-vi) is 4. In certain embodiments m5 of formula (D-vi) is 5. In certain embodiments m5 of formula (D-vi) is 6. In certain embodiments m5 of formula (D-vi) is 7.

In certain embodiments a moiety $—X^{0E}—SP—X^{0F}—CL-X^{0F}—SP—X^{0E}—$ has the structure of formula (D-vii)

(D-vii)

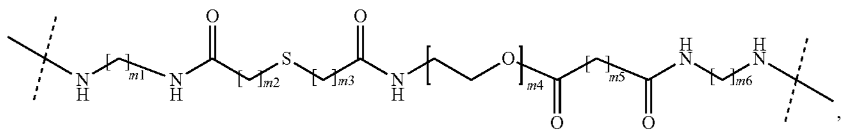

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-vii) is an integer selected from the group consisting of 2, 3, 4, 5 and 6. In certain embodiments m1 of formula (D-vii) is 3. In certain embodiments m2 of formula (D-vii) is an integer selected from the group consisting of 1, 2, 3, 4 and 5. In certain embodiments m2 of formula (D-vii) is 1. In certain embodiments m2 of formula (D-vii) is 2. In certain embodiments m3 of formula (D-vii) is an integer selected from the group consisting of 1, 2, 3, 4 and 5. In certain embodiments m3 of formula (D-vii) is 1. In certain embodiments m3 of formula (D-vii) is 2. In certain embodiments m4 of formula (D-vii) is an integer selected from the group consisting of 1, 2, 3, 4, 5, 6, 7, 8, 9 and 10. In certain embodiments m4 of formula (D-vii) is 1. In certain embodiments m4 of formula (D-vii) is 2. In certain embodiments m4 of formula (D-vii) is 3. In certain embodiments m4 of formula (D-vii) is 4. In certain embodiments m5 of formula (D-vii) is an integer selected from 2, 3, 4, 5, 6, 7, 8, 9 and 10. In certain embodiments m5 of formula (D-vii) is 3. In certain embodiments m5 of formula (D-vii) is 4. In certain embodiments m5 of formula (D-vii) is 5. In certain embodiments m5 of formula (D-vii) is 6. In certain embodiments m5 of formula (D-vii) is 7. In certain embodiments m6 of formula (D-vii) is an integer selected from the group consisting of 2, 3, 4, 5 and 6. In certain embodiments m6 of formula (D-vii) is 3.

In certain embodiments —CL- is of formula (D-viii)

(D-viii)

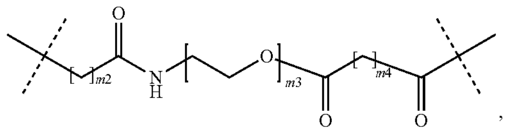

wherein dashed lines indicate attachment to a moiety $—X^{0F}—$;

m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-viii) is an integer selected from the group consisting of 2, 3, 4, 5 and 6. In certain embodiments m1 of formula (D-viii) is 3. In certain embodiments m2 is an integer selected from the group consisting of 1, 2, 3, 4 and 5. In certain embodiments m2 of formula (D-viii) is 2. In certain embodiments m2 of formula (D-viii) is 5. In certain embodiments m3 of formula (D-viii) is an integer selected from the group consisting of 1, 2, 3, 4, 5, 6, 7, 8, 9 and 10. In certain embodiments m3 of formula (D-viii) is an integer selected from the group consisting of 1, 2, 3 and 4. In certain embodiments m3 of formula (D-viii) is 1. In certain embodiments m3 of formula (D-viii) is 2. In certain embodiments m3 of formula (D-viii) is 3. In certain embodiments m3 of formula (D-viii) is 4. In certain embodiments m4 of formula (D-viii) is an integer selected from the group consisting of 2, 3, 4, 5, 6, 7, 8, 9 and 10. In certain embodiments m4 of formula (D-viii) is an integer selected from the group consisting of 3, 4, 5, 6 and 7. In certain embodiments m4 of formula (D-viii) is 3. In certain embodiments m4 of formula (D-viii) is 4. In certain embodiments m4 of formula (D-viii) is 5. In certain embodiments m4 of formula (D-viii) is 6. In certain embodiments m4 of formula (D-viii) is 7. In certain embodiments m5 of formula (D-viii) is an integer selected from 2, 3, 4, 5 and 6. In certain embodiments m5 of formula (D-viii) is 3.

In certain embodiments a moiety $—X^{0E}—SP—X^{0F}—CL-X^{0F}—SP—X^{0E}—$ has the structure of formula (D-ix)

(D-ix)

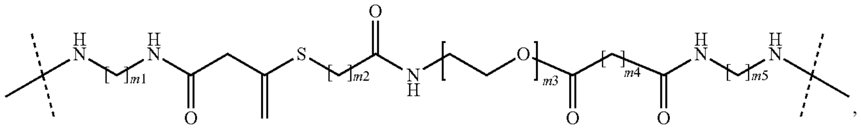

wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-ix) is an integer selected from the group consisting of 2, 3, 4, 5 and 6. In certain embodiments m1 of formula (D-ix) is 3. In certain embodiments m2 is an integer selected from the group consisting of 1, 2, 3, 4 and 5. In certain embodiments m2 of formula (D-ix) is 2. In certain embodiments m2 of formula (D-ix) is 5. In certain embodiments m3 of formula (D-ix) is an integer selected from the group consisting of 1, 2, 3, 4, 5, 6, 7, 8, 9 and 10. In certain embodiments m3 of formula (D-ix) is an integer selected from the group consisting of 1, 2, 3 and 4. In certain embodiments m3 of formula (D-ix) is 1. In certain embodiments m3 of formula (D-ix) is 2. In certain embodiments m3 of formula (D-ix) is 3. In certain embodiments m3 of formula (D-ix) is 4. In certain embodiments m4 of formula (D-ix) is an integer selected from the group consisting of 2, 3, 4, 5, 6, 7, 8, 9 and 10. In certain embodiments m4 of formula (D-ix) is an integer selected from the group consisting of 3, 4, 5, 6 and 7. In certain embodiments m4 of formula (D-ix) is 3. In certain embodiments m4 of formula (D-ix) is 4. In certain embodiments m4 of formula (D-ix) is 5. In certain embodiments m4 of formula (D-ix) is 6. In certain embodiments m4 of formula (D-ix) is 7. In certain embodiments m5 of formula (D-ix) is an integer selected from 2, 3, 4, 5 and 6. In certain embodiments m5 of formula (D-ix) is 3.

In certain embodiments —CL- is of formula (D-x)

(D-x)

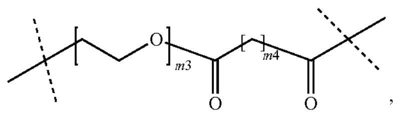

dashed lines indicate attachment to a moiety —$X^{0F}$—;

m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-x) is an integer selected from the group consisting of 1, 2, 3, 4, 5, 6, 7, 8, 9 and 10. In certain embodiments m3 of formula (D-x) is an integer selected from the group consisting of 1, 2, 3 and 4. In certain embodiments m3 of formula (D-x) is 1. In certain embodiments m3 of formula (D-x) is 2. In certain embodiments m3 of formula (D-x) is 3. In certain embodiments m3 of formula (D-x) is 4. In certain embodiments m4 of formula (D-x) is an integer selected from the group consisting of 2, 3, 4, 5, 6, 7, 8, 9 and 10. In certain embodiments m4 of formula (D-x) is an integer selected from the group consisting of 3, 4, 5, 6 and 7. In certain embodiments m4 of formula (D-x) is 3. In certain embodiments m4 of formula (D-x) is 4. In certain embodiments m4 of formula (D-x) is 5. In certain embodiments m4 of formula (D-x) is 6. In certain embodiments m4 of formula (D-x) is 7.

In certain embodiments a moiety —$X^{0E}$—SP—$X^{0F}$—$CL^{P}$-$X^{0F}$—SP—$X^{0E}$— has the structure of formula (D-xi)

(D-xi)

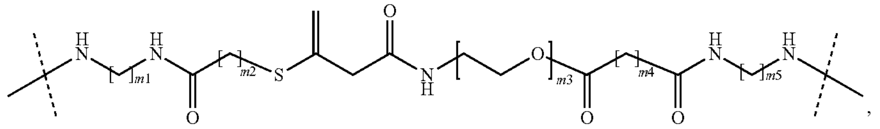

wherein dashed lines indicate attachment to the carbonyl of the hyaluronic acid; and each m1, m2, m3, m4 and m5 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xi) is an integer selected from the group consisting of 2, 3, 4, 5 and 6. In certain embodiments m1 of formula (D-xi) is 3. In certain embodiments m2 is an integer selected from the group consisting of 1, 2, 3, 4 and 5. In certain embodiments m2 of formula (D-xi) is 2. In certain embodiments m2 of formula (D-xi) is 5. In certain embodiments m3 of formula (D-xi) is an integer selected from the group consisting of 1, 2, 3, 4, 5, 6, 7, 8, 9 and 10. In certain embodiments m3 of formula (D-xi) is an integer selected from the group consisting of 1, 2, 3 and 4. In certain embodiments m3 of formula (D-xi) is 1. In certain embodiments m3 of formula (D-xi) is 2. In certain embodiments m3 of formula (D-xi) is 3. In certain embodiments m3 of formula (D-xi) is 4. In certain embodiments m4 of formula (D-xi) is an integer selected from the group consisting of 2, 3, 4, 5, 6, 7, 8, 9 and 10. In certain embodiments m4 of formula (D-xi) is an integer selected from the group consisting of 3, 4, 5, 6 and 7. In certain embodiments m4 of formula (D-xi) is 3. In certain embodiments m4 of formula (D-xi) is 4. In certain embodiments m4 of formula (D-xi) is 5. In certain embodiments m4 of formula (D-xi) is 6. In certain embodiments m4 of formula (D-xi) is 7. In certain embodiments m5 of formula (D-xi) is an integer selected from 2, 3, 4, 5 and 6. In certain embodiments m5 of formula (D-xi) is 3.

In certain embodiments —CL- is of formula (D-xii)

(D-xii)

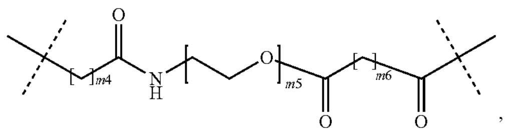

wherein dashed lines indicate attachment to a moiety —$X^{0F}$—;

m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m4 of formula (D-xii) is an integer selected from the group consisting of 1, 2, 3, 4 and 5. In certain embodiments m4 of formula (D-xii) is 1. In certain embodiments m4 of formula (D-xii) is 5. In certain embodiments m5 of formula (D-xii) is an integer selected from 1, 2, 3, 4, 5, 6, 7, 8, 9 and 10. In certain embodiments m5 of formula (D-xii) is an integer selected from the group consisting of 1, 2, 3 and 4. In certain embodiments m5 of formula (D-xii) is 1. In certain embodiments m5 of formula (D-xii) is 2. In certain embodiments m5 of formula (D-xii) is 3. In certain embodiments m5 of formula (D-xii) is 4. In certain embodiments m6 of formula (D-xii) is an integer selected from the group consisting of 2, 3, 4, 5, 6, 7, 8, 9 and 10. In certain embodiments m6 of formula (D-xii) is an integer selected from the group consisting of 3, 4, 5, 6 and 7. In certain embodiments m6 of formula (D-xii) is 3. In certain embodiments m6 of formula (D-xii) is 4. In certain embodiments m6 of formula (D-xii) is 5. In certain embodiments m6 of formula (D-xii) is 6. In certain embodiments m6 of formula (D-xii) is 7.

In certain embodiments a moiety —$X^{0E}$—SP—$X^{0F}$—CL-$X^{0F}$—SP—$X^{0E}$— has the structure of formula (D-xiii)

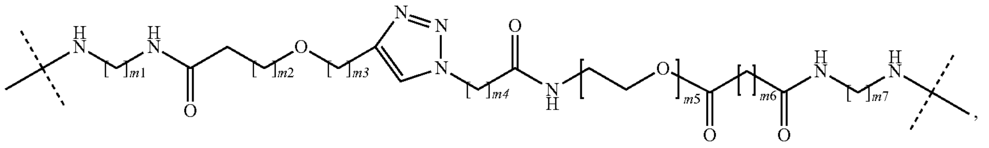

(D-xiii)

wherein dashed lines indicate attachment to the carbonyl of the hyaluronic acid; and m1, m2, m3, m4, m5, m6 and m7 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xiii) is an integer selected from the group consisting of 2, 3, 4, 5 and 6. In certain embodiments m1 of formula (D-xiii) is 3. In certain embodiments m2 of formula (D-xiii) is an integer selected from the group consisting of 1, 2, 3, 4 and 5. In certain embodiments m2 of formula (D-xiii) is 1. In certain embodiments m3 of formula (D-xiii) is an integer selected from the group consisting of 1, 2, 3, 4 and 5. In certain embodiments m3 of formula (D-xiii) is 1. In certain embodiments m4 of formula (D-xiii) is an integer selected from the group consisting of 1, 2, 3, 4 and 5. In certain embodiments m4 of formula (D-xiii) is 1. In certain embodiments m4 of formula (D-xiii) is 5. In certain embodiments m5 of formula (D-xiii) is an integer selected from 1, 2, 3, 4, 5, 6, 7, 8, 9 and 10. In certain embodiments m5 of formula (D-xiii) is an integer selected from the group consisting of 1, 2, 3 and 4. In certain embodiments m5 of formula (D-xiii) is 1. In certain embodiments m5 of formula (D-xiii) is 2. In certain embodiments m5 of formula (D-xiii) is 3. In certain embodiments m5 of formula (D-xiii) is 4. In certain embodiments m6 of formula (D-xiii) is an integer selected from the group consisting of 2, 3, 4, 5, 6, 7, 8, 9 and 10. In certain embodiments m6 of formula (D-xiii) is an integer selected from the group consisting of 3, 4, 5, 6 and 7. In certain embodiments m6 of formula (D-xiii) is 3. In certain embodiments m6 of formula (D-xiii) is 4. In certain embodiments m6 of formula (D-xiii) is 5. In certain embodiments m6 of formula (D-xiii) is 6. In certain embodiments m6 of formula (D-xiii) is 7. In certain embodiments m7 of formula (D-xiii) is an integer selected from the group consisting of 2, 3, 4, 5 and 6. In certain embodiments m7 of formula (D-xiii) is 3. In certain embodiments m7 of formula (D-xiii) is 4.

In certain embodiments —CL- is of formula (D-xiv)

(D-xiv)

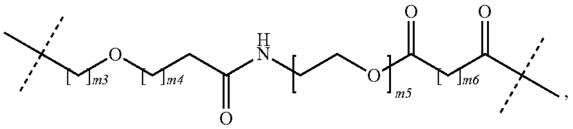

wherein dashed lines indicate attachment to a moiety —$X^{0F}$—;

m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-xiv) is an integer selected from the group consisting of 1, 2, 3, 4 and 5. In certain embodiments m3 is 1. In certain embodiments m3 of formula (D-xiv) is 5. In certain embodiments m4 of formula (D-xiv) is an integer selected from the group consisting of 1, 2, 3, 4 and 5. In certain embodiments m4 of formula (D-xiv) is 1. In certain embodiments m5 is an integer selected from the group consisting of 1, 2, 3, 4, 5, 6, 7, 8, 9 and 10. In certain embodiments m5 of formula (D-xiv) is an integer selected from the group consisting of 1, 2, 3 and 4. In certain embodiments m5 of formula (D-xiv) is 1. In certain embodiments m5 of formula (D-xiv) is 2. In certain embodiments m5 of formula (D-xiv) is 3. In certain embodiments m5 of formula (D-xiv) is 4. In certain embodiments m6 of formula (D-xiv) is an integer selected from the group consisting of 2, 3, 4, 5, 6, 7, 8, 9 and 10. In certain embodiments m6 of formula (D-xiv) is 3. In certain embodiments m6 of formula (D-xiv) is 4. In certain embodiments m6 of formula (D-xiv) is 5. In certain embodiments m6 of formula (D-xiv) is 6. In certain embodiments m6 of formula (D-xiv) is 7.

In certain embodiments a moiety —$X^{0E}$—SP—$X^{0F}$—CL-$X^{0F}$—SP—$X^{0E}$— has the structure of formula (D-xv)

(D-xv)

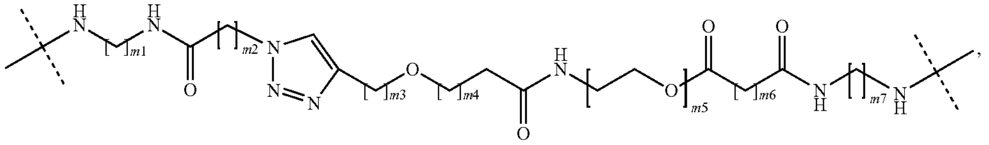

wherein dashed lines indicate attachment to the carbonyl of the hyaluronic acid; and m1, m2, m3, m4, m5, m6 and m7 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xv) is an integer selected from the group consisting of 2, 3, 4, 5 and 6. In certain embodiments m1 of formula (D-xv) is 3. In certain embodiments of m2 of formula (D-xv) is an integer selected from the group consisting of 1, 2, 3, 4 and 5. In certain embodiments m2 of formula (D-xv) is 1. In certain embodiments m3 of formula (D-xv) is an integer selected from the group consisting of 1, 2, 3, 4 and 5. In certain embodiments m3 is 1. In certain embodiments m3 of formula (D-xv) is 5. In certain embodiments m4 of formula (D-xv) is an integer selected from the group consisting of 1, 2, 3, 4 and 5. In certain embodiments m4 of formula (D-xv) is 1. In certain embodiments m5 is an integer selected from the group consisting of 1, 2, 3, 4, 5, 6, 7, 8, 9 and 10. In certain embodiments m5 of formula (D-xv) is an integer selected from the group consisting of 1, 2, 3 and 4. In certain embodiments m5 of formula (D-xv) is 1. In certain embodiments m5 of formula (D-xv) is 2. In certain embodiments m5 of formula (D-xv) is 3. In certain embodiments m5 of formula (D-xv) is 4. In certain embodiments m6 of formula (D-xv) is an integer selected from the group consisting of 2, 3, 4, 5, 6, 7, 8, 9 and 10. In certain embodiments m6 of formula (D-xv) is 3. In certain embodiments m6 of formula (D-xv) is 4. In certain embodiments m6 of formula (D-xv) is 5. In certain embodiments m6 of formula (D-xv) is 6. In certain embodiments m6 of formula (D-xv) is 7. In certain embodiments m7 of formula (D-xv) is an integer selected from the group consisting of 2, 3, 4, 5 and 6. In certain embodiments m7 of formula (D-xv) is 4.

In certain embodiments —CL- is of formula (D-xvi)

(D-xvi)

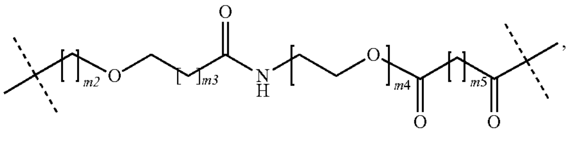

wherein dashed lines indicate attachment to a moiety —$X^{0F}$—;

m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments of m2 of formula (D-xvi) is an integer selected from the group consisting of 1, 2, 3, 4 and 5. In certain embodiments m2 of formula (D-xvi) is 1. In certain embodiments m3 of formula (D-xvi) is an integer selected from the group consisting of 1, 2, 3, 4 and 5. In certain embodiments m3 is 1. In certain embodiments m4 of formula (D-xvi) is an integer selected from the group consisting of 1, 2, 3, 4, 5, 6, 7, 8, 9 and 10. In certain embodiments m4 of formula (D-xvi) is an integer selected from the group consisting of 1, 2, 3 and 4. In certain embodiments m4 of formula (D-xvi) is 1. In certain embodiments m4 of formula (D-xvi) is 2. In certain embodiments m4 of formula (D-xvi) is 3. In certain embodiments m4 of formula (D-xvi) is 4. In certain embodiments m5 is an integer selected from the group consisting of 2, 3, 4, 5, 6, 7, 8, 9 and 10. In certain embodiments m5 of formula (D-xvi) is an integer selected from the group consisting of 3, 4, 5, 6, and 7. In certain embodiments m5 of formula (D-xvi) is 3. In certain embodiments m5 of formula (D-xvi) is 4. In certain embodiments m5 of formula (D-xvi) is 5. In certain embodiments m5 of formula (D-xvi) is 6. In certain embodiments m5 of formula (D-xvi) is 7.

In certain embodiments a moiety —$X^{0E}$—SP—$X^{0F}$—$CL^{P}$-$X^{0F}$—SP—$X^{0E}$— has the structure of formula (D-xvii)

(D-xvii)

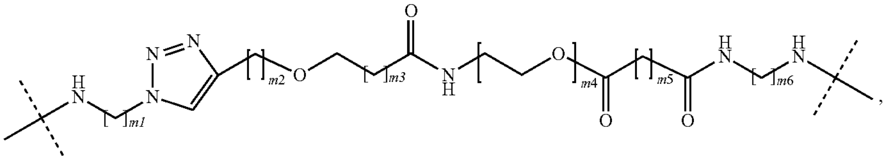

wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xvii) is an integer selected from the group consisting of 2, 3, 4, 5 and 6. In certain embodiments m1 of formula (D-xvii) is 3. In certain embodiments m1 of formula (D-xvii) is 4. In certain embodiments of m2 of formula (D-xvii) is an integer selected from the group consisting of 1, 2, 3, 4 and 5. In certain embodiments m2 of formula (D-xvii) is 1. In certain embodiments m3 of formula (D-xvii) is an integer selected from the group consisting of 1, 2, 3, 4 and 5. In certain embodiments m3 is 1. In certain embodiments m4 of formula (D-xvii) is an integer selected from the group consisting of 1, 2, 3, 4, 5, 6, 7, 8, 9 and 10. In certain embodiments m4 of formula (D-xvii) is an integer selected from the group consisting of 1, 2, 3 and 4. In certain embodiments m4 of formula (D-xvii) is 1. In certain embodiments m4 of formula (D-xvii) is 2. In certain embodiments m4 of formula (D-xvii) is 3. In certain embodiments m4 of formula (D-xvii) is 4. In certain embodiments m5 of formula (D-xvii) is an integer selected from the group consisting of 2, 3, 4, 5, 6, 7, 8, 9 and 10. In certain embodiments m5 of formula (D-xvii) is an integer selected from the group consisting of 3, 4, 5, 6, and 7. In certain embodiments m5 of formula (D-xvii) is 3. In certain embodiments m5 of formula (D-xvii) is 4. In certain embodiments m5 of formula (D-xvii) is 5. In certain embodiments m5 of formula (D-xvii) is 6. In certain embodiments m5 of formula (D-xvii) is 7. In certain embodiments m6 of formula (D-xvii) is an integer selected from the group consisting of 2, 3, 4, 5 and 6. In certain embodiments m6 of formula (D-xvii) is 3.

In certain embodiments —CL- is of formula (D-xviii)

(D-xviii)

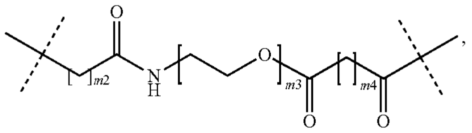

wherein dashed lines indicate attachment to a moiety —$X^{0F}$—;

m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D-xviii) is an integer selected from the group consisting of 1, 2, 3, 4 and 5. In certain embodiments m2 of formula (D-xviii) is 1. In certain embodiments m3 of formula (D-xviii) is an integer selected from the group consisting of 1, 2, 3, 4, 5, 6, 7, 8, 9 and 10. In certain embodiments m3 of formula (D-xviii) is an integer selected from the group consisting of 1, 2, 3 and 4. In certain embodiments m3 of formula (D-xviii) is 1. In certain embodiments m3 of formula (D-xviii) is 2. In certain embodiments m3 of formula (D-xix) is 3. In certain embodiments m3 of formula (D-xviii) is 4. In certain embodiments m4 of formula (D-xviii) is an integer selected from the group consisting of 2, 3, 4, 5, 6, 7, 8, 9 and 10. In certain embodiments m4 of formula (D-xviii) is an integer selected from the group consisting of 3, 4, 5, 6 and 7. In certain embodiments m4 of formula (D-xviii) is 3. In certain embodiments m4 of formula (D-xviii) is 4. In certain embodiments m4 of formula (D-xviii) is 5. In certain embodiments m4 of formula (D-xviii) is 6.

In certain embodiments a moiety —$X^{0E}$—SP—$X^{0F}$—CL-$X^{0F}$—SP—$X^{0E}$— has the structure of formula (D-xix)

(D-xix)

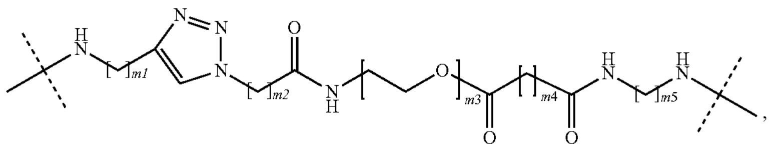

wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xix) is an integer selected from the group consisting of 1, 2, 3, 4, 5, 6, 7 and 8. In certain embodiments m1 of formula (D-xix) is 1. In certain embodiments m2 of formula (D-xix) is an integer selected from the group consisting of 1, 2, 3, 4 and 5. In certain embodiments m2 of formula (D-xix) is 1. In certain embodiments m3 of formula (D-xix) is an integer selected from the group consisting of 1, 2, 3, 4, 5, 6, 7, 8, 9 and 10. In certain embodiments m3 of formula (D-xix) is an integer selected from the group consisting of 1, 2, 3 and 4. In certain embodiments m3 of formula (D-xix) is 1. In certain embodiments m3 of formula (D-xix) is 2. In certain embodiments m3 of formula (D-xix) is 3. In certain embodiments m3 of formula (D-xix) is 4. In certain embodiments m4 of formula (D-xix) is an integer selected from the group consisting of 2, 3, 4, 5, 6, 7, 8, 9 and 10. In certain embodiments m4 of formula (D-xix) is an integer selected from the group consisting of 3, 4, 5, 6 and 7. In certain embodiments m4 of formula (D-xix) is 3. In certain embodiments m4 of formula (D-xix) is 4. In certain embodiments m4 of formula (D-xix) is 5. In certain embodiments m4 of formula (D-xix) is 6. In certain embodiments m4 of formula (D-xix) is 7. In certain embodiments m5 of formula (D-xix) is an integer selected from the group consisting of 2, 3, 4, 5 and 6. In certain embodiments m5 of formula (D-xix) is 3.

In certain embodiments —CL- is of formula (D-xx)

(D-xx)

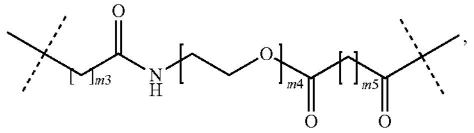

wherein dashed lines indicate attachment to a moiety $—X^{0F}—$;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-xx) is an integer selected from the group consisting of the group 2, 3, 4, 5, 6, 7, 8, 9 and 10. In certain embodiments m3 of formula (D-xx) is an integer selected from the group consisting of 3, 4, 5, 6 and 7. In certain embodiments m3 of formula (D-xx) is 3. In certain embodiments m3 is 4. In certain embodiments m3 of formula (D-xx) is 5. In certain embodiments m3 of formula (D-xx) is 6. In certain embodiments m3 of formula (D-xxi is 7. In certain embodiments m4 of formula (D-xx) is an integer selected from the group consisting of 1, 2, 3, 4, 5, 6, 7, 8, 9 and 10. In certain embodiments m4 of formula (D-xx) is an integer selected from the group consisting of 1, 2, 3 and 4. In certain embodiments m4 of formula (D-xx) is 1. In certain embodiments m4 of formula (D-xx) is 2. In certain embodiments m4 of formula (D-xx) is 3. In certain embodiments m4 of formula (D-xx) is 4. In certain embodiments m5 of formula (D-xx) is an integer selected from the group consisting of 2, 3, 4, 5, 6, 7, 8, 9 and 10. In certain embodiments m5 of formula (D-xx) is an integer selected from the group consisting of 3, 4, 5, 6 and 7. In certain embodiments m5 of formula (D-xx) is 3. In certain embodiments m5 of formula (D-xx) is 4. In certain embodiments m5 of formula (D-xx) is 5. In certain embodiments m5 of formula (D-xx) is 6. In certain embodiments m5 of formula (D-xx) is 7.

In certain embodiments a moiety $—X^{0E}—SP—X^{0F}—CL^{P}-X^{0F}—SP—X^{0E}—$ has the structure of formula (D-xxi) or (D-xxi')

In certain embodiments m1 of formula (D-xxi) or (D-xxi') is an integer selected from the group consisting of 2, 3, 4, 5 and 6. In certain embodiments m1 of formula (D-xxi) or (D-xxi') is 3. In certain embodiments m1 of formula (D-xxi) or (D-xxi') is 4. In certain embodiments m2 of formula (D-xxi) or (D-xxi') is an integer selected from the group consisting of 1, 2, 3, 4 and 5. In certain embodiments m2 of formula (D-xxi) or (D-xxi') is 1. In certain embodiments m3 of formula (D-xxi) or (D-xxi') is an integer selected from the group consisting of the group 2, 3, 4, 5, 6, 7, 8, 9 and 10. In certain embodiments m3 of formula (D-xxi) or (D-xxi') is an integer selected from the group consisting of 3, 4, 5, 6 and 7. In certain embodiments m3 of formula (D-xxi) or (D-xxi') is 3. In certain embodiments m3 is 4. In certain embodiments m3 of formula (D-xxi) or (D-xxi') is 5. In certain embodiments m3 of formula (D-xxi) or (D-xxi') is 6. In certain embodiments m3 of formula (D-xxi) or (D-xxi') is 7. In certain embodiments m4 of formula (D-xxi) or (D-xxi') is an integer selected from the group consisting of 1, 2, 3, 4, 5 6, 7, 8, 9 and 10. In certain embodiments m4 of formula (D-xxi) or (D-xxi') is an integer selected from the group consisting of 1, 2, 3 and 4. In certain embodiments m4 of formula (D-xxi) or (D-xxi') is 1. In certain embodiments m4 of formula (D-xxi) or (D-xxi') is 2. In certain embodiments m4 of formula (D-xxi) or (D-xxi') is 3. In certain embodiments m4 of formula (D-xxi) or (D-xxi') is 4. In certain embodiments m5 of formula (D-xxi) or (D-xxi') is an integer selected from the group consisting of 2, 3, 4, 5, 6, 7, 8, 9 and 10. In certain embodiments m5 of formula (D-xxi) or (D-xxi') is an integer selected from the group consisting of 3, 4, 5, 6 and 7. In certain embodiments m5 of formula (D-xxi) or (D-xxi') is 3. In certain embodiments m5 of formula (D-xxi) or (D-xxi') is 4. In certain embodiments m5 of formula (D-xxi) or (D-xxi') is 5. In certain embodiments (D-xxi)

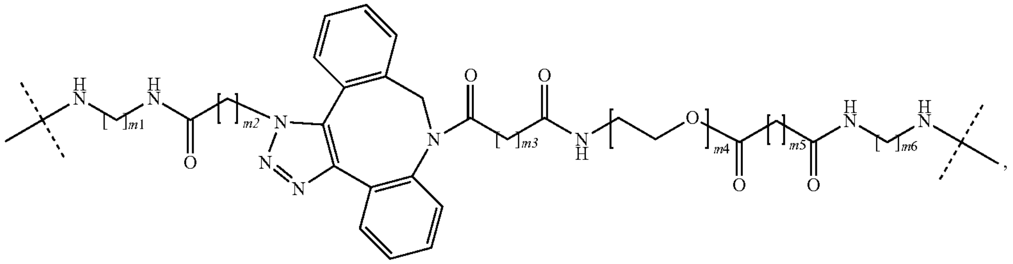

(D-xxi')

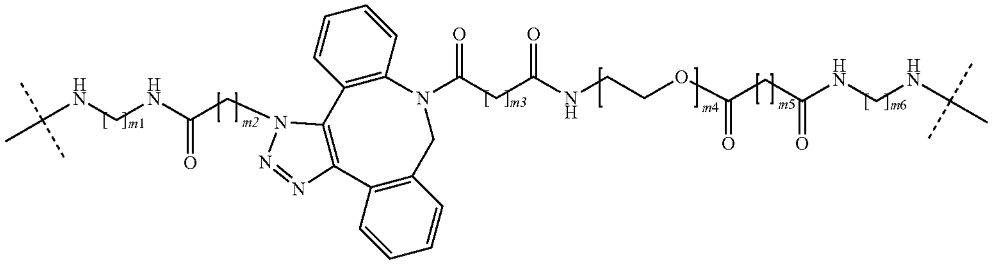

wherein dashed lines indicate attachment to the carbonyl of the hyaluronic acid; and each m1, m2, m3, m4, m5 and m6 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

m5 of formula (D-xxi) or (D-xxi') is 6. In certain embodiments m5 of formula (D-xxi) or (D-xxi') is 7. In certain embodiments m6 of formula (D-xxi) or (D-xxi') is an integer selected from the group consisting of 2, 3, 4, 5 and 6. In certain embodiments m6 of formula (D-xxi) or (D-xxi') is 3. In certain embodiments m6 of formula (D-xxi) or (D-xxi') is 4.

In certain embodiments —CL- is of formula (D-xxii)

(D-xxii)

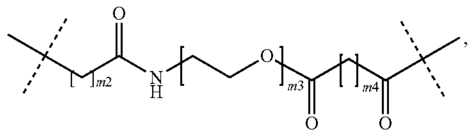

embodiments m4 (D-xxiii) or (D-xxiii') is an integer selected from the group consisting of 3, 4, 5, 6 and 7. In certain embodiments m4 (D-xxiii) or (D-xxiii') is 3. In certain embodiments m4 is 4. In certain embodiments m4 (D-xxiii) or (D-xxiii') is 5. In certain embodiments m4 (D-xxiii) or (D-xxiii') is 6. In certain embodiments m4 (D-xxiii) or (D-xxiii') is 7.

In certain embodiments a moiety $—X^{0E}—SP—X^{0F}—CL-X^{0F}—SP—X^{0E}—$ has the structure of formula (D-xxiii) or (D-xxiii')

(D-xxiii)

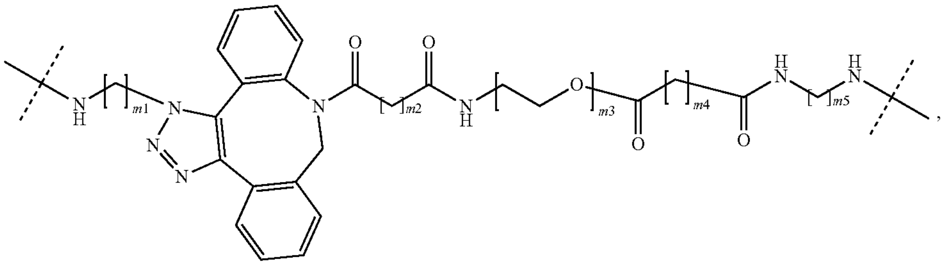

(D-xxiii')

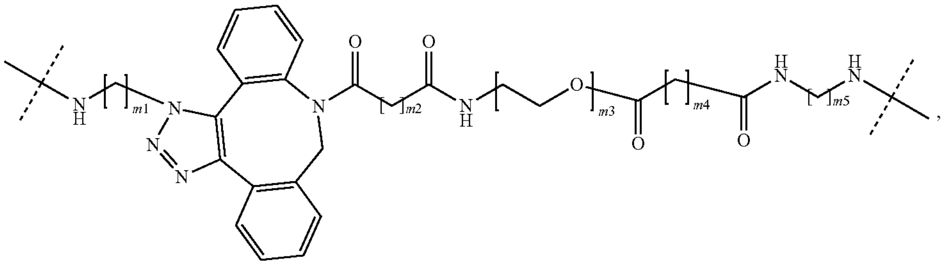

wherein dashed lines indicate attachment to a moiety $—X^{0F}—$;

m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 (D-xxiii) or (D-xxiii') is an integer selected from the group consisting of 2, 3, 4, 5, 6, 7, 8, 9, and 10. In certain embodiments m2 (D-xxiii) or (D-xxiii') is an integer selected from the group consisting of 3, 4, 5, 6 and 7. In certain embodiments m2 (D-xxiii) or (D-xxiii') is 3. In certain embodiments m2 (D-xxiii) or (D-xxiii') is 4. In certain embodiments m2 (D-xxiii) or (D-xxiii') is 5. In certain embodiments m2 (D-xxiii) or (D-xxiii') is 6. In certain embodiments m2 (D-xxiii) or (D-xxiii') is 7. In certain embodiments m3 (D-xxiii) or (D-xxiii') is an integer selected from the group consisting of 1, 2, 3, 4, 5, 6, 7, 8, 9 and 10. In certain embodiments m3 (D-xxiii) or (D-xxiii') is is an integer selected from the group consisting of 1, 2, 3 and 4. In certain embodiments m3 (D-xxiii) or (D-xxiii') is 1. In certain embodiments m3 (D-xxiii) or (D-xxiii') is 2. In certain embodiments m3 (D-xxiii) or (D-xxiii') is 3. In certain embodiments m3 (D-xxiii) or (D-xxiii') is 4. In certain embodiments m4 (D-xxiii) or (D-xxiii') is an integer selected from the group consisting of 2, 3, 4, 5, 6, 7, 8, 9 and 10. In certain wherein dashed lines indicate attachment to the carbonyl of the hyaluronic acid; and m1, m2, m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxiii) or (D-xxiii') is an integer selected from the group consisting of 1, 2, 3, 4 and 5. In certain embodiments m1 (D-xxiii) or (D-xxiii') is 1. In certain embodiments m2 (D-xxiii) or (D-xxiii') is an integer selected from the group consisting of 2, 3, 4, 5, 6, 7, 8, 9, and 10. In certain embodiments m2 (D-xxiii) or (D-xxiii') is an integer selected from the group consisting of 3, 4, 5, 6 and 7. In certain embodiments m2 (D-xxiii) or (D-xxiii') is 3. In certain embodiments m2 (D-xxiii) or (D-xxiii') is 4. In certain embodiments m2 (D-xxiii) or (D-xxiii') is 5. In certain embodiments m2 (D-xxiii) or (D-xxiii') is 6. In certain embodiments m2 (D-xxiii) or (D-xxiii') is 7. In certain embodiments m3 (D-xxiii) or (D-xxiii') is an integer selected from the group consisting of 1, 2, 3, 4, 5, 6, 7, 8, 9 and 10. In certain embodiments m3 (D-xxiii) or (D-xxiii') is an integer selected from the group consisting of 1, 2, 3 and 4. In certain embodiments m3 (D-xxiii) or (D-xxiii') is 1. In certain embodiments m3 (D-xxiii) or (D-xxiii') is 2. In certain embodiments m3 (D-xxiii) or (D-xxiii') is 3. In certain embodiments m3 (D-xxiii) or (D-xxiii') is 4. In certain embodiments m4 (D-xxiii) or (D-xxiii') is an integer selected from the group consisting of 2, 3, 4, 5, 6, 7, 8, 9 and 10. In certain embodiments m4 (D-xxiii) or (D-xxiii') is an integer selected from the group consisting of 3, 4, 5, 6 and 7. In certain embodiments m4 (D-xxiii) or (D-xxiii') is 3. In certain embodiments m4 is 4. In certain embodiments m4 (D-xxiii) or (D-xxiii') is 5. In certain embodiments m4 (D-xxiii) or (D-xxiii') is 6. In certain embodiments m4 (D-xxiii) or (D-xxiii') is 7. In certain embodiments m5 (D-xxiii) or (D-xxiii') is an integer selected from the group consisting of 2, 3, 4, 5 and 6. In certain embodiments m5 (D-xxiii) or (D-xxiii') is 3. In certain embodiments m5 (D-xxiii) or (D-xxiii') is 4.

from the group consisting of 2, 3, 4, 5, 6, 7, 8, 9 and 10. In certain embodiments m5 of formula (D-xxiv) is an integer selected from the group consisting of 3, 4, 5, 6 and 7. In certain embodiments m5 of formula (D-xxiv) is 3. In certain embodiments m5 of formula (D-xxiv) is 4. In certain embodiments m5 of formula (D-xxiv) is 5. In certain embodiments m5 of formula (D-xxiv) is 6. In certain embodiments m5 of formula (D-xxiv) is 7.

In certain embodiments a moiety —$X^{0E}$—SP—$X^{0F}$—CL-$X^{0F}$—SP—$X^{0E}$— has the structure of formula (D-xxv) or (D-xxv')

(D-xxv)

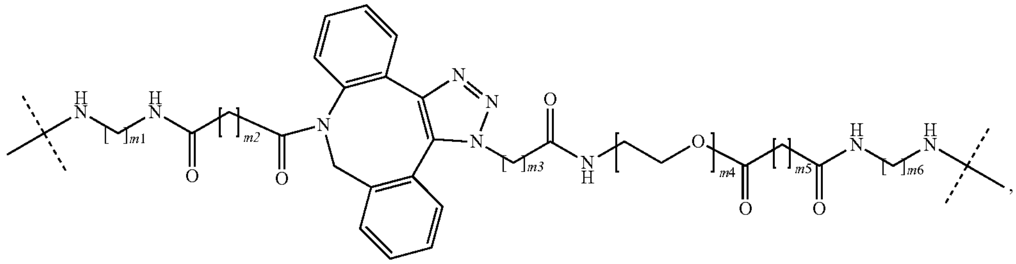

(D-xxvi)

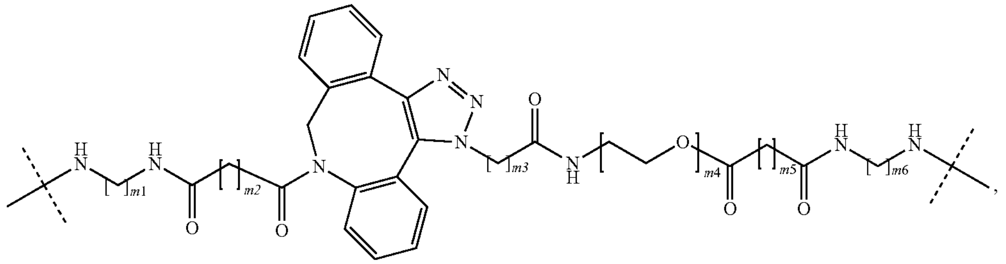

In certain embodiments —$CL^P$- is of formula (D-xxiv)

(D-xxiv)

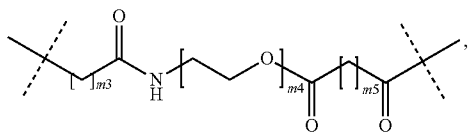

wherein dashed lines indicate attachment to a moiety —$X^{0F}$—;

m3, m4 and m5 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m3 of formula (D-xxiv) is an integer selected from the group consisting of 1, 2, 3, 4 and 5. In certain embodiments m3 of formula (D-xxiv) is 1. In certain embodiments m4 of formula (D-xxiv) is an integer selected from the group consisting of 1, 2, 3, 4, 5, 6, 7, 8, 9 and 10. In certain embodiments m4 of formula (D-xxiv) is an integer selected from the group consisting of 1, 2, 3 and 4. In certain embodiments m4 of formula (D-xxiv) is 1. In certain embodiments m4 of formula (D-xxiv) is 2. In certain embodiments m4 of formula (D-xxiv) is 3. In certain embodiments m4 of formula (D-xxiv) is 4. In certain embodiments m5 of formula (D-xxiv) is an integer selected wherein dashed lines indicate attachment to the carbonyl of the hyaluronic acid; and m1, m2, m3, m4, m5 and m6 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxv) or (D-xxv') is an integer selected from the group consisting of 2, 3, 4, 5 and 6. In certain embodiments m1 of formula (D-xxv) or (D-xxv') is 3. In certain embodiments m1 of formula (D-xxv) or (D-xxv') is 4. In certain embodiments m2 of formula (D-xxv) or (D-xxv') is an integer selected from the group consisting of 2, 3, 4, 5, 6, 7, 8, 9, and 10. In certain embodiments m2 of formula (D-xxv) or (D-xxv') is an integer selected from the group consisting of 3, 4, 5, 6 and 7. In certain embodiments m2 of formula (D-xxv) or (D-xxv') is 3. In certain embodiments m2 of formula (D-xxv) or (D-xxv') is 4. In certain embodiments m2 of formula (D-xxv) or (D-xxv') is 5. In certain embodiments m2 of formula (D-xxv) or (D-xxv') is 6. In certain embodiments m2 of formula (D-xxv) or (D-xxv') is 7. In certain embodiments m3 of formula (D-xxv) or (D-xxv') is an integer selected from the group consisting of 1, 2, 3, 4 and 5. In certain embodiments m3 of formula (D-xxv) or (D-xxv') is 1. In certain embodiments m4 of formula (D-xxv) or (D-xxv') is an integer selected from the group consisting of 1, 2, 3, 4, 5, 6, 7, 8, 9 and 10. In certain embodiments m4 of formula (D-xxv) or (D-xxv') is an integer selected from the group consisting of 1, 2, 3 and 4. In certain embodiments m4 of formula (D-xxv) or (D-xxv') is 1. In certain embodiments m4 of formula (D-xxv) or (D-xxv') is 2. In certain embodiments m4 of formula (D-xxv) or (D-xxv') is 3. In certain embodiments m4 of formula (D-xxv) or (D-xxv') is 4. In certain embodiments m5 of formula (D-xxv) or (D-xxv') is an integer selected from the group consisting of 2, 3, 4, 5, 6, 7, 8, 9 and 10. In certain embodiments m5 of formula (D-xxv) or (D-xxv') is an integer selected from the group consisting of 3, 4, 5, 6 and 7. In certain embodiments m5 of formula (D-xxv) or (D-xxv') is 3. In certain embodiments m5 of formula (D-xxv) or (D-xxv') is 4. In certain embodiments m5 of formula (D-xxv) or (D-xxv') is 5. In certain embodiments m5 of formula (D-xxv) or (D-xxv') is 6. In certain embodiments m5 of formula (D-xxv) or (D-xxv') is 7. In certain embodiments m6 of formula (D-xxv) or (D-xxv') is an integer selected from 2, 3, 4 5 and 6. In certain embodiments m6 of formula (D-xxv) or (D-xxv') is 3. In certain embodiments m6 of formula (D-xxv) or (D-xxv') is 4.

In certain embodiments —$CL^P$- is of formula (D-xxvi)

(D-xxvi)

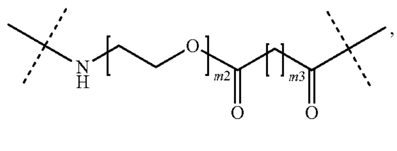

wherein dashed lines indicate attachment to a moiety —$X^{0F}$;

m2 and m3 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D-xxvi) is an integer selected from the group consisting of 1, 2, 3, 4, 5, 6, 7, 8, 9 and 10. In certain embodiments m2 of formula (D-xxvi) is an integer selected from the group consisting of 1, 2, 3 and 4. In certain embodiments m2 of formula (D-xxvi) is 1. In certain embodiments m2 of formula (D-xxvi) is 2. In certain embodiments m2 of formula (D-xxvi) is 3. In certain embodiments m2 of formula (D-xxvi) is 4. In certain embodiments m3 of formula (D-xxvi) is an integer selected from the group consisting of 2, 3, 4, 5, 6, 7, 8, 9 and 10. In certain embodiments m3 of formula (D-xxvi) is an integer selected from the group consisting of 3, 4, 5, 6 and 7. In certain embodiments m3 of formula (D-xxvi) is 3. In certain embodiments m3 of formula (D-xxvi) is 4. In certain embodiments m3 of formula (D-xxvi) is 5. In certain embodiments m3 of formula (D-xxvi) is 6. In certain embodiments m3 of formula (D-xxvi) is 7.

In certain embodiments a moiety —$X^{0E}$—SP—$X^{0F}$—CL-$X^{0F}$—SP—$X^{0E}$— has the structure of formula (D-xxvii) or (D-xxvii')

(D-xxvii)

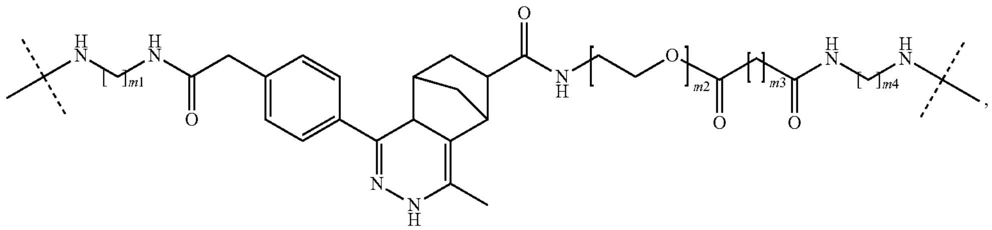

(D-xxvii')

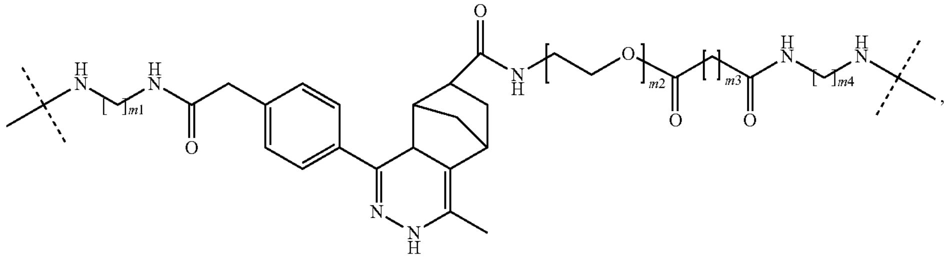

wherein dashed lines indicate attachment to the carbonyl of the hyaluronic acid; and m1, m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxvii) or (D-xxvii') is an integer selected from the group consisting of 2, 3, 4, 5 and 6. In certain embodiments m1 of formula (D-xxvii) or (D-xxvii') is 3. In certain embodiments m1 of formula (D-xxvii) or (D-xxvii') is 4. In certain embodiments m2 of formula (D-xxvii) or (D-xxvii') is an integer selected from the group consisting of 1, 2, 3, 4, 5, 6, 7, 8, 9 and 10. In certain embodiments m2 of formula (D-xxvii) or (D-xxvii') is an integer selected from the group consisting of 1, 2, 3 and 4. In certain embodiments m2 of formula (D-xxvii) or (D-xxvii') is 1. In certain embodiments m2 of formula (D-xxvii) or (D-xxvii') is 2. In certain embodiments m2 of formula (D-xxvii) or (D-xxvii') is 3. In certain embodiments m2 of formula (D-xxvii) or (D-xxvii') is 4. In certain embodiments m3 of formula (D-xxvii) or (D-xxvii') is an integer selected from the group consisting of 2, 3, 4, 5, 6, 7, 8, 9 and 10. In certain embodiments m3 of formula (D-xxvii) or (D-xxvii') is an integer selected from the group consisting of 3, 4, 5, 6 and 7. In certain embodiments m3 of formula (D-xxvii) or (D-xxvii') is 3. In certain embodiments m3 of formula (D-xxvii) or (D-xxvii') is 4. In certain embodiments m3 of formula (D-xxvii) or (D-xxvii') is 5. In certain embodiments m3 of formula (D-xxvii) or (D-xxvii') is 6. In certain embodiments m3 of formula (D-xxvii) or (D-xxvii') is 7. In certain embodiments m4 of formula (D-xxvii) or (D-xxvii') is an integer selected from the group consisting of 2, 3, 4, 5 and 6. In certain embodiments m4 of formula (D-xxvii) or (D-xxvii') is 3. In certain embodiments m4 of formula (D-xxvii) or (D-xxvii') is 4.

In certain embodiments —CL- is of formula (D-xxviii)

(D-xxviii)

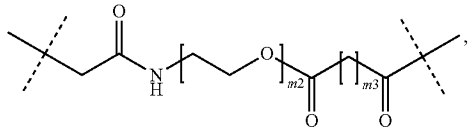

wherein dashed lines indicate attachment to a moiety —$X^{0F}$—;

m2 and m3 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m2 of formula (D-xxviii) is an integer selected from the group consisting of 1, 2, 3, 4, 5, 6, 7, 8, 9 and 10. In certain embodiments m2 of formula (D-xxviii) is an integer selected from the group consisting of 1, 2, 3 and 4. In certain embodiments m2 of formula (D-xxviii) is 1. In certain embodiments m2 of formula (D-xxviii) is 2. In certain embodiments m2 of formula (D-xxviii) is 3. In certain embodiments m2 of formula (D-xxviii) is 4. In certain embodiments m3 of formula (D-xxviii) is an integer selected from the group consisting of 2, 3, 4, 5, 6, 7, 8, 9 and 10. In certain embodiments m3 of formula (D-xxviii) is an integer selected from the group consisting of 3, 4, 5, 6 and 7. In certain embodiments m3 of formula (D-xxviii) is 3. In certain embodiments m3 of formula (D-xxviii) is 4. In certain embodiments m3 of formula (D-xxviii) is 5. In certain embodiments m3 of formula (D-xxviii) is 6. In certain embodiments m3 of formula (D-xxviii) is 7.

In certain embodiments a moiety —$X^{0E}$—SP—$X^{0F}$—CL-$X^{0F}$—SP—$X^{0E}$— has the structure of formula (D-xxix) or (D-xxix')

(D-xxix)

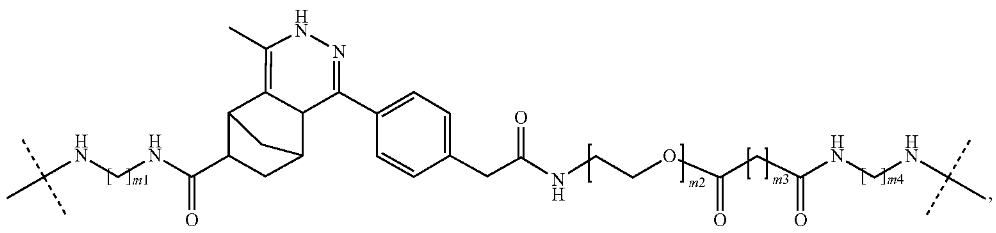

(D-xxix')

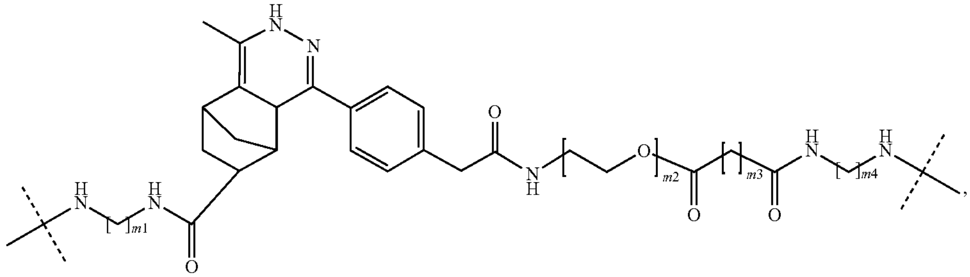

wherein dashed lines indicate attachment to the carbonyl of the hyaluronic acid; and m1, m2, m3 and m4 are independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments m1 of formula (D-xxix) or (D-xxix') is an integer selected from the group consisting of 2, 3, 4, 5 and 6. In certain embodiments m1 of formula (D-xxix) or (D-xxix') is 3. In certain embodiments m1 of formula (D-xxix) or (D-xxix') is 4. In certain embodiments m2 of formula (D-xxix) or (D-xxix') is an integer selected from the group consisting of 1, 2, 3, 4, 5, 6, 7, 8, 9 and 10. In certain embodiments m2 of formula (D-xxix) or (D-xxix') is an integer selected from the group consisting of 1, 2, 3 and 4. In certain embodiments m2 of formula (D-xxix) or (D-xxix') is 1. In certain embodiments m2 of formula (D-xxix) or (D-xxix') is 2. In certain embodiments m2 of formula (D-xxix) or (D-xxix') is 3. In certain embodiments m2 of formula (D-xxix) or (D-xxix') is 4. In certain embodiments m3 of formula (D-xxix) or (D-xxix') is an integer selected from the group consisting of 2, 3, 4, 5, 6, 7, 8, 9 and 10. In certain embodiments m3 of formula (D-xxix) or (D-xxix') is an integer selected from the group consisting of 3, 4, 5, 6 and 7. In certain embodiments m3 of formula (D-xxix) or (D-xxix') is 3. In certain embodiments m3 of formula (D-xxix) or (D-xxix') is 4. In certain embodiments m3 of formula (D-xxix) or (D-xxix') is 5. In certain embodiments m3 of formula (D-xxix) or (D-xxix') is 6. In certain embodiments m3 of formula (D-xxix) or (D-xxix') is 7. In certain embodiments m4 of formula (D-xxix) or (D-xxix') is an integer selected from the group consisting of 2, 3, 4, 5 and 6. In certain embodiments m4 of (D-xxix) or (D-xxix') is 3. In certain embodiments m4 of formula (D-xxix) or (D-xxix') is 4.

In a second embodiment the moiety —CL- is selected from the group consisting of (C-i)

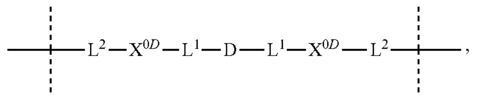

(C-ii)

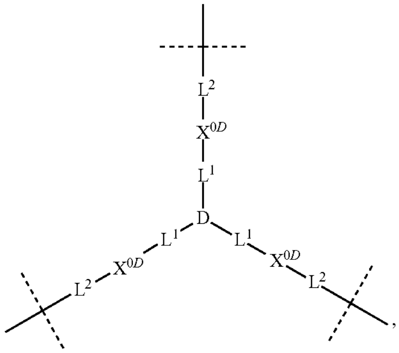

wherein each dashed line indicates attachment to a moiety $—X^{0F}—$; and $-L^1-$, $-L^2-$, $—X^{0D}—$ and -D are used as defined for $Z^2$.

It is understood that in formula (C-i) two functional groups of the drug are conjugated to one moiety $-L^1-$ each and that in formula (C-ii) three functional groups of the drug are conjugated to one moiety $-L^1-$ each. The moiety —CL- of formula (C-i) connects two moieties $Z^3$ and the moiety —CL- of formula (C-ii) connects three moieties $Z^3$, which may be on the same or different hyaluronic acid strand. In this embodiment —CL- comprises at least two degradable bonds, if —CL- is of formula (C-i) or at least three degradable bonds, if —CL- is of formula (C-ii), namely the degradable bonds that connect D with a moiety $-L^1-$. A conjugate may only comprise moieties —CL- of formula (C-i), may only comprise moieties —CL- of formula (C-ii) or may comprise moieties —CL- of formula (C-i) and formula (C-ii).

Accordingly, a conjugate of this second embodiment comprises crosslinked hyaluronic acid strands to which a plurality of drug moieties are covalently and reversibly conjugated, wherein the conjugate comprises a plurality of connected units selected from the group consisting of $Z^1$

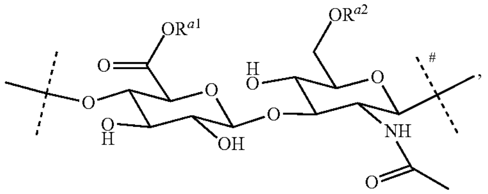

-continued $Z^2$

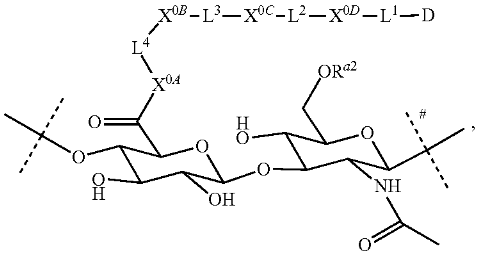

and $Z^3$

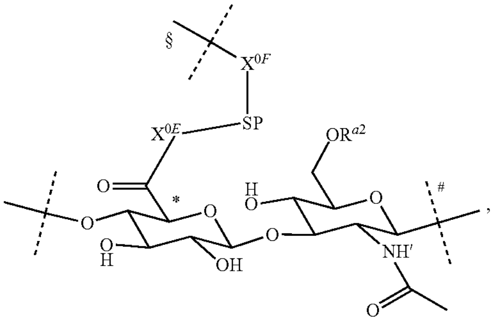

wherein an unmarked dashed line indicates a point of attachment to an adjacent unit at a dashed line marked with # or to a hydrogen;

a dashed line marked with # indicates a point of attachment to an adjacent unit at an unmarked dashed line or to a hydroxyl;

a dashed line marked with § indicates a point of connection between at least two units $Z^3$ via a moiety —CL-;

each —CL- comprises at least one degradable bond between the two carbon atoms marked with the * connected by a moiety —CL- and each —CL- is independently selected from the group consisting of formula (C-i) and (C-ii)

(C-i)

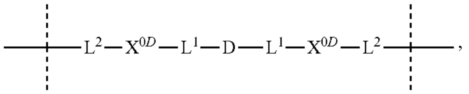

(C-ii)

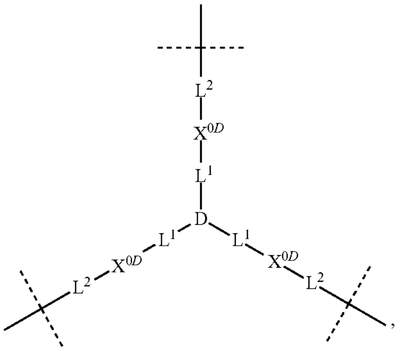

wherein dashed lines indicate attachment to a moiety $—X^{0F}—$ of a unit $Z^3$;

-D, $-L^1-$, $-L^2-$, $-L^3-$, $-L^4-$, —SP—, $—X^{0A}—$, $—X^{0B}—$, $—X^{0C}—$, $—X^{0D}—$, $—X^{0E}—$, $—X^{0F}—$, $—R^{a1}$ and $—R^{a2}$ are used as defined for $Z^1$, $Z^2$ and $Z^3$;

wherein all units $Z^1$ present in the conjugate may be the same or different;

all units $Z^2$ present in the conjugate may be the same or different;

all units $Z^3$ present in the conjugate may be the same or different;

the number of $Z^1$ units ranges from 1% to 98% of the total number of units present in the conjugate;

the number of $Z^2$ units ranges from 0% to 98% of the total number of units present in the conjugate;

the number of $Z^3$ units ranges from 1% to 97% of the total number of units present in the conjugate, provided that at least one unit $Z^3$ is present per strand which is connected to at least one unit $Z^3$ on a different hyaluronic acid strand.

The conjugate according to this second embodiment may also comprise units selected from the group consisting of $Z^4$, $Z^5$, $Z^6$, $Z^7$, $Z^8$, $Z^9$ and $Z^{10}$ as described above. For $Z^4$ variable a is 1 and b is 0 for a moiety —CL- of formula (C-i), and if —CL- is of formula (C-ii) variable a may be 1 with b being also 1 or variable a may be 2 with b being 0.

This embodiment has the effect that for synthesizing a conjugate of the present invention there is no need to separate monoconjugates $Y^{0G}$-$L^2$-$X^{0D}$-$L^1$-D from bisconjugates $Y^{0G}$-$L^2$-$X^{0D}$-$L^1$-D-$L^1$-$X^{0D}$-$L^2$-$Y^{0G}$ or even trisconjugates, in which three moieties $Y^{0G}$-$L^2$-$X^{0D}$-$L^1$- are conjugated to one moiety D. A mixture of both or all three can directly be used for conjugation: Conjugation of a monoconjugate $Y^{0G}$-$L^2$-$X^{D}$-$L^1$-D to a unit $Z^7$ results in the formation of a unit $Z^2$, whereas the bis- and/or trisconjugate are conjugated to units $Z^5$ to thus enable crosslinking and result in the formation of units $Z^3$. $—Y^{0G}$ is a functional group, which is used as defined as for $—Y^{0A}$, $—Y^{0B}$, $—Y^{0C}$ and $—Y^{0D}$ below. Such synthesis may also be done with mixtures comprising higher conjugates, such as tetra-, penta-, hexa- or heptaconjugates, and such embodiments for —CL-, i.e. moieties —CL- in which one moiety D is conjugated to four, five, six or seven or more moieties $-L^1-$, are also included in the present invention. Accordingly, also covered are conjugates comprising a moiety —CL- in the form of tetra-, penta-, hexa- and/or hepta- or higher conjugates.

In a conjugate according to this second embodiment the number of units $Z^2$ ranges from 0 to 70% of all units present in the conjugate, such as from 2 to 15%, from 2 to 10%, from 16 to 39, from 40 to 65%, or from 50 to 60% of all units present in the conjugate.

In a conjugate according to this second embodiment the number of units $Z^3$ ranges from 1 to 30% of all units present in the conjugate, such as from 2 to 5%, from 5 to 20%, from 10 to 18%, or from 14 to 18% of all units present in the conjugate.

In a conjugate according to this second embodiment the number of units $Z^1$ ranges from 10 to 97% of all units present in the conjugate, such as from 20 to 40%, such as from 25 to 35%, such as from 41 to 95%, such as from 45 to 90%, such as from 50 to 70% of all units present in the conjugate.

More specific embodiments for -D, $-L^1-$, $-L^2-$, $-L^3-$, $-L^4-$, —SP—, $—X^{0A}—$, $—X^{0B}—$, $—X^{0C}—$, $—X^{0D}—$, $—X^{0E}—$, $—X^{0F}—$, $—R^{a1}$ and $—R^{a2}$ of the second embodiment are as described elsewhere herein.

In a third embodiment the moiety —CL- is a moiety (D-i)

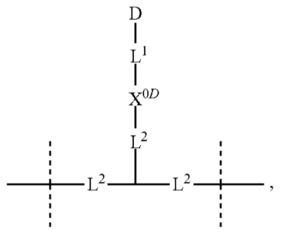

wherein each dashed line indicates attachment to a moiety $—X^{0F}—$ of a unit $Z^3$.

It is understood that a moiety $—CL^P-$ of formula (D-i) comprises at least one branching point, which branching point may be selected from the group consisting of

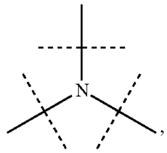,

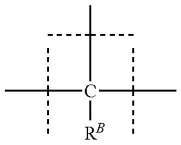

and

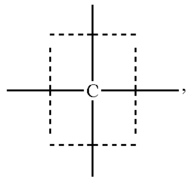, wherein dashed lines indicate attachment to an arm; and $—R^B$ is selected from the group consisting of —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $—R^B1$, which are the same or different, and wherein $C_{1-6}$ alkyl, $C_{2-6}$ alkenyl and $C_{2-6}$ alkynyl are optionally interrupted with —C(O)O—, —O—, —C(O)—, $—C(O)N(R^{B2})—$, $—S(O)_2N(R^{B2})—$, $—S(O)N(R^{B2})—$, $—S(O)_2—$, —S(O)—, $—N(R^{B2})S(O)_2N(R^{B2a})—$, —S—, $—N(R^{B2})—$, $—OC(OR^{B2})(R^{B2a})$, $—N(R^{B2})C(O)N(R^{B2a})—$, and $—OC(O)N(R^{B2})—$; wherein $—R^{B1}$, $—R^{B2}$ and $—R^{B2a}$ are selected from —H, $C_{1-6}$ alkyl, $C_{2-6}$ alkenyl and $C_{2-6}$ alkynyl.

In certain embodiments $—R^B$ is selected from the group consisting of —H, methyl and ethyl.

Accordingly, a conjugate of the third embodiment comprises crosslinked hyaluronic acid strands to which a plurality of drug moieties are covalently and reversibly conjugated, wherein the conjugate comprises a plurality of connected units selected from the group consisting of $Z^1$

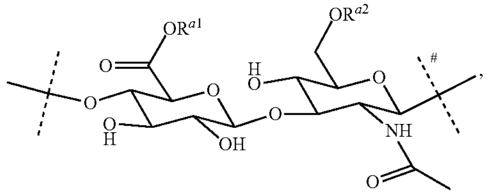

-continued $Z^2$

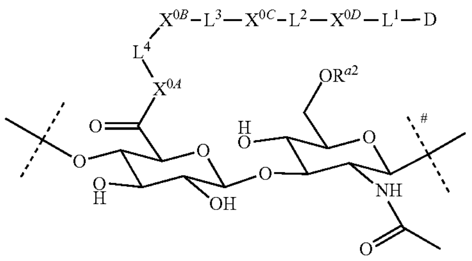

and $Z^3$

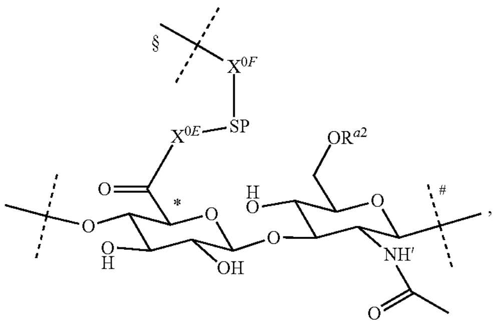

wherein an unmarked dashed line indicates a point of attachment to an adjacent unit at a dashed line marked with # or to a hydrogen;

a dashed line marked with # indicates a point of attachment to an adjacent unit at an unmarked dashed line or to a hydroxyl;

a dashed line marked with § indicates a point of connection between two units $Z^3$ via a moiety —CL -;

each —CL - comprises at least one degradable bond between the two carbon atoms marked with the * connected by a moiety —CL - and each —CL - is independently of formula (D-i)

(D-i)

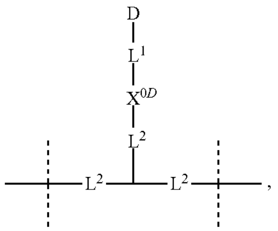

wherein dashed lines indicate attachment to a moiety $—X^{0F}—$ of a unit $Z^3$;

-D, $-L^1-$, $-L^2-$, $-L^3-$, $-L^4-$, —SP—, $—X^{0A}—$, $—X^{0B}—$, $X^{0C}—$, $—X^{0D}—$, $—X^{0E}—$, $—X^{0F}—$, $—R^{a1}$ and $—R^{a2}$ are used as defined for $Z^1$, $Z^2$ and $Z^3$;

wherein all units $Z^1$ present in the conjugate may be the same or different;

all units $Z^2$ present in the conjugate may be the same or different;

all units $Z^3$ present in the conjugate may be the same or different;

the number of units $Z^1$ ranges from 1% to 99% of the total number of units present in the conjugate;

the number of units $Z^2$ ranges from 0% to 98% of the total number of units present in the conjugate; and the number of units $Z^3$ ranges from 1% to 97% of the total number of units present in the conjugate, provided that at least one unit $Z^3$ is present per strand.

The conjugate according to this third embodiment may also comprise units selected from the group consisting of $Z^4$, $Z^5$, $Z^6$, $Z^7$, $Z^8$, $Z^9$ and $Z^{10}$ as described above. For $Z^4$ variable a is 1 and variable b is 0 in this third embodiment.

In a conjugate according to this third embodiment the number of units $Z^2$ ranges from 0 to 70% of all units present in the conjugate, such as from 2 to 15%, from 2 to 10%, from 16 to 39, from 40 to 65%, or from 50 to 60% of all units present in the conjugate.

In a conjugate according to this third embodiment the number of units $Z^3$ ranges from 1 to 30% of all units present in the conjugate, such as from 2 to 5%, from 5 to 20%, from 10 to 18%, or from 14 to 18% of all units present in the conjugate.

In a conjugate according to this third embodiment the number of units $Z^1$ ranges from 10 to 97% of all units present in the conjugate, such as from 20 to 40%, such as from 25 to 35%, such as from 41 to 95%, such as from 45 to 90%, such as from 50 to 70% of all units present in the conjugate.

In this third embodiment —CL- comprises a moiety $-L^2-X^{0C}-L^1-D$, so the presence of units $Z^2$ is optional in this embodiment. In certain embodiment no units $Z^2$ are present in the third embodiment. In certain embodiments the conjugate according to the third embodiment also comprises units $Z^2$. The presence of units $Z^2$ may have the effect that in case of a high drug loading is desired, which in this embodiment also means a high degree of crosslinking, an undesired high degree of crosslinking can be avoided by the presence of units $Z^2$.

More specific embodiments for -D, $-L^1-$, $-L^2-$, $-L^3-$, $-L^4-$, —SP—, $—X^{0A}—$, $—X^{0B}—$, $—X^{0C}—$, $—X^{0D}—$, $—X^{0E}—$, $—X^{0F}—$, $—R^{a1}$ and $—R^{a2}$ of the second embodiment are as described elsewhere herein.

In certain embodiments each $—X^{0A}—$ and $—X^{0E}—$ is independently either absent or selected from the group consisting of (x-1)

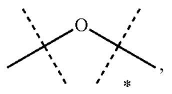

(x-2)

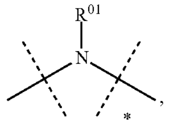

(x-3)

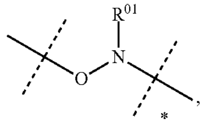

(x-4)

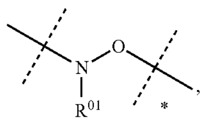

-continued (x-5)

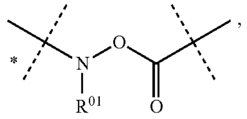

(x-6)

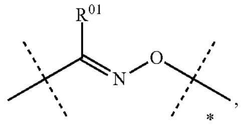

(x-7)

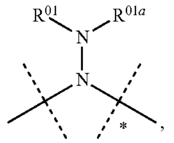

(x-8)

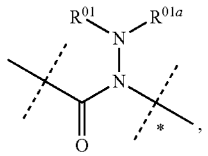

(x-9)

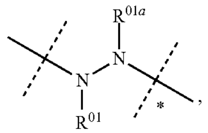

(x-10)

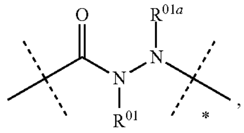

(x-11)

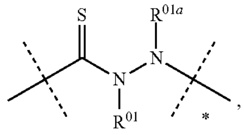

(x-12)

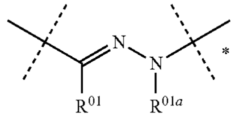

(x-13)

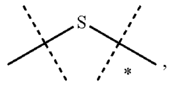

(x-14)

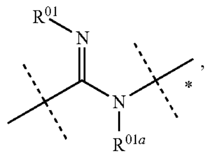

(x-15)

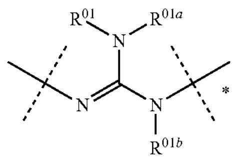

and

-continued (x-16)

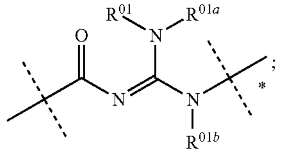

wherein unmarked dashed lines indicate attachment to $-L^4-$ for $—X^{0A}—$ and to —SP— for $—X^{0E}—$; dashed lines marked with an asterisk indicate attachment to the carbonyl of the hyaluronic acid;

each $—R^{01}$, $—R^{01a}$ and $—R^{01b}$ is independently selected from the group consisting of halogen, —H, —CN, $-T^0$, $C_{1-50}$ alkyl, $C_{2-50}$ alkenyl, and $C_{2-50}$ alkynyl; wherein $-T^0$, $C_{1-50}$ alkyl, $C_{2-50}$ alkenyl, and $C_{2-50}$ alkynyl are optionally substituted with one or more $—R^{02}$, which are the same or different, and wherein $C_{1-50}$ alkyl, $C_{2-50}$ alkenyl, and $C_{2-50}$ alkynyl are optionally interrupted by one or more groups selected from the group consisting of $-T^0-$, —C(O)O—, —O—, —C(O)—, —C(O)N$(R0^3)$—, $—S(O)_2N(R^{03})—$, $—S(O)N(R^{03})—$, $—S(O)_2—$, —S(O)—, $—N(R^{03})S(O)_2N(R^{03a})—$, —S—, $—N(R^{03})—$, $—OC(OR^{03})(R^{03a})—$, $—N(R^{03})C(O)N(R^{03a})—$, and $—OC(O)N(R^{03})—$;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more $—R^{02}$, which are the same or different; and each $—R^{02}$, $—R^{03}$ and $—R^{03a}$ is independently selected from the group consisting of —H and $C_{1-6}$ alkyl; wherein $C_{1-6}$ alkyl is optionally substituted with one or more halogen, which are the same or different.

In certain embodiments each $—X^{0A}—$ and $—X^{0E}—$ is independently a linkage selected from the group consisting of formula x-1, x-2, x-3, x-4, x-6, x-9, x-10, x-11, x-12, x-13, x-14, x-15 and x-16, In certain embodiments each $—X^{0A}—$ and $—X^{0E}—$ is independently a linkage selected from the group consisting of formula x-1, x-2, x-3, x-4, x-6, x-9, x-10, x-12, x-13 and x-15.

In certain embodiments each $—X^{0A}—$ and $—X^{0E}—$ is independently a linkage selected from the group consisting of formula x-1, x-2, x-9 and x-10.

In certain embodiments each $—X^{0A}—$ and $—X^{0E}—$ is independently a linkage selected from the group consisting of formula x-1, x-2 and x-10.

In certain embodiments $—X^{0A}—$ is of formula x-1. In certain embodiments $—X^{0A}—$ is of formula x-2. In certain embodiments $—X^{0A}—$ is of formula x-3. In certain embodiments $—X^{0A}—$ is of formula x-4. In certain embodiments $—X^{0A}—$ is of formula x-5. In certain embodiments $—X^{0A}—$ is of formula x-6. In certain embodiments $—X^{0A}—$ is of formula x-7. In certain embodiments $—X^{0A}—$ is of formula x-8. In certain embodiments $—X^{0A}—$ is of formula x-9. In certain embodiments $—X^{0A}—$ is of formula x-10. In certain embodiments $—X^{0A}—$ is of formula x-11. In certain embodiments $—X^{0A}—$ is of formula x-12. In certain embodiments $—X^{0A}—$ is of formula x-13. In certain embodiments $—X^{0A}—$ is of formula x-14. In certain embodiments $—X^{0A}—$ is of formula x-15. In certain embodiments $—X^{0A}—$ is of formula x-16.

In certain embodiments $—X^{0E}—$ is of formula x-1. In certain embodiments $—X^{0E}—$ is of formula x-2. In certain embodiments —$X^{0E}$— is of formula x-3. In certain embodiments —$X^{0E}$— is of formula x-4. In certain embodiments —$X^{0E}$— is of formula x-5. In certain embodiments —$X^{0E}$— is of formula x-6. In certain embodiments —$X^{0E}$— is of formula x-7. In certain embodiments —$X^{0E}$— is of formula x-8. In certain embodiments —$X^{0E}$— is of formula x-9. In certain embodiments $X^{0E}$— is of formula x-10. In certain embodiments —$X^{0E}$— is of formula x-11. In certain embodiments —$X^{0E}$— is of formula x-12. In certain embodiments —$X^{0E}$— is of formula x-13. In certain embodiments —$X^{0E}$— is of formula x-14. In certain embodiments —$X^{0E}$— is of formula x-15. In certain embodiments $X^{0E}$— is of formula x-16.

In certain embodiments each —$X^{0B}$—, —$X^{0C}$—, —$X^{0D}$— and —$X^{0F}$— is independently either absent or selected from the group consisting of (x-17)

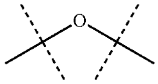

(x-18)

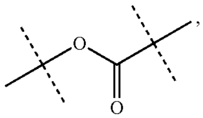

(x-19)

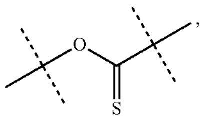

(x-20)

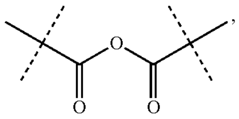

(x-21)

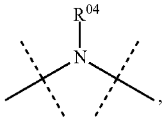

(x-22)

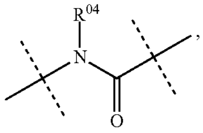

(x-23)

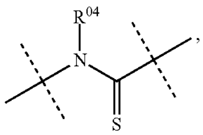

(x-24)

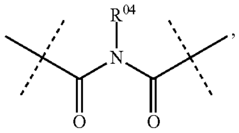

(x-25)

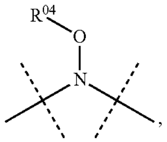

-continued (x-26)

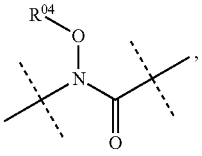

(x-27)

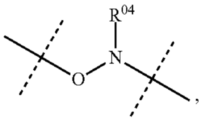

(x-28)

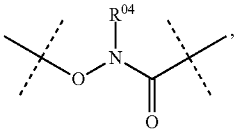

(x-29)

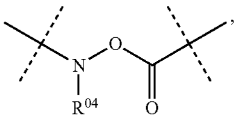

(x-30)

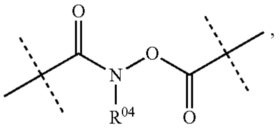

(x-31)

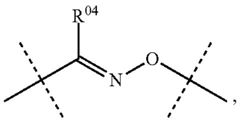

(x-32)

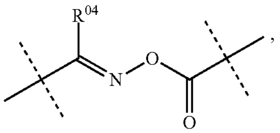

(x-33)

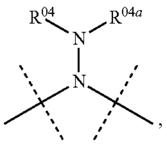

(x-34)

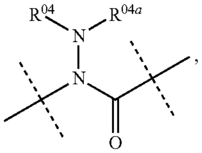

(x-35)

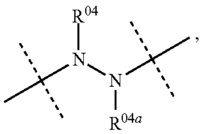

(x-36)

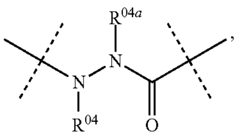

-continued
(x-37)
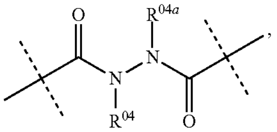
(x-38)
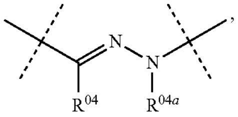
(x-39)
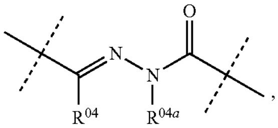
(x-40)
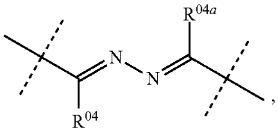
(x-41)
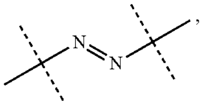
(x-42)
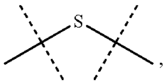
(x-43)
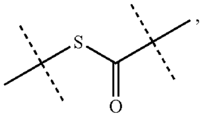
(x-44)
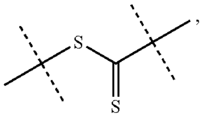
(x-45)
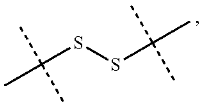
(x-46)
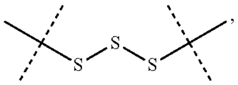
(x-47)
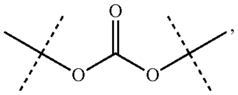
(x-48)
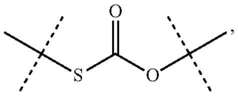
(x-49)
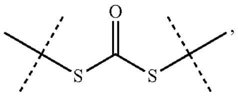
-continued
(x-50)
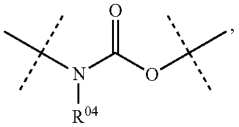
(x-51)
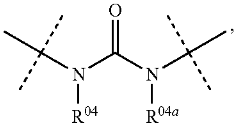
(x-52)
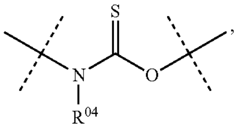
(x-53)
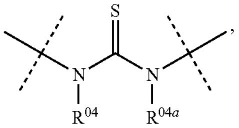
(x-54)
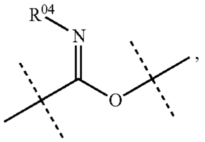
(x-55)
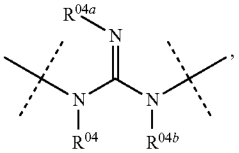
(x-56)
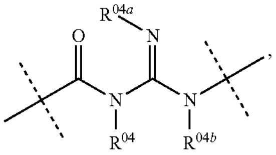
(x-57)
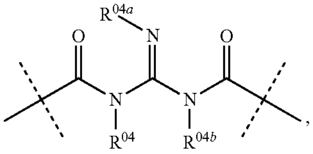
(x-58)
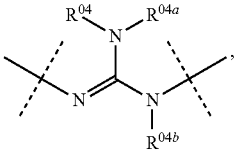
(x-59)
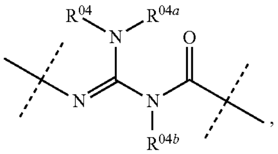

-continued
(x-60)
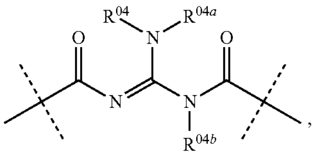
(x-61)
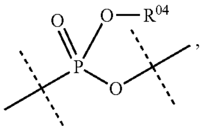
(x-62)
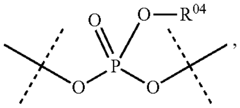
(x-63)
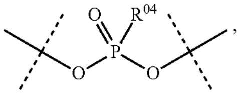
(x-64)
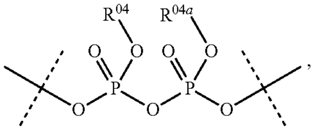
(x-65)
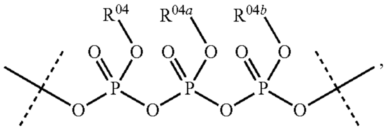
(x-66)
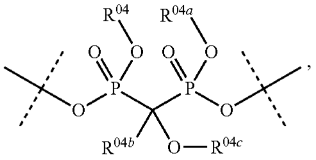
(x-67)
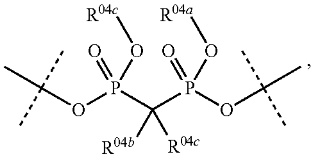
(x-68)
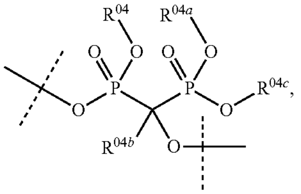
(x-69)
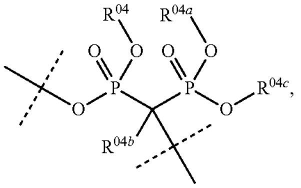
-continued
(x-70)
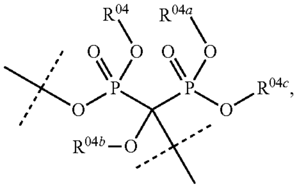
(x-71)
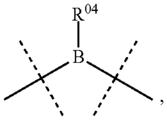
(x-72)
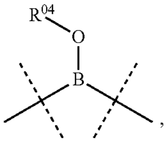
(x-73)
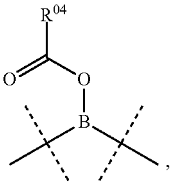
(x-74)
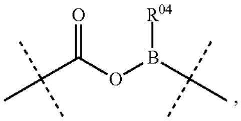
(x-75)
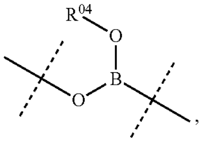
(x-76)
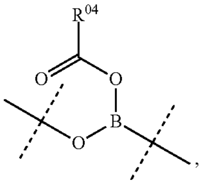
(x-77)
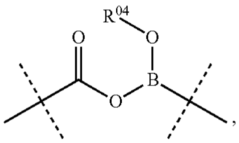
(x-78)
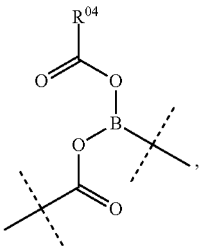

-continued
(x-79)
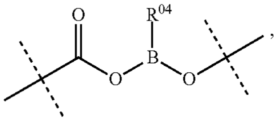
(x-80)
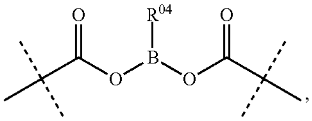
(x-81)
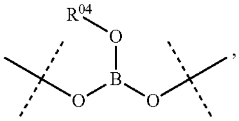
(x-82)
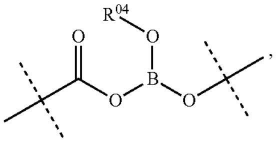
(x-83)
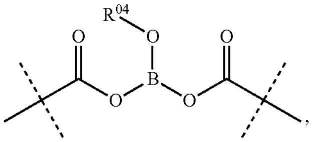
(x-84)
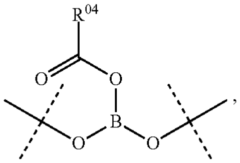
(x-85)
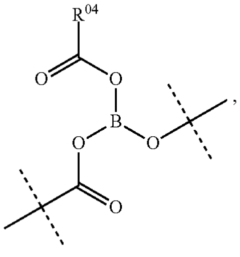
(x-86)
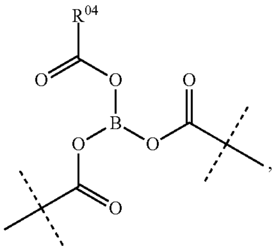
(x-87)
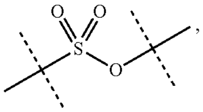
-continued
(x-88)
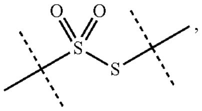
(x-89)
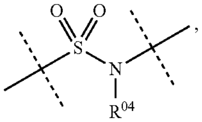
(x-90)
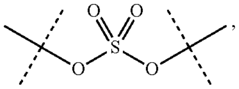
(x-91)
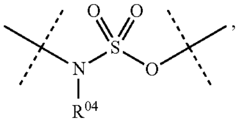
(x-92)
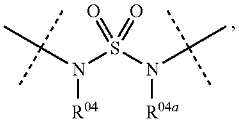
(x-93)
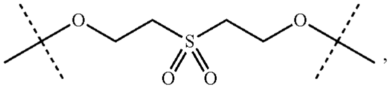
(x-94)
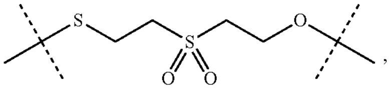
(x-95)
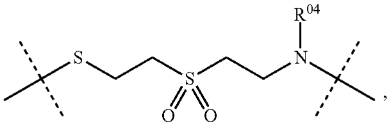
(x-96)
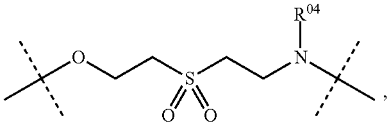
(x-97)
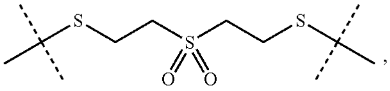
(x-98)
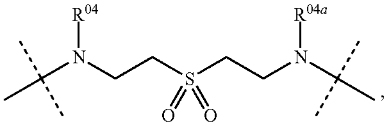
(x-99)
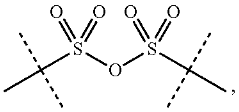
(x-100)
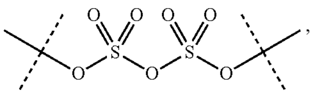

-continued
(x-101)
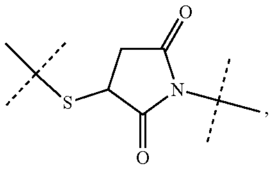
(x-102)
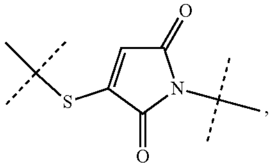
(x-103)
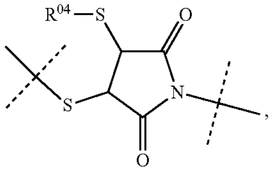
(x-104)
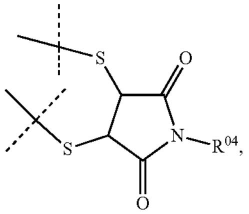
(x-105)
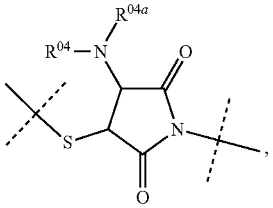
(x-106)
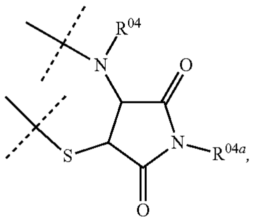
(x-107)
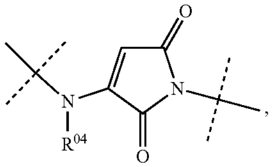
(x-108)
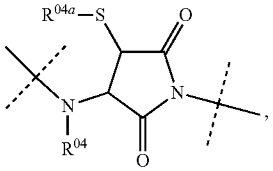
-continued
(x-109)
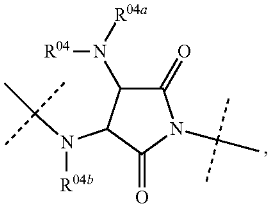
(x-110)
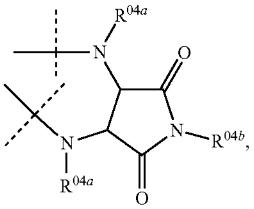
(x-111)
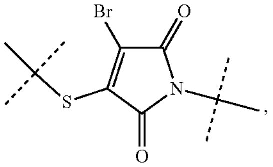
(x-112)
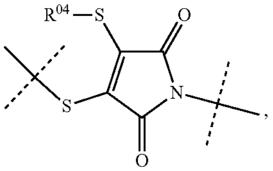
(x-113)
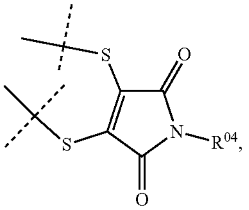
(x-114)
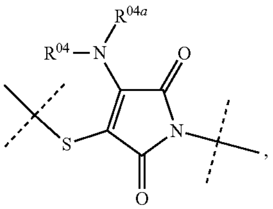
(x-115)
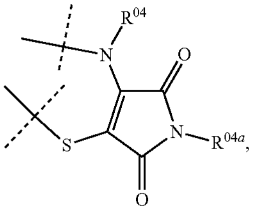
(x-116)
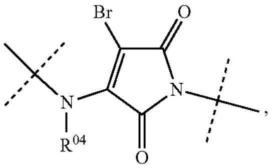

-continued
(x-117)
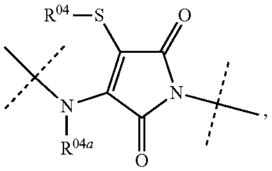
(x-118)
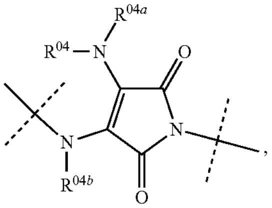
(x-119)
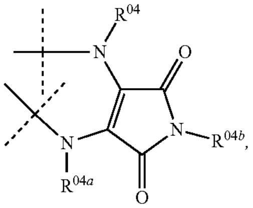
(x-120)
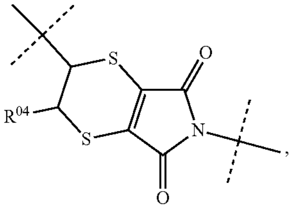
(x-121)
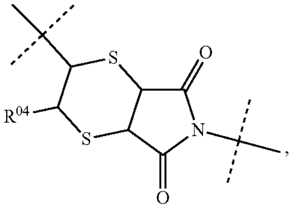
(x-122)
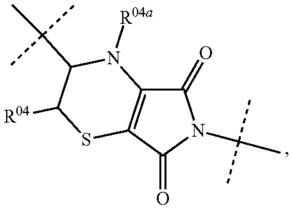
(x-123)
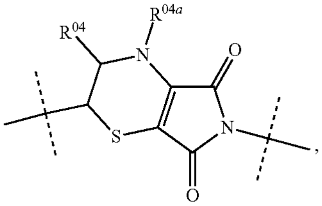
-continued
(x-124)
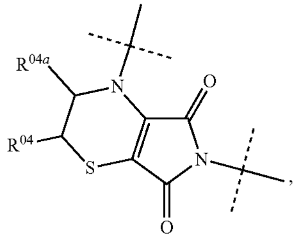
(x-125)
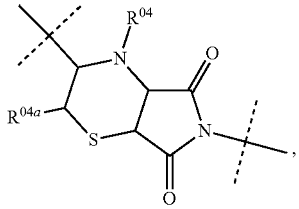
(x-126)
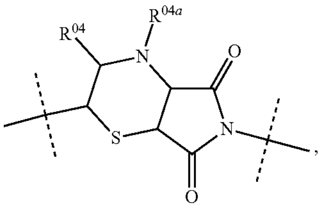
(x-127)
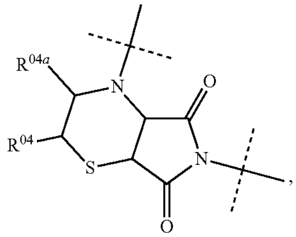
(x-128)
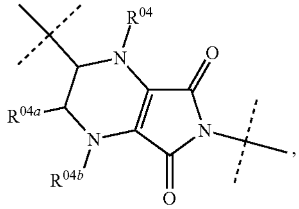
(x-129)
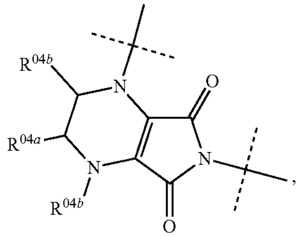
(x-130)
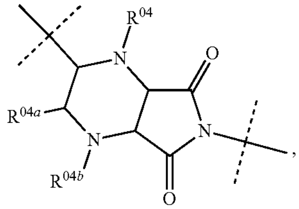

-continued
(x-131)
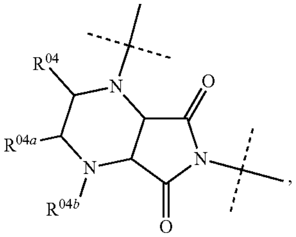
(x-132)
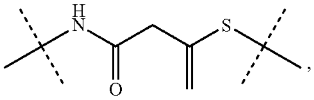
(x-133)
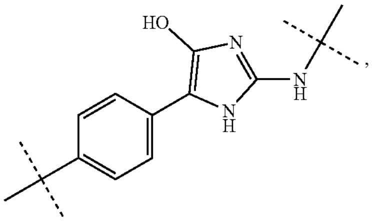
(x-134)
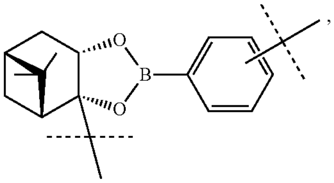
(x-135)
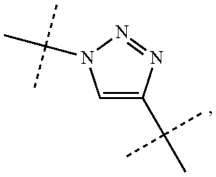
(x-136)
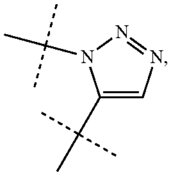
(x-137)
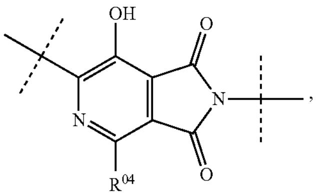
(x-138)
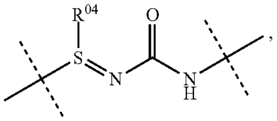
-continued
(x-139)
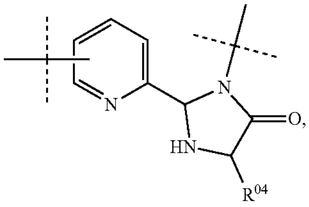
(x-140)
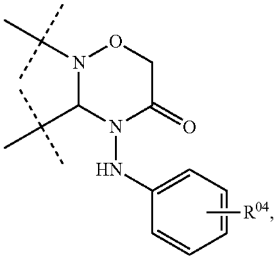
(x-141)
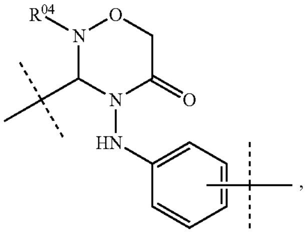
(x-142)
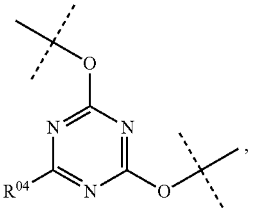
(x-143)
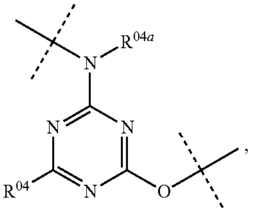
(x-144)
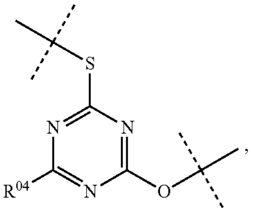
(x-145)
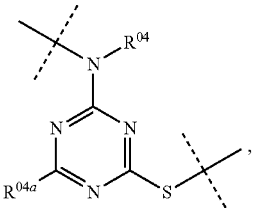

-continued
(x-146)
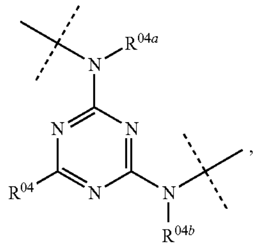
(x-147)
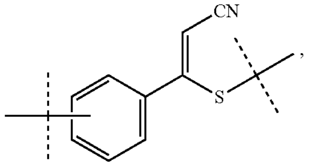
(x-148)
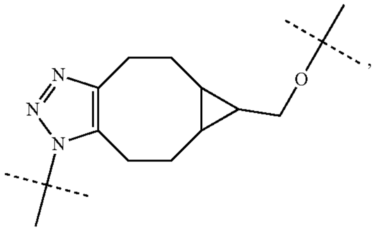
(x-149)
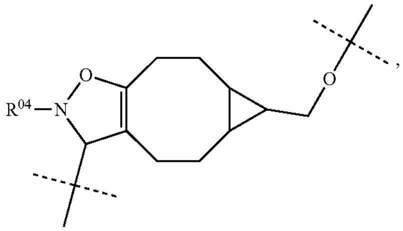
(x-150)
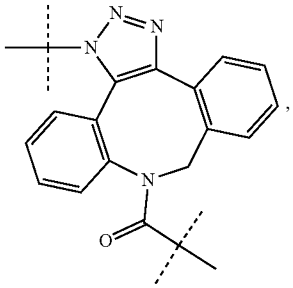
(x-151)
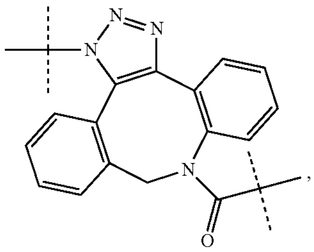
-continued
(x-152)
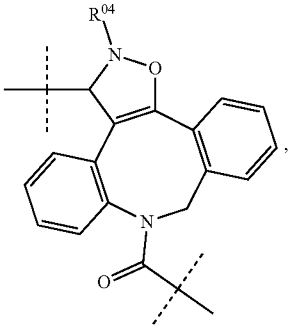
(x-153)
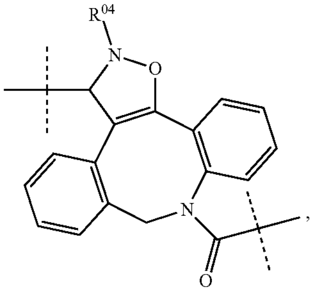
(x-154)
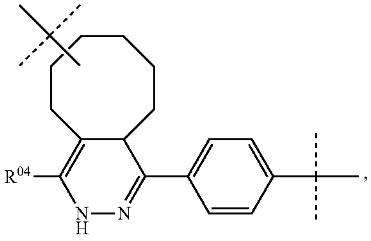
(x-155)
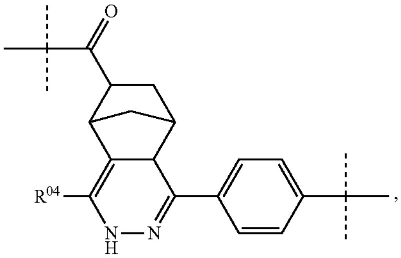
(x-156)
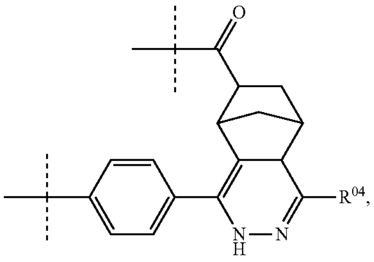
(x-157)
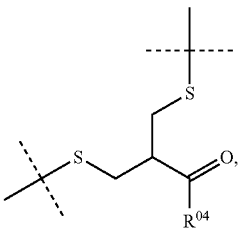

-continued
(x-158)
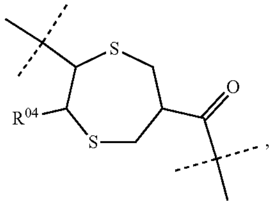
(x-159)
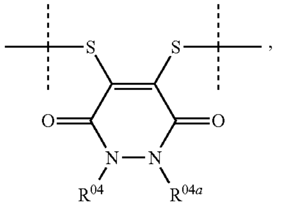
(x-160)
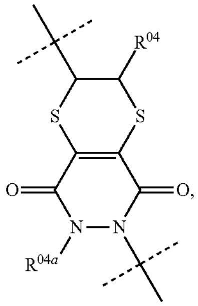
(x-161)
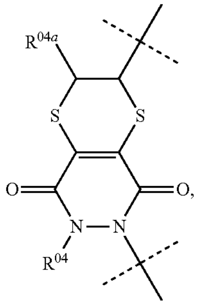
(x-162)
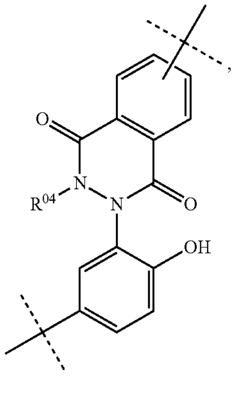
-continued
(x-163)
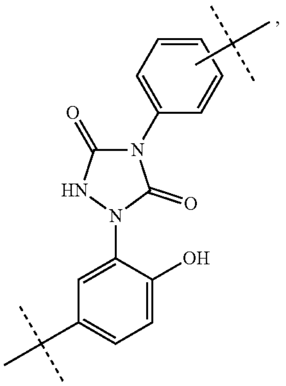
(x-164)
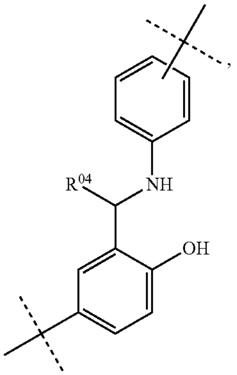
(x-165)
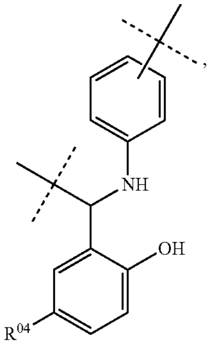
(x-166)
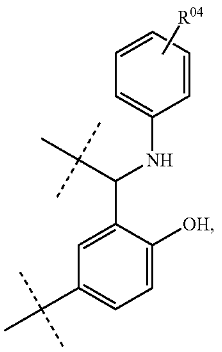
(x-167)
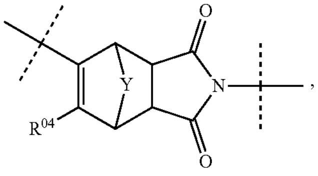

-continued (x-168)

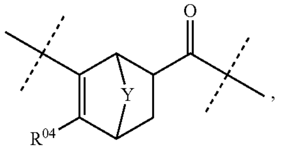

(x-169)

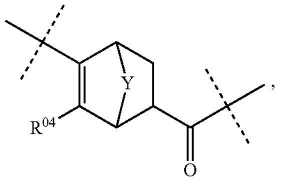

(x-170)

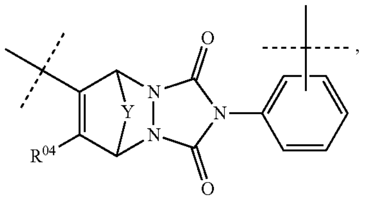

(x-171)

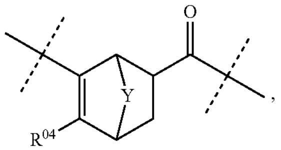

(x-172)

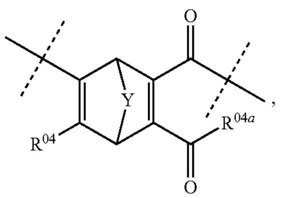

(x-173)

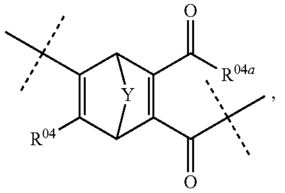

(x-174)

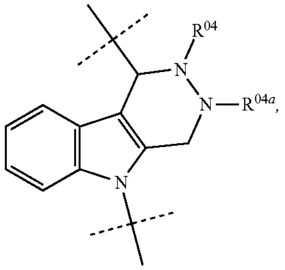

-continued (x-175)

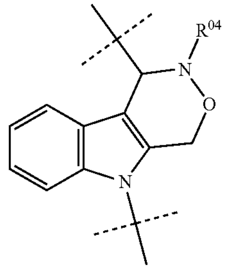

and (x-176)

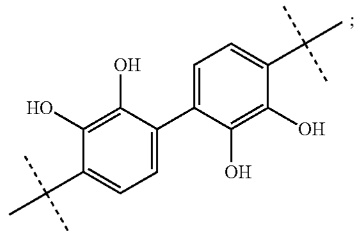

wherein

Y is selected from the group consisting of —O—, —S—, —$NR^{05}$—, —$CR^{05}R^{05a}$;

each —$R^{04}$, —$R^{04a}$, —$R^{04b}$, —$R^{04c}$, —$R^{05}$ and —$R^{05a}$ is independently selected from the group consisting of halogen, —H, —CN, -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more —$R^{06}$, which are the same or different, and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R0^7$)—, —$S(O)_2N(R^{07})$—, —$S(O)N(R^{07})$—, —$S(O)_2$—, —S(O)—, —$N(R^{07})S(O)_2N(R^{07a})$—, —S—, —$N(R^{07})$—, —$OC(OR^{07})(R^{07a})$—, —$N(R^{07})C(O)N(R^{07a})$—, and —$OC(O)N(R^{07})$—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{06}$, which are the same or different; and each —$R^{06}$, —$R^{07}$ and —$R^{07a}$ is independently selected from the group consisting of —H and $C_{1-6}$ alkyl; wherein $C_{1-6}$ alkyl is optionally substituted with one or more halogen, which are the same or different.

In certain embodiments each —$X^{0B}$—, $X^{0C}$—, —$X^{0D}$— and —$X^{0F}$— is independently a linkage selected from the group consisting of formula x-17, x-18, x-19, x-20, x-21, x-22, x-23, x-25, x-26, x-27, x-28, x-29, x-30, x-31, x-32, x-35, x-36, x-37, x-38, x-39, x-41, x-42, x-43, x-45, x-46, x-47, x-48, x-49, x-50, x-51, x-52, x-53, x-54, x-55, x-56, x-57, x-58, x-59, x-60, x-61, x-62, x-64, x-65, x-66, x-75, x-76, x-77, x-78, x-79, x-80, x-81, x-82, x-83, x-84, x-85, x-87, x-88, x-89, x-90, x-91, x-92, x-93, x-97, x-98, x-101, x-102, x-103, x-104, x-105, x-106, x-107, x-108, x-109, x-110, x-111, x-112, x-113, x-114, x-115, x-116, x-117, x-118, x-119, x-132, x-133, x-134, x-135, x-137, x-138, x-139, x-140, x-141, x-142, x-146, x-147, x-148, x-150, x-151, x-154, x-155, x-156, x-157, x-159, x-160, x-161, x-162, x-163, x-167, x-170, x-174, x-175 and x-176.

In certain embodiments each —$X^{0B}$—, $X^{0C}$—, —$X^{0D}$— and —$X^{0F}$— is independently a linkage selected from the group consisting of formula x-17, x-18, x-21, x-22, x-23, x-26, x-28, x-29, x-31, x-32, x-36, x-37, x-38, x-41, x-42, x-43, x-45, x-47, x-48, x-49, x-50, x-51, x-52, x-53, x-54, x-56, x-57, x-59, x-60, x-61, x-62, x-64, x-65, x-66, x-75, x-77, x-79, x-80, x-81, x-82, x-83, x-87, x-88, x-89, x-90, x-91, x-92, x-93, x-97, x-98, x-101, x-102, x-103, x-104, x-111, x-112, x-113, x-132, x-133, x-134, x-135, x-137, x-138, x-139, x-140, x-141, x-142, x-146, x-147, x-148, x-150, x-151, x-154, x-155, x-156, x-157, x-159, x-160, x-161, x-162, x-163, x-167, x-170, x-174, x-175 and x-176.

In certain embodiments each —$X^{0B}$—, —$X^{0C}$—, —$X^{0D}$— and —$X^{0F}$— is independently a linkage selected from the group consisting of formula x-17, x-18, x-21, x-22, x-31, x-36, x-37, x-38, x-42, x-45, x-47, x-50, x-51, x-54, x-56, x-59, x-88, x-89, x-90, x-91, x-92, x-93, x-97, x-101, x-102, x-104, x-113, x-132, x-135, x-147, x-148, x-150, x-151, x-154, x-155, x-156, x-157, x-159, x-163, x-167, x-170, x-174, x-175 and x-176.

In certain embodiments each —$X^{0B}$—, —$X^{0C}$—, —$X^{0D}$— and —$X^{0F}$— is independently a linkage selected from the group consisting of formula x-18, x-22, x-37, x-45, x-47, x-50, x-51, x-101, x-135, x-148, x-150 and x-151.

In certain embodiments —$X^{0B}$— is of formula x-18. In certain embodiments —$X^{0B}$— is of formula x-22. In certain embodiments $X^{0B}$— is of formula x-37. In certain embodiments —$X^{0B}$— is of formula x-45. In certain embodiments —$X^{0B}$— is of formula x-47. In certain embodiments —$X^{0B}$— is of formula x-50. In certain embodiments —$X^{0B}$— is of formula x-51. In certain embodiments —$X^{0B}$— is of formula x-101. In certain embodiments —$X^{0B}$— is of formula x-135. In certain embodiments —$X^{0B}$— is of formula x-148. In certain embodiments —$X^{0B}$— is of formula x-150. In certain embodiments —$X^{0B}$— is of formula x-151.

In certain embodiments —$X^{0C}$— is of formula x-18. In certain embodiments —$X^{0C}$— is of formula x-22. In certain embodiments —$X^{0C}$— is of formula x-37. In certain embodiments —$X^{0C}$— is of formula x-45. In certain embodiments —$X^{0C}$— is of formula x-47. In certain embodiments —$X^{0C}$— is of formula x-50. In certain embodiments —$X^{0C}$— is of formula x-51. In certain embodiments —$X^{0C}$— is of formula x-101. In certain embodiments —$X^{0C}$— is of formula x-135. In certain embodiments —$X^{0C}$— is of formula x-148. In certain embodiments —$X^{0C}$— is of formula x-150. In certain embodiments —$X^{0C}$— is of formula x-151.

In certain embodiments —$X^{0D}$— is of formula x-18. In certain embodiments —$X^{0D}$— is of formula x-22. In certain embodiments —$X^{0D}$— is of formula x-37. In certain embodiments —$X^{0D}$— is of formula x-45. In certain embodiments —$X^{0D}$— is of formula x-47. In certain embodiments —$X^{0D}$— is of formula x-50. In certain embodiments —$X^{0D}$— is of formula x-51. In certain embodiments —$X^{0D}$— is of formula x-101. In certain embodiments —$X^{0D}$— is of formula x-135. In certain embodiments —$X^{0D}$— is of formula x-148. In certain embodiments —$X^{0D}$— is of formula x-150. In certain embodiments —$X^{0D}$— is of formula x-151.

In certain embodiments —$X^{0F}$— is of formula x-18. In certain embodiments —$X^{0F}$— is of formula x-22. In certain embodiments —$X^{0F}$— is of formula x-37. In certain embodiments —$X^{0F}$— is of formula x-45. In certain embodiments —$X^{0F}$— is of formula x-47. In certain embodiments —$X^{0F}$— is of formula x-50. In certain embodiments —$X^{0F}$— is of formula x-51. In certain embodiments —$X^{0F}$— is of formula x-101. In certain embodiments —$X^{0F}$— is of formula x-135. In certain embodiments —$X^{0F}$— is of formula x-148. In certain embodiments —$X^{0F}$— is of formula x-150. In certain embodiments $X^{0F}$— is of formula x-151.

In certain embodiments each —$Y^{0A}$, —$Y^{0B}$, —$Y^{0C}$, —$Y^{0D}$ is individually selected from the group consisting of (y-1)

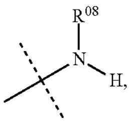

(y-2)

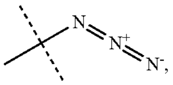

(y-3)

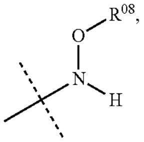

(y-4)

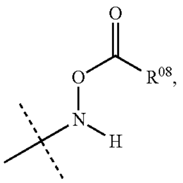

(y-5)

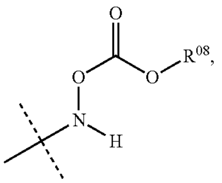

(y-6)

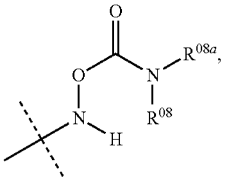

(y-7)

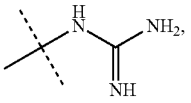

(y-8)

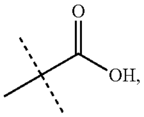

(y-9)

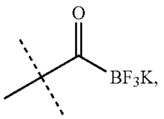

(y-10)

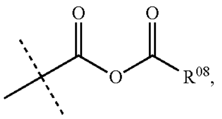

-continued
(y-11)
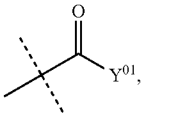
(y-12)
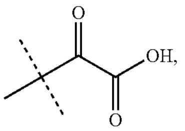
(y-13)
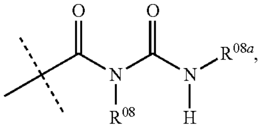
(y-14)
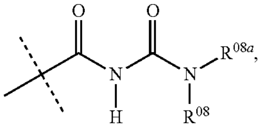
(y-15)
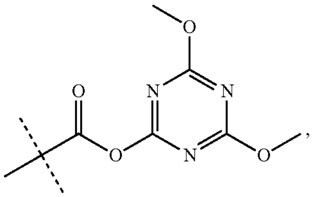
(y-16)
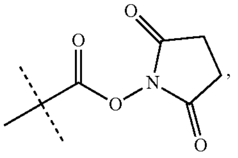
(y-17)
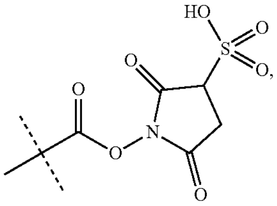
(y-18)
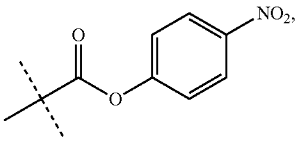
(y-19)
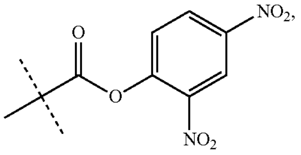
(y-20)
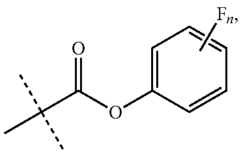
-continued
(y-21)
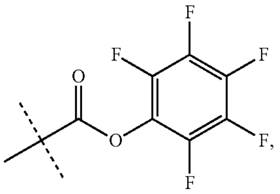
(y-22)
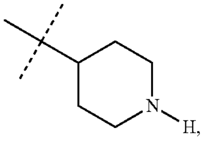
(y-22a)
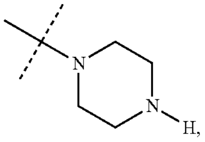
(y-23)
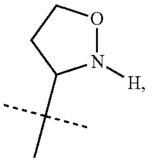
(y-24)
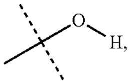
(y-25)
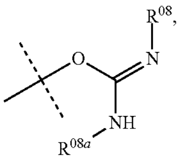
(y-26)
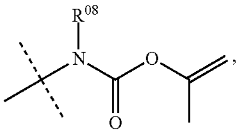
(y-27)
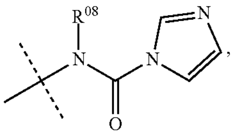
(y-28)
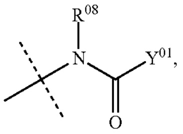
(y-29)
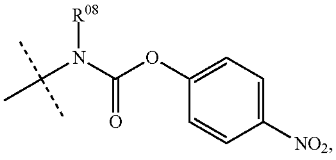

-continued
(y-30)
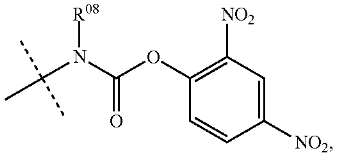
(y-31)
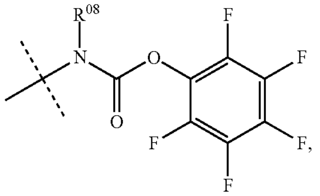
(y-32)
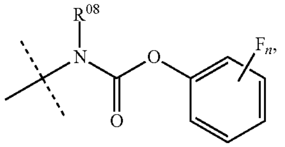
(y-33)
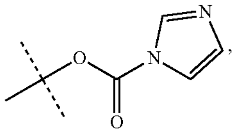
(y-34)
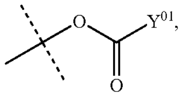
(y-35)
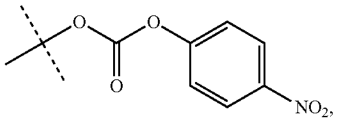
(y-36)
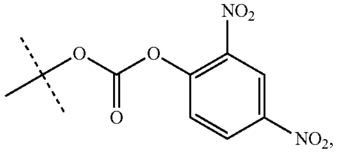
(y-37)
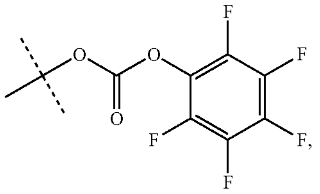
(y-38)
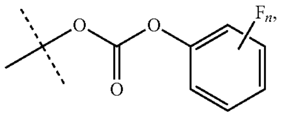
(y-39)
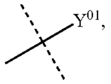
(y-40)
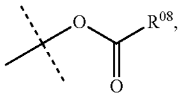
-continued
(y-41)
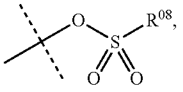
(y-42)
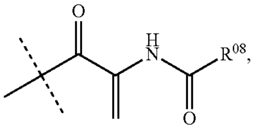
(y-43)
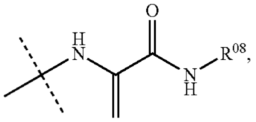
(y-44)
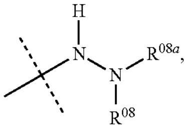
(y-45)
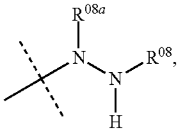
(y-46)
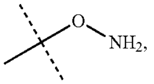
(y-47)
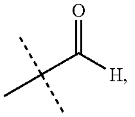
(y-48)
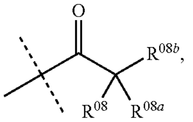
(y-49)
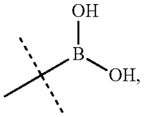
(y-50)
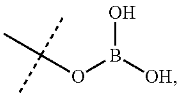
(y-51)
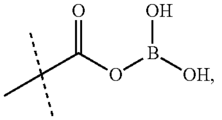
(y-52)
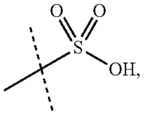

-continued
(y-53)
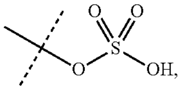
(y-54)
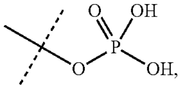
(y-55)
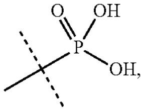
(y-56)
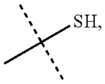
(y-57)
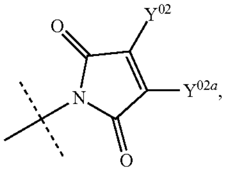
(y-58)
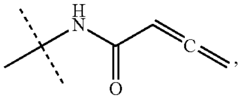
(y-59)
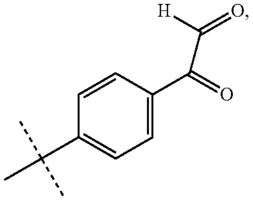
(y-60)
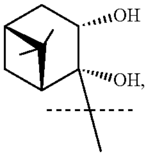
(y-61)
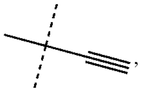
(y-62)
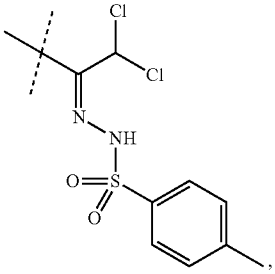
-continued
(y-63)
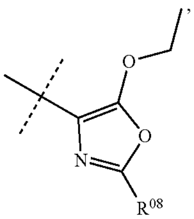
(y-64)
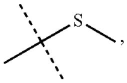
(y-65)
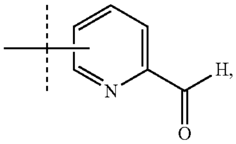
(y-66)
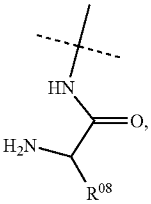
(y-67)
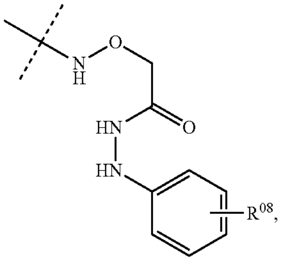
(y-68)
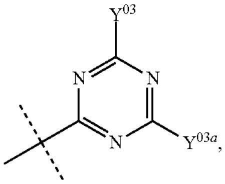
(y-69)
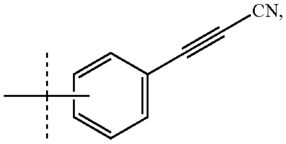
(y-70)
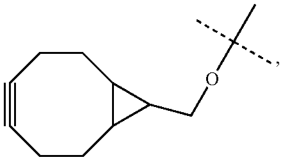

-continued
(y-71)
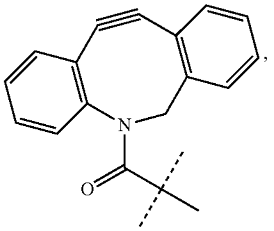
(y-72)
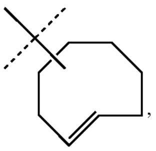
(y-73)
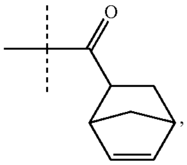
(y-74)
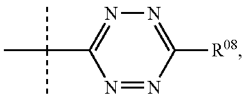
(y-75)
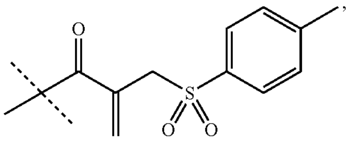
(y-76)
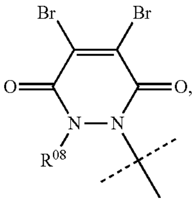
(y-77)
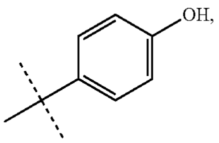
(y-78)
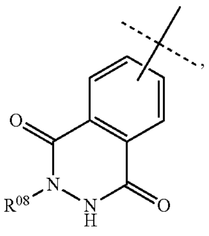
-continued
(y-79)
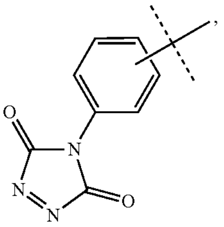
(y-80)
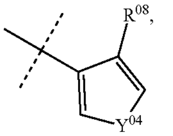
(y-81)
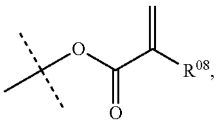
(y-82)
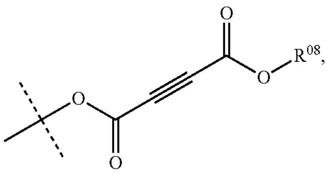
(y-83)
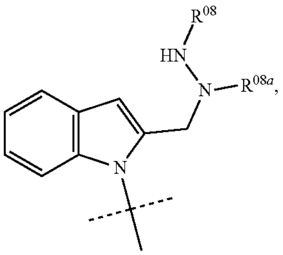
(y-84)
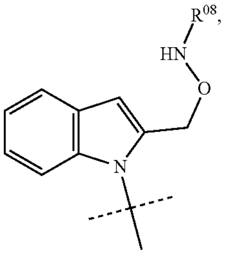
(y-85)
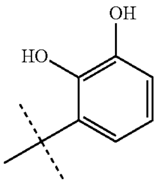
and
(y-86)
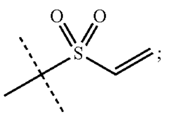
wherein
each —$R^{08}$, —$R^{08a}$ and —$R^{08b}$ is independently selected from the group consisting of halogen, —H, —CN, -$T^0$, $C_{1-50}$ alkyl, $C_{2-50}$ alkenyl, and $C_{2-50}$ alkynyl; wherein $-T^0$, $C_{1-50}$ alkyl, $C_{2-50}$ alkenyl, and $C_{2-50}$ alkynyl are optionally substituted with one or more $—R^{09}$ which are the same or different, and wherein $C_{1-50}$ alkyl, $C_{2-50}$ alkenyl, and $C_{2-50}$ alkynyl are optionally interrupted by one or more groups selected from the group consisting of $-T^0-$, —C(O)O—, —O—, —C(O)—, —C(O)N($R^{010}$)—, —$S(O)_2N(R^{010})$—, —$S(O)N(R^{010})$—, —$S(O)_2$—, —S(O)—, —$N(R^{010})S(O)_2N(R^{010a})$—, —S—, —$N(R^{010})$—, —$OC(OR^{010})(R^{010a})$—, —$N(R^{010})C(O)N(R^{010a})$—, and —$OC(O)N(R^{010})$—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more $—R^{09}$, which are the same or different;

each $—R^{09}$, $—R^{010}$ and $—R^{010a}$ is independently selected from the group consisting of —H and $C_{1-6}$ alkyl; wherein $C_{1-6}$ alkyl is optionally substituted with one or more halogen, which are the same or different;

each $T^y$ is independently a ring comprising 5, 6 or 7 atoms of which at least one is a heteroatom;

each $—Y^{01}$ is independently selected from the group consisting of —F, —Cl, —Br and —I; each n is independently 1, 2, 3 or 4;

each $—Y^{02}$ and $—Y^{02a}$ is independently selected from the group consisting of —H and —Br;

each $—Y^{03}$ and $—Y^{03a}$ is independently selected from the group consisting of —F, —Cl, —Br, —I, —OR, $—NR^{011}R^{011a}$ and $—SR^{011}$;

each $—Y^{04}—$ is independently selected from —O—, —S—, $—NR^{011}—$, $—CR^{011}R^{011a}—$; and each $—R^{011}$ and $—R^{011a}$ is independently selected from the group consisting of halogen, —H, —CN, $-T^0$, $C_{1-50}$ alkyl, $C_{2-50}$ alkenyl, and $C_{2-50}$ alkynyl; wherein $-T^0$, $C_{1-50}$ alkyl, $C_{2-50}$ alkenyl, and $C_{2-50}$ alkynyl are optionally substituted with one or more $—R^{012}$, which are the same or different, and wherein $C_{1-50}$ alkyl, $C_{2-50}$ alkenyl, and $C_{2-50}$ alkynyl are optionally interrupted by one or more groups selected from the group consisting of $-T^0-$, —C(O)O—, —O—, —C(O)—, —C(O)N($R^{013}$)—, —$S(O)_2N(R^{013})$—, —$S(O)N(R^{013})$—, —$S(O)_2$—, —S(O)—, —$N(R^{013})S(O)_2N(R^{013a})$—, —S—, —$N(R^{013})$—, —$OC(OR^{013})(R^{013a})$—, —$N(R^{013})C(O)N(R^{013a})$—, and —$OC(O)N(R^{013})$—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more $—R^{012}$, which are the same or different; and each $—R^{012}$, $—R^{013}$ and $—R^{013a}$ is independently selected from the group consisting of —H and $C_{1-6}$ alkyl; wherein $C_{1-6}$ alkyl is optionally substituted with one or more halogen, which are the same or different.

In certain embodiments each $—Y^{0A}$, $—Y^{0B}$, $—Y^{0C}$, $—Y^{0D}$ and $—Y^{0E}$ is independently a functional group selected from the group consisting of formula y-1, y-2, y-3, y-7, y-8, y-9, y-10, y-11, y-12, y-13, y-14, y-15, y-16, y-17, y-18, y-21, y-22, y-22a, y-23, y-24, y-27, y-28, y-29, y-31, y-33, y-35, y-37, y-39, y-40, y-41, y-42, y-43, y-45, y-46, y-47, y-49, y-52, y-53, y-54, y-55, y-56, y-57, y-59, y-61, y-62, y-64, y-70, y-71, y-72, y-73, y-74, y-77, y-79, y-80, y-85 and y-86.

In certain embodiments each $—Y^{0A}$, $—Y^{0B}$, $—Y^{0C}$, $—Y^{0D}$ and $—Y^{0E}$ is independently a functional group selected from the group consisting of formula y-1, y-2, y-3, y-7, y-8, y-9, y-12, y-13, y-14, y-15, y-16, y-17, y-18, y-21, y-22, y-22a, y-23, y-24, y-27, y-28, y-29, y-31, y-39, y-45, y-46, y-47, y-52, y-53, y-54, y-55, y-56, y-57, y-59, y-61, y-68, y-70, y-71, y-72, y-73, y-74, y-77, y-79, y-80, y-85 and y-86.

In certain embodiments each $—Y^{0A}$, $—Y^{0B}$, $—Y^{0C}$, $—Y^{0D}$ and $—Y^{0E}$ is independently a functional group selected from the group consisting of formula y-1, y-2, y-7, y-8, y-9, y-13, y-14, y-15, y-16, y-21, y-22, y-22a, y-24, y-39, y-56, y-57, y-60, y-70, y-71 and y-86.

In certain embodiments each $—Y^{0A}$, $—Y^{0B}$, $—Y^{0C}$, $—Y^{0D}$ and $—Y^{0E}$ is independently a functional group selected from the group consisting of formula y-1, y-2, y-8, y-9, y-13, y-14, y-16, y-22, y-22a, y-39, y-56, y-57, y-61, y-70, y-71 and y-86.

In certain embodiments each $—Y^{0A}$, $—Y^{0B}$, $—Y^{0C}$, $—Y^{0D}$ and $—Y^{0E}$ is independently a functional group selected from the group consisting of formula y-1, y-2, y-8, y-9, y-16, y-22, y-22a, y-39, y-56, y-57, y-61, y-70, y-71 and y-86.

In certain embodiments $—Y^{0A}$ is of formula y-1. In certain embodiments $—Y^{0A}$ is of formula y-2. In certain embodiments $—Y^{0A}$ is of formula y-8. In certain embodiments $—Y^{0A}$ is of formula y-9. In certain embodiments $—Y^{0A}$ is of formula y-16. In certain embodiments $—Y^{0A}$ is of formula y-22. In certain embodiments $—Y^{0A}$ is of formula y-22a. In certain embodiments $—Y^{0A}$ is of formula y-39. In certain embodiments $—Y^{0A}$ is of formula y-56. In certain embodiments $—Y^{0A}$ is of formula y-57. In certain embodiments $—Y^{0A}$ is of formula y-61. In certain embodiments $—Y^{0A}$ is of formula y-70. In certain embodiments $—Y^{0A}$ is of formula y-71. In certain embodiments $—Y^{0A}$ is of formula y-86.

In certain embodiments $—Y^{0B}$ is of formula y-1. In certain embodiments $—Y^{0B}$ is of formula y-2. In certain embodiments $—Y^{0B}$ is of formula y-8. In certain embodiments $—Y^{0B}$ is of formula y-9. In certain embodiments $—Y^{0B}$ is of formula y-16. In certain embodiments $—Y^{0B}$ is of formula y-22. In certain embodiments $—Y^{0B}$ is of formula y-22a. In certain embodiments $—Y^{0B}$ is of formula y-39. In certain embodiments $—Y^{0B}$ is of formula y-56. In certain embodiments $—Y^{0B}$ is of formula y-57. In certain embodiments $—Y^{0B}$ is of formula y-61. In certain embodiments $—Y^{0B}$ is of formula y-70. In certain embodiments $—Y^{0B}$ is of formula y-71. In certain embodiments $—Y^{0B}$ is of formula y-86.

In certain embodiments $—Y^{0C}$ is of formula y-1. In certain embodiments $—Y^{0C}$ is of formula y-2. In certain embodiments $—Y^{0C}$ is of formula y-8. In certain embodiments $—Y^{0C}$ is of formula y-9. In certain embodiments $—Y^{0C}$ is of formula y-16. In certain embodiments $—Y^{0C}$ is of formula y-22. In certain embodiments $—Y^{0C}$ is of formula y-22a. In certain embodiments $—Y^{0C}$ is of formula y-39. In certain embodiments $—Y^{0C}$ is of formula y-56. In certain embodiments $—Y^{0C}$ is of formula y-57. In certain embodiments $—Y^{0C}$ is of formula y-61. In certain embodiments $—Y^{0C}$ is of formula y-70. In certain embodiments $—Y^{0C}$ is of formula y-71. In certain embodiments $—Y^{0C}$ is of formula y-86.

In certain embodiments $—Y^{0D}$ is of formula y-1. In certain embodiment $—Y^{0D}$ is of formula y-2. In certain embodiments $—Y^{0D}$ is of formula y-8. In certain embodiments $—Y^{0D}$ is of formula y-9. In certain embodiments $—Y^{0D}$ is of formula y-16. In certain embodiments $—Y^{0D}$ is of formula y-22. In certain embodiments $—Y^{0D}$ is of formula y-22a. In certain embodiments $—Y^{0D}$ is of formula y-39. In certain embodiments —$Y^{0D}$ is of formula y-56. In certain embodiments —$Y^{0D}$ is of formula y-57. In certain embodiments —$Y^{0D}$ is of formula y-61. In certain embodiments —$Y^{0D}$ is of formula y-70. In certain embodiments —$Y^{0D}$ is of formula y-71. In certain embodiments —$Y^{0D}$ is of formula y-86.

In certain embodiments —$Y^{0E}$ is of formula y-1. In certain embodiments —$Y^{0E}$ is of formula y-2. In certain embodiments —$Y^{0E}$ is of formula y-8. In certain embodiments —$Y^{0E}$ is of formula y-9. In certain embodiments —$Y^{0E}$ is of formula y-16. In certain embodiments —$Y^{0E}$ is of formula y-22. In certain embodiments —$Y^{0E}$ is of formula y-22a. In certain embodiments —$Y^{0E}$ is Of formula y-39. In certain embodiments —$Y^{0E}$ is of formula y-56. In certain embodiments —$Y^{0E}$ of of formula y-57. In certain embodiments —$Y^{0E}$ is of formula y-61. In certain embodiments —$Y^{0E}$ is of formula y-70. In certain embodiments —$Y^{0E}$ is of formula y-71. In certain embodiments —$Y^{0E}$ is of formula y-86.

In certain embodiments —$Y^{0F}$ is selected from the group consisting of (y-87)

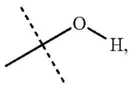

(y-88)

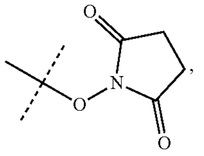

(y-89)

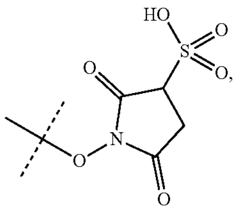

(y-90)

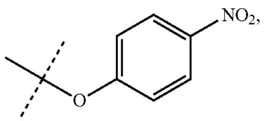

(y-91)

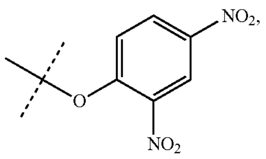

(y-92)

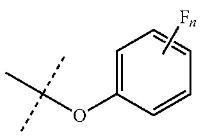

and

-continued (y-93)

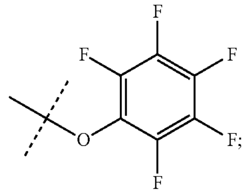

wherein each n is independently 1, 2, 3, or 4.

In certain embodiments each —$Y^{0F}$ is independently a functional group selected from the group consisting of formula y-87, y-88, y-89, y-90 and y-91.

In certain embodiments each —$Y^{0F}$ is independently a functional group selected from the group consisting of formula y-87, y-88 and y-93.

In certain embodiments all —$Y^{0F}$ present in the conjugates of the present invention are of formula y-87. In certain embodiments all —$Y^{0F}$ present in the conjugates of the present invention are of formula y-88. In certain embodiments all —$Y^{0F}$ present in the conjugates of the present invention are of formula y-93.

In certain embodiments each —$Y^{0F}$ is independently a functional group selected from the group consisting of formula y-87 and y-88.

Each —$Y^{0H}$ is independently selected from the group consisting of (y'-1)

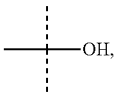

(y'-2)

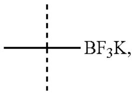

(y'-3)

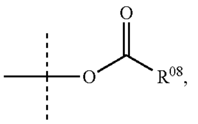

(y'-4)

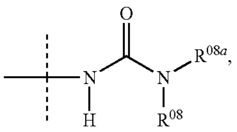

(y'-5)

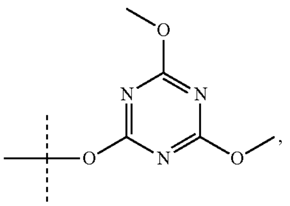

(y'-6)

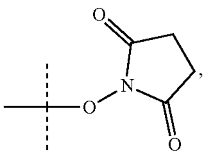

-continued (y'-7)

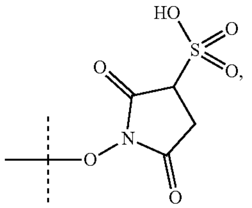

(y'-8)

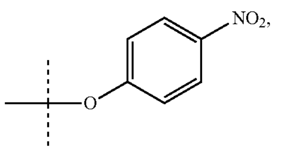

(y'-9)

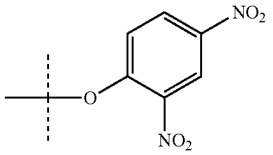

and (y'-10)

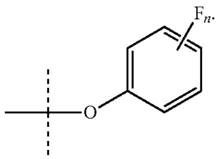

In certain embodiments —$Y^{0H}$ is of formula y'-1. In certain embodiments —$Y^{0H}$ is of formula y'-2. In certain embodiments —$Y^{0H}$ is of formula y'-3. In certain embodiments —$Y^{0H}$ is of formula y'-4. In certain embodiments —$Y^{0H}$ is of formula y'-5. In certain embodiments —$Y^{0H}$ is of formula y'-6. In certain embodiments —$Y^{0H}$ is of formula y'-7. In certain embodiments —$Y^{0H}$ is of formula y'-8. In certain embodiments —$Y^{0H}$ is of formula y'-9. In certain embodiments —$Y^{0H}$ is of formula y'-10.

The pharmaceutical compositions of the present invention comprise a conjugate of the present invention and at least one excipient. It is understood that more than one type of conjugate of the present invention may be present in such pharmaceutical composition.

In certain embodiments all moieties —$X^{0D}$— of units $Z^2$ und $Z^9$ are identical. In certain embodiments a conjugate of the present invention comprises more than one type of —$X^{0D}$—, such as two, three or four different types of —$X^{0D}$—. In certain embodiment one hyaluronic acid strand comprises only one type of —$X^{0D}$—. In certain embodiments the conjugates comprise a first type of hyaluronic acid strands with a first type of —$X^{0D}$— and a second type of hyaluronic acid strands with a second type of —$X^{0D}$— and optionally a third type of hyaluronic acid strand with a third type of —$X^{0D}$ and optionally a fourth type of hyaluronic acid strand with a fourth type of —$X^{0D}$—.

In certain embodiments —$X^{0D}$— of units $Z^2$ und $Z^9$ is a stable linkage, i.e -$L^1$- and —$X^{0D}$-$L^2$- are connected through a stable linkage.

In certain embodiments —$X^{0D}$— of units $Z^2$ und $Z^9$ is absent, in which case the moiety -$L^2$-$X^{0D}$-$L^1$- is a moiety -$L^2$-$L^1$-, wherein the bond between -$L^2$- and -$L^1$- is a stable bond.

-$L^2$- of $Z^2$, $Z^8$ and $Z^9$ is absent or a spacer moiety.

In certain embodiments -$L^2$- of $Z^2$, $Z^8$ and $Z^9$ is absent.

In certain embodiments -$L^2$- of $Z^2$, $Z^8$ and $Z^9$ is a spacer moiety.

In certain embodiments -$L^2$- of $Z^2$, $Z^8$ and $Z^9$ does not comprise a degradable bond, i.e. all bonds of -$L^2$- are stable bonds.

In certain embodiments -$L^2$- of $Z^2$, $Z^8$ and $Z^9$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2$N($R^{y3}$)—, —S(O)N($R^{y3}$)—, —$S(O)_2$—, —S(O)—, —N($R^{y3}$)$S(O)_2$N($R^{y3a}$)—, —S—, —N($R^{y3}$)—, —OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —$S(O)_2$N(Re)—, —S(O)N($R^{y4}$)—, —$S(O)_2$—, —S(O)—, —N($R^{y4}$)$S(O)_2$N($R^{y4a}$)—, —S—, —N($R^{y4}$)—, —OC($OR^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (=O), —$COOR^{y5}$, —$OR^{y5}$, —C(O)$R^{y5}$, —C(O)N($R^{y5}R^{y5a}$), —$S(O)_2$N($R^{y5}R^{y5a}$), —S(O)N($R^{y5}R^{y5a}$), —$S(O)_2R^{y5}$, —S(O)$R^{y5}$, —N($R^{y5}$)$S(O)_2$N($R^{y5a}R^{y5b}$), —$SR^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)$OR^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different, provided that -$L^2$- is attached to —$X^{0C}$— and —$X^{0D}$— via a carbon atom of -$L^2$-.

In certain embodiments -$L^2$- of $Z^2$, $Z^8$ and $Z^9$ is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —$S(O)_2$N($R^{y3}$)—, —S(O)N($R^{y3}$)—, —$S(O)_2$—, —S(O)—, —N($R^{y3}$)$S(O)_2$N($R^{y3a}$)—, —S—, —$N(R^{y3})$—, —$OC(OR^{y3})(R^{y3a})$—, —$N(R^{y3})C(O)N(R^{y3a})$—, and —$OC(O)N(R^{y3})$—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —$C(O)N(R^{y4})$—, —$S(O)_2N(Re)$—, —$S(O)N(R^{y4})$—, —$S(O)_2$—, —S(O)—, —$N(R^{y4})S(O)_2N(R^{y4a})$—, —S—, —$N(R^{y4})$—, —$OC(OR^{y4})(R^{y4a})$—, —$N(R^{y4})C(O)N(R^{y4a})$—, and —$OC(O)N(R^{y4})$—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (═O), —$COOR^{y5}$, —$OR^{y5}$, —$C(O)R^{y5}$, —$C(O)N(R^{y5}R^{y5a})$, —$S(O)_2N(R^{y5}R^{y5a})$, —$S(O)N(R^{y5}R^{y5a})$, —$S(O)_2R^{y5}$, —$S(O)R^{y5}$, —$N(R^{y5})S(O)_2N(R^{y5a}R^{y5b})$, —$SR^{y5}$, —$N(R^{y5}R^{y5a})$, —$NO_2$, —$OC(O)R^{y5}$, —$N(R^{y5})C(O)R^{y5a}$, —$N(R^{y5})S(O)_2R^{y5a}$, —$N(R^{y5})S(O)R^{y5a}$, —$N(R^{y5})C(O)OR^{y5a}$, —$N(R^{y5})C(O)N(R^{y5a}R^{y5b})$, —$OC(O)N(R^{y5}R^{y5a})$, and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^5$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^2$- is attached to —$X^{0C}$— and —$X^{0D}$— via a carbon atom of -$L^2$-.

In certain embodiments -$L^2$- of $Z^2$, $Z^8$ and $Z^9$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —$C(O)N(R^{y3})$—, —$S(O)_2N(R^{y3})$—, —$S(O)N(R^{y3})$—, —$S(O)_2$—, —S(O)—, —$N(R^{y3})S(O)_2N(R^{y3a})$—, —S—, —$N(R^{y3})$—, —$OC(OR^{y3})(R^{y3a})$—, —$N(R^{y3})C(O)N(R^{y3a})$—, and —$OC(O)N(R^{y3})$—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; each —$R^{y2}$ is independently selected from the group consisting of halogen and $C_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^2$- is attached to —$X^{0C}$— and —$X^{0D}$— via a carbon atom of -$L^2$-.

In certain embodiments -$L^2$- of $Z^2$, $Z^8$ and $Z^9$ is a $C_{1-20}$ alkyl chain, which is optionally interrupted by one or more groups independently selected from —O—, -T-, —$N(R^{y3})$— and —$C(O)N(R^{y1})$—; and which $C_{1-20}$ alkyl chain is optionally substituted with one or more groups independently selected from —OH, -T, —$N(R^{y3})$— and —$C(O)N(R^{y6}R^{y6a})$; wherein —$R^{y1}$, —$R^{y6}$, —$R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that -$L^2$- is attached to —$X^{0C}$— and —$X^{0D}$— via a carbon atom of -$L^2$-.

In certain embodiments -$L^2$- of $Z^2$, $Z^8$ and $Z^9$ has a molecular weight ranging from 14 g/mol to 750 g/mol.

In certain embodiments -$L^2$- of $Z^2$, $Z^8$ and $Z^9$ has a chain length ranging from 1 to 20 atoms.

In certain embodiments -$L^2$- of $Z^2$, $Z^8$ and $Z^9$ is a $C_{1-10}$ alkyl. In certain embodiments -$L^2$- of $Z^2$, $Z^8$ and $Z^9$ is a $C_1$ alkyl. In certain embodiments -$L^2$- of $Z^2$, $Z^8$ and $Z^9$ is a $C_2$ alkyl. In certain embodiments -L 2- of $Z^2$, $Z^8$ and $Z^9$ is a $C_8$ alkyl. In certain embodiments -$L^2$- of $Z^2$, $Z^8$ and $Z^9$ is a $C_4$ alkyl. In certain embodiments -$L^2$- of $Z^2$, $Z^8$ and $Z^9$ is a $C_C$ alkyl. In certain embodiments -$L^2$- of $Z^2$, $Z^8$ and $Z^9$ is a $C_6$ alkyl. In certain embodiments -$L^2$- of $Z^2$, $Z^8$ and $Z^9$ is a $C_7$ alkyl. In certain embodiments -$L^2$- of $Z^2$, $Z^8$ and $Z^9$ is a $C_8$ alkyl. In certain embodiments -$L^2$- of $Z^2$, $Z^8$ and $Z^9$ is a $C_9$ alkyl. In certain embodiments -$L^2$- of $Z^2$, $Z^8$ and $Z^9$ is a $C_{10}$ alkyl.

In certain embodiments all moieties —$X^{0C}$— are identical. In certain embodiments the conjugates comprise more than one type of —$X^{0C}$—, such as two, three or four different types of —$X^{0C}$—. In certain embodiment one hyaluronic acid strand comprises only one type of —$X^{0C}$—. In certain embodiments the conjugates comprise a first type of hyaluronic acid strands with a first type of —$X^{0C}$— and a second type of hyaluronic acid strands with a second type of —$X^{0C}$— and optionally a third type of hyaluronic acid strand with a third type of —$X^{0C}$— and optionally a fourth type of hyaluronic acid strand with a fourth type of —$X^{0C}$—.

In certain embodiments —$X^{0C}$— is absent.

In certain embodiments —$X^{0C}$— is a stable linkage, i.e -$L^2$- and -$L^3$- are connected through a stable linkage.

In certain embodiments —$X^{0C}$— is a moiety selected from the group consisting of

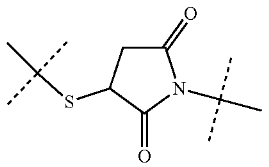

and

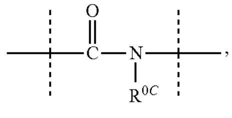

, wherein

—$R^{0C}$ selected from the group consisting of —H and $C_{1-6}$ alkyl.

In certain embodiments $—X^{0C}—$ is

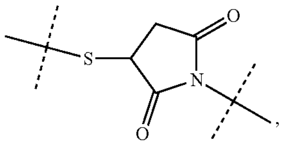

wherein the dashed lines indicate attachment to $-L^2-$ and $-L^3-$, respectively.

More specifically, in certain embodiments $—X^{0C}—$ is

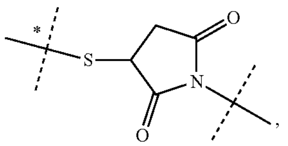

wherein the dashed line marked with the asterisk indicates attachment to $-L^2-$ and the unmarked dashed line indicates attachment to $-L^3-$.

$-L^3-$ is absent or a spacer moiety. In certain embodiments $-L^3-$ does not comprise a reversible linkage, i.e. all linkages in $-L^3-$ are stable linkages.

In certain embodiments $-L^3-$ is absent.

In certain embodiments $-L^3-$ is a spacer moiety.

In certain embodiments $-L^3-$ does not comprise a degradable bond, i.e. all bonds of $-L^3-$ are stable bonds.

In certain embodiments $-L^3-$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $—R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y4})—$, $—S(O)_2N(Re)—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$; each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

each $—R^{y2}$ is independently selected from the group consisting of halogen, —CN, oxo (=O), $—COOR^{y5}$, $—OR^{y5}$, $—C(O)R^{y5}$, $—C(O)N(R^{y5}R^{y5a})$, $—S(O)_2N(R^{y5}R^{y5a})$, $—S(O)N(R^{y5}R^{y5a})$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3a}$, $—R^{y4}$, $—R^{y4a}$, $—R^{y5}$, $—R^{y5a}$ and $—R^{y5b}$ is independently selected from the group consisting of —H, and $C_{1-6}$ alkyl, wherein $C_{1-6}$ alkyl is optionally substituted with one or more halogen, which are the same or different, provided that $-L^3-$ is attached to $—X^{0B}—$ and $—X^{0C}—$ via a carbon atom of $-L^3-$.

In certain embodiments $-L^3-$ is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $—R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more $—R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, $—C(O)N(R^{y4})—$, $—S(O)_2N(Re)—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

$—R^{y2}$ is selected from the group consisting of halogen, —CN, oxo (=O), $—COOR^{y5}$, $—OR^{y5}$, $—C(O)R^{y5}$, $—C(O)N(R^{y5}R^{y5a})$, $—S(O)_2N(R^{y5}R^{y5a})$, $—S(O)N(R^{y5}R^{y5a})$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^3$, $—R^{y3a}$, $—R^{y4}$, $—R^{y4a}$, $—R^5$, $—R^{y5a}$ and $—R^{y5b}$ is independently of each other selected from the group consisting of —H, and $C_{1-6}$ alkyl; wherein $C_{1-6}$ alkyl is optionally substituted with one or more halogen, which are the same or different, provided that $-L^3-$ is attached to $—X^{0B}—$ and $—X^{0C}—$ via a carbon atom of $-L^3-$.

In certain embodiments $-L^3-$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2N(R^{y3})$—, —S(O)N($R^{y3}$)—, —$S(O)_2$—, —S(O)—, —N($R^{y3}$)$S(O)_2N(R^{y3a})$—, —S—, —N($R^{y3}$)—, —OC($OR^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen and $C_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that -$L^3$- is attached to —$X^{0B}$— and —$X^{0C}$— via a carbon atom of -$L^3$-.

In certain embodiments -$L^3$- is a $C_{1-20}$ alkyl chain, which is optionally interrupted by one or more groups independently selected from —O—, -T-, —N($R^{y3}$)— and —C(O)N($R^{y1}$)—; and which $C_{1-20}$ alkyl chain is optionally substituted with one or more groups independently selected from —OH, -T, —N($R^{y3}$)— and —C(O)N($R^{y6}R^{y6a}$); wherein —$R^{y1}$, —$R^{y6}$, —$R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that -$L^3$- is attached to —$X^{0B}$— and —$X^{0C}$— via a carbon atom of -$L^3$-.

In certain embodiments -$L^3$- has a molecular weight ranging from 14 g/mol to 750 g/mol.

In certain embodiments -$L^3$- has a chain length ranging from 1 to 20 atoms.

In certain embodiments -$L^3$- is a $C_{1-10}$ alkyl. In certain embodiments -$L^3$- is a $C_1$ alkyl. In certain embodiments -$L^3$- is a $C_2$ alkyl. In certain embodiments -$L^3$- is a $C_3$ alkyl. In certain embodiments -$L^3$- is a $C_4$ alkyl. In certain embodiments -$L^3$- is a $C_5$ alkyl. In certain embodiments -$L^3$- is a $C_6$ alkyl. In certain embodiments -$L^3$- is a $C_7$ alkyl. In certain embodiments -$L^3$- is a $C_8$ alkyl. In certain embodiments -$L^3$- is a $C_9$ alkyl. In certain embodiments -$L^3$- is a $C_{10}$ alkyl.

In certain embodiments all moieties —$X^{0B}$— are identical. In certain embodiments a conjugate or the present invention comprises more than one type of —$X^{0B}$—, such as two, three or four different types of —$X^{0B}$—. In certain embodiment one hyaluronic acid strand comprises only one type of —$X^{0B}$—. In certain embodiments the conjugates comprise a first type of hyaluronic acid strands with a first type of —$X^{0B}$— and a second type of hyaluronic acid strands with a second type of —$X^{0B}$— and optionally a third type of hyaluronic acid strand with a third type of —$X^{0B}$— and optionally a fourth type of hyaluronic acid strand with a fourth type of —$X^{0B}$—.

In certain embodiments —$X^{0B}$— is absent.

In certain embodiments —$X^{0B}$— is a stable linkage, i.e -$L^3$- and -$L^4$- are connected through a stable linkage.

In certain embodiments —$X^{0B}$— is a moiety selected from the group consisting of

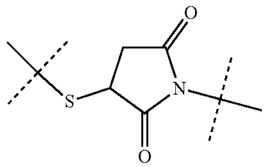

and

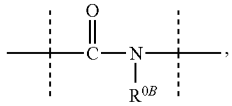, wherein

—$R^{0B}$ selected from the group consisting of —H and $C_{1-10}$ alkyl.

In certain embodiments —$R^{0B}$ is a —H. In certain embodiments —$R^{0B}$ is a $C_{1-10}$ alkyl. In certain embodiments —$R^{0B}$ is a C alkyl. In certain embodiments —$R^{0B}$ is a $C_2$. In certain embodiments —$R^{0B}$ is a $C_3$ alkyl. In certain embodiments —$R^{0B}$ is a $C_4$ alkyl. In certain embodiments —$R^{0B}$ is a $C_5$ alkyl. In certain embodiments —$R^{0B}$ is a C6 alkyl. In certain embodiments —$R^{0B}$ is a $C_7$ alkyl. In certain embodiments —$R^{0B}$ is a $C_8$ alkyl. In certain embodiments —$R^{0B}$ is a $C_9$ alkyl. In certain embodiments —RB is a $C_{10}$ alkyl.

In certain embodiments —$X^{0B}$—

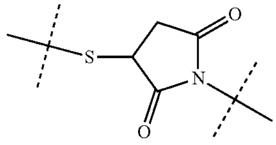, wherein the dashed lines indicate attachment to -$L^3$- and -$L^4$-, respectively.

In certain embodiments —$X^{0B}$— is

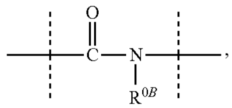, wherein the dashed lines indicate attachment to -$L^3$- and -$L^4$-, respectively.

In certain embodiments —$X^{0B}$— is

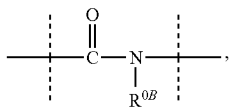, wherein the dashed line marked with the asterisk indicates attachment to -$L^3$- and the unmarked dashed line indicates attachment to -$L^4$-.

-$L^4$- is absent or a spacer moiety. In certain embodiments -$L^4$- does not comprise a reversible linkage, i.e. all linkages in -$L^4$- are stable linkages.

In certain embodiments -$L^4$- is absent.

In certain embodiments -$L^4$- is a spacer moiety.

In certain embodiments $-L^4-$ does not comprise a degradable bond, i.e. all bonds of $-L^4-$ are stable bonds.

In certain embodiments $-L^4-$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $—R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y4})—$, $—S(O)_2N(R^{y4})—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

each $—R^{y2}$ is independently selected from the group consisting of halogen, —CN, oxo (=O), $—COOR^{y5}$, $—OR^{y5}$, $—C(O)R^{y5}$, $—C(O)N(R^{y5}R^{y5a})$, $—S(O)_2N(R^{y5}R^{y5a})$, $—S(O)N(R^{y5}R^{y5a})$, $—S(O)_2R^{y5}$, $—S(O)R^{y5}$, $—N(R^{y5})S(O)_2N(R^{y5a}R^{y5}b)$, $—SR^5$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3a}$, $R^4$, $—R^{y4a}$, $—R^5$, $—R^{y5a}$ and $—R^{y5b}$ is independently selected from the group consisting of —H, and $C_{1-6}$ alkyl, wherein $C_{1-6}$ alkyl is optionally substituted with one or more halogen, which are the same or different, provided that $-L^4-$ is attached to $—X^{0A}—$ and $—X^{0B}—$ via a carbon atom of $-L^4-$.

In certain embodiments $-L^4-$ is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more $—R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more $—R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, $—C(O)N(R^{y4})—$, $—S(O)_2N(Re)—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

$—R^{y2}$ is selected from the group consisting of halogen, —CN, oxo (=O), $—COOR^{y5}$, $—OR^5$, $—C(O)R^{y5}$, $—C(O)N(R^{y5}R^{y5a})$, $—S(O)_2N(R^{y5}R^{y5a})$, $—S(O)N(R^{y5}R^{y5a})$, $—S(O)_2R^{y5}$, $—S(O)R^{y5}$, $—N(R^{y5})S(O)_2N(R^{y5a}R^{y5b})$, $—SR^{y5}$, $—N(R^{y5}R^{y5a})$, $—NO_2$, $—OC(O)R^{y5}$, $—N(R^{y5})C(O)R^{y5a}$, $—N(R^{y5})S(O)_2R^{y5a}$, $—N(R^{y5})S(O)R^{y5a}$, $—N(R^{y5})C(O)OR^{y5a}$, $—N(R^{y5})C(O)N(R^{y5a}R^{y5b})$, $—OC(O)N(R^{y5}R^{y5a})$, and $C_{1-6}$ alkyl; wherein $C_{1-6}$ alkyl is optionally substituted with one or more halogen, which are the same or different; and each $—R^{y3}$, $—R^{y3a}$, $—R^{y4}$, $—R^{y4a}$, $—R^{y5}$, $—R^{y5a}$ and $—R^{y5b}$ is independently of each other selected from the group consisting of —H, and $C_{1-6}$ alkyl; wherein $C_{1-6}$ alkyl is optionally substituted with one or more halogen, which are the same or different, provided that $-L^4-$ is attached to $—X^{0A}—$ and $—X^{0B}—$ via a carbon atom of $-L^4-$.

In certain embodiments $-L^4-$ is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; each $—R^{y2}$ is independently selected from the group consisting of halogen and $C_{1-6}$ alkyl; and each $—R^3$, $—R^{y3a}$, $—R^{y4}$, $—R^{y4a}$, $R^5$, $—R^{y5a}$ and $—R^{y5b}$ is independently of each other selected from the group consisting of —H, and $C_{1-6}$ alkyl; wherein $C_{1-6}$ alkyl is optionally substituted with one or more halogen, which are the same or different, provided that $-L^4-$ is attached to $—X^{0A}—$ and $—X^{0B}—$ via a carbon atom of $-L^4-$.

In certain embodiments $-L^4-$ is a $C_{1-20}$ alkyl chain, which is optionally interrupted by one or more groups independently selected from —O—, -T-, $—N(R^{y3})—$ and —C(O)

N($R^{y1}$)—; and which $C_{1-20}$ alkyl chain is optionally substituted with one or more groups independently selected from —OH, -T, —N($R^{y3}$)— and —C(O)N($R^{y6}R^{y6a}$); wherein —$R^{y1}$, —$R^{y6}$, —$R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that -$L^4$- is attached to —$X^{0A}$— and —$X^{0B}$— via a carbon atom of -$L^4$-.

In certain embodiments -$L^4$- has a molecular weight ranging from 14 g/mol to 750 g/mol.

In certain embodiments -$L^4$- has a chain length ranging from 1 to 20 atoms.

In certain embodiments -$L^4$- is a $C_{1-10}$ alkyl. In certain embodiments -$L^4$- is a $C_1$ alkyl. In certain embodiments -$L^4$- is a $C_2$ alkyl. In certain embodiments -$L^4$- is a $C_3$ alkyl. In certain embodiments -$L^4$- is a $C_4$ alkyl. In certain embodiments -$L^4$- is a $C_5$ alkyl. In certain embodiments -$L^4$- is a $C_6$ alkyl. In certain embodiments -$L^4$- is a $C_7$ alkyl. In certain embodiments -$L^4$- is a $C_8$ alkyl. In certain embodiments -$L^4$- is a $C_9$ alkyl. In certain embodiments -$L^4$- is a $C_{10}$ alkyl.

In certain embodiments all moieties $X^{0A}$— are identical. In certain embodiments the conjugates comprise more than one type of —$X^{0A}$—, such as two, three or four different types of —$X^{0A}$—. In certain embodiment one hyaluronic acid strand comprises only one type of —$X^{0A}$—. In certain embodiments the conjugates comprise a first type of hyaluronic acid strands with a first type of —$X^{0A}$— and a second type of hyaluronic acid strands with a second type of —$X^{0A}$— and optionally a third type of hyaluronic acid strand with a third type of —$X^{0A}$— and optionally a fourth type of hyaluronic acid strand with a fourth type of —$X^{0A}$—.

In certain embodiments —$X^{0A}$ is absent.

In certain embodiments $X^{0A}$— forms together with the carbonyl to which it is attached a stable linkage, i.e -$L^4$- and the remainder of the unit $Z^2$ are connected through a stable linkage.

In certain embodiments $X^{0A}$— is

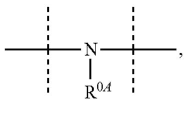

wherein the dashed lines indicate attachment to -$L^4$- and to the remainder of $Z^2$, respectively; and —$R^{0A}$ selected from the group consisting of —H, methyl, ethyl, propyl, isobutyl, n-butyl, sec-butyl, isobutyl, tert-butyl, pentyl, 2-methylbutan-2-yl, 2,2-dimethylpropyl, 3-methylbutyl, pentan-2-yl, pentan-3-yl, 3-methylbutan-2-yl and 2-methylbutyl.

In certain embodiments —$X^{0A}$— is

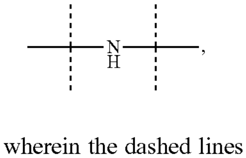

wherein the dashed lines indicate attachment to -$L^4$- and to the remainder of $Z^2$, respectively.

In certain embodiments the only reversible bond in a moiety —$X^{0A}$-$L^4$-$X^{0B}$-$L^3$-$X^{0C}$-$L^2$-$X^{0D}$-$L^1$-D is the bond that connects -$L^1$- and -D, which leads to the drug being released in its free form.

In certain embodiments the moiety —$X^{0A}$-$L^4$-$X^{0B}$-$L^3$-$X^{0C}$-$L^2$-$X^{0D}$— is of formula (i)

(i)

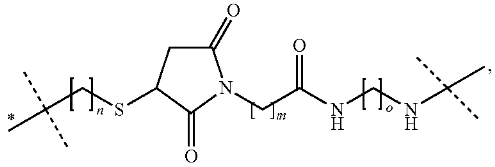

wherein the dashed line marked with the asterisk indicates attachment to -$L^1$-;

the unmarked dashed line indicates attachment to the remainder of $Z^2$;

n is selected from the group consisting of 0, 1, 2, 3, 4, 5, 6, 7, 8, 9, 10, 11, 12, 13, 14, 15, 16, 17 and 18;

m is selected from the group consisting of 1, 2, 3, 4, 5, 6, 7, 8, 9, 10, 11, 12, 13, 14, 15, 16, 17 and 18;

o is selected from the group consisting of 1, 2, 3, 4, 5, 6, 7, 8, 9, 10, 11, 12, 13, 14, 15, 16, 17 and 18; and wherein the moiety of formula (i) is optionally further substituted.

It is understood that in formula (i) —$X^{0D}$— is absent.

In certain embodiments n of formula (i) is selected from the group consisting of 3, 4, 5, 6, 7, 8, and 9. In certain embodiments n of formula (i) is 3, 4, 5, 6, or 7. In certain embodiments n of formula (i) is 3. In certain embodiments n of formula (i) is 4. In certain embodiments n of formula (i) is 5. In certain embodiments n of formula (i) is 6.

In certain embodiments m of formula (i) is selected from the group consisting of 1, 2, 3, 4, 5, 6 or 7. In certain embodiments m of formula (i) is 1, 2, 3, 4 or 5. In certain embodiments m of formula (i) is 1. In certain embodiments m of formula (i) is 2. In certain embodiments m of formula (i) is 3. In certain embodiments m of formula (i) is 4.

In certain embodiments o of formula (i) is selected from the group consisting of 1, 2, 3, 4, 5, 6 or 7. In certain embodiments o of formula (i) is 1, 2, 3, 4 or 5. In certain embodiments o of formula (i) is 1. In certain embodiments o of formula (i) is 2. In certain embodiments o of formula (i) is 3. In certain embodiments o of formula (i) is 4.

In certain embodiments the moiety —$X^{0A}$-$L^4$-$X^{0B}$-$L^3$-$X^{0C}$-$L^2$-$X^{0D}$-$L^1$- is selected from the group consisting of (Ia-i)

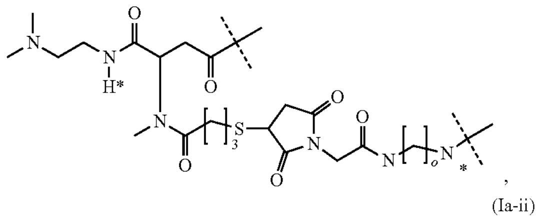

, (Ia-ii)

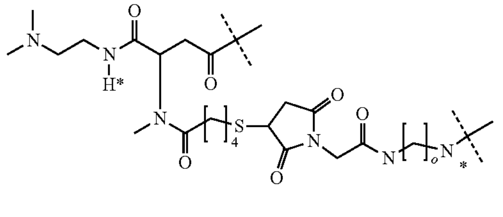

-continued
(Ia-iii)
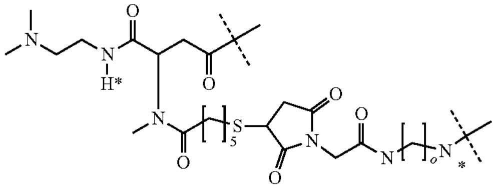
(Ia-iv)
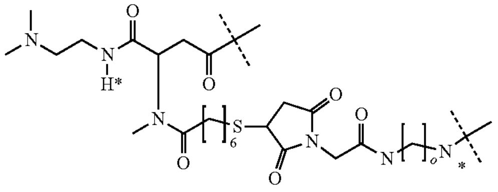
,
(Ib-i)
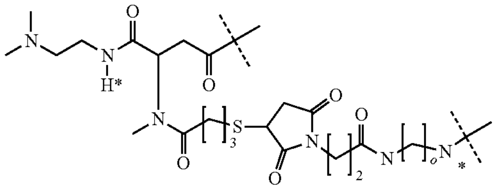
,
(Ib-ii)
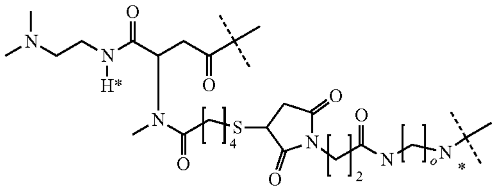
,
(Ib-iii)
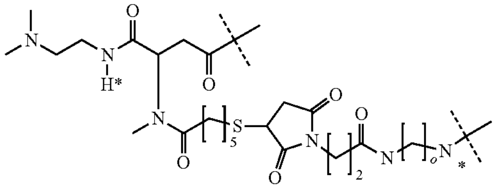
,
(Ib-iv)
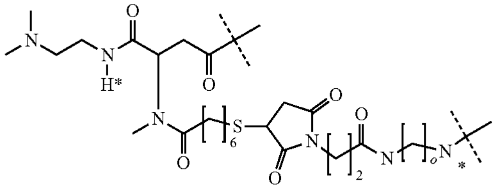
,
(Ic-i)
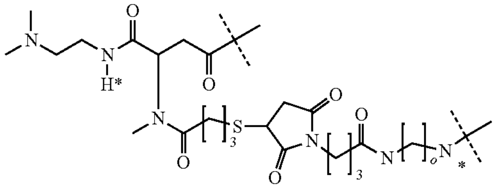
,
-continued
(Ic-ii)
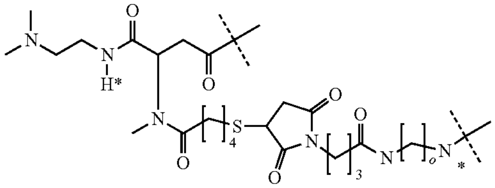
,
(Ic-iii)
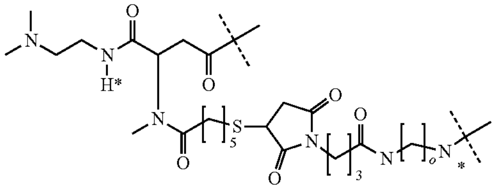
,
(Ic-iv)
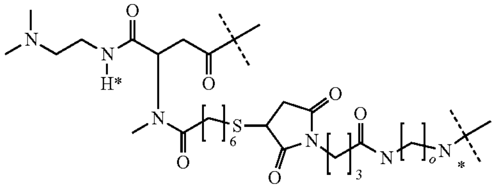
,
(Id-i)
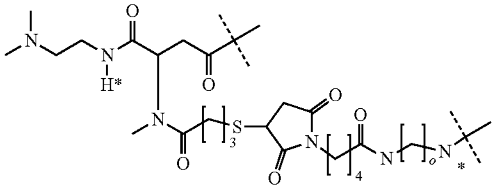
,
(Id-ii)
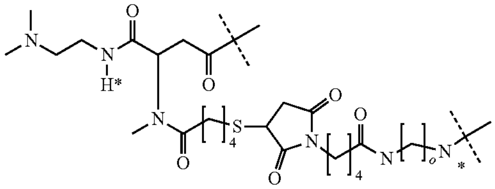
,
(Id-iii)
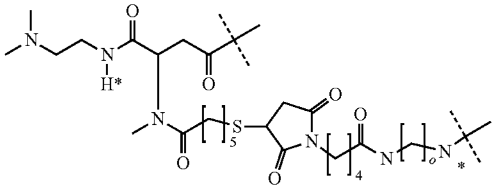
,
(Id-iv)
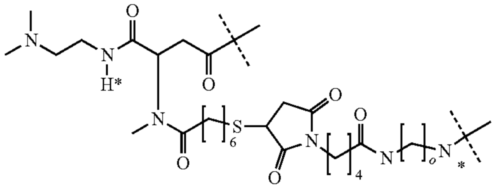
,
wherein
the unmarked dashed line indicates the attachment to a nitrogen of -D by forming an amide bond;

o is selected from the group consisting of 1, 2, 3 and 4; and the dashed line marked with the asterisk indicates attachment to the remainder of $Z^2$.

In certain embodiments the moiety —$X^{0A}$-$L^4$-$X^{0B}$-$L^3$-$X^{0C}$-$L^2$-$X^{0D}$-$L^1$- is of formula (Ia-i) with o being 1. In certain embodiments the moiety —$X^{0A}$-$L^4$-$X^{0B}$-$L^3$-$X^{0C}$-$L^2$-$X^{0D}$-$L^1$- is of formula (Ia-i) with o being 2. In certain embodiments the moiety —$X^{0A}$-$L^4$-$X^{0B}$-$L^3$-$X^{0C}$-$L^2$-$X^{0D}$-$L^1$- is of formula (Ia-i) with o being 3. In certain embodiments the moiety —$X^{0A}$-$L^4$-$X^{0B}$-$L^3$-$X^{0C}$-$L^2$-$X^{0D}$-$L^1$- is of formula (Ia-i) with o being 4.

In certain embodiments the moiety —$X^{0A}$-$L^4$-$X^{0B}$-$L^3$-$X^{0C}$-$L^2$-$X^{0D}$-$L^1$- is of formula (Ia-ii) with o being 1. In certain embodiments the moiety —$X^{0A}$-$L^4$-$X^{0B}$-$L^3$-$X^{0C}$-$L^2$-$X^{0D}$-$L^1$- is of formula (Ia-ii) with o being 2. In certain embodiments the moiety —$X^{0A}$-$L^4$-$X^{0B}$-$L^3$-$X^{0C}$-$L^2$-$X^{0D}$-$L^1$- is of formula (Ia-ii) with o being 3. In certain embodiments the moiety —$X^{0A}$-$L^4$-$X^{0B}$-$L^3$-$X^{0C}$-$L^2$-$X^{0D}$-$L^1$- is of formula (Ia-ii) with o being 4.

In certain embodiments the moiety —$X^{0A}$-$L^4$-$X^{0B}$-$L^3$-$X^{0C}$-$L^2$-$X^{0D}$-$L^1$- is of formula (Ia-iii) with o being 1. In certain embodiments the moiety —$X^{0A}$-$L^4$-$X^{0B}$-$L^3$-$X^{0C}$-$L^2$-$X^{0D}$-$L^1$- is of formula (Ia-iii) with o being 2. In certain embodiments the moiety —$X^{0A}$-$L^4$-$X^{0B}$-$L^3$-$X^{0C}$-$L^2$-$X^{0D}$-$L^1$- is of formula (Ia-iii) with o being 3. In certain embodiments the moiety —$X^{0A}$-$L^4$-$X^{0B}$-$L^3$-$X^{0C}$-$L^2$-$X^{0D}$-$L^1$- is of formula (Ia-iii) with o being 4.

In certain embodiments the moiety —$X^{0A}$-$L^4$-$X^{0B}$-$L^3$-$X^{0C}$-$L^2$-$X^{0D}$-$L^1$- is of formula (Ia-iv) with o being 1. In certain embodiments the moiety —$X^{0A}$-$L^4$-$X^{0B}$-$L^3$-$X^{0C}$-$L^2$-$X^{0D}$-$L^1$- is of formula (Ia-iv) with o being 2. In certain embodiments the moiety —$X^{0A}$-$L^4$-$X^{0B}$-$L^3$-$X^{0C}$-$L^2$-$X^{0D}$-$L^1$- is of formula (Ia-iv) with o being 3. In certain embodiments the moiety —$X^{0A}$-$L^4$-$X^{0B}$-$L^3$-$X^{0C}$-$L^2$-$X^{0D}$-$L^1$- is of formula (Ia-iv) with o being 4.

In certain embodiments the moiety —$X^{0A}$-$L^4$-$X^{0B}$-$L^3$-$X^{0C}$-$L^2$-$X^{0D}$-$L^1$- is of formula (Ib-i) with o being 1. In certain embodiments the moiety —$X^{0A}$-$L^4$-$X^{0B}$-$L^3$-$X^{0C}$-$L^2$-$X^{0D}$-$L^1$- is of formula (Ib-i) with o being 2. In certain embodiments the moiety —$X^{0A}$-$L^4$-$X^{0B}$-$L^3$-$X^{0C}$-$L^2$-$X^{0D}$-$L^1$- is of formula (Ib-i) with o being 3 In certain embodiments the moiety —$X^{0A}$-$L^4$-$X^{0B}$-$L^3$-$X^{0C}$-$L^2$-$X^{0D}$-$L^1$- is of formula (Ib-i) with o being 4.

In certain embodiments the moiety —$X^{0A}$-$L^4$-$X^{0B}$-$L^3$-$X^{0C}$-$L^2$-$X^{0D}$-$L^1$- is of formula (Ib-ii) with o being 1. In certain embodiments the moiety —$X^{0A}$-$L^4$-$X^{0B}$-$L^3$-$X^{0C}$-$L^2$-$X^{0D}$-$L^1$- is of formula (Ib-ii) with o being 2. In certain embodiments the moiety —$X^{0A}$-$L^4$-$X^{0B}$-$L^3$-$X^{0C}$-$L^2$-$X^{0D}$-$L^1$- is of formula (Ib-ii) with o being 3. In certain embodiments the moiety —$X^{0A}$-$L^4$-$X^{0B}$-$L^3$-$X^{0C}$-$L^2$-$X^{0D}$-$L^1$- is of formula (Ib-ii) with o being 4.

In certain embodiments the moiety —$X^{0A}$-$L^4$-$X^{0B}$-$L^3$-$X^{0C}$-$L^2$-$X^{0D}$-$L^1$- is of formula (Ib-iii) with o being 1. In certain embodiments the moiety —$X^{0A}$-$L^4$-$X^{0B}$-$L^3$-$X^{0C}$-$L^2$-$X^{0D}$-$L^1$- is of formula (Ib-iii) with o being 2. In certain embodiments the moiety —$X^{0A}$-$L^4$-$X^{0B}$-$L^3$-$X^{0C}$-$L^2$-$X^{0D}$-$L^1$- is of formula (Ib-iii) with o being 3. In certain embodiments the moiety —$X^{0A}$-$L^4$-$X^{0B}$-$L^3$-$X^{0C}$-$L^2$-$X^{0D}$-$L^1$- is of formula (Ib-iii) with o being 4.

In certain embodiments the moiety —$X^{0A}$-$L^4$-$X^{0B}$-$L^3$-$X^{0C}$-$L^2$-$X^{0D}$-$L^1$- is of formula (Ib-iv) with o being 1. In certain embodiments the moiety —$X^{0A}$-$L^4$-$X^{0B}$-$L^3$-$X^{0C}$-$L^2$-$X^{0D}$-$L^1$- is of formula (Ib-iv) with o being 2. In certain embodiments the moiety —$X^{0A}$-$L^4$-$X^{0B}$-$L^3$-$X^{0C}$-$L^2$-$X^{0D}$-$L^1$- is of formula (Ib-iv) with o being 3. In certain embodiments the moiety —$X^{0A}$-$L^4$-$X^{0B}$-$L^3$-$X^{0C}$-$L^2$-$X^{0D}$-$L^1$- is of formula (Ib-iv) with o being 4.

In certain embodiments the moiety —$X^{0A}$-$L^4$-$X^{0B}$-$L^3$-$X^{0C}$-$L^2$-$X^{0D}$-$L^1$- is of formula (Ic-i) with o being 1. In certain embodiments the moiety —$X^{0A}$-$L^4$-$X^{0B}$-$L^3$-$X^{0C}$-$L^2$-$X^{0D}$-$L^1$- is of formula (Ic-i) with o being 2. In certain embodiments the moiety —$X^{0A}$-$L^4$-$X^{0B}$-$L^3$-$X^{0C}$-$L^2$-$X^{0D}$-$L^1$- is of formula (Ic-i) with o being 3. In certain embodiments the moiety —$X^{0A}$-$L^4$-$X^{0B}$-$L^3$-$X^{0C}$-$L^2$-$X^{0D}$-$L^1$- is of formula (Ic-i) with o being 4.

In certain embodiments the moiety —$X^{0A}$-$L^4$-$X^{0B}$-$L^3$-$X^{0C}$-$L^2$-$X^{0D}$-$L^1$- is of formula (Ic-ii) with o being 1. In certain embodiments the moiety —$X^{0A}$-$L^4$-$X^{0B}$-$L^3$-$X^{0C}$-$L^2$-$X^{0D}$-$L^1$- is of formula (Ic-ii) with o being 2. In certain embodiments the moiety —$X^{0A}$-$L^4$-$X^{0B}$-$L^3$-$X^{0C}$-$L^2$-$X^{0D}$-$L^1$- is of formula (Ic-ii) with o being 3. In certain embodiments the moiety —$X^{0A}$-$L^4$-$X^{0B}$-$L^3$-$X^{0C}$-$L^2$-$X^{0D}$-$L^1$- is of formula (Ic-ii) with o being 4.

In certain embodiments the moiety —$X^{0A}$-$L^4$-$X^{0B}$-$L^3$-$X^{0C}$-$L^2$-$X^{0D}$-$L^1$- is of formula (Ic-iii) with o being 1. In certain embodiments the moiety —$X^{0A}$-$L^4$-$X^{0B}$-$L^3$-$X^{0C}$-$L^2$-$X^{0D}$-$L^1$- is of formula (Ic-iii) with o being 2. In certain embodiments the moiety —$X^{0A}$-$L^4$-$X^{0B}$-$L^3$-$X^{0C}$-$L^2$-$X^{0D}$-$L^1$- is of formula (Ic-iii) with o being 3. In certain embodiments the moiety —$X^{0A}$-$L^4$-$X^{0B}$-$L^3$-$X^{0C}$-$L^2$-$X^{0D}$-$L^1$- is of formula (Ic-iii) with o being 4.

In certain embodiments the moiety —$X^{0A}$-$L^4$-$X^{0B}$-$L^3$-$X^{0C}$-$L^2$-$X^{0D}$-$L^1$- is of formula (Ic-iv) with o being 1. In certain embodiments the moiety —$X^{0A}$-$L^4$-$X^{0B}$-$L^3$-$X^{0C}$-$L^2$-$X^{0D}$-$L^1$- is of formula (Ic-iv) with o being 2. In certain embodiments the moiety —$X^{0A}$-$L^4$-$X^{0B}$-$L^3$-$X^{0C}$-$L^2$-$X^{0D}$-$L^1$- is of formula (Ic-iv) with o being 3. In certain embodiments the moiety —$X^{0A}$-$L^4$-$X^{0B}$-$L^3$-$X^{0C}$-$L^2$-$X^{0D}$-$L^1$- is of formula (Ic-iv) with o being 4.

In certain embodiments the moiety —$X^{0A}$-$L^4$-$X^{0B}$-$L^3$-$X^{0C}$-$L^2$-$X^{0D}$-$L^1$- is of formula (Id-i) with o being 1. In certain embodiments the moiety —$X^{0A}$-$L^4$-$X^{0B}$-$L^3$-$X^{0C}$-$L^2$-$X^{0D}$-$L^1$- is of formula (Id-i) with o being 2. In certain embodiments the moiety —$X^{0A}$-$L^4$-$X^{0B}$-$L^3$-$X^{0C}$-$L^2$-$X^{0D}$-$L^1$- is of formula (Id-i) with o being 3. In certain embodiments the moiety —$X^{0A}$-$L^4$-$X^{0B}$-$L^3$-$X^{0C}$-$L^2$-$X^{0D}$-$L^1$- is of formula (Id-i) with o being 4.

In certain embodiments the moiety —$X^{0A}$-$L^4$-$X^{0B}$-$L^3$-$X^{0C}$-$L^2$-$X^{0D}$-$L^1$- is of formula (Id-ii) with o being 1. In certain embodiments the moiety —$X^{0A}$-$L^4$-$X^{0B}$-$L^3$-$X^{0C}$-$L^2$-$X^{0D}$-$L^1$- is of formula (Id-ii) with o being 2. In certain embodiments the moiety —$X^{0A}$-$L^4$-$X^{0B}$-$L^3$-$X^{0C}$-$L^2$-$X^{0D}$-$L^1$- is of formula (Id-ii) with o being 3. In certain embodiments the moiety —$X^{0A}$-$L^4$-$X^{0B}$-$L^3$-$X^{0C}$-$L^2$-$X^{0D}$-$L^1$- is of formula (Id-ii) with o being 4.

In certain embodiments the moiety —$X^{0A}$-$L^4$-$X^{0B}$-$L^3$-$X^{0C}$-$L^2$-$X^{0D}$-$L^1$- is of formula (Id-iii) with o being 1. In certain embodiments the moiety —$X^{0A}$-$L^4$-$X^{0B}$-$L^3$-$X^{0C}$-$L^2$-$X^{0D}$-$L^1$- is of formula (Id-iii) with o being 2. In certain embodiments the moiety —$X^{0A}$-$L^4$-$X^{0B}$-$L^3$-$X^{0C}$-$L^2$-$X^{0D}$-$L^1$- is of formula (Id-iii) with o being 1. In certain embodiments the moiety —$X^{0A}$-$L^4$-$X^{0B}$-$L^3$-$X^{0C}$-$L^2$-$X^{0D}$-$L^1$- is of formula (Id-iii) with o being 4.

In certain embodiments the moiety —$X^{0A}$-$L^4$-$X^{0B}$-$L^3$-$X^{0C}$-$L^2$-$X^{0D}$-$L^1$- is of formula (Id-iv) with o being 1. In certain embodiments the moiety —$X^{0A}$-$L^4$-$X^{0B}$-$L^3$-$X^{0C}$-$L^2$-$X^{0D}$-$L^1$- is of formula (Id-iv) with o being 2. In certain embodiments the moiety —$X^{0A}$-$L^4$-$X^{0B}$-$L^3$-$X^{0C}$-$L^2$-$X^{0D}$-$L^1$- is of formula (Id-iv) with o being 3. In certain embodiments the moiety —$X^{0A}$-$L^4$-$X^{0B}$-$L^3$-$X^{0C}$-$L^2$-$X^{0D}$-$L^1$- is of formula (Id-iv) with o being 4.

In certain embodiments the moiety $—X^{0A}$-$L^4$-$X^{0B}$-$L^3$-$X^{0C}$-$L^2$-$X^{0D}$-$L^1$- is of formula (Ie-i).

(Ie-i)

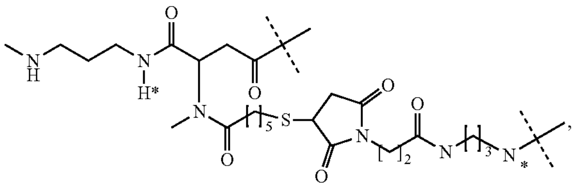

wherein the unmarked dashed line indicates the attachment to a nitrogen of -D by forming an amide bond; and the dashed line marked with the asterisk indicates attachment to the remainder of $Z^2$.

In certain embodiments all moieties $—X^{0F}—$ are identical. In certain embodiments the conjugates comprise more than one type of $—X^{0F}—$, such as two, three or four different types of $—X^{0F}—$. In certain embodiment one hyaluronic acid strand comprises only one type of $—X^{0F}—$. In certain embodiments the conjugates comprise a first type of hyaluronic acid strands with a first type of $—X^{0F}—$ and a second type of hyaluronic acid strands with a second type of $—X^{0F}—$ and optionally a third type of hyaluronic acid strand with a third type of $—X^{0F}—$ and optionally a fourth type of hyaluronic acid strand with a fourth type of $—X^{0F}—$.

In certain embodiments $—X^{0F}—$ is absent.

In certain embodiments $—X^{0F}—$ is a stable linkage, i.e —SP— is connected to —CL- through a stable linkage.

In certain embodiments $—X^{0F}—$ is an amide bond, in particular an amide of formula (F)

(F)

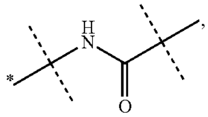

wherein the dashed line marked with the asterisk indicates attachment to —SP— and the unmarked dashed line indicates attachment to —CL-.

In certain embodiments the conjugate comprises a first type of hyaluronic acid strand in which $—X^{0F}—$ is an amide bond, in particular an amide bond of formula (F), and a second type of hyaluronic acid strand in which $—X^{0F}—$ is of formula (F-i)

(F-i)

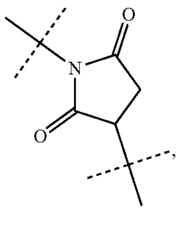

wherein dashed lines indicate attachment to —SP— and —CL-.

In particular, in the second type of hyaluronic acid strand $—X^{0F}—$ is of formula (F-ii)

(F-ii)

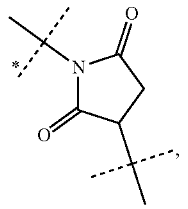

wherein the dashed line marked with the asterisk indicates attachment to —SP— and the unmarked dashed line indicates attachment to —CL-.

—SP— is absent or a spacer moiety. In certain embodiments —SP— does not comprise a reversible linkage, i.e. all linkages in —SP— are stable linkages.

In certain embodiments —SP— is absent.

In certain embodiments —SP— is a spacer moiety.

In certain embodiments —SP— does not comprise a degradable bond, i.e. all bonds of —SP— are stable bonds. In certain embodiments at least one of the at least one degradable bond in the direct connection between two carbon atoms marked with the * connected by a moiety —CL- is provided by —SP—.

In certain embodiments —SP— is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $—R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y3})—$, $—S(O)_2N(R^{y3})—$, $—S(O)N(R^{y3})—$, $—S(O)_2—$, —S(O)—, $—N(R^{y3})S(O)_2N(R^{y3a})—$, —S—, $—N(R^{y3})—$, $—OC(OR^{y3})(R^{y3a})—$, $—N(R^{y3})C(O)N(R^{y3a})—$, and $—OC(O)N(R^{y3})—$;

$—R^{y1}$ and $—R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $—R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^{y4})—$, $—S(O)_2N(R^{y4})—$, $—S(O)N(R^{y4})—$, $—S(O)_2—$, —S(O)—, $—N(R^{y4})S(O)_2N(R^{y4a})—$, —S—, $—N(R^{y4})—$, $—OC(OR^{y4})(R^{y4a})—$, $—N(R^{y4})C(O)N(R^{y4a})—$, and $—OC(O)N(R^{y4})—$;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $—R^{y2}$, which are the same or different;

each $—R^{y2}$ is independently selected from the group consisting of halogen, —CN, oxo (=O), $—COOR^{y5}$, $—OR^{y5}$, $—C(O)R^{y5}$, $—C(O)N(R^{y5}R^{y5a})$, $—S(O)_2N(R^{y5}R^{y5a})$, $—S(O)N(R^{y5}R^{y5a})$, $—S(O)_2R^{y5}$, $—S(O)R^{y5}$, $—N(R^{y5})S(O)_2N(R^{y5a}R^{y5b})$, $—SR^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different, provided that —SP— is attached to —$X^{0E}$— and —$X^{0F}$— via a carbon atom of —SP—.

In certain embodiments —SP— is a spacer moiety selected from the group consisting of -T-, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —$S(O)_2$N($R^{y3}$)—, —S(O)N($R^{y3}$)—, —$S(O)_2$—, —S(O)—, —N($R^{y3}$)$S(O)_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —$S(O)_2$N($R^{y4}$)—, —S(O)N($R^{y4}$)—, —$S(O)_2$—, —S(O)—, —N($R^{y4}$)$S(O)_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

—$R^{y2}$ is selected from the group consisting of halogen, —CN, oxo (=O), —COO$R^{y5}$, —O$R^{y5}$, —C(O)$R^{y5}$, —C(O)N($R^{y5}R^{y5a}$), —$S(O)_2$N($R^{y5}R^{y5a}$), —S(O)N($R^{y5}R^{y5a}$), —$S(O)_2R^{y5}$, —S(O)$R^{y5}$, —N($R^{y5}$)$S(O)_2$N($R^{y5a}R^{y5b}$), —S$R^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that —SP— is attached to —$X^{0E}$— and —$X^{0F}$ via a carbon atom of —SP—.

In certain embodiments —SP— is a spacer moiety selected from the group consisting of -T-, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2$N($R^{y3}$)—, —S(O)N($R^{y3}$)—, —$S(O)_2$—, —S(O)—, —N($R^{y3}$)$S(O)_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen and $C_{1-6}$ alkyl; and each —$R^{y}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different, provided that —SP— is attached to —$X^{0E}$— and —$X^{0F}$— via a carbon atom of —SP—.

In certain embodiments —SP— is a $C_{1-20}$ alkyl chain, which is optionally interrupted by one or more groups independently selected from —O—, -T-, —N($R^{y3}$)— and —C(O)N($R^{y1}$)—; and which $C_{1-20}$ alkyl chain is optionally substituted with one or more groups independently selected from —OH, -T, —N($R^{y3}$)— and —C(O)N($R^{y6}R^{y6a}$); wherein —$R^{y1}$, —$R^{y6a}$, —$R^{y6a}$ are independently selected from the group consisting of H and $C_{1-4}$ alkyl, wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, provided that —SP— is attached to —$X^{0E}$— and $X^{0F}$— via a carbon atom of —SP—.

In certain embodiments —SP— has a molecular weight ranging from 14 g/mol to 750 g/mol.

In certain embodiments —SP— has a chain lengths ranging from 1 to 20 atoms.

In certain embodiments all moieties —SP— of a conjugate are identical.

In certain embodiments —SP— is a $C_{1-10}$ alkyl. In certain embodiments —SP— is a $C_1$ alkyl. In certain embodiments —SP— is a $C_2$ alkyl. In certain embodiments —SP— is a $C_3$ alkyl. In certain embodiments —SP— is a $C_4$ alkyl. In certain embodiments —SP— is a $C_5$ alkyl. In certain embodiments —SP— is a $C_6$ alkyl. In certain embodiments —SP— is a $C_7$ alkyl. In certain embodiments —SP— is a $C_8$ alkyl. In certain embodiments —SP— is a $C_9$ alkyl. In certain embodiments —SP— is a $C_{10}$ alkyl.

In certain embodiments —SP— is a moiety of formula (E)

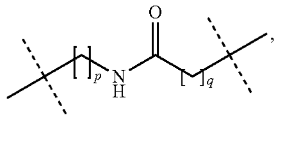

(E)

wherein dashed lines indicate attachment to —$X^{0E}$— and —$X^{0F}$—;

p is an integer selected from the group consisting of 1, 2, 3, 4, 5, 6, 7, 8, 9, 10, 11, 12, 13, 14 and 15; and q is an integer selected from the group consisting of 1, 2, 3, 4, 5, 6, 7, 8, 9, 10, 11, 12, 13, 14 and 15.

In certain embodiments —SP— is a moiety of formula (E-i)

(E-i)

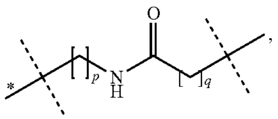

wherein dashed the dashed line indicate attachment to —$X^{0E}$— and the unmarked dashed line indicates attachment to —$X^{0F}$—;

p is an integer selected from the group consisting of 1, 2, 3, 4, 5, 6, 7, 8, 9, 10, 11, 12, 13, 14 and 15; and q is an integer selected from the group consisting of 1, 2, 3, 4, 5, 6, 7, 8, 9, 10, 11, 12, 13, 14 and 15.

In certain embodiments p of formula (E) or (E-i) is selected from the group consisting of 1, 2, 3, 4, 5, 6, 7 and 8. In certain embodiments p of formula (E) or (E-i) is selected from the group consisting of 2, 3, 4, 5, and 6. In certain embodiments p of formula (E) or (E-i) is 2. In certain embodiments p of formula (E) or (E-i) is 3. In certain embodiments p of formula (E) or (E-i) is 4. In certain embodiments p of formula (E) or (E-i) is 5.

In certain embodiments q of formula (E) or (E-i) is selected from the group consisting of 1, 2, 3, 4, 5, 6, 7 and 8. In certain embodiments q of formula (E) or (E-i) is selected from the group consisting of 1, 2, 3, 4 and 5. In certain embodiments q of formula (E) or (E-i) is 1. In certain embodiments q of formula (E) or (E-i) is 2. In certain embodiments q of formula (E) or (E-i) is 3. In certain embodiments q of formula (E) or (E-i) is 4. In certain embodiments q of formula (E) or (E-i) is 5.

In certain embodiments p of formula (E) or (E-i) is 3 and q of formula (E) or (E-i) is 2.

In certain embodiments a conjugate comprises more than one type of —SP—, such as two, three or four different types of —SP—. In certain embodiment one hyaluronic acid strand comprises only one type of —SP—. In certain embodiments a conjugate comprise a first type of hyaluronic acid strands with a first type of —SP— and a second type of hyaluronic acid strands with a second type of —SP— and optionally a third type of hyaluronic acid strand with a third type of —SP— and optionally a fourth type of hyaluronic acid strand with a fourth type of —SP—.

In certain embodiments the conjugate comprises a first type of hyaluronic acid strand in which —SP— is $C_{1-10}$ alkyl, such as a methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl or 3,3-dimethylpropyl. In particular —SP— of the first type of hyaluronic acid is n-propyl. In certain embodiments such conjugate comprises a second type of hyaluronic acid strand in which —SP— is of formula (E), in particular of formula (E-i) and in particular of formula (E-i) in which p is 3 and q is 2.

In certain embodiments all moieties —$X^{0E}$— are identical. In certain embodiments the conjugates comprise more than one type of —$X^{0E}$—, such as two, three or four different types of —$X^{0E}$—. In certain embodiment one hyaluronic acid strand comprises only one type of —$X^{0E}$—. In certain embodiments the conjugates comprise a first type of hyaluronic acid strands with a first type of —$X^{0E}$— and a second type of hyaluronic acid strands with a second type of —$X^{0E}$— and optionally a third type of hyaluronic acid strand with a third type of —$X^{0E}$— and optionally a fourth type of hyaluronic acid strand with a fourth type of —$X^{0E}$—.

In certain embodiments —$X^{0E}$— is a stable linkage, i.e —SP— is connected to the remainder of a unit $Z^3$ through a stable linkage.

In certain embodiments a moiety —$X^{0E}$—SP—$X^{0F}$—$CL^P$-$X^{0F}$—SP—$X^{0E}$— has the structure of formula (G-i)

(G-i)

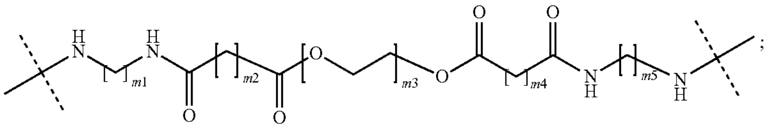

wherein dashed lines indicate attachment to the carbonyl of the hyaluronic acid; and each m1, m2, m3, m4 and m5 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments each m1 of formula (G-i) is individually selected from the group consisting of 1, 2, 3, 4, 5, 6, 7 and 8. In certain embodiments each m1 of formula (G-i) is individually selected from the group consisting of 1, 2, 3, 4 and 5. In certain embodiments m1 of formula (G-i) is 1. In certain embodiments m1 of formula (G-i) is 2. In certain embodiments m1 of formula (G-i) is 3. In certain embodiments m1 of formula (G-i) is 4. In certain embodiments m1 of formula (G-i) is 5.

In certain embodiments each m2 of formula (G-i) is individually selected from the group consisting of 1, 2, 3, 4, 5, 6, 7 and 8. In certain embodiments each m2 of formula (G-i) is individually selected from the group consisting of 1, 2, 3, 4 and 5. In certain embodiments m2 of formula (G-i) is 1. In certain embodiments m2 of formula (G-i) is 2. In certain embodiments m2 of formula (G-i) is 3. In certain embodiments m2 of formula (G-i) is 4. In certain embodiments m2 of formula (G-i) is 5.

In certain embodiments each m3 of formula (G-i) is individually selected from the group consisting of 0, 1, 2, 3, 4, 5, 6, 7 and 8. In certain embodiments each m3 of formula (G-i) is individually selected from the group consisting of 0, 1, 2, 3, 4 and 5. In certain embodiments m3 of formula (G-i) is 0. In certain embodiments m3 of formula (G-i) is 1. In certain embodiments m3 of formula (G-i) is 2. In certain embodiments m3 of formula (G-i) is 3. In certain embodiments m3 of formula (G-i) is 4. In certain embodiments m3 of formula (G-i) is 5.

In certain embodiments each m4 of formula (G-i) is individually selected from the group consisting of 0, 1, 2, 3, 4, 5, 6, 7 and 8. In certain embodiments each m4 of formula (G-i) is individually selected from the group consisting of 0, 1, 2, 3, 4 and 5. In certain embodiments m4 of formula (G-i) is 0. In certain embodiments m4 of formula (G-i) is 1. In certain embodiments m4 of formula (G-i) is 2. In certain embodiments m4 of formula (G-i) is 3. In certain embodiments m4 of formula (G-i) is 4. In certain embodiments m4 of formula (G-i) is 5.

In certain embodiments each m5 of formula (G-i) is individually selected from the group consisting of 0, 1, 2, 3, 4, 5, 6, 7 and 8. In certain embodiments m5 of formula (G-i) is selected from the group consisting of 0, 1, 2, 3, 4 and 5. In certain embodiments m5 of formula (G-i) is 0. In certain embodiments m5 of formula (G-i) is 1. In certain embodiments m5 of formula (G-i) is 2. In certain embodiments m5 of formula (G-i) is 3. In certain embodiments m5 of formula (G-i) is 4. In certain embodiments m5 of formula (G-i) is 5.

In certain embodiments m1, m2, m3, m4 and m5 are 3.

In certain embodiments a moiety $—X^{0E}—SP—X^{0F}—CL^{P}-X^{0F}—SP—X^{0E}—$ has the structure of formula (G-ii)

certain embodiments m2 of formula (G-ii) is 3. In certain embodiments m2 of formula (G-ii) is 4. In certain embodiments m2 of formula (G-ii) is 5.

In certain embodiments each m3 of formula (G-ii) is individually selected from the group consisting of 1, 2, 3, 4, 5, 6, 7 and 8. In certain embodiments each m3 of formula (G-ii) is individually selected from the group consisting of 1, 2, 3, 4 and 5. In certain embodiments m3 of formula (G-ii) is 1. In certain embodiments m3 of formula (G-ii) is 2. In certain embodiments m3 of formula (G-ii) is 3. In certain embodiments m3 of formula (G-ii) is 4. In certain embodiments m3 of formula (G-ii) is 5.

In certain embodiments each m4 of formula (G-ii) is individually selected from the group consisting of 1, 2, 3, 4, 5, 6, 7 and 8. In certain embodiments each m4 of formula (G-ii) is individually selected from the group consisting of 1, 2, 3, 4 and 5. In certain embodiments m4 of formula (G-ii) is 1. In certain embodiments m4 of formula (G-ii) is 2. In certain embodiments m4 of formula (G-ii) is 3. In certain embodiments m4 of formula (G-ii) is 4. In certain embodiments m4 of formula (G-ii) is 5.

In certain embodiments each m5 of formula (G-ii) is individually selected from the group consisting of 1, 2, 3, 4, 5, 6, 7, 8, 9, 10, 11, 12, 13 and 14. In certain embodiments (G-ii)

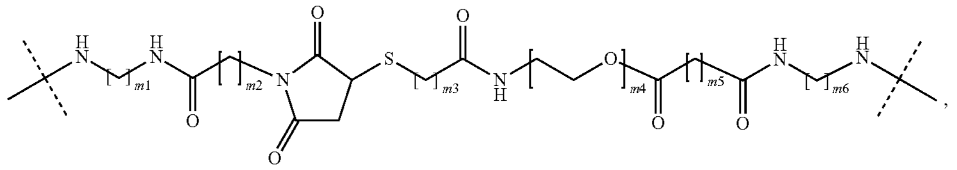

wherein dashed lines indicate attachment to the carbonyl of the hyaluronic acid; and each m1, m2, m3, m4, m5 and m6 is independently an integer selected from the group consisting of 1, 2, 3, 4, 5, 6, 7, 8, 9, 10, 11, 12, 13, 14, 15, 16, 17, 18, 19, 20, 21, 22, 23, 24 and 25.

In certain embodiments each m1 of formula (G-ii) is individually selected from the group consisting of 1, 2, 3, 4, 5, 6, 7 and 8. In certain embodiments each m1 of formula (G-ii) is individually selected from the group consisting of 1, 2, 3, 4 and 5. In certain embodiments m1 of formula (G-ii) is 1. In certain embodiments m1 of formula (G-ii) is 2. In certain embodiments m1 of formula (G-ii) is 3. In certain embodiments m1 of formula (G-ii) is 4. In certain embodiments m1 of formula (G-ii) is 5.

In certain embodiments each m2 of formula (G-ii) is individually selected from the group consisting of 1, 2, 3, 4, 5, 6, 7 and 8. In certain embodiments each m2 of formula (G-ii) is individually selected from the group consisting of 1, 2, 3, 4 and 5. In certain embodiments m2 of formula (G-ii) is 1. In certain embodiments m2 of formula (G-ii) is 2. In each m5 of formula (G-ii) is individually selected from the group consisting of 1, 2, 3, 4, 5, 6, 7, 8, 9 and 10. In certain embodiments m5 of formula (G-ii) is 3. In certain embodiments m5 of formula (G-ii) is 4. In certain embodiments m5 of formula (G-ii) is 5. In certain embodiments m5 of formula (G-ii) is 6. In certain embodiments m5 of formula (G-ii) is 7. In certain embodiments m5 of formula (G-ii) is 8. In certain embodiments m5 of formula (G-ii) is 9. In certain embodiments m5 of formula (G-ii) is 10.

In certain embodiments each m6 of formula (G-ii) is individually selected from the group consisting of 1, 2, 3, 4, 5, 6, 7 and 8. In certain embodiments each m6 of formula (G-ii) is individually selected from the group consisting of 1, 2, 3, 4 and 5. In certain embodiments m6 of formula (G-ii) is 1. In certain embodiments m6 of formula (G-ii) is 2. In certain embodiments m6 of formula (G-ii) is 3. In certain embodiments m6 of formula (G-ii) is 4. In certain embodiments m6 of formula (G-ii) is 5.

In certain embodiments m1 and m6 of formula (G-ii) are 3, m2, m3 and m4 of formula (G-ii) are 2 and m5 is 7.

In certain embodiments a moiety $—X^{0A}-L^{4}-X^{0B}-L^{3}-X^{0C}-L^{2}-X^{0D}-L^{1}-D$ is of formula (H-i)

(H-i)

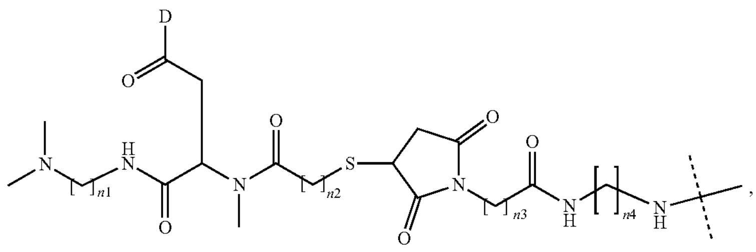

wherein the dashed line indicates attachment to the carbonyl of the hyaluronic acid;

-D is used as defined above;

each n1 is independently an integer selected from the group consisting of 2 or 3; and n2, n3 and n4 is independently an integer selected from the group consisting of 1, 2, 3, 4, 5, 6, 7, 8, 9, 10, 11, 12, 13, 14, 15 and 16.

In certain embodiments n1 of formula (H-i) is 2. In certain embodiments n1 of formula (H-i) is 3.

In certain embodiments n2 of formula (H-i) is an integer selected from the group consisting of 1, 2, 3, 4, 5, 6, 7 and 8. In certain embodiments n2 of formula (H-i) is an integer selected from the group consisting of 2, 3, 4, 5, and 6. In certain embodiments n2 of formula (H-i) is 2. In certain embodiments n2 of formula (H-i) is 3. In certain embodiments n2 of formula (H-i) is 4. In certain embodiments n2 of formula (H-i) is 5.

In certain embodiments n3 of formula (H-i) is an integer selected from the group consisting of 1, 2, 3, 4, 5, 6, 7, 8, 9 and 10. In certain embodiments n3 of formula (H-i) is an integer selected from the group consisting of 1, 2, 3, 4, 5 and 6. In certain embodiments n3 of formula (H-i) is 1. In certain embodiments n3 of formula (H-i) is 2. In certain embodiments n3 of formula (H-i) is 3. In certain embodiments n3 of formula (H-i) is 4. In certain embodiments n3 of formula (H-i) is 5. In certain embodiments n3 of formula (H-i) is 6.

In certain embodiments n4 of formula (H-i) is an integer selected from the group consisting of 1, 2, 3, 4, 5, 6, 7, 8, 9 and 10. In certain embodiments n4 of formula (H-i) is an integer selected from the group consisting of 1, 2, 3, 4, 5 and 6. In certain embodiments n4 of formula (H-i) is 1. In certain embodiments n4 of formula (H-i) is 2. In certain embodiments n4 of formula (H-i) is 3. In certain embodiments n4 of formula (H-i) is 4. In certain embodiments n4 of formula (H-i) is 5. In certain embodiments n4 of formula (H-i) is 6.

In certain embodiments n1 and n3 of formula (H-i) are 2, n2 of formula (H-i) is 5 and n4 of formula (H-i) is 3.

In certain embodiments a moiety $—X^{0A}-L^4-X^{0B}-L^3-X^{0C}-L^2-X^{0D}-L^1-D$ is of formula (H-ii)

(H-ii)

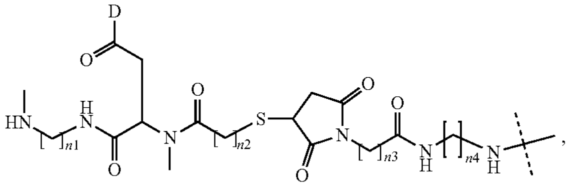

wherein the dashed line indicates attachment to the carbonyl of the hyaluronic acid;

-D is used as defined above;

each n1 is independently an integer selected from the group consisting of 2 or 3; and n2, n3 and n4 is independently an integer selected from the group consisting of 1, 2, 3, 4, 5, 6, 7, 8, 9, 10, 11, 12, 13, 14, 15 and 16.

In certain embodiments n1 of formula (H-ii) is 2. In certain embodiments n1 of formula (H-ii) is 3.

In certain embodiments n2 of formula (H-ii) is an integer selected from the group consisting of 1, 2, 3, 4, 5, 6, 7 and 8. In certain embodiments n2 of formula (H-ii) is an integer selected from the group consisting of 2, 3, 4, 5, and 6. In certain embodiments n2 of formula (H-ii) is 2. In certain embodiments n2 of formula (H-ii) is 3. In certain embodiments n2 of formula (H-ii) is 4. In certain embodiments n2 of formula (H-ii) is 5.

In certain embodiments n3 of formula (H-ii) is an integer selected from the group consisting of 1, 2, 3, 4, 5, 6, 7, 8, 9 and 10. In certain embodiments n3 of formula (H-ii) is an integer selected from the group consisting of 1, 2, 3, 4, 5 and 6. In certain embodiments n3 of formula (H-ii) is 1. In certain embodiments n3 of formula (H-ii) is 2. In certain embodiments n3 of formula (H-ii) is 3. In certain embodiments n3 of formula (H-ii) is 4. In certain embodiments n3 of formula (H-ii) is 5. In certain embodiments n3 of formula (H-ii) is 6.

In certain embodiments n4 of formula (H-ii) is an integer selected from the group consisting of 1, 2, 3, 4, 5, 6, 7, 8, 9 and 10. In certain embodiments n4 of formula (H-ii) is an integer selected from the group consisting of 1, 2, 3, 4, 5 and 6. In certain embodiments n4 of formula (H-ii) is 1. In certain embodiments n4 of formula (H-ii) is 2. In certain embodiments n4 of formula (H-ii) is 3. In certain embodiments n4 of formula (H-ii) is 4. In certain embodiments n4 of formula (H-ii) is 5. In certain embodiments n4 of formula (H-ii) is 6.

In certain embodiments n1 and n4 of formula (H-ii) are 3, n2 of formula (H-ii) is 5 and n3 of formula (H-ii) is 2.

If Z is a hyaluronic acid-based hydrogel, the present invention also relates to a method of preparing a pharmaceutical formulation comprising a conjugate of the first or second aspect or the compound of the third aspect comprising crosslinked hyaluronic acid strands to which a plurality of drug moieties are covalently conjugated, wherein the method comprises the steps of (a) providing said conjugate or compound;

(b) subjecting the conjugate or compound of step (a) to a solution comprising a buffering agent, a surfactant and a salt comprising multivalent ions, to which a swelling agent is added after addition of said solution;

(c) homogenizing the admixture of step (b);

(d) deswelling the conjugate or compound of step (c) in a deswelling solution comprising at least a deswelling agent;

(e) isolating the conjugate or compound from the admixture of step (d);

(f) subjecting the conjugate or compound of step (e) to a solution comprising a buffering agent, a surfactant, a salt comprising multivalent ions, a hydrophilic polymer of a molecular weight higher than 10 kDa, a density-modifying agent and a polarity-modifying agent, to which a swelling agent is added after addition of said solution;

(g) homogenizing the admixture of step (f);

(h) deswelling the conjugate or compound of step (g) in a deswelling solution comprising at least a deswelling agent;

(i) isolating the conjugate or compound from the admixture of step (h); and wherein, there may be optional washing steps between steps (c) and (d), (f) and (g), and (g) and (h).

It was surprisingly found that this method allows for the formulation of such conjugates and compounds of the first, second and third embodiment.

It is understood that in step (b) the solution that comprises a buffering agent, a surfactant and a salt comprising multivalent ions may provide swelling to the conjugate, before the addition of the swelling agent.

It is also understood that in step (f) the solution that comprises a buffering agent, a surfactant, a salt comprising multivalent ions, a hydrophilic polymer of a molecular weight higher than 10 kDa, a density-modifying agent and a polarity-modifying agent may provide swelling to the conjugate of step (e), before the addition of the swelling agent.

As used herein, the term "buffer" or "buffering agent" refers to a chemical compound that maintains the pH in a desired range. Physiologically tolerated buffers are, for example acetate, adipate, alanine, ammonium, arginine, ascorbate, aspartate, benzoate, bicarbonate, carbonate, citrate, diethanolamine, edetate, ethylenediamine, fumarate, gluconate, glutamate, glycine, guanidine, histidine, lactate, lysine, malate, metaphosphate, pentetate, phosphate, pyruvate, sorbate, succinate, tartrate, tromethamine and α-ketoglutarate. Antacids such as $CaCO_3$, $Mg(OH)_2$ or $ZnCO_3$ may be also used.

As used herein, the term "surfactant" or "surfactant agent" refers to a chemical compound that reduces the surface tension of a liquid to which it is added.

As used herein, the term "density-modifying agent" refers to a chemical compound that modifies the density of a liquid to which it is added. The density-modifying agent may also serve as a polarity-modifying agent.

As used herein, the term "polarity-modifying agent" refers to a chemical compound that modifies the polarity of a liquid to which it is added. The polarity-modifying agent may also serve as a density-modifying agent.

As used herein, the term "swelling agent" refers to a fluid used to swell a gel, network or solid so that the gel, network or solid may increase their volume after swelling such as by at least 1.1, 1.5, 2, 5, 10, 50, 100 or 1000 times their volume in the non-swollen state.

As used herein, the term "deswelling agent" refers to a fluid used to reduce the swelling of a gel, network or solid so that the gel, network or solid may decrease their volume after deswelling such as by at least 1.1, 1.5, 2, 5, 10, 50, 100 or 1000 times their volume in the swollen state.

As used herein, the term "polar protic solvent" refers to a solvent which comprises bonds between atoms with different electronegativities, has large dipole moments and has at least one hydrogen atom directly bound to an electronegative atom such as an oxygen, nitrogen or sulfur atom.

As used herein, the term "polar aprotic solvent" refers to a solvent which comprises bonds between atoms with different electronegativities, has large dipole moments and has at least one hydrogen atom directly bound to an electronegative atom such as an oxygen, nitrogen or sulfur atom.

As used herein, the term "homogenization" refers to any process that is used to make a mixture of two mutually non-miscible compounds the same throughout.

As used herein, the term "formulation", "pharmaceutical formulation", "admixture" or "composition" refers to a formulation containing one or more active ingredients and one or more excipients, as well as any product which results, directly or indirectly, from combination, complexation or aggregation of any two or more of the ingredients of the formulation, or from dissociation of one or more of the ingredients, or from other types of reactions or interactions of one or more of the ingredients. It is understood that said active ingredients may also be present in the form of inactive conjugates or compounds, from which the active ingredient is released.

As used herein, the term "reconstitution" means the addition of a liquid to a dry pharmaceutical formulation in order to bring back the original form of a formulation, such as a solution or suspension.

As used herein, the term "reconstituted formulation" refers to the formulation obtained upon reconstitution of a dry pharmaceutical formulation by addition of a reconstitution solution.

As used herein, the term "reconstitution solution" refers to the liquid used to reconstitute the dry pharmaceutical formulation prior to administration to a patient in need thereof.

The conjugate or compound is subjected to a solution comprising a buffering agent. Exemplary buffering agents may be selected from the group consisting of histidine, 1,3-diaminopropane, 1,4-diaminopropane, 1,4-piperazinediethanesulfonic acid (PIPES), 2-(cyclohexylamino)ethanesulfonic acid (CHES), 2-(N-morpholino)ethanesulfonic acid (MES), 2-[bis(2-hydroxyethyl)amino]-2-(hydroxymethyl)propane-1,3-diol[(BTM), 2-amino-2-methylpropan-1-ol (AMP), 2-bis(2-hydroxyethyl)amino-2-(hydroxymethyl)-1,3-propanediol (BIS-TRIS), 2-hydroxy-3-[tris(hydroxymethyl)methylamino]-1-propanesulfonic acid (TAPSO), 3-(cyclohexylamino)-1-propanesulfonic acid (CAPS), 3-(N,N-bis[2-hydroxyethyl]amino)-2-hydroxypropanesulfonic acid (DIPSO), 3-(N-morpholino)propanesulfonic acid (MOPS), 3-[4-(2-hydroxyethyl)piperazin-1-yl]propane-1-sulfonic acid (HEPPS), 3-{[1,3-dihydroxy-2-(hydroxymethyl)propan-2-yl]amino}propane-1-sulfonic acid (TAPS), acetamidoglycine, acetic acid, aconitic acid, adipic acid, alanine, ammonia, arginine, ascorbic acid, aspartic acid, benzoic acid, besylic acid, boric acid, butyric acid, carbonic acid, cholamine, citraconic acid, citric acid, diethanolamine, ethanolamine, ethylenediamine, ethylenediaminetetraacetic acid (EDTA), formic acid, fumaric acid, gluconic acid, glutamic acid, glutaric acid, glycine, glycinamide, glycylglycine, guanidine, histamine, imidazole, isobutyric acid, lactic acid, lysine, maleic acid, malic acid, malonic acid, metaphosphoric acid, N-(2-acetamido)-2-aminoethanesulfonic acid (ACES), N-(2-acetamido)-iminodiacetic acid (ADA), N-(2-hydroxy-1,1-bis(hydroxymethyl)ethyl)glycine (TRICINE), N-(2-Hydroxyethyl)piperazine-N-(4- butanesulfonic acid) (HEPBS), N-(2-hydroxyethyl)piperazine-N'-(2-ethanesulfonic acid) (HEPES), N-[tris(hydroxymethyl)methyl]-2-aminoethanesulfonic acid (TES), nitrilotriacetic acid (NTA), oxalic acid, pentetic acid (DTPA), phosphoric acid, piperazine, piperidine, pivalic acid, propionic acid, pyridine, pyrrolidine, pyruvic acid, quinoline, sorbic acid, spermidine, spermine, squaric acid, succinic acid, tartronic acid, tetramic acid, tetronic acid, tosylic acid, triethanolamine (TEA), trimethylamine, tromethamine (TRIS), tryptamine, tryptophan, tyramine, tyrosine, α-ketoglutaric acid, β-hydroxy-4-morpholinepropanesulfonic acid (MOPSO) and mixtures thereof.

It is clear to the person skilled in the art that the corresponding conjugate acids, bases or salts of the buffering agents and mixtures thereof are also included.

In certain embodiments, the buffering agent is selected from the group consisting of histidine, 1,3-diaminopropane, 2-(N-morpholino)ethanesulfonic acid (MES), 2-bis(2-hydroxyethyl)amino-2-(hydroxymethyl)-1,3-propanediol (BIS-TRIS), acetic acid, adipic acid, ammonia, arginine, boric acid, carbonic acid, citric acid, diethanolamine, ethanolamine, ethylenediamine, formic acid, gluconic acid, glutaric acid, glycine, glycinamide, guanidine, histamine, imidazole, lysine, malic acid, N-(2-hydroxy-1,1-bis(hydroxymethyl)ethyl)glycine (TRICINE), N-(2-hydroxyethyl)piperazine-N'-(2-ethanesulfonic acid) (HEPES), N-[tris(hydroxymethyl)methyl]-2-aminoethanesulfonic acid (TES), phosphoric acid, piperazine, propionic acid, pyruvic acid, spermidine, spermine, succinic acid, tartronic acid, triethanolamine (TEA), tromethamine (TRIS), tyrosine and mixtures thereof.

In certain embodiments, the buffering agent is selected from the group consisting of histidine, acetic acid, ammonia, arginine, citric acid, diethanolamine, ethylenediamine, gluconic acid, glycine, guanidine, imidazole, lysine, N-(2-hydroxyethyl)piperazine-N'-(2-ethanesulfonic acid) (HEPES), phosphoric acid, piperazine, spermidine, spermine, succinic acid, tartronic acid, triethanolamine (TEA), tromethamine (TRIS) and mixtures thereof.

In certain embodiments, the buffering agent is selected from the group consisting of histidine, arginine, diethanolamine, guanidine, spermidine and tromethamine (TRIS).

In certain embodiments, the buffering agent is selected from the group consisting of histidine, arginine and tromethamine (TRIS).

In certain embodiments, the buffering agent is histidine.

As defined herein, the term "histidine" is intended to encompass both D-histidine and L-histidine and mixtures thereof. In certain embodiments, the term "histidine" refers to L-histidine. In certain embodiments, the term "histidine" refers to D-histidine. In certain embodiments, the term "histidine" refers to a mixture of L-histidine and D-histidine.

In certain embodiments, the buffering agent is L-histidine.

The buffering agent maintains the pH of a solution within a desired range. In certain embodiments, the pH of the solutions of steps (b) and (f) is not higher than 9. In certain embodiments, the pH of the solutions of steps (b) and (f) is from about pH 3 to about pH 9. In certain embodiments, the pH of the solutions of steps (b) and (f) is from about pH 4 to about pH 8. In certain embodiments, the pH of the solutions of steps (b) and (f) is from about pH 5 to about pH 7. In certain embodiments, the pH of the solutions of steps (b) and (f) is about 6. In certain embodiments, the pH of the solutions of steps (b) and (f) is 6.0.

The buffering agent may be added in an amount of about 0.01 mM to about 500 mM. In certain embodiments, the buffering agent has a concentration ranging from about 0.5 mM to about 350 mM. In certain embodiments, the buffering agent has a concentration ranging from about 1 mM to about 250 mM. In certain embodiments, the buffering agent has a concentration ranging from about 5 mM to 100 mM. In certain embodiments, the buffering agent has a concentration ranging from about 10 mM to 50 mM. In certain embodiments, the buffering agent has a concentration of about 20 mM. In certain embodiments, the buffering agent has a concentration of 20 mM.

The conjugate is subjected to a solution comprising a surfactant. Exemplary surfactants may be selected from the group consisting polyoxyethylenesorbitan monooleate (Polysorbate 80, Tween® 80 and Tween® 80R); alcohols such as propanol, butanol, pentanol, hexanol, heptanol or octanol; alkyl and aryl amine salts such as primary amine salts, quaternary amine salts, secondary amine salts or tertiary amine salts; alkyl dimethyl betaines; alkyl ethoxylate sulfates; alkyl phenyl polyoxyethylene ethers such as Octoxynol 9, Triton X-100, Igepal™ or Nonidet P40; alkyl phosphates such as monoalkylphosphates or dialkylphosphates; alkyl polyoxyethylene ethers such as Laureth-4, Laureth-9, Laureth-23, Ceteth-2, Ceteth-10, Ceteth-20, Ceteareth-6, Ceteareth-20, Ceteareth-25, Steareth-2, Steareth-10, Steareth-20, Oleth-2, Oleth-10, Oleth-20, Deceth-10 or Trideceth-10; alkyl sulfates such as sodium dodecylsulfate (SDS); alkyl xanthates; bile acid salts such as cholic acid sodium salt or deoxycholic acid sodium salt; cationic lipids such as cetyl trimethylammonium bromide, cetyl trimethylammonium chloride, dioctadecyl dimethyl ammonium bromide, dioctadecyl dimethyl ammonium chloride, 1,2-diacyl-3-trimethylammonium propane, 1,2-diacyl-3-dimethyl ammonium propane, [2,3-bis(oleoyl)propyl] trimethyl ammonium chloride or [N—(N-dimethylaminoethane)-carbamoyl]cholesterol, dioleoyl); dialkyl sulfosuccinate salts such as Aerosol OT; Ethylenediamine tetrakis(ethoxylate-block-propoxylate) tetrols such as Tetronic 304, Tetronic 904, Tetronic 90R4 or Tetronic 1304; fatty acids such as palmitic acid, oleic acid, lauric acid, myristic acid, stearic acid, arachidic acid, behenic acid, lignoceric acid, palmitoleic acid, linoleic acid, linolenic acid or arachidonic acid and salts thereof such as sodium or potassium salts; glycosides such as octyl glucoside or dodecyl maltoside; linear and branched alkylbenzene sulfonates; poly(ethylene glycol)-block-poly(propylene glycol)-block-poly(ethylene glycol)s such as Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188 (Pluronic® F68), Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 benzoate or Poloxamer 182 dibenzoate; polyoxyethylenesorbitan esters such as polyethyleneoxy(40)-sorbitol hexaoleate ester, polyoxyethylenesorbitan monolaurate (Polysorbate 20, Tween® 20 and Tween® 21), polyoxyethylenesorbitan monopalmitate (Polysorbate 40, Tween® 40), polyoxyethylenesorbitan monostearate (Polysorbate 60, Tween® 60 and Tween® 61), polyoxyethylenesorbitan trioleate (Polysorbate 85, Tween® 85) or polyoxyethylenesorbitan tristearate (Polysorbate 65, Tween® 65); polyvinyl alcohol; polyvinylpyrrolidone; sorbitan esters such as sorbitan monolaurate (Span® 20), sorbitan monooleate (Span® 80), sorbitan monopalmitate (Span® 40), sorbitan monostearate (Span® 60), sorbitan sequioleate (Span® 83), sorbitan trioleate (Span® 85) or sorbitan tristearate (Span® 65); starch and their derivatives and mixtures thereof.

In certain embodiments, the surfactant is selected from the group consisting of polyoxyethylenesorbitan monooleate (Polysorbate 80, Tween® 80 and Tween® 80R), alkyl phenyl polyoxyethylene ethers such as Octoxynol 9, Triton X-100, Igepal™ or Nonidet P40; alkyl polyoxyethylene ethers such as Laureth-9, Ceteth-10, Ceteareth-20, Steareth-10, Oleth-10, Deceth-10 or Trideceth-10; alkyl sulfates such as sodium dodecylsulfate (SDS); bile acid salts such as cholic acid sodium salt or deoxycholic acid sodium salt; cationic lipids such as cetyl trimethylammonium chloride, dioctadecyl dimethyl ammonium chloride, 1,2-diacyl-3-trimethylammonium propane, 1,2-diacyl-3-dimethyl ammonium propane or [2,3-bis(oleoyl)propyl] trimethyl ammonium chloride; Ethylenediamine tetrakis(ethoxylate-block-propoxylate) tetrols such as Tetronic 90R4; glycosides such as octyl glucoside or dodecyl maltoside; poly(ethylene glycol)-block-poly(propylene glycol)-block-poly(ethylene glycol)s such as Poloxamer 101, Poloxamer 188 (Pluronic® F68) or Poloxamer 288; polyoxyethylenesorbitan esters such as polyethyleneoxy(40)-sorbitol hexaoleate ester, polyoxyethylenesorbitan monolaurate (Polysorbate 20, Tween® 20 and Tween® 21); polyvinyl alcohol; polyvinylpyrrolidone; sorbitan esters such as sorbitan monolaurate (Span® 20) or sorbitan monooleate (Span® 80) and mixtures thereof.

In certain embodiments, the surfactant is selected from the group consisting of polyoxyethylenesorbitan monooleate (Polysorbate 80, Tween® 80 and Tween® 80R), alkyl phenyl polyoxyethylene ethers such as Triton X-100; alkyl polyoxyethylene ethers such as Laureth-9 and Ceteth-10; alkyl sulfates such as sodium dodecylsulfate (SDS); bile acid salts such as cholic acid sodium salt; cationic lipids such as cetyl trimethylammonium chloride; Ethylenediamine tetrakis(ethoxylate-block-propoxylate) tetrols such as Tetronic 90R4; glycosides such as octyl glucoside; poly(ethylene glycol)-block-poly(propylene glycol)-block-poly(ethylene glycol)s such as Poloxamer 188 (Pluronic® F68); polyoxyethylenesorbitan esters such as polyoxyethylenesorbitan monolaurate (Polysorbate 20, Tween® 20 and Tween® 21) and mixtures thereof.

In certain embodiments, the surfactant is selected from the group consisting of polyoxyethylenesorbitan monooleate (Polysorbate 80, Tween® 80 and Tween® 80R) poly(ethylene glycol)-block-poly(propylene glycol)-block-poly(ethylene glycol)s such as Poloxamer 188 (Pluronic F68) and polyoxyethylenesorbitan esters such as polyoxyethylenesorbitan monolaurate (Polysorbate 20, Tween® 20 and Tween® 21) and mixtures thereof.

In certain embodiments, the surfactant is a polyoxyethylenesorbitan monooleate, such as polysorbate 80.

The surfactant may be added in an amount of about 0.01% (w/w) to about 10% (w/w). In certain embodiments, the surfactant is added in an amount of about 0.1% (w/w) to about 7% (w/w). In certain embodiments, the surfactant is added in an amount of about 1% (w/w) to about 5% (w/w). In certain embodiments, the surfactant is added in an amount of about 1.5% (w/w) to about 3.0% (w/w). In certain embodiments, the surfactant is added in an amount of about 2% (w/w). In certain embodiments, the surfactant is added in an amount of 2% (w/w).

The conjugate or compound is subjected to a solution comprising a salt comprising multivalent ions. Exemplary salts may be selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate or calcium sulfate; aluminium salts and complexes such as aluminium acetate, aluminium ascorbate, aluminium bromide, aluminium carbonate, aluminium chloride, aluminium citrate, aluminium dihydrogen phosphate, aluminium disulfate, aluminium fluoride, aluminium formate, aluminium fumarate, aluminium gluconate, aluminium hydrogen carbonate, aluminium hydrogenphosphate, aluminium hydrogen sulfate, aluminium hydroxide, aluminium iodide, aluminium lactate, aluminium levulinate, aluminium malate, aluminium malonate, aluminium nitrate, aluminium oxalate, aluminium phosphate, aluminium propionate or aluminium sulfate; barium salts and complexes such as barium acetate, barium ascorbate, barium bromide, barium carbonate, barium chloride, barium citrate, barium dihydrogen phosphate, barium disulfate, barium fluoride, barium formate, barium fumarate, barium gluconate, barium hydrogen carbonate, barium hydrogenphosphate, barium hydrogen sulfate, barium hydroxide, barium iodide, barium lactate, barium levulinate, barium malate, barium malonate, barium nitrate, barium oxalate, barium phosphate, barium propionate or barium sulfate; copper(II) salts and complexes such as copper(II) acetate, copper(II) ascorbate, copper(II) bromide, copper(II) carbonate, copper(II) chloride, copper (II) citrate, copper(II) dihydrogen phosphate, copper(II) disulfate, copper(II) fluoride, copper(II) formate, copper(II) fumarate, copper(II) gluconate, copper(II) hydrogen carbonate, copper(II) hydrogenphosphate, copper(II) hydrogen sulfate, copper(II) hydroxide, copper(II) iodide, copper(II) lactate, copper(II) levulinate, copper(II) malate, copper(II) malonate, copper(II) nitrate, copper(II) oxalate, copper(II) phosphate, copper(II) propionate or copper(II) sulfate; iron (II) salts and complexes such as iron(II) acetate, iron(II) ascorbate, iron(II) bromide, iron(II) carbonate, iron(II) chloride, iron(II) citrate, iron(II) dihydrogen phosphate, iron(II) disulfate, iron(II) fluoride, iron(II) formate, iron(II) fumarate, iron(II) gluconate, iron(II) hydrogen carbonate, iron(II) hydrogenphosphate, iron(II) hydrogen sulfate, iron (II) hydroxide, iron(II) iodide, iron(II) lactate, iron(II) levulinate, iron(II) malate, iron(II) malonate, iron(II) nitrate, iron(II) oxalate, iron(II) phosphate, iron(II) propionate or iron(II) sulfate; iron(III) salts and complexes such as iron (III) acetate, iron(III) ascorbate, iron(III) bromide, iron(III) carbonate, iron(III) chloride, iron(III) citrate, iron(III) dihydrogen phosphate, iron(III) disulfate, iron(III) fluoride, iron (III) formate, iron(III) fumarate, iron(III) gluconate, iron(III) hydrogen carbonate, iron(III) hydrogenphosphate, iron(III) hydrogen sulfate, iron(III) hydroxide, iron(III) iodide, iron (III) lactate, iron(III) levulinate, iron(III) malate, iron(III) malonate, iron(III) nitrate, iron(III) oxalate, iron(III) phosphate, iron(III) propionate and iron(III) sulfate; lanthanum salts and complexes such as lanthanum acetate, lanthanum ascorbate, lanthanum bromide, lanthanum carbonate, lanthanum chloride, lanthanum citrate, lanthanum dihydrogen phosphate, lanthanum disulfate, lanthanum fluoride, lanthanum formate, lanthanum fumarate, lanthanum gluconate, lanthanum hydrogen carbonate, lanthanum hydrogenphosphate, lanthanum hydrogen sulfate, lanthanum hydroxide, lanthanum iodide, lanthanum lactate, lanthanum levulinate, lanthanum malate, lanthanum malonate, lanthanum nitrate, lanthanum oxalate, lanthanum phosphate, lanthanum propionate or lanthanum sulfate; magnesium salts and complexes such as magnesium acetate, magnesium ascorbate, magnesium bromide, magnesium carbonate, magnesium chloride, magnesium citrate, magnesium dihydrogen phosphate, magnesium disulfate, magnesium fluoride, magnesium formate, magnesium fumarate, magnesium gluconate, magnesium hydrogen carbonate, magnesium hydrogenphosphate, magnesium hydrogen sulfate, magnesium hydroxide, magnesium iodide, magnesium lactate, magnesium levulinate, magnesium malate, magnesium malonate, magnesium nitrate, magnesium oxalate, magnesium phosphate, magnesium propionate or magnesium sulfate; manganese(II) salts and complexes such as manganese(II) acetate, manganese (II) ascorbate, manganese(II) bromide, manganese(II) carbonate, manganese(II) chloride, manganese(II) citrate, manganese(II) dihydrogen phosphate, manganese(II) disulfate, manganese(II) fluoride, manganese(II) formate, manganese (II) fumarate, manganese(II) gluconate, manganese(II) hydrogen carbonate, manganese(II) hydrogenphosphate, manganese(II) hydrogen sulfate, manganese(II) hydroxide, manganese(II) iodide, manganese(II) lactate, manganese(II) levulinate, manganese(II) malate, manganese(II) malonate, manganese(II) nitrate, manganese(II) oxalate, manganese (II) phosphate, manganese(II) propionate or manganese(II) sulfate; scandium salts and complexes such as scandium acetate, scandium ascorbate, scandium bromide, scandium carbonate, scandium chloride, scandium citrate, scandium dihydrogen phosphate, scandium disulfate, scandium fluoride, scandium formate, scandium fumarate, scandium gluconate, scandium hydrogen carbonate, scandium hydrogenphosphate, scandium hydrogen sulfate, scandium hydroxide, scandium iodide, scandium lactate, scandium levulinate, scandium malate, scandium malonate, scandium nitrate, scandium oxalate, scandium phosphate, scandium propionate and scandium sulfate; strontium salts and complexes such as strontium acetate, strontium ascorbate, strontium bromide, strontium carbonate, strontium chloride, strontium citrate, strontium dihydrogen phosphate, strontium disulfate, strontium fluoride, strontium formate, strontium fumarate, strontium gluconate, strontium hydrogen carbonate, strontium hydrogenphosphate, strontium hydrogen sulfate, strontium hydroxide, strontium iodide, strontium lactate, strontium levulinate, strontium malate, strontium malonate, strontium nitrate, strontium oxalate, strontium phosphate, strontium propionate or strontium sulfate; zinc salts and complexes such as zinc acetate, zinc ascorbate, zinc bromide, zinc carbonate, zinc chloride, zinc citrate, zinc dihydrogen phosphate, zinc disulfate, zinc fluoride, zinc formate, zinc fumarate, zinc gluconate, zinc hydrogen carbonate, zinc hydrogenphosphate, zinc hydrogen sulfate, zinc hydroxide, zinc iodide, zinc lactate, zinc levulinate, zinc malate, zinc malonate, zinc nitrate, zinc oxalate, zinc phosphate, zinc propionate, zinc sulfate and mixtures thereof.

In certain embodiments, the salt is selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate or calcium sulfate; iron(II) salts and complexes such as iron(II) acetate, iron(II) ascorbate, iron(II) bromide, iron(II) carbonate, iron(II) chloride, iron (II) citrate, iron(II) dihydrogen phosphate, iron(II) disulfate, iron(II) fluoride, iron(II) formate, iron(II) fumarate, iron(II) gluconate, iron(II) hydrogen carbonate, iron(II) hydrogenphosphate, iron(II) hydrogen sulfate, iron(II) hydroxide, iron(II) iodide, iron(II) lactate, iron(II) levulinate, iron(II) malate, iron(II) malonate, iron(II) nitrate, iron(II) oxalate, iron(II) phosphate, iron(II) propionate or iron(II) sulfate; lanthanum salts and complexes such as lanthanum acetate, lanthanum ascorbate, lanthanum bromide, lanthanum carbonate, lanthanum chloride, lanthanum citrate, lanthanum dihydrogen phosphate, lanthanum disulfate, lanthanum fluoride, lanthanum formate, lanthanum fumarate, lanthanum gluconate, lanthanum hydrogen carbonate, lanthanum hydrogenphosphate, lanthanum hydrogen sulfate, lanthanum hydroxide, lanthanum iodide, lanthanum lactate, lanthanum levulinate, lanthanum malate, lanthanum malonate, lanthanum nitrate, lanthanum oxalate, lanthanum phosphate, lanthanum propionate or lanthanum sulfate; magnesium salts and complexes such as magnesium acetate, magnesium ascorbate, magnesium bromide, magnesium carbonate, magnesium chloride, magnesium citrate, magnesium dihydrogen phosphate, magnesium disulfate, magnesium fluoride, magnesium formate, magnesium fumarate, magnesium gluconate, magnesium hydrogen carbonate, magnesium hydrogenphosphate, magnesium hydrogen sulfate, magnesium hydroxide, magnesium iodide, magnesium lactate, magnesium levulinate, magnesium malate, magnesium malonate, magnesium nitrate, magnesium oxalate, magnesium phosphate, magnesium propionate or magnesium sulfate; zinc salts and complexes such as zinc acetate, zinc ascorbate, zinc bromide, zinc carbonate, zinc chloride, zinc citrate, zinc dihydrogen phosphate, zinc disulfate, zinc fluoride, zinc formate, zinc fumarate, zinc gluconate, zinc hydrogen carbonate, zinc hydrogenphosphate, zinc hydrogen sulfate, zinc hydroxide, zinc iodide, zinc lactate, zinc levulinate, zinc malate, zinc malonate, zinc nitrate, zinc oxalate, zinc phosphate, zinc propionate, zinc sulfate and mixtures thereof.

In certain embodiments, the salt is selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate or calcium sulfate; magnesium salts and complexes such as magnesium acetate, magnesium ascorbate, magnesium bromide, magnesium carbonate, magnesium chloride, magnesium citrate, magnesium dihydrogen phosphate, magnesium disulfate, magnesium fluoride, magnesium formate, magnesium fumarate, magnesium gluconate, magnesium hydrogen carbonate, magnesium hydrogenphosphate, magnesium hydrogen sulfate, magnesium hydroxide, magnesium iodide, magnesium lactate, magnesium levulinate, magnesium malate, magnesium malonate, magnesium nitrate, magnesium oxalate, magnesium phosphate, magnesium propionate, magnesium sulfate and mixtures thereof.

In certain embodiments, the salt is selected from the group consisting of calcium salts and complexes such as calcium chloride, calcium acetate, calcium ascorbate, calcium bromide, calcium carbonate, calcium citrate, calcium dihydrogen phosphate, calcium disulfate, calcium fluoride, calcium formate, calcium fumarate, calcium gluconate, calcium hydrogen carbonate, calcium hydrogenphosphate, calcium hydrogen sulfate, calcium hydroxide, calcium iodide, calcium lactate, calcium levulinate, calcium malate, calcium malonate, calcium nitrate, calcium oxalate, calcium phosphate, calcium propionate and calcium sulfate.

In certain embodiments, the salt is selected from the group consisting of calcium salts and complexes such as calcium chloride, calcium acetate, calcium ascorbate, calcium citrate, calcium gluconate, calcium lactate, calcium levulinate, calcium malate and calcium malonate.

In certain embodiments, the salt is calcium chloride.

The salt may be added in an amount of about 0.01 mM to about 500 mM. In certain embodiments, the salt has a concentration ranging from about 0.1 mM to about 350 mM. In certain embodiments, the salt has a concentration ranging from about 1 mM to about 250 mM.

In certain embodiments, the salt has a concentration ranging from about 5 mM to 100 mM. In certain embodiments, the salt has a concentration ranging from about 10 mM to 75 mM. In certain embodiments, the salt has a concentration of about 50 mM. In certain embodiments, the salt has a concentration of 50 mM.

A swelling agent is added to the conjugate or compound after addition of a solution comprising a buffering agent, a surfactant and a salt comprising multivalent ions.

In certain embodiments, the swelling agent is a polar aprotic solvent. Exemplary swelling agents may be selected from the group consisting of dimethyl sulfoxide, 1,2-dimethoxyether, 1,3-dimethyl-2-imidazolidinone, 1,3-dioxolane, 1,4-dioxane, 2,5-dimethyltetrahydrofuran, 2-methyltetrahydrofuran, 4-acetyl morpholine, 4-propionyl morpholine, acetone, acetonitrile, diethyl carbonate, diethyl ether, dimethyl carbonate, ethyl acetate, ethyl formate, ethyl lactate, ethylene carbonate, gamma-butyrolactone, gamma-valerolactone, hexamethylphosphoramide, methyl acetate, methyl carbonate, monomethyl ether acetate, N,N'-dimethylpropyleneurea, N,N-dimethylacetamide, N,N-dimethylformamide, N-formyl morpholine, N-methyl-2-pyrrolidone, propylene carbonate, sulfolane, tetrahydrofuran, tetrahydropyran, tripyrrolidinophosphoric acid triamide and mixtures thereof.

In certain embodiments, the swelling agent may be selected from the group consisting of dimethyl sulfoxide, 1,3-dimethyl-2-imidazolidinone, 4-acetyl morpholine, 4-propionyl morpholine, hexamethylphosphoramide, N,N'-dimethylpropyleneurea, N,N-dimethylacetamide, N,N-dimethylformamide, N-formyl morpholine, N-methyl-2-pyrrolidone, sulfolane, tripyrrolidinophosphoric acid triamide and mixtures thereof.

In certain embodiments, the swelling agent may be selected from the group consisting of dimethyl sulfoxide, N,N-dimethylacetamide, N,N-dimethylformamide, N-methyl-2-pyrrolidone and sulfolane.

In certain embodiments, the swelling agent is dimethyl sulfoxide.

The swelling agent may be added in an amount of about 10% (v/v) to about 99% (v/v). In certain embodiments, the swelling agent is added in an amount of about 30% (v/v) to about 97% (v/v). In certain embodiments, the swelling agent is added in an amount of about 50% (v/v) to about 95% (v/v). In certain embodiments, the swelling agent is added in an amount of about 80% (v/v) to about 90% (v/v). In certain embodiments, the swelling agent is added in an amount of about 87% (v/v). In certain embodiments, the swelling agent is added in an amount of about 85% (v/v). In certain embodiments, the swelling agent is added in an amount of about 83% (v/v). In certain embodiments, the swelling agent is added in an amount of 87% (v/v). In certain embodiments, the swelling agent is added in an amount of 850 (v/v). In certain embodiments, the swelling agent is added in an amount of 83% o (v/v).

The conjugate or compound is subjected to a deswelling solution comprising at least a deswelling agent.

In certain embodiments, a deswelling agent is a polar protic solvent.

Exemplary deswelling agents may be selected from the group consisting of ethanol, 1,4-butanediol, acetic acid, cyclohexanol, diethylene glycol, diethylene glycol monoethyl ether, diethylene glycol monomethyl ether, ethylene diamine, ethylene glycol, ethylene glycol monoethyl ether, ethylene glycol monomethyl ether, formamide, formic acid, glycerine, isobutanol, isopropanol, methanesulfonic acid, methanol, n-butanol, n-hexanol, n-pentanol, n-propanol, propionic acid, propylene diamine, propylene glycol, propylene glycol monoethyl ether, propylene glycol monomethyl ether, sec-butanol, t-butanol, triethylene glycol monoethyl ether, triethylene glycol monomethyl ether, triethylene glycol, trifluoroacetic acid, water and mixtures thereof.

In certain embodiments, the deswelling agent may be selected from the group consisting of ethanol, 1,4-butanediol, diethylene glycol, ethylene glycol, formamide, glycerine, isobutanol, isopropanol, methanol, n-butanol, n-hexanol, n-pentanol, n-propanol, propylene glycol, sec-butanol, t-butanol and mixtures thereof.

In certain embodiments, the deswelling agent may be selected from the group consisting of ethanol, isopropanol, methanol and n-propanol.

In certain embodiments, the deswelling agent is ethanol.

The deswelling agent may be added in an amount of about 10% (v/v) to about 99% (v/v). In certain embodiments, the deswelling agent is added in an amount of about 30% (v/v) to about 97% (v/v). In certain embodiments, the deswelling agent is added in an amount of about 50% (v/v) to about 95% (v/v). In certain embodiments, the deswelling agent is added in an amount of about 70% (v/v) to about 90% (v/v). In certain embodiments, the deswelling agent is added in an amount of about 87% (v/v). In certain embodiments, the deswelling agent is added in an amount of about 80% (v/v). In certain embodiments, the deswelling agent is added in an amount of about 74% (v/v). In certain embodiments, the deswelling agent is added in an amount of 87.50 (v/v). In certain embodiments, the deswelling agent is added in an amount of 80% o (v/v). In certain embodiments, the deswelling agent is added in an amount of 74% o (v/v).

In certain embodiments, the conjugate or compound is subjected to a solution comprising a hydrophilic polymer of a molecular weight higher than 10 kDa. Exemplary hydrophilic polymers may be selected from the group consisting of hyaluronic acids and derivatives, functionalized hyaluronic acids, 2-methacryloyl-oxyethyl phosphoryl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly (glycolic acids), poly(hydroxyethyl acrylates), poly(hydroxyethyl-oxazolines), poly(hydroxymethacrylates), poly (hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carboxymethyl celluloses, hydroxypropyl methylcelluloses, chitins, chitosans, dextrans, dextrins, gelatins, gellans, pullulans, mannans, pectins, rhamnogalacturonans, starches, hydroxyalkyl starches, hydroxyethyl starches and other carbohydrate-based polymers, xylans, copolymers and mixtures thereof.

In certain embodiments, the hydrophilic polymer may be selected from the group consisting of hyaluronic acids and derivatives, functionalized hyaluronic acids, poly(acrylic acids), poly(ethylene glycol), poly(glycolic acids), poly(lactic acids), poly(lactic-co-glycolic acids), poly(propylene glycols), poly(vinyl alcohols), poly(vinylpyrrolidones), carboxymethyl celluloses, hydroxypropyl methylcelluloses, chitosans, dextrans, dextrins, *pullulans*, hydroxyalkyl starches, hydroxyethyl starches and other carbohydrate-based polymers, xylans, copolymers and mixtures thereof.

In certain embodiments, the hydrophilic polymer may be selected from the group consisting of hyaluronic acids, carboxymethyl celluloses, hydroxypropyl methylcelluloses, chitosans, dextrans, pullulans, hydroxyethyl starches and mixtures thereof.

In certain embodiments, the hydrophilic polymer is hyaluronic acid.

The hydrophilic polymer may be added in an amount of about 0.01 g/l to about 100 g/l. In certain embodiments, the hydrophilic polymer has a concentration ranging from about 0.1 g/l to about 50 g/l. In certain embodiments, the hydrophilic polymer has a concentration ranging from about 0.5 g/l to about 10 g/l. In certain embodiments, the hydrophilic polymer has a concentration ranging from about 1 g/l to about 5 g/1. In certain embodiments, the hydrophilic polymer has a concentration of about 2 g/l. In certain embodiments, the hydrophilic polymer has a concentration of 2 g/l.

In certain embodiments, the conjugate or compound may be subjected to a solution comprising a density-modifying agent.

Exemplary density-modifying agents may be selected from the group consisting of trehalose, arabitol, cellobiose, dextrose, erythritol, fructose, fucitol, fucose, galactitol, gentiobiose, iditol, inositol, isomalt, isomaltose, isomaltulose, lactitol, lactose, lactulose, laminaribiose, maltitol, maltose, maltotetraitol, maltotriitol, maltulose, mannitol, mannose, melibiose, neohesperidose, neotrehalose, nigerose, polyglycitol, potassium chloride, potassium sulfate, raffinose, ribitol, rutinose, sambubiose, sodium chloride, sodium sulfate, sophorose, sorbitol, sucrose, threitol, volemitol, xylitol and mixtures thereof.

In certain embodiments, the density-modifying agent may be selected from the group consisting of trehalose, erythritol, inositol, isomaltose, lactose, maltitol, mannitol, sodium chloride, sodium sulfate, sorbitol, sucrose, xylitol and mixtures thereof.

In certain embodiments, the density-modifying agent may be selected from the group consisting of trehalose, lactose, mannitol, sorbitol, sucrose and mixtures thereof.

In certain embodiments, the density-modifying agent is trehalose.

As defined herein, the term "trehalose" is intended to encompass all salts and hydration states of trehalose, such as trehalose anhydrous or trehalose dihydrate. In certain embodiments, the term "trehalose" refers to trehalose anhydrous.

In certain embodiments, the term "trehalose" refers to trehalose dihydrate.

The density-modifying agent may be added in an amount of about 0.1% (w/w) to about 25% (w/w). In certain embodiments, the density-modifying agent is added in an amount of about 1% (w/w) to about 20% (w/w). In certain embodiments, the density-modifying agent is added in an amount of about 2% (w/w) to about 10% (w/w). In certain embodiments, the density-modifying agent is added in an amount of about 5% (w/w). In certain embodiments, the density-modifying agent is added in an amount of 5% (w/w).

In certain embodiments, the conjugate or compound may be subjected to a solution comprising a polarity-modifying agent.

In certain embodiments, the polarity-modifying agent is selected from the group consisting of polar protic and polar aprotic solvents.

Exemplary polarity-modifying agents may be selected from the group consisting of propylene glycol, acetonitrile, dimethyl sulfoxide, ethanol, ethylene glycol, ethylene glycol monomethyl ether, glycerol, isopropanol, methanol, N,N-dimethylformamide, n-propanol and mixtures thereof.

In certain embodiments, the polarity-modifying agent may be selected from the group consisting of propylene glycol, dimethyl sulfoxide, ethanol, ethylene glycol, glycerol and mixtures thereof.

In certain embodiments, the polarity-modifying agent may be selected from the group consisting of propylene glycol, ethanol, glycerol and mixtures thereof.

In certain embodiments, the polarity-modifying agent is propylene glycol.

As defined herein, the term "propylene glycol" is intended to encompass (R)-1,2-dihydroxypropane, (S)-1,2-dihydroxypropane, (RS)-1,2-dihydroxypropane and mixtures thereof. In certain embodiments, the term "propylene glycol" refers to (R)-1,2-dihydroxypropane. In certain embodiments, the term "propylene glycol" refers to (S)-1,2-dihydroxypropane. In certain embodiments, the term "propylene glycol" refers to (RS)-1,2-dihydroxypropane.

In certain embodiments, the polarity-modifying agent is (RS)-1,2-dihydroxypropane.

The polarity-modifying agent may be added in an amount of about 0.1% (w/w) to about 75% (w/w). In certain embodiments, the polarity-modifying agent is added in an amount of about 1% (w/w) to about 50% (w/w). In certain embodiments, the polarity-modifying agent is added in an amount of about 2% (w/w) to about 35% (w/w). In certain embodiments, the polarity-modifying agent is added in an amount of about 5% (w/w) to about 20% (w/w). In certain embodiments, the polarity-modifying agent is added in an amount of about 10% (w/w). In certain embodiments, the polarity-modifying agent is added in an amount of 10% (w/w).

In certain embodiments, homogenization may be achieved by mechanical methods such as extrusion, injection, atomization, shearing, molding or emulsion-templating, sonication, vortexing, manual grinding or combined procedures thereof.

In certain embodiments, isolation of the conjugate may be achieved by evaporation of a liquid solution comprising the conjugate, lyophilization, filtration, centrifugation or combined procedures thereof.

In certain embodiments, the method of preparing a pharmaceutical formulation comprises the steps of (a) providing said conjugate or compound;

(b) subjecting the conjugate or compound of step (a) to a solution comprising L-histidine, polysorbate 80 and $CaCl_2$ to which dimethyl sulfoxide is added after addition of said solution;

(c) homogenizing the admixture of step (b);

(d) deswelling the conjugate or compound of step (c) in ethanol, acetic acid and polysorbate 80;

(e) isolating the conjugate or compound from the admixture of step (d);

(f) subjecting the conjugate or compound of step (e) to a solution comprising L-histidine, polysorbate 80, $CaCl_2$, hyaluronic acid of a molecular weight higher than 10 kDa, trehalose dihydrate and (RS)-1,2-dihydroxypropane, to which dimethyl sulfoxide is added after addition of said solution;

(g) homogenizing the admixture of step (f);

(h) deswelling the conjugate or compound d of step (g) in ethanol;

(i) isolating the conjugate or compound from the admixture of step (h); and wherein, there may be optional washing steps between steps (c) and (d), (f) and (g), and (g) and (h).

In certain embodiments the pharmaceutical formulation obtained by the process is dried, such as by lyophilization or by treating the conjugate in a high vacuum.

Prior to applying such dry pharmaceutical formulation to a patient in need thereof, the dry pharmaceutical formulation is reconstituted. Reconstitution of the dry pharmaceutical formulation into a reconstituted formulation is done by adding a predefined amount of reconstitution solution to the dry pharmaceutical formulation. Therefore, a further aspect of the present invention is a method of reconstituting the dry pharmaceutical formulation, wherein the method comprises the step of (a) contacting the dry pharmaceutical formulation with a reconstitution solution.

The present invention also relates to a reconstituted pharmaceutical formulation obtainable from the method of reconstituting said dry pharmaceutical formulation.

Reconstitution may take place in the container in which the dry pharmaceutical formulation comprising the conjugate is provided, such as in a vial; syringe, such as a dual-chamber syringe; ampoule; cartridge, such as a dual-chamber cartridge; or the dry pharmaceutical formulation may be transferred to a different container and is then reconstituted.

In certain embodiments, the container in which the reconstitution of the dry pharmaceutical formulation takes place is a vial. In certain embodiments, the container in which the reconstitution of the dry pharmaceutical formulation takes place is a syringe. In certain embodiments, the container in which the reconstitution of the dry pharmaceutical formulation takes place is a dual-chamber syringe. In certain embodiments, the container in which the reconstitution of the dry pharmaceutical formulation takes place is a cartridge. In certain embodiments, the container in which the reconstitution of the dry pharmaceutical formulation takes place is a dual-chamber cartridge. In certain embodiments, the dry pharmaceutical formulation is provided in a first chamber of the dual-chamber syringe and the reconstitution solution is provided in a second chamber of the dual-chamber syringe. In certain embodiments, the dry pharmaceutical formulation is provided in a first chamber of the dual-chamber cartridge and the reconstitution solution is provided in a second chamber of the dual-chamber cartridge.

The reconstitution solution is a sterile liquid, such as water or buffer, which may comprise further additives, such as preservatives and/or antimicrobials. In certain embodiments, the reconstituted solution comprises one or more preservative and/or antimicrobial. In certain embodiments, the reconstituted solution comprises one or more excipient. In certain embodiments, the reconstitution solution is sterile water. In certain embodiments, the reconstitution solution is sterile water comprising 0.7-1.1% benzylalcohol. In certain embodiments, the reconstitution solution is sterile water comprising 0.9% benzylalcohol.

The buffering agent maintains the pH of the reconstituted formulation within a desired range.

In certain embodiments, the pH of the reconstituted formulation is not higher than 9. In certain embodiments, the pH of the reconstituted formulation is from about pH 3 to about pH 9. In certain embodiments, the pH of the reconstituted formulation is from about pH 4 to about pH 6. In certain embodiments, the pH of the reconstituted formulation is from about pH 4.5 to about pH 5.5.

In certain embodiments, the buffering agent has a concentration ranging from 1 to 50 mM in the reconstituted formulation. In certain embodiments, the buffering agent has a concentration ranging from 2 to 30 mM in the reconstituted formulation. In certain embodiments, the buffering agent has a concentration ranging from 5 to 20 mM in the reconstituted formulation.

In certain embodiments, the buffering agent has a concentration of about 10 mM in the reconstituted formulation.

In general a pharmaceutical composition of the present invention has a pH ranging from pH 3 to pH 8, such as ranging from pH 4 to pH 6 or ranging from pH 4 to pH 5. In certain embodiments the pharmaceutical composition has a pH of about 4. In certain embodiments the pharmaceutical composition has a pH of about 4.5. In certain embodiments the pharmaceutical composition has a pH of about 5.

In certain embodiments such pharmaceutical composition is a suspension composition.

In certain embodiments such pharmaceutical is a dry composition. It is understood that such dry composition may be obtained by drying, such as lyophilizing, a suspension composition.

Suitable excipients for the pharmaceutical may be categorized as, for example, buffering agents, isotonicity modifiers, preservatives, stabilizers, anti-adsorption agents, oxidation protection agents, viscosifiers/viscosity enhancing agents, anti-agglomeration agents or other auxiliary agents. However, in some cases, one excipient may have dual or triple functions.

Excipient may be selected from the group consisting of (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;

(ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral compositions benefit from the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the composition's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: retard settling of the particles and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone; such block copolymers as well as the abovementioned poloxamers may exhibit reverse thermal gelation behavior, meaning they are fluid state at room temperature to facilitate administration and gel state above sol-gel transition temperature at body temperature after injection;

(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs;

(ix) Anti-agglomeration agents, such as propylene glycol; and (x) Other auxiliary agents: such as wetting agents, viscosity modifiers, antibiotics; acids and bases such as hydrochloric acid and sodium hydroxide are auxiliary agents necessary for pH adjustment during manufacture.

In certain embodiments the conjugate or the pharmaceutically acceptable salt thereof or the pharmaceutical composition comprising said conjugate or its pharmaceutically acceptable salt of the first aspect of the present invention are for use in a method of preventing an infection.

In certain embodiments the conjugate or the pharmaceutically acceptable salt thereof or the pharmaceutical composition comprising said conjugate or its pharmaceutically acceptable salt of the first aspect are for use in a method of treating an infection.

In certain embodiments such infection is in a body compartment. Such body compartment may be selected from the group consisting of body cavities, body spaces, brain or parts thereof, ear or parts thereof, nose, throat, sinuses, lung or parts thereof, abdomen, bone, skin, muscle, abscess, small intestine, large intestine, cyst, uterus, amniotic sac and joint.

Such body compartment may be any cavity of the human body, such as the oral cavity, cranial cavity, spinal cavity, dorsal cavity, thoracic cavity, pericardial cavity, abdominal cavity, ventral cavity, retroperitoneal space, abdominopelvic cavity, pelvic cavity and its enclosed organs.

In certain embodiments such body compartment is selected from the group consisting of the retropharyngeal space, retropalatial space, mediastinal space, retrosternal space, pleural space, retroperitoneal space, prevesical space, paravesical space, vesicocervical space, rectovaginal space, pararectal space, presacral space, subphrenic space, subhepatic space, supramesocolic space and inframesocolic space.

In certain embodiments the body compartment is the brain or one or more parts of it. In certain embodiments the body compartment is the ear or one or more parts of it, such as the middle ear. In certain embodiments the body compartment is the nose, throat, and sinuses. In certain embodiments the body compartment is the lung or parts of it. In certain embodiments the body compartment is the abdomen. In certain embodiments the body compartment is bone, such as the pelvis. In certain embodiments the body compartment is the skin. In certain embodiments the body compartment is muscles. In certain embodiments the body compartment is an abscess. In certain embodiments the body compartment is the small intestine, such as the duodenum, ileum and jejunum. In certain embodiments the body compartment is the large intestine, such as the colon, appendix and rectum. In certain embodiments the body compartment is a cyst. In certain embodiments the body compartment is the uterus. In certain embodiments the body compartment is the amniotic sac. In certain embodiments the body compartment is a joint.

The present invention also relates to the use of the sustained-release compound of the second or third aspect as a medicament, such as a medicament for the prevention or treatment of joint infections. In certain embodiments the present invention relates to the use of the sustained-release compound of the second or third aspect as a medicament for the prevention of joint infections. In certain embodiments the present invention relates to the use of the sustained-release compound of the second or third aspect as a medicament for the treatment of joint infections.

The present invention further relates to the conjugate of the second and the compound of the third aspect of present invention for use in a method of preventing or treating a joint infection.

In certain embodiments the present invention relates to the conjugate of the second and the compound of the third aspect of present invention for use in a method of preventing a joint infection. In certain embodiments the present invention relates to the conjugate of the second and the compound of the third aspect of present invention for use in a method of treating a joint infection.

If the infection is in a joint, the conjugate according to the first and second aspect and the compound of the third aspect of the present invention may be administered via intraarticular injection.

In certain embodiments the volume of such an intraarticular injection is no more than 12 ml, such as no more than 11 ml, such as no more than 10 ml or such as no more than 9 ml such as no more than 8 ml.

The joint of a joint infection may in certain embodiments be a synovial joint. Such synovial joint may be selected from the group consisting of hinge joints and ball and socket joints. In certain embodiments the joint is a hinge joint. In certain embodiments the joint is a ball and socket joint.

Examples for a synovial joint are knee, hip, shoulder, elbow, foot, hand, sternoclavicular joint and vertebral articulations.

Examples for a joint of the knee are tibiofemoral joint and patellofemoral joint.

Examples for a joint of the shoulder are glenohumeral joint and acromioclavicular joint.

Examples for a joint of the elbow are humero-ulnar joint, humero-radial joint and radio-ulnar joint.

It is understood that the term "joints of the foot" also covers joints of the toes. Examples for a joint of the foot are ankle, subtalar and talocalcaneal joint.

It is understood that the term "joints of the hand" also covers joints of the fingers. Example for a joint of the hand are wrist, intercarpal joint, midcarpal joint, carpometacarpal joint and metacarpophalangeal joint.

Examples for a vertebral articulation are zygapophyseal joints, temporomandibular joints and sacroiliac joints.

In certain embodiments the joint is selected from the group consisting of knee, hip, shoulder, elbow and ankle. In certain embodiments the joint is a knee. In certain embodiments the joint is a hip. In certain embodiments the joint is a shoulder.

In certain embodiments the joint infection is a joint infection related to a surgical implant.

Examples for such surgical implant are pins, rods, screws, artificial joints, mesh, clips, sutures, wires, tubes, catheters, pumps, filters, prostheses, plates, fasteners, washers, bolts, seeds, beads, staples, nails, shunts, cuffs, buttons, ports, cement, fixators, stents, fillers, wax, wraps, weights, stimulators, anchors, expanders, guidewires, fillers, polymers, film, fixators, drains, lines and cones.

In certain embodiments the surgical implant is an artificial joint. In certain embodiments the surgical implant is a prosthesis.

In certain embodiments surgical implants are at least partially made from one or more material selected from the group consisting of metals, ceramics, natural polymers, artificial polymers, bone cement, foreign organic material, artificial tissue and natural tissue. Such natural tissue may be selected from the group consisting of ligament, skin, muscle and bone.

In certain embodiments the natural tissue is bone.

In certain embodiments the conjugate or the pharmaceutically acceptable salt thereof or the pharmaceutical composition comprising said conjugate or its pharmaceutically acceptable salt of the first and second aspect or the compound of the third aspect are for use in a method of preventing a joint infection, in particular a surgical implant-related joint infection. In such case the conjugate or the pharmaceutically acceptable salt thereof or the pharmaceutical composition comprising said conjugate or its pharmaceutically acceptable salt of the first or second aspect or the compound of the third aspect may be administered to the joint prior, during or after the implantation of the surgical implant. In certain embodiments it is administered prior to the implantation a surgical implant. In certain embodiments it is administered during the implantation of a surgical implant. In certain embodiments it is administered after the implantation of a surgical implant, such as for example no more than 1 hour after the implantation, no later than 2 hours after the implantation, no later than 5 hours after the implantation, no later than 10 hours after the implantation, no later than 24 hours after the implantation, no later than 48 hours after the implantation or no later than 72 hours after the implantation, no later than 96 hours after the implantation, no later than a week after the implantation, no later than two weeks after the implantation, no later than three weeks after the implantation, no later than four weeks after the implantation, no later than six weeks after the implantation or no later than eight weeks after the implantation. In certain embodiments it may be administered later than two months after the implantation.

In certain embodiments the joint infection, in particular a joint infection related to surgical implants, comprises the presence of a biofilm in said infected joint, in particular a biofilm on at least one surface of the surgical implant. Such biofilm may comprise organisms selected from the group consisting of bacteria, mycobacteria and fungi. Accordingly, in certain embodiments the method of preventing or treating a joint infection also comprises the preventing of biofilm formation or the eradication of an existing biofilm.

In certain embodiments such biofilm comprises bacteria. Such bacteria may be gram-positive or gram-negative. They may be aerobic or anaerobic bacteria. In certain embodiments the biofilm comprises multiple different species. In certain embodiments the biofilm comprises one predominant species, to which at least 80%, such as at least 85%, at least 90%, at least 92%, at least 95%, at least 96%, at least 97%, at least 98% or at least 99%, of all bacteria present in the biofilm belong.

Examples for gram-positive bacteria are *Staphylococcus, Streptococcus, Enterococcus, Clostridium, Bacillus, Listeria* and lactic acid bacteria, such as *Staphylococcus aureus, Staphylococcus epidermidis, Staphylococcus saprophyticus, Streptococcus pneumoniae, Streptococcus pyogenes, Streptococcus agalactiae, Streptococcus dysgalactiae, Streptococcus viridans, Enterococcus faecalis, Enterococcus faecium, Clostridium tetani, Clostridium botulinum, Clostridium perfringes, Clostridium difficile, Bacillus anthracis, Listeria monocytogenes* and *Propionibacterium acnes.*

Examples for gram-negative bacteria are Enterobacteriaceae, Vibrionaceae, Pseudomonadaceae, Bacteroidaceae, *Actinomyces, Neisseria, Hemophilus, Bordetella, Legionella, Treponema, Borrelia, Chlamydia, Rickettsia, Ehrlichia, Mycoplasma* and *Burkholderia*, such as *Salmonella* species, *Shigella dysenteriae, Klebsiella pneumoniae, Escherichia coli, Escherichia faecalis, Vibrio cholera, Campylobacter jejuni, Pseudomonas aeruginosa, Bacteroides fragilis, Neisseria meningitidis, Neisseria gonorrhoeae, Haemophilus influenza, Actinomyces isrealli, Mycoplasma pneumoniae, Acinetobacter baumanii, Citrobacter, Achromobacter* and *Stenotrophomonas.*

In certain embodiments the biofilm comprises mycobacteria.

In certain embodiments the biofilm comprises fungi. Such fungi may be molds or yeasts.

Examples for fungi are *Candida, Aspergillus, Cryptococcus, Trichosporon, Coccidioides*, and *Pneumocystis*, such as *Candida albicans, Candida parapsilosis, Candida tropicalis, Candida parapsilosis, Candida glabrata; Aspergillus fumigatus, Coccioides immitis, Coccioides neoformans, Trichosporon asahii*, and *Pneumocystis carinii.*

Preferably, administration of the sustained-release compounds of the present invention occurs via intraarticular injection into the infected joint. Accordingly, administration occurs via intraarticular injection into the joints described above.

Intraarticular injection allows the administration of significantly lower doses of the antibiotic compared to, for example, systemic administration of the same drug, which reduces the risks of side effects.

In certain embodiment administration of the conjugates of the present invention, their pharmaceutically acceptable salts or the pharmaceutical composition comprising said conjugates or their pharmaceutically acceptable salts occurs via external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, direct delivery to the brain via an implanted device allowing delivery of the conjugates of the present invention to brain tissue or brain fluids such as via an Ommaya Reservoir, direct intracerebroventricular injection or infusion, injection or infusion into brain or brain associated regions, injection into the subchoroidal space, retro-orbital injection and ocular instillation.

In certain embodiment administration occurs at the infection site. In certain embodiments administration occurs close to the infection site.

In certain embodiments administration of the conjugates of the present invention, their pharmaceutically acceptable salts or the pharmaceutical composition comprising said conjugates or their pharmaceutically acceptable salts occurs via intraarticular injection into the infected joint. Accordingly, administration occurs via intraarticular injection into the joints described above.

Such localized administration of a depot in the form of the conjugates of the present invention at or close to the infection site allows the administration of significantly lower doses of the antibiotic compared to, for example, systemic administration of the same drug, which reduces the risks of side effects.

In a further aspect the present invention relates to a method of preventing or treating a patient suffering from an infection, such as an infection of a body compartment, such as a joint infection and in particular a joint infection related to a surgical implant, comprising administering an effective amount of the conjugate of the present invention, the pharmaceutically acceptable salt thereof or the pharmaceutical composition comprising said conjugate or its pharmaceutically acceptable salt to the patient. Embodiments are as described above.

In a further aspect the present invention relates to the use of the conjugate of the present invention, the pharmaceutically acceptable salt thereof or the pharmaceutical composition comprising said conjugate or its pharmaceutically acceptable salt for the manufacture of a medicament for the prevention or treatment of an infection, such as an infection in a body compartment, such as a joint infection and in particular a joint infection related to a surgical implant. Embodiments are as described above.

EXAMPLES

Materials and Methods

All materials were commercially available except where stated otherwise.

Rp-HPLC Purification:

For preparative RP-HPLC a Waters 600 controller and a 2487 Dual Absorbance Detector was used, equipped with the following column: Waters XBridge™ BEH300 Prep C18 10 μm, 150 ×30 mm, flow rate 40 mL/min. Gradients of solvent system A (water containing 0.1% TFA v/v) and solvent system B (acetonitrile containing 0.1% TFA v/v) were used. Products were detected at 215 nm. HPLC fractions containing product were pooled and lyophilized if not stated otherwise.

Flash Chromatography:

Flash chromatography purifications were performed on an Isolera One system or an Isolera Four system from Biotage AB, Sweden, using Biotage KP-Sil silica cartridges and $CH_2Cl_2$/MeOH, $CH_2Cl_2$/ACN, $CH_2Cl_2$/THF, n-heptane/ethyl acetate or n-heptane/methyl acetate as eluents. Products were detected at 215 nm, 254 nm or 280 nm.

RP-LPLC Purification:

Low pressure RP chromatography purifications were performed on an Isolera One system or an Isolera Four system from Biotage AB, Sweden, using Biotage SNAP C18 cartridges. Gradients of solvent system A (water containing 0.1% TFA v/v) and solvent system B (acetonitrile containing 0.1% TFA v/v) were used. Products were detected at 215 nm. LPLC fractions containing product were pooled and lyophilized if not stated otherwise.

Analytical Methods

UPLC-MS Analysis:

Analytical ultra-performance LC(UPLC)-MS was performed on a Waters Acquity system or an Agilent 1290 Infinity II equipped with a Waters BEH300 C18 column (2.1×50 mm, 1.7 μm particle size or 2.1×100 mm, 1.7 μm particle size; solvent A: water containing 0.04% TFA (v/v), solvent B: acetonitrile containing 0.05% TFA (v/v) or solvent A: water containing 0.1% FA (v/v), solvent B: acetonitrile containing 0.1% FA (v/v)) coupled to an LTQ Orbitrap Discovery mass spectrometer from Thermo Scientific or coupled to a Waters Micromass ZQ or coupled to Single Quad MS System from Agilent or coupled to an Agilent Triple Quad 6460 system.

SEC Analysis:

Size-exclusion chromatography (SEC) was performed on an Agilent 1260 system, equipped with a Sepax Zenix SEC-150 column (150 Å, 7.8×300 mm; isocratic: 60:40 v/v mixture of water containing 0.05% TFA and acetonitrile containing 0.04% TFA) with detection at 215 nm and 280 nm.

OPA Assay for Amine Content Determination:

Amine content of the amine-HA was determined by reacting the free amino groups with o-phthalaldehyde (OPA) and N-acetylcysteine under alkaline conditions and photometric quantification of the formed chromophores, as methodically described by Molnir-Perl (Ed.) (2015), Journal of Chromatography Library 70: 405-444.

Amine Content Determination on the PEG-Hydrogel Beads:

Amino group content of the PEG-hydrogel was determined by conjugation of an Fmoc-amino acid to the free amino groups on the hydrogel and subsequent Fmoc-determination as described by Gude, M., J. Ryf, et al. (2002) Letters in Peptide Science 9(4): 203-206.

Maleimide Content Determination on the PEG-Hydrogel Beads:

Maleimide group content of the PEG-hydrogel was determined by conjugation of Fmoc-cysteine to the maleimide residues on the hydrogel and subsequent Fmoc-determination following a procedure, which is based on Gude, M., Ryf, J. et al. (2002) Letters in Peptide Science 9(4): 203-206 and Smyth, D. G., Blumenfeld, O. O., Konigsberg, W. (1964) Biochemical Journal 91: 589.

Quantitative Amino Acid Analysis (QAAA):

Quantitative amino acid analysis was performed to determine the amount of daptomycin in a sample matrix with unknown content. For the content determination, a material sample containing daptomycin was hydrolysed using a TFA/HCl mixture and microwave irradiation. The resulting single amino acids was dye labelled and analysed chromatographically. The contents of aspartic acid, alanine and ornithine were calculated using calibration curves of the respective amino acid standards. The amount of daptomycin was calculated using the averaged content values of aspartic acid, alanine and omithine.

Daptomycin Content by UV Measurement:

For determination of the daptomycin content of a transient daptomycin-linker HA-hydrogel conjugate, the sample is completely hydrolyzed under strongly alkaline conditions and the UV absorption of the resulting sample at 360 nm is used to calculate the daptomycin content.

Hydrogel Degradation Kinetics:

A hydrogel sample was incubated with degradation buffer of the desired pH in a water bath at the desired temperature. For each sampling time-point, the reaction mixture was homogenized, centrifuged, supernatant was withdrawn, filtered through a syringe filter and transferred into a sterile Eppendorf tube. Samples were further incubated at the same temperature. At the end of the incubation time, all samples were quenched with acetic acid, and analysed chromatographically. The obtained peak areas of the individual samples were used to calculate degradation kinetics.

Example 1

Synthesis of Linker Reagent 1f

Linker Reagent 1f was Synthesized According to the Following Scheme:

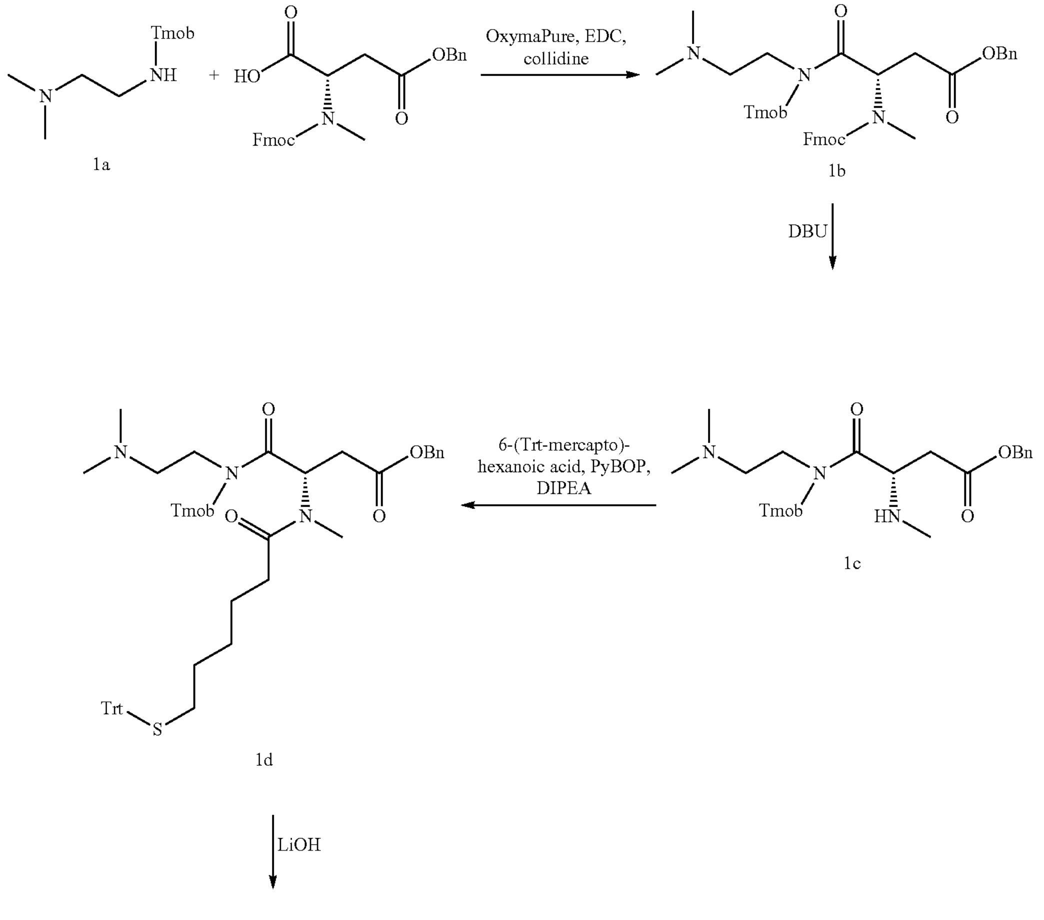

1a 1b 1c 1d

-continued

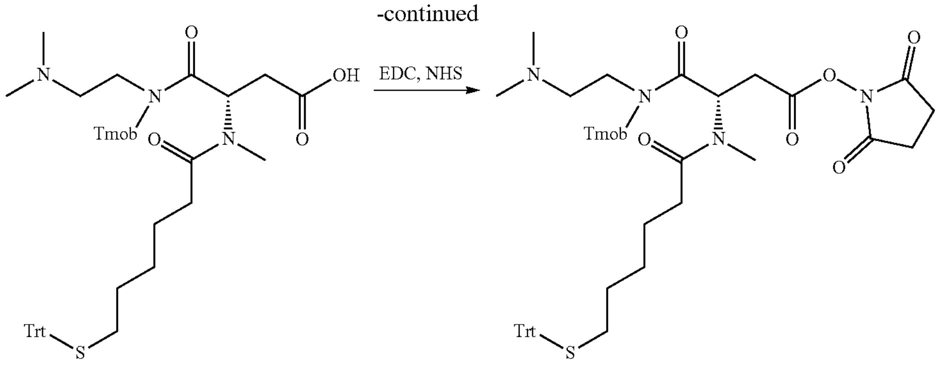

1e 1f

To a solution of N,N-dimethylethylenediamine (2.00 g, 22.69 mmol) and $NaCNBH_3$ (1.35 g, 21.55 mmol) in MeOH (40 mL) was added 2,4,6-trimethoxybenzaldehyde (4.23 g, 21.55 mmol) over two hours. After complete addition, the mixture was stirred at r.t. for 1 hour, acidified with 1 M HCl (60 mL) and stirred for further 30 min. To the reaction mixture saturated $NaHCO_3$ solution (70 mL) was added and the solution was extracted with $CH_2Cl_2$ (5×150 mL). The combined organic phases were dried over $Na_2SO_4$, filtered and the solvents were evaporated in vacuo. The resulting N,N-dimethyl-N'-Tmob-ethylenediamine 1a was dried in high vacuum and used in the next reaction step without further purification.

To a solution of Fmoc-N-Me-Asp(OBn)-OH (4.63 g, 10.07 mmol) in $CH_2Cl_2$ (108 mL) EDC (2.51 g, 13.09 mmol), OxymaPure® (2.00 g, 14.09 mmol) and 2,4,6-collidine (2.53 mL, 2.32 g, 19.13 mmol) were added and the mixture was stirred for 5 min. A solution of crude 1a (3.00 g, max. 11.18 mmol) in $CH_2Cl_2$ (27 mL) was added and the solution was stirred at r.t. for 1 hour. The reaction was quenched by addition of 0.1 M HCl (300 mL) and the acidified mixture was extracted with $CH_2Cl_2$ (5×40 mL). The combined organic layers were washed with saturated $NaHCO_3$ solution (2×90 mL). The organic phase was dried over $Na_2SO_4$, filtered and the solvent was evaporated in vacuo. Crude 1b was purified by flash chromatography.

Yield: 5.31 g (7.48 mmol, 74% over two steps)

MS: m/z 710.23=$[M+H]^+$, (calculated monoisotopic mass: [M]=709.34.)

To a solution of 1b (5.31 g, 7.48 mmol) in THF (53 mL) DBU (1.31 mL, 1.33 g, 8.75 mmol) was added and the solution was stirred at r.t. for 12 min. The reaction mixture was submitted to flash chromatography and 1c was isolated from the product fractions by evaporation of the solvents in vacuo.

Yield: 3.16 g (6.48 mmol, 87%)

MS: m/z 488.13=$[M+H]^+$, (calculated monoisotopic mass: [M]=487.27.)

To a solution of 1c (3.16 g, 6.48 mmol), PyBOP (4.05 g, 7.78 mmol) and DIPEA (3.39 mL, 2.51 g, 19.44 mmol) in $CH_2Cl_2$ (32 mL), a solution of 6-tritylmercaptohexanoic acid (3.04 g, 7.78 mmol) in $CH_2Cl_2$ (32 mL) was added and the mixture was stirred for 24 hours. Additional 6-tritylmercaptohexanoic acid (633 mg, 1.62 mmol) and PyBOP (843 mg, 1.62 mmol) were added and the mixture was stirred for additional 5 hours. After dilution with $CH_2Cl_2$ (600 mL), the organic layer was washed with 0.1 M HCl (3×300 mL) and brine (300 mL), dried over $Na_2SO_4$, filtered and the solvent was evaporated in vacuo. Crude 1d was purified by flash chromatography.

Yield: 5.06 g (5.88 mmol, 91%)

MS: m/z 860.45=$[M+H]^+$, (calculated monoisotopic mass: [M]=859.42.)

To a solution of 1d in a mixture of THF (61 mL) and water (61 mL) LiOH (423 mg, 17.66 mmol) was added and the solution was stirred at r.t. for six hours. After dilution with $CH_2Cl_2$ (500 mL), the organic layer was washed with a mixture of 0.1 M HCl/brine (1:1 v/v, 3×300 mL). The aqueous layers were re-extracted with $CH_2Cl_2$ (5×100 mL). The combined organic layers were washed with brine (200 mL), dried over $Na_2SO_4$, filtered and the solvents were evaporated in vacuo. Crude 1e was dried in high vacuum and used without further purification in the next step.

To a solution of crude 1e (5.05 g, max. 6.56 mmol) in $CH_2Cl_2$ (60 mL), NHS (1.13 g, 9.85 mmol) and EDC(1.89 g, 9.85 mmol) were added and the mixture was stirred at r.t. for 130 min. After evaporation of the solvent in vacuo, the residue was dissolved in a mixture of MeCN/water/TFA (8:2:0.002 v/v, 10 mL) and the resulting solution was purified by automated RP-LPLC to yield pure if after lyophilization.

Yield: 4.15 g (4.52 mmol, 76%, 96% purity by UV215)

MS: m/z 867.44=$[M+H]^+$, (calculated monoisotopic mass: [M]=866.39.)

Example 2

Synthesis of Cross-Linker Reagent 2b

Cross-Linker Reagent 2b was Synthesized According to the Following Scheme:

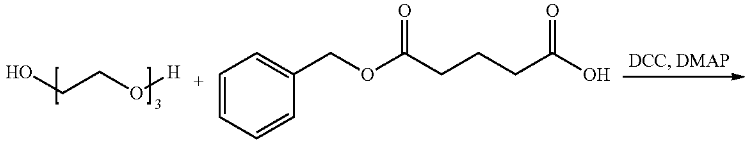

-continued

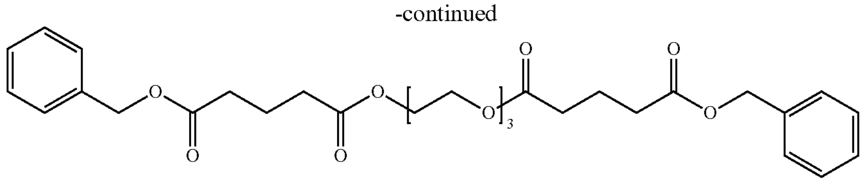

2a

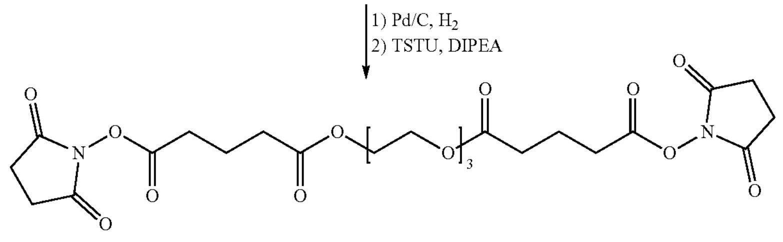

2b

To a cooled solution of triethylene glycol (5.00 g, 33.29 mmol), glutaric acid monobenzyl ester (22.20 g, 99.88 mmol) and DMAP (0.20 g, 1.66 mmol) in $CH_2Cl_2$ (100 mL) DCC(20.61 g, 99.88 mmol) was added and the mixture was stirred at 0° C. for 5 min, then at r.t. for additional 30 min. After filtration, the filtrate was diluted with $CH_2Cl_2$ (500 mL) and the organic layer was washed with a mixture of saturated $NaHCO_3$ solution/water (1:1 v/v, 2×500 mL) and brine (250 mL). The organic phase was dried over $MgSO_4$, filtrated and all volatiles were evaporated in vacuo. Crude 2a was purified by flash chromatography.

Yield: 13.64 g (24.42 mmol. 73%)

MS: m/z 559.08=$[M+H]^+$, (calculated monoisotopic mass: [M]=558.25.)

To a solution of 2a (13.64 g, 24.42 mmol) in THF (55 mL) palladium on charcoal (10% Pd, 1.04 g) was added and the mixture was stirred under a hydrogen gas atmosphere at 50° C. for two hours. The reaction mixture was filtered through a pad of Celite 503, which was flushed with additional THF (50 mL). The combined filtrates were split in half and to each solution TSTU (14.70 g, 48.84 mmol) and DIPEA (8.51 mL, 6.31 g, 48.84 mmol) were added and both reaction mixtures were stirred at r.t. for 16 hours. Both reaction mixtures were combined and filtered through a glass filter funnel, which was flushed with additional THF (50 mL). After removal of all volatiles from the combined organic layers, the residue was dissolved in $CH_2Cl_2$ (500 mL). The solution was washed with 0.5 M phosphate buffer pH 7.4 (2×500 mL), 0.5 M HCl (3×250 mL) and brine (2×250 mL). The organic phase was dried over $MgSO_4$, filtered and all volatiles were evaporated in vacuo. Crude 2b was purified by flash chromatography.

Yield: 10.79 g (18.84 mmol, 77%, 98% purity by UV215)

MS: m/z 573.00=$[M+H]^+$, (calculated monoisotopic mass: [M]=572.19.)

Example 3

Synthesis of Amine-HAs 3, 3' and 3"

Synthesis of Compound 3 in 1 g Scale

To a solution of hyaluronic acid sodium salt (90-130 kDa, 1.00 g, 2.49 mmol COOH eqv.) in 100 mM MES 400 mM 1,3-diaminopropane buffer pH 5.5 (125 mL) HOBt×$H_2O$ (1.15 g, 7.48 mmol) was added. EDC (2.87 g, 14.96 mmol) was added to the mixture and it was stirred at r.t. overnight. Sodium acetate trihydrate (16.97 g) was added to the reaction mixture and the solution was partitioned between twelve 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum for 50 min. The crude material was dissolved in water (80 mL) and 4 M NaOH (26.67 mL) was added. The resulting mixture was stirred at r.t. for two hours before AcOH (6.10 mL) was added while stirring. The solution was partitioned between ten 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum overnight. The obtained material was dissolved in 10% TFA (w/w) in water (50 mL). The solution was partitioned between ten 50 mL Falcon tubes. To each tube isopropanol (ad 50 mL) was added, the tubes were shaken and centrifuged. The supernatants were decanted, and the pellets were washed with isopropanol (40 mL each tube) and dried in high vacuum overnight to yield amine-HA 3 as white solid. The amine content of the material was determined by photometric measurement after chemical derivatization (OPA-assay).

Yield: 1.09 g (TFA salt, 87%, amine-content: 1.422 mmol/g, 71% DS)

Synthesis of Compound 3' in 2 g Scale

To a solution of hyaluronic acid sodium salt (90-130 kDa, 2.00 g, 4.99 mmol COOH eqv.) in 100 mM MES 400 mM 1,3-diaminopropane buffer pH 5.5 (250 mL) HOBt×$H_2O$ (2.29 g, 14.96 mmol) was added. EDC (5.74 g, 29.93 mmol) was added to the mixture and it was stirred at r.t. overnight. Sodium acetate trihydrate (33.94 g) was added to the reaction mixture and the solution was partitioned between twenty-eight 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum for 60 min. The crude material was dissolved in water (160 mL) and 4 M NaOH (53.34 mL) was added. The resulting mixture was stirred at r.t. for two hours before AcOH (12.20 mL) was added while stirring. The solution was partitioned between twenty-two 50 mL Falcon tubes. To each tube absolute EtOH (ad 50 mL) was added, the tubes were shaken and centrifuged. The supernatants were decanted, and the pellets were washed with 80% v/v EtOH (40 mL each tube) and absolute EtOH (40 mL each tube). The residues were dried in high vacuum overnight. 1.92 g of the obtained material were dissolved in 10% TFA (w/w) in water (96.6 mL). The solution was partitioned between eighteen 50 mL Falcon tubes. To each tube isopropanol (ad 50 mL) was added, the tubes were shaken and centrifuged. The supernatants were decanted, and the pellets were washed with isopropanol (40 mL each tube) and dried in high vacuum for 65 hours to yield amine-HA 3". The amine content of the material was determined by photometric measurement after chemical derivatization (OPA-assay).

Yield: 2.13 g (TFA salt, 86, amine-content: 1.400 mmol/g, 70% DS)

Synthesis of Compound 3" in 2 g Scale

The synthesis of amine-HA 3" was carried out as described for compound 3' to yield compound 3" as white solid. The amine content of the material was determined by photometric measurement after chemical derivatization (OPA-assay).

Yield: 2.06 g (TFA salt, 83, amine-content: 1.413 mmol/g, 71% DS)

Example 4

Synthesis of Daptomycin Linker Thiol 4b

Daptomycin Linker Thiol 4b was Synthesized According to the Following Scheme:

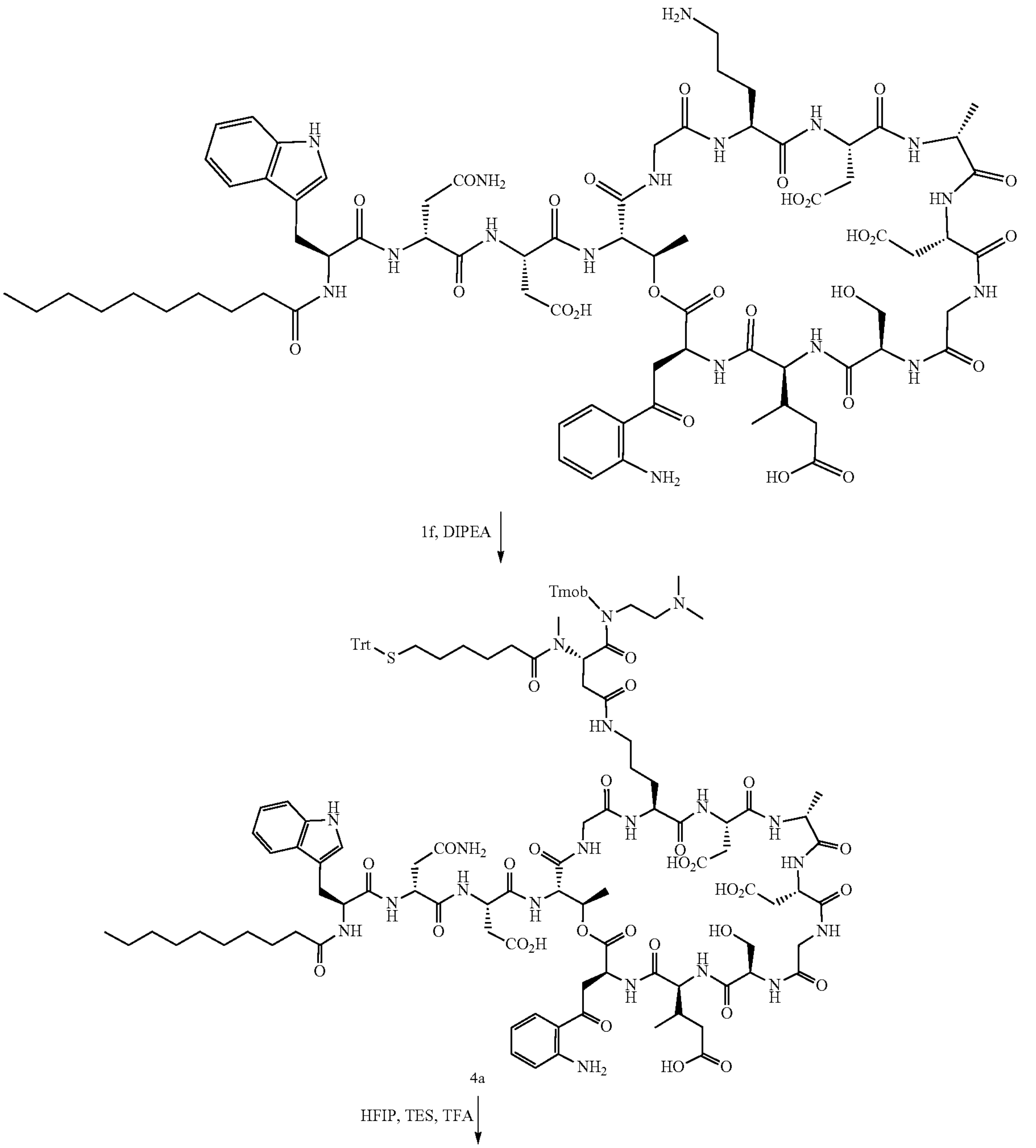

4a

-continued

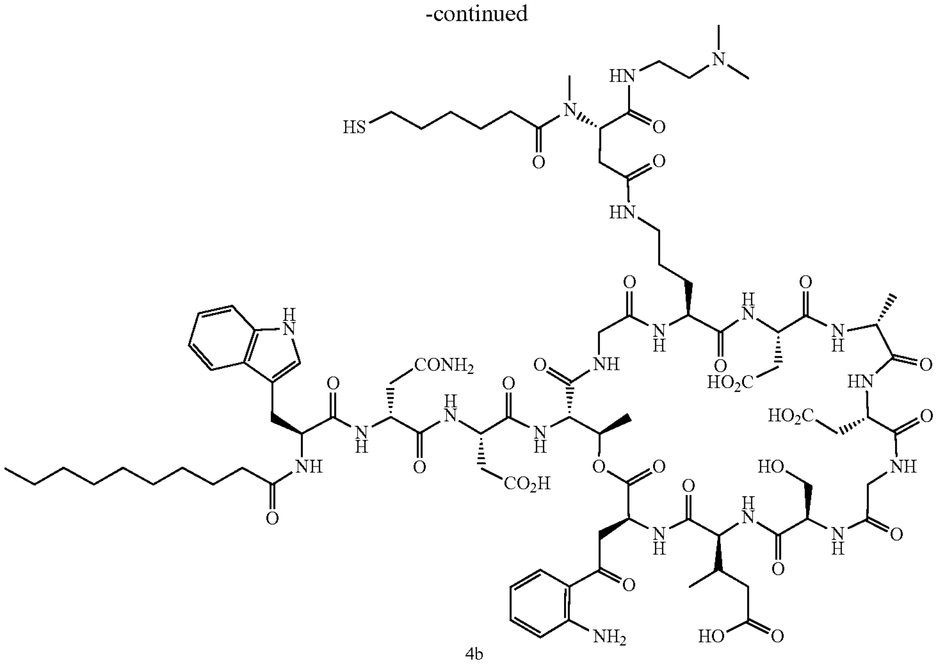

4b

To a mixture of daptomycin (1.08 g, approx. 0.63 mmol) and if (0.99 g, 1.01 mmol) in DMSO (38 mL) DIPEA (0.97 mL, 0.72 g, 5.69 mmol) was added and it was stirred for 380 min. After quenching with TFA (0.44 mL, 0.66 g, 5.69 mmol), the mixture was added to MTBE in 50 mL Falcon tubes (1 mL solution and 40 mL MTBE per tube) to precipitate the conjugate. The tubes were shaken and centrifuged. After decanting the supernatants, the residues were combined and dried in high vacuum overnight. Crude 4a was used for the next step without further purification.

Crude 4a (2.50 g, max. 0.63 mmol) was dissolved in a mixture of HFIP/TES (39:1 v/v, 57 mL) and the solution was stirred at r.t. for 5 min. TFA (4.01 mL) was added and the reaction mixture was stirred at r.t. for two hours. All volatiles were removed in vacuo and the residue was dissolved in a mixture of DCM/TFA (98:2 v/v, 3.0 mL). The solution was added to MTBE in 50 mL Falcon tubes (1 mL solution and 40 mL MTBE per tube) to precipitate the material. The tubes were shaken and centrifuged. After decanting the supernatants, the combined residues were dried in high vacuum overnight. Crude 4b was purified by RP-LPLC to afford pure and mixed product fractions. Pure product fractions were lyophilized to afford a first crop of pure linker thiol. The mixed fractions were additionally purified by preparative RP-HPLC to afford a second crop of pure linker thiol. Both product batches were combined to afford pure 4b.

Yield: 1.00 g (0.46 mmol, 72%, 99% purity at 215 nm)

MS: m/z 975.92=$[M+2H]^{2+}$, (calculated monoisotopic mass: [M]=1948.89.)

Example 5

Synthesis of Transient Daptomycin-Linker HA-Hydrogel Conjugates 5, 5', 5a, 5b, 5c and 5d

Synthesis of 5 (Molar Ratio of Amines/Maleimides/Thiols/Cross-Linker=1.3:1:1:0.3)

All reagent solutions in DMSO were separately filtered through sterile 0.22 μm PTFE syringe filters before the actual hydrogel conjugate synthesis.

A solution of 3" in DMSO (50 mg/mL, 13.00 mL) was mixed with a solution of 4b in DMSO (200 mg/mL, 7.70 mL), a solution of N-succinimidyl 3-maleimidopropionate in DMSO (50 mg/mL, 3.76 mL) and a solution of 2b in DMSO (50 mg/mL, 1.21 mL) in a 50 mL Falcon tube. The yellow solution was drawn into a 30 mL Luer Lock syringe. DIPEA (1.20 mL) was added to the mixture in the 30 mL syringe through the syringe tip, the syringe was closed with a sterile screw cap and vigorously shaken for 30 seconds. An 18G blunt cannula was mounted onto the syringe and the solidifying reaction mixture was transferred into three 10 mL Luer Lock syringes. Due to the increasing viscosity of the mixture, the 18G blunt cannula was exchanged for a 14G cannula after filling the first syringe. The three 10 mL Luer Lock syringes were closed with sterile caps and stored at r.t., in the dark overnight. The gel portions in the syringes were shred into particles by passing them through two stainless steel mesh plates (144 μm mesh size, 3.7 mm diameter) in row, which were fixed with PTFE O-rings in three LL connectors that were mounted on the syringes. The particulate gel portions were directly injected into three portions of EtOH/AcOH (98:2 v/v, 3×35 mL) in 50 mL Falcon tubes. The tubes were vigorously shaken until free-floating particle suspension were obtained. After a short settling time, the slightly turbid supernatants were removed from the dense particle suspensions. The solid conjugate was collected in two 20 mL syringe reactors and was washed with EtOH/AcOH (98:2 v/v, 5×10 mL each) and absolute EtOH (5×10 mL each). After expelling the liquids completely from the suspensions, two sterile 0.22 μm PTFE syringe filters were attached and the materials were dried in high vacuum at r.t. overnight to yield 1642 mg intermediate 1 as yellow powder.

Intermediate 1 (1642 mg) was briefly soaked in 20 mM histidine, 100 mM $CaCl_2$, 2% Tween® 80 buffer pH 6.0 (39.4 mL) in a sterile plastic bottle by gentle swirling. To the pre-swollen suspension, DMSO (200 mL) was added. After complete addition, the bottle was vigorously shaken, and the gel suspension was transferred into six Falcon tubes. After gentle centrifugation, the clear supernatants were removed.

To each tube DMSO (20 mL per tube) was added, the tubes were shaken and centrifuged again gently. After removal of the clear supernatants, DMSO (4 mL per tube) was added and the tubes were gently agitated to afford homogeneous suspensions. The combined suspensions were injected in six portions though a 25G nanoneedle (Japan Bio Products Co., Ltd.) into 2% v/v AcOH and 1% v/v Tween® 80 in absolute EtOH (6×35 mL) in six 50 mL Falcon tubes. The injected suspensions were distributed between twelve 50 mL Falcon tubes in 25 mL portions. To the tubes 2% v/v AcOH and 1% v/v Tween® 80 in absolute EtOH (25 mL per tube) was added. The tubes were vigorously shaken and left standing shortly. The slightly turbid supernatants were removed from the dense suspensions and the latter were combined in two 20 mL syringe reactors. The solids were washed with 2% v/v AcOH and 1% v/v Tween® 80 in absolute EtOH (5×10 mL per syringe) and 2% v/v AcOH in absolute EtOH (5×10 mL per syringe). After expelling the liquids completely from the suspensions without pressing the particles together, two sterile 0.22 μm PTFE syringe filters were attached to the syringe reactors and the materials were dried in high vacuum at r.t. overnight to yield 1626 mg intermediate 2 as yellow granules.

Intermediate 2 (1626 mg) was soaked in 20 mM histidine, 10% α,α-trehalose, 0.2% 1 MDa native hyaluronic acid, 10% propylene glycol, 2% Tween® 80 pH 6.0 (13.17 mL) in two equal portions in 50 mL Falcon tubes for 15 minutes. DMSO (40 mL per tube) was added and the tubes were shaken vigorously for approximately four hours. After dilution with additional DMSO (20 mL), the combined suspensions were subsequently injected through a 14 G and a 25G nanoneedle (Japan Bio Products Co., Ltd.) into absolute EtOH (10×35 mL) in equal portions in ten 50 mL Falcon tubes. The tubes with the injected suspensions were vigorously shaken and left standing for sedimentation. The clear supernatants were removed from the dense suspensions and the latter were combined in a 20 mL syringe reactor. The solid was washed with absolute EtOH (10×10 mL). After expelling the liquid completely from the suspension without pressing the particles together, a sterile 0.22 μm PTFE syringe filter was attached to the syringe reactor and the material was dried in high vacuum at r.t. overnight to yield 1174 mg conjugate 5 as fine, yellow powder. The daptomycin content of 5 was determined by QAAA.

Yield: 1174 mg (51%, daptomycin content: 459 mg/g)

Synthesis of 5' (Molar Ratio of Amines/Maleimides/Thiols/Cross-Linker=1.3:1:1:0.3)

The synthesis of 5' was carried out as described for compound 5, using a solution of 3' in DMSO (50 mg/mL, 13.00 mL), a solution of 4b in DMSO (200 mg/mL, 7.62 mL), a solution of N-succinimidyl 3-maleimidopropionate in DMSO (50 mg/mL, 3.73 mL), a solution of 2b in DMSO (50 mg/mL, 1.20 mL) and DIPEA (1.21 mL) to give compound 5' as fine, yellow powder. The daptomycin content of 5' was determined by UV measurement after total hydrolysis.

Yield: 1262 mg (55%, daptomycin content: 483 mg/g)

Synthesis of 5a (Molar Ratio of Amines/Maleimides/Thiols/Cross-Linker=1.3:1:1:0.3)

A solution of 3 in DMSO (50 mg/mL, 2499 μL) was mixed with a solution of 4b in DMSO (200 mg/mL, 1490 μL), a solution of N-succinimidyl 3-maleimidopropionate in DMSO (50 mg/mL, 728 μL) and a solution of 2b in DMSO (50 mg/mL, 235 μL) in a 50 mL Falcon tube. To test the mixture for filterability, an aliquot of approx. 1.2 mL was passed through a sterile 0.22 μm PTFE syringe filter. The filtrate was combined with the remaining portion of the solution and the mixture was drawn into a 10 mL syringe. DIPEA (240 μL) was added to the solution, the syringe was closed and vigorously shaken for 30 seconds. The syringe with the reaction mixture was stored at r.t. in the dark overnight. The gel in the syringe was shred into particles by passing it through two stainless steel mesh plates (144 μm mesh size, 3.7 mm diameter) in row, which were fixed with PTFE O-rings in three LL connectors that were mounted on the syringe. The particulate gel was directly injected into a portion of EtOH/AcOH (98:2 v/v, 40 mL) in a 50 mL Falcon tube. The syringe and the shredding line were flushed with a small portion of EtOH/AcOH (98:2 v/v, 4 mL) and the washing liquid was combined with the suspension in the Falcon tube. The tube was vigorously shaken until a free-floating particle suspension was obtained. The suspension was transferred into a 10 mL syringe reactor with PP frit in portions until the whole material was present in the syringe reactor. The particles were washed with EtOH/AcOH (98:2 v/v, 15×8 mL). After expelling all liquids, hydrogel 5a was dried in high vacuum for 8 hours. The daptomycin content of 5a was determined by QAAA.

Yield: 301 mg (68%, daptomycin content: 489 mg/g)

Synthesis of 5b (Molar Ratio of Amines/Maleimides/Thiols/Cross-Linker=1.02:1:1:0.02)

A solution of 3 in DMSO (50 mg/mL, 240 μL) was mixed with a solution of 4b in DMSO (200 mg/mL, 182 μL), a solution of N-succinimidyl 3-maleimidopropionate in DMSO (50 mg/mL, 89.1 μL) and a solution of 2b in DMSO (50 mg/mL, 1.9 μL) in a 2 mL Eppendorf tube. DIPEA (26.4 μL) was added to the solution, the tube was shaken, centrifuged and left standing at r.t. in the dark for gelation overnight. The gel was transferred into a 2 mL LL syringe and passed through two stainless steel mesh plates (144 μm mesh size, 3.7 mm diameter) in row, which were fixed with PTFE O-rings in three LL connectors that were mounted on the syringe. The particulate gel was directly injected into a portion of EtOH/AcOH (98:2 v/v, 10 mL) in a 15 mL Falcon tube. The syringe and the shredding line were flushed with a small portion of EtOH/AcOH (98:2 v/v, 2 mL) and the washing liquid was combined with the suspension in the Falcon tube. The tube was vigorously shaken until a free-floating particle suspension was obtained, then centrifuged. After decanting the supernatant, the particles were suspended in EtOH/AcOH (98:2 v/v, 10 mL) and transferred into a 10 mL syringe reactor with PP frit in portions until the whole material was present in the syringe reactor. The particles were washed with EtOH/AcOH (98:2 v/v, 5×8 mL). After expelling all liquids, hydrogel 5b was dried in high vacuum overnight. The daptomycin content of 5b was determined by QAAA.

Yield: 40 mg (810%, daptomycin content: 570 mg/g)

Synthesis of 5c (Molar Ratio of Amines/Maleimides/Thiols/Cross-Linker=1.05:1:1:0.05)

A solution of 3 in DMSO (50 mg/mL, 240 μL) was mixed with a solution of 4b in DMSO (200 mg/mL, 177 μL), a solution of N-succinimidyl 3-maleimidopropionate in DMSO (50 mg/mL, 86.5 μL) and a solution of 2b in DMSO (50 mg/mL, 4.7 μL) in a 2 mL Eppendorf tube. DIPEA (25.9 μL) was added to the solution, the tube was shaken, centrifuged and left standing at r.t. in the dark for gelation overnight. Work-up was carried out as described for compound 5b. The daptomycin content of 5c was determined by QAAA.

Yield: 40 mg (83%, daptomycin content: 564 mg/g)

Synthesis of 5d (Molar Ratio of Ratio Amines/Maleimides/Thiols/Cross-Linker=1.1:1:1:0.1)

A solution of 3 in DMSO (50 mg/mL, 240 μL) was mixed with a solution of 4b in DMSO (200 mg/mL, 168.9 μL), a solution of N-succinimidyl 3-maleimidopropionate in DMSO (50 mg/mL, 82.6 μL) and a solution of 2b in DMSO (50 mg/mL, 8.9 μL) in a 2 mL Eppendorf tube. DIPEA (25.2 μL) was added to the solution, the tube was shaken, centrifuged and left standing at r.t. in the dark for gelation overnight. Work-up was carried out as described for compound 5b. The daptomycin content of 5d was determined by QAAA.

Yield: 37 mg (80%, daptomycin content: 476 mg/g)

Example 6

Synthesis of Cross-Linker Reagent 6d

Cross-linker reagent 6d was synthesized according to the following scheme. Theoretical calculations of the Mw of the polydisperse PEG conjugates were exemplarily performed for a PEG 1000 with 23 ethylene glycol units that has a Mw of 1031.22 g/mol (exact mass: 1030.61 g/mol):

Glutaric acid monobenzyl ester (40.0 g, 180 mmol), ethylene glycol (101 mL, 1.80 mol) and DMAP (2.20 g; 18.0 mmol) were dissolved in $CH_2Cl_2$ (400 mL). DCC (44.6 g, 216 mmol) was added to the solution, and the mixture was stirred at room temperature for one hour. The reaction mixture was filtered and the filter cake was washed with additional $CH_2Cl_2$ (50 mL). The filtrate was washed with 0.1 N hydrochloric acid (2×250 mL) and brine (1×250 mL). The organic phase was dried over $MgSO_4$, filtered and all volatiles were evaporated in vacuo. The residue was purified by flash chromatography to afford intermediate 6a.

Yield: 41.9 g (157 mmol, 87%)

MS: m/z 267.00=$[M+H]^+$, (calculated monoisotopic mass: [M]=266.16.)

Intermediate 6a (41.0 g, 154 mmol), glutaric acid anhydride (31.6 g, 277 mmol) and DMAP (3.76 g, 30.8 mmol) were dissolved in $CH_2Cl_2$ (164 mL). DIPEA, (53.8 mL, 308 mmol) was added and the mixture was stirred at r.t. for two hours. The mixture was washed with 1 M hydrochloric acid (lx 400 mL, lx 200 mL) and brine (200 mL). The organic phase was dried over $MgSO_4$, filtered and all volatiles were evaporated in vacuo. The residue was purified by flash chromatography to afford intermediate 6b.

Yield: 34.9 g (91.7 mmol, 60%)

MS: m/z 381.05=$[M+H]^+$, (calculated monoisotopic mass: [M]=380.15.)

Poly(ethylene glycol) (PEG 1000, 19.0 g), intermediate 6b (25.3 g, 66.5 mmol) and DMAP (116 mg, 0.95 mmol) were dissolved in $CH_2Cl_2$ (95 mL). DCC (13.7 g, 66.50 mmol) was added at 0° C. and the mixture was afterwards

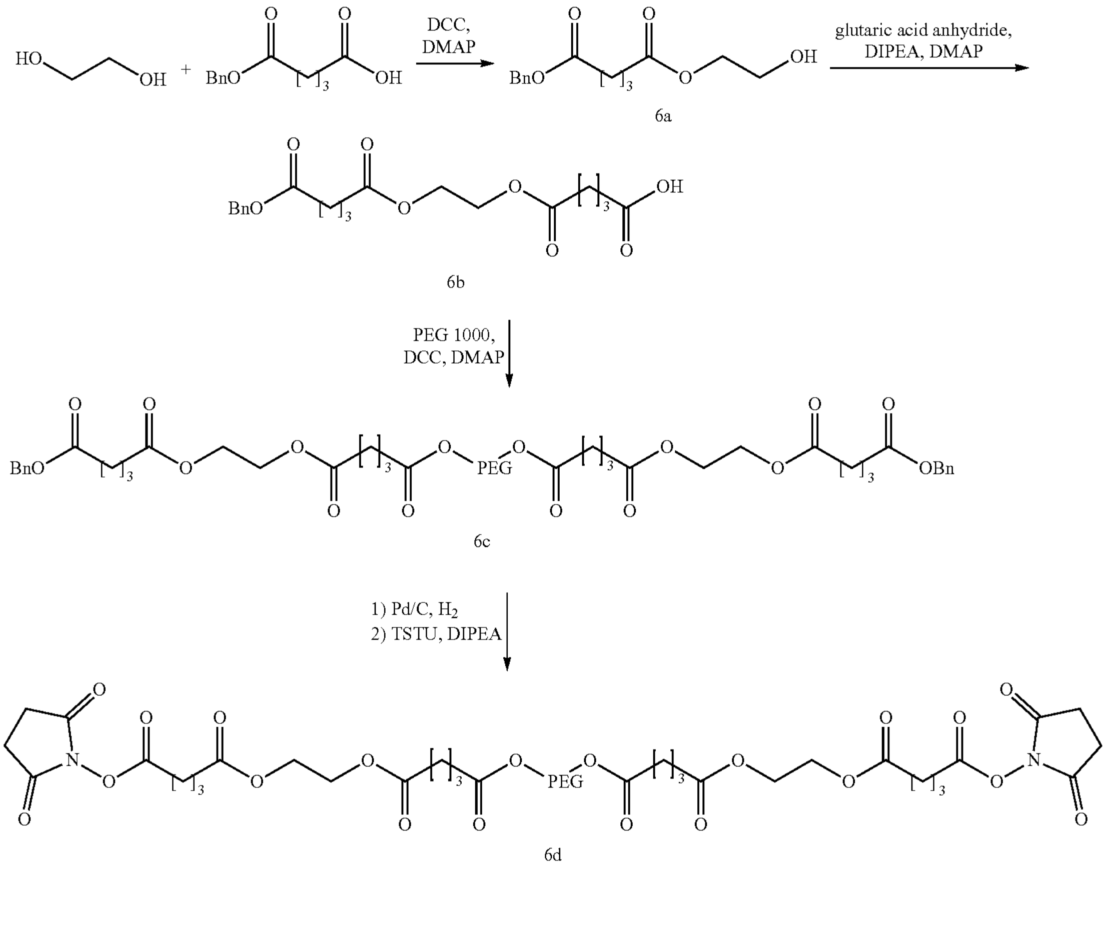

stirred at r.t. for 16 hours. The mixture was diluted with MTBE (95 mL), filtered and all volatiles of the filtrate were evaporated in vacuo. The residue was dissolved in $CH_2Cl_2$ (120 mL) and the solution was diluted with MTBE (1800 mL) and n-heptane (100 mL) and split in two halves. The mixtures were cooled to −20° C. for 20 h. The supernatants were decanted and the precipitates suspended in a −20° C. cold mixture of MTBE/n-heptane (9:1 v/v, 2× approx. 900 mL). The mixtures were stored at -20° C. for one hour before supernatants were decanted. The precipitates were again suspended in a −20° C. cold mixture of MTBE/n-heptane (9:1 v/v, 2× approx. 900 mL) and the resulting suspensions were combined and filtered. The filter cake was washed with a −20° C. cold mixture of MTBE/n-heptane (9:1 v/v, 500 mL) and was afterwards dried in high vacuum to afford pure intermediate 6c.

Yield: 28.2 g

MS: m/z 878.33=[M+2H]2+, (calculated monoisotopic mass: [M]=1754.89.)

Compound 6c (28.1 g, 16.0 mmol) was dissolved in THF (281 mL) and palladium on charcoal (10% Pd, 0.68 g) was added. The reaction mixture was stirred at 50° C. under a hydrogen atmosphere for one hour. The mixture was filtered through a pad of Celite 503, which was flushed with additional THF (50 mL). To the combined filtrates, TSTU (19.3 g, 64.0 mmol) and DIPEA (11.2 mL, 64.0 mmol) were added and the reaction mixture was stirred at r.t. for three hours. The mixture was filtered and the filter cake was washed with THF (50 mL). All volatiles were removed from the combined filtrates in vacuo and the residue was dissolved in $CH_2Cl_2$ (1200 mL). The solution was washed with 0.5 M phosphate buffer pH 7.4 (2×600 mL) and brine (2×200 mL) and was afterwards dried over $MgSO_4$. After filtration, all volatiles were removed in vacuo to afford crude NHS ester. The crude material was dissolved in toluene (1000 mL) and the solution was split in two halves. To each portion MTBE (450 mL) was added and the resulting mixtures were stored at −20° C. overnight. The supernatants were decanted and the solids were collected by filtration and washed with −20° C. cold MTBE (500 mL). The filter residue was transferred into a 100 mL flask and dried for 4 h in high vacuum. The residue was dissolved in $CH_2Cl_2$ (600 mL) and the solution was split in three portions. To each portion MTBE (800 mL) was added and the resulting mixtures were stored at −20° C. overnight. The supernatants were decanted from the precipitated oils and all volatiles were removed. The residues were combined with the precipitated oils and the combined crude material was dissolved in THF (1200 mL) and the solution was split in four portions. To each portion MTBE (700 mL) was added and the resulting mixtures were stored at −25° C. overnight. The supernatants were decanted and the solids were collected by filtration and washed with −20° C. cold MTBE (1000 mL). Pure cross-linker reagent 6d was obtained after drying in high vacuum.

Yield: 17.5 g

MS: m/z 885.25=[M+2H]2+, (calculated monoisotopic mass: [M]=1768.83.)

Example 7

Synthesis of Backbone Reagent 7

Backbone reagent 7 was synthesized as HCl salt using L-lysine building blocks, analogously to an earlier described procedure (WO2013/053856, example 1, compound 1g therein):

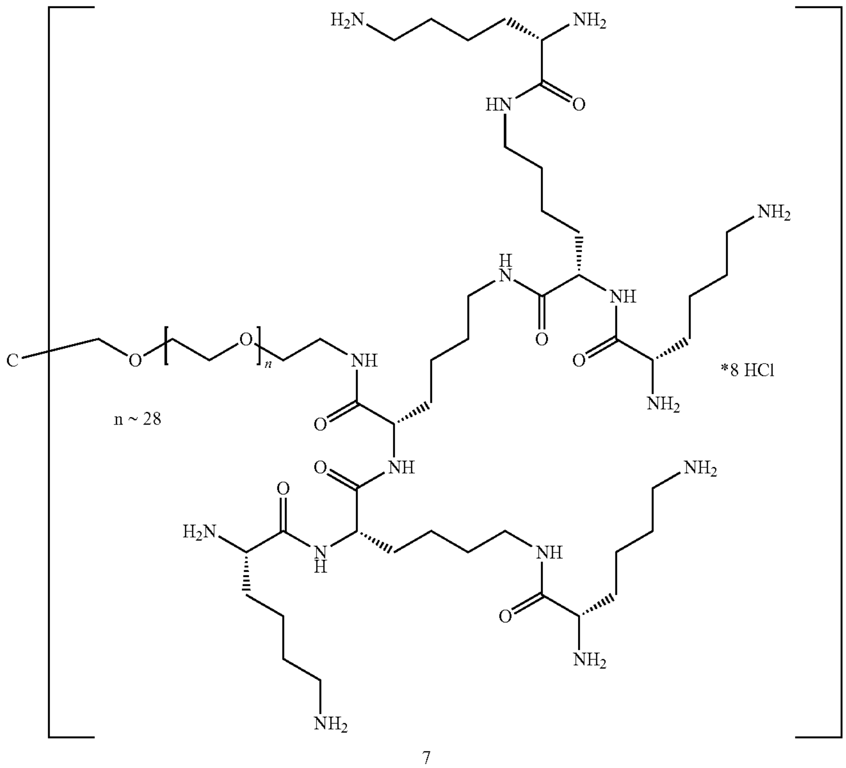

7

Example 8

Synthesis of PEG-Hydrogel Beads 8a, 8b, and 8c Containing Free Amino Groups

The weights of the PEG-hydrogel beads 8a, 8b and 8c were estimated by the volume of the aqueous hydrogel bead suspensions, calculating with 1 g of the dry PEG-hydrogel beads 8a, 8b or 8c swelling to a volume of approx. 20 mL under aqueous conditions. All liquids, solvents and reagent solutions were filtered through 0.2 μm PES filters (for aqueous solutions) or 0.2 μm PTFE filters (all others) before use.

A cylindrical 250 mL reactor with bottom outlet, diameter 60 mm, equipped with baffles, was charged with an emulsion of Cithrol™ DPHS (0.25 g) in heptane (75 mL). The reactor content was stirred with a pitch-blade stirrer, diameter 45 mm, at 520 rpm, at r.t.. A solution of cross-linker 6d (3129 mg) and backbone reagent 7 (2600 mg) in DMSO (22.92 g) was added to the reactor and stirred for 10 min to form an emulsion. TMEDA (11.6 mL) was added to effect polymerization and the mixture was stirred at r.t. for 16 h. Acetic acid (17.8 mL) was added while stirring. After 10 min, a sodium chloride solution (15 wt %, 90 mL) was added under stirring. After 10 min, the stirrer was stopped and phases were allowed to separate. After 30 min, the aqueous phase containing the PEG-hydrogel beads was drained.

For bead size fractionation, the water-hydrogel suspension was diluted with ethanol (40 mL) and wet-sieved on 125, 100, 75, 63, and 50 μm (mesh opening) stainless steel sieves, diameter 200 mm using a sieving machine for 15 min. Sieving amplitude was 1.5 mm, liquid flow was 300 mL/min. First, a sodium chloride solution (20 wt %, 3000 mL), then water (1000 mL) was used as the liquid for wet-sieving. The bead fractions on the different sieves were transferred into 50 mL Falcon tubes (max. 14 mL bead suspension per tube) and successively washed with AcOH (0.1% v/v, 3×~40 mL) and ethanol (5-7×~40 mL) by addition, shaking, centrifugation and decantation. The bead fractions were transferred into 20 mL syringes with PE frits (max. ≈600 mg hydrogel beads per syringe) and dried in high vacuum for 16 hours to yield amine hydrogels 8a, 8b and 8c. The amine content of the hydrogels was determined for bead fraction 8a, representatively for all batches, by conjugation of an Fmoc-amino acid to the free amino groups on the hydrogel and subsequent Fmoc determination.

Yields: 8a (63 μm sieve fraction): ~ 125 mg
8b (75 μm sieve fraction): ~ 600 mg
8c (100 μm sieve fraction): ~ 1400 mg
Amine content: 0.877 mmol/g Example 9

Synthesis of Transient Daptomycin-Linker PEG-Hydrogel Conjugate 9b

Amine hydrogel beads 8c (approx. 600 mg) were placed into a 20 mL syringe reactor with PE frit. The beads were washed with NMP (3×12 mL) and NMP/DIPEA (98:2 v/v, 2×12 mL) and all solvents were expelled afterwards. N-succinimidyl 3-maleimidopropionate (416 mg, 1.56 mmol) was dissolved in NMP (7.2 mL) and the resulting solution was drawn to the hydrogel in the syringe reactor. The suspension was allowed to incubate for two hours at r.t. under gentle agitation. The liquids were expelled and the hydrogel beads were washed with NMP (5×12 mL), AcOH (0.1% v/v, 5×12 mL) and ethanol (5×12 mL). Maleimide hydrogel 9a was obtained by drying in high vacuum for 5 days. The maleimide content of the functionalized PEG-hydrogel beads 9a was determined by conjugation of Fmoc-cysteine to the maleimide residues on the hydrogel and subsequent Fmoc determination.

Yield: not determined
Maleimide content: 0.7166 mmol/g

A suspension of the maleimide functionalized hydrogel beads 9a (346 mg, 0.248 mmol maleimides) in buffer (100 mM succinate, 0.05% Tween 20, pH 5.5, 15.0 mL) in a 50 mL Falcon tube was agitated for 5 min and then centrifuged. A part of the supernatant (approx. 11 mL) was discarded and a solution of daptomycin linker thiol 4b (820 mg, 0.376 mmol) in buffer (100 mM succinate, 0.05% Tween 20, pH 5.5, 32.8 mL) was added to the hydrogel suspension. The tube was agitated at r.t. and protected from light for 22 hours. The tube was centrifuged and the supernatant was partially removed to leave approx. 2 mL supernatant above the dense bead suspension. The beads were transferred into a 20 ml syringe reactor with a PE frit. The hydrogel beads were successively washed with buffer (100 mM succinate, 0.05% Tween 20, pH 5.5, 10×10 mL), AcOH (0.1% v/v, 10×10 mL), NMP/AcOH (97:3 v/v, 10×10 mL) and ethanol (10×10 mL). The transient daptomycin-linker PEG-hydrogel conjugate 9b was obtained after drying in high vacuum overnight. The daptomycin content of 9b was determined by QAAA.

Yield: 821 mg (99%, daptomycin content: 470.1 mg/g)

Example 10

Linker Release Kinetics for Transient Daptomycin-Linker Hydrogel Conjugates

The linker kinetics with respect to the daptomycin species release from transient daptomycin-linker hydrogel conjugates were investigated by incubation of transient daptomycin-linker HA-conjugate 5 and transient daptomycin-linker PEG-conjugate 9b at pH 7.4 and 37° C. Daptomycin is prone to hydrolytic degradation and some minor different degradation pathways upon aqueous incubation. For determination of the linker kinetics on the carriers, the supernatants of the incubated suspensions were analyzed by UPLC at 215 nm and all daptomycin-related peaks were taken into account for the calculation of the linker kinetics. The half-lifes of the linker with respect to daptomycin species release have been determined to be two weeks for the transient daptomycin-linker PEG-hydrogel conjugate 9b and eleven days for the transient daptomycin-linker HA-conjugate 5.

Example 11

Stability of Daptomycin in Transient Daptomycin-Linker Hydrogel Conjugates

The relative stability of the covalently bound daptomycin in the transient daptomycin-linker hydrogel conjugates towards hydrolytic and other degradation pathways in comparison to free daptomycin was investigated. For that purpose, free daptomycin, transient daptomycin-linker HA-conjugate 5 and transient daptomycin-linker PEG-conjugate 9b were incubated at pH 7.4 and 37° C. The supernatants of the carrier samples were exchanged five times within a week and the daptomycin purity in these samples was analyzed by UPLC. In parallel, analytical samples of the free daptomycin control solution were also analyzed by UPLC at the same incubation times. The purity of daptomycin in the samples was calculated as the ratio of the peak area of the intact daptomycin peak at 215 nm relative to the area sum of all daptomycin-related peaks identified at 215 nm. It was found that within the first 7 days of incubation under physiological conditions, the purity of the daptomycin, which was continuously released from transient daptomycin-linker hydrogel conjugates was constantly at around 85%, whereas the purity of the free daptomycin in the solution control sample dropped to 72% at day seven.

Example 12

Degradation Study of Transient Daptomycin-Linker Hydrogel Conjugates

The transient daptomycin-linker hydrogel conjugates were analyzed regarding carrier degradation. For that purpose, transient daptomycin-linker HA-conjugates 5, 5b, 5c, 5d and transient daptomycin-linker PEG-conjugate 9b were incubated at pH 7.4 and 37° C. The samples were visually checked for the presence of the solid carrier particles daily. As soon as no particles could be detected in the sample anymore, the material was deemed to be fully degraded to soluble products. It was found that the transient daptomycin-linker PEG-hydrogel conjugate 9b was fully degraded after about 40 days and the transient daptomycin-linker HA-hydrogel conjugate 5 was fully degraded after about 55 days. The less cross-linked, transient daptomycin-linker HA-conjugates 5b and 5c were fully degraded after about 36 days and conjugate 5d needed more than 49 days for full degradation.

Example 13

In Vitro Biofilm Eradication Study

This study was performed to investigate the daptomycin concentration required to fully eradicate biofilms when constantly exposed to daptomycin for one or three days. The screening was done using a Calgary Biofilm Device (CBD) as described in Ceri, H., et al. (1999) Journal of Clinical Microbiology 37(6): 1771-1776. Biofilms were grown in tryptic soy broth (TSB) using a Methicillin-sensitive *Staphylococcus aureus* (MSSA) MN8 strain. Aliquots of a diluted culture of this bacterial strain in TSB, obtained from an inoculum of the respective strain on trypticase soy agar plates (TSA), were transferred to all but the negative control wells of flat-bottom 96-well microtiter plates. The bacterial biofilms were formed by immersing lids with pegs into the 96-well microtiter plates, followed by incubation for 24, 48 and 72 hours at 37° C. The differently aged biofilms were subsequently transferred into new microtiter plates using TSB media with addition of 12 mg/mL bovine serum albumin (BSA) and 50 μg/mL calcium as $CaCl_2$. Daptomycin was added to the media as required to obtain concentrations of 2-1458 μg/mL. The plates were incubated for one or three days at 37° C. The biofilms were detached from the pegs by centrifugation, generating bacterial suspensions in the wells of the microtiter plates. The optical densities of these suspensions were measured (OD600) to determine the biofilm eradication concentrations. All measurements were performed in triplicates. It was found that biofilms of all ages were eradicated after 24 hours exposure to 486 μg/mL daptomycin. When biofilms were exposed for three days, only 162 μg/mL daptomycin was needed to fully eradicate biofilms.

Example 14

Quantification of Daptomycin Concentrations in Rabbit Plasma

Daptomycin concentrations in rabbit plasma after IA administration of either PEG-hydrogel conjugate 9b or transient daptomycin-linker HA-hydrogel conjugate 5 and different residence times of the materials were determined after plasma protein precipitation via liquid chromatography separation and detection by LC-MS. As internal standard deuterated daptomycin-D5 peptide was used. LC-MS analysis was carried out by using an UHPLC system coupled to a triple quadrupole mass spectrometer via an ESI probe. Chromatography was performed on a C18 analytical UHPLC column. UPLC grade water containing 0.1% formic acid (v/v) was used as mobile phase A and UPLC grade acetonitrile with 0.1% formic acid as mobile phase B. The gradient system comprised a linear increase from 20% B to 45% B in 10 min. Mass analysis was performed in MRM mode with the selected transitions for daptomycin and the internal standard daptomycin-D5.

Calibration standards of daptomycin in blank plasma were prepared as follows: thawed 1K2-EDTA rabbit plasma was homogenized. The daptomycin formulation was spiked into blank plasma at concentrations between 1000 ng/mL and 2 ng/mL. These solutions were used for the generation of a calibration curve. Calibration curves were weighted $1/x^2$.

For sample preparation, 70 μL of rabbit plasma sample were spiked with 20 μL of internal standard solution. Subsequently, the mixture was spiked with 40 μL of 0.5 M citrate buffer pH 4.0 and incubated for 30 min at room temperature. Protein precipitation was carried out by addition of 270 μL of room temperature methanol. 200 μL of the supernatant were transferred into a new well-plate and evaporated to dryness (under a gentle nitrogen stream at 45° C.). 50 μL of reconstitution solvent ($H_2O$/MeOH 1:1+1.0% FA) were used to dissolve the residue by intensive shaking. 10 μL were injected into the LC-MS system.

Example 15

Pharmacokinetic Profiles of Daptomycin in New Zealand White Rabbits after Intraarticular (IA) Injections with Transient Daptomycin-Linker Hydrogel Conjugates This study was performed in order to investigate the systemic pharmacokinetics of daptomycin in male New Zealand White (NZW) rabbits following intraarticular administration of either transient daptomycin-linker PEG-hydrogel conjugate 9b or transient daptomycin-linker HA-hydrogel conjugate 5. Animals (n=9 per group) received a single IA injection of 300 μL transient daptomycin-linker PEG-hydrogel conjugate 9b formulation (15 mg daptomycin nominal) or 300 μl of a formulation of transient daptomycin-linker HA-hydrogel conjugate (5; 15 mg daptomycin nominal) in the right knee and 300 μL vehicle in the left knee. Three animals from each group were sacrificed three days, two weeks, and six weeks after dosing. Blood samples for PK analysis were collected and processed to plasma at predose and 0.5, 1, 2, 4, 8, 12, 24, 48, 72, 96, 120, 144, 168, 336 hours post dose (PK blood samples were only collected until 72 hours post dose from animals with three days inlife). Moreover, blood was collected for clinical chemistry and hematology at predose, day three, day seven*, week two*, and week six* (*in the appropriate groups). Visual inspection and palpation (such as reddening/swelling) were performed in the first seven days after injection. Hereafter, visual inspection and palpation was done once a week. Upon sacrifice all knees were sampled for histopathological examination.

Results: Dose administrations were well tolerated with no visible signs of discomfort during administration and following administration. No dose site reactions were observed any time throughout the study and all animals showed normal behavior and no knee swelling or warming. After intraarticular injection of either transient daptomycin-linker PEG-hydrogel conjugate 9b or transient daptomycin-linker HA-hydrogel conjugate 5, sustained PK plasma concentrations above 100 ng/mL were detected over the time course of one week after injection.

Example 16

Quantification of Daptomycin Concentrations in Rabbit Synovial Liquid

Rabbit synovial liquid was sampled after IA administration of transient daptomycin-linker HA-hydrogel conjugate 5' and different residence times of the materials from incised rabbit knee capsules with an Ecoflo perfusion catheter set after cutting of the butterfly needle. During collection the synovial fluid stayed in the catheter and did not enter the syringe. The fluid in the perfusion catheter was collected by flushing the perfusion catheter vigorously with air. 100 μL of the synovial liquid were transferred to a centrifugation filter (PVDF membrane with 5.0 μm pore size) and centrifuged for 4 min at 12,000 g. The filtrate was diluted with K2-EDTA rabbit plasma and after dilution analyzed for daptomycin content as described for plasma samples in example 14.

Example 17

Synovial Liquid Determination of Daptomycin in New Zealand White Rabbits after Intraarticular (IA) Injections with Transient Daptomycin-Linker Hydrogel Conjugate 5'

This study was performed in order to investigate the synovial liquid concentrations of daptomycin in male New Zealand White (NZW) rabbits following intraarticular administration of transient daptomycin-linker HA-hydrogel conjugate 5'. Animals (n=3 per group) received a single IA injection of 300 μL of a formulation of transient daptomycin-linker HA-hydrogel conjugate 5' (15 mg daptomycin nominal) in the left knee. The study consisted of three groups with different in-life phases. Animals from group 1 were sacrificed after three days, animals from group 2 were sacrificed after four days, and animals from group 3 were sacrificed five days after dosing. At sacrifice, synovial liquid was sampled from the left knee and stored frozen until analysis.

Results: All animals showed a good clinical condition throughout the study without local side effects. After intraarticular injection of transient daptomycin-linker HA-hydrogel conjugate 5', average synovial liquid concentrations of 58.1 μg/mL daptomycin were determined three days after dosing in animals from group 1, average synovial liquid concentrations of 111 μg/mL daptomycin were determined four days after dosing in animals from group 2, and average synovial liquid concentrations of 102 μg/mL daptomycin were determined five days after dosing in animals from group 3.

Two additional experiments indicate that the determined daptomycin levels can be considered as minimal values of daptomycin in rabbit synovial liquid. First, spiking experiments with bovine synovial fluid showed recovery values of around 50% using the same sample preparation method (centrifugation filter PVDF membrane with 5.0 μm pore size). Second, in an additional experiment, the extraction of one whole rabbit synovial fluid sample with organic solvent revealed significantly higher free daptomycin concentration in this native, unfiltered synovial fluid sample compared to the concentrations which have been determined in the filtered samples.

ABBREVIATIONS

ACN Acetonitrile
AcOH Acetic Acid
Asp Aspartic Acid
Bn Benzyl
BSA Bovine Serum Albumin
CBD Calgary Biofilm Device
DBU 1,8-Diazabicyclo[5.4.0]undec-7-ene
DCC Dicyclohexylcarbodiimide
DCM Dichloromethane
DIPEA N,N-Diisopropylethylamine
DMAP 4-(Dimethylamino)pyridine
DMSO Dimethyl Sulfoxide
DPHS Dipolyhydroxystearate
DS Degree of Substitution
EDC N-(3-Dimethylaminopropyl)-N'-ethylcarbodiimide Hydrochloride
EDTA Ethylenediaminetetraacetic Acid
eqv. Equivalents
ESI Electrospray Ionization
EtOH Ethanol
FA Formic Acid
Fmoc Fluorenylmethyloxycarbonyl
HA Hyaluronic Acid
HFIP 1,1,1,3,3,3-Hexafluoro-2-propanol
HOBt 1-Hydroxybenzotriazole
HPLC High-Performance Liquid Chromatography
IA Intraarticular
LC Liquid Chromatography
LC-MS Mass Spectrometry Coupled Liquid Chromatography
LL Luer Lock
LPLC Low Pressure Liquid Chromatography
MeCN Acetonitrile
MeOH Methanol
MES 2-(N-Morpholino)ethanesulfonic acid
MRM Multiple Reaction Monitoring
MSSA Methicillin-sensitive *Staphylococcus aureus*
MTBE tert-Butyl Methyl Ether
Mw Molecular Weight
NHS N-Hydroxysuccinimide
NMP N-Methyl-2-pyrrolidone
NZW New Zealand White Rabbits
OD600 Optical Density Measured at 600 nm Wavelength
OPA o-Phthalaldehyde
OxymaPure® Ethyl cyano(hydroxyimino)acetate
PE Polyethylene
PEG Poly(ethylene glycol)
PES Polyethersulfone
PK Pharmacokinetic/s
PP polypropylene
PTFE Polytetrafluoroethylene
PVDF Polyvinylidene Difluoride
PyBOP Benzotriazol-1-yl-oxytripyrrolidinophosphonium Hexafluorophosphate
QAAA Quantitative Amino Acid Analysis
RP Reversed Phase
RP-HPLC Reversed Phase High-Performance Liquid Chromatography
RP-LPLC Reversed Phase Low Pressure Liquid Chromatography
r.t. Room Temperature SEC Size-exclusion chromatography
TES Triethylsilane
TFA Trifluoroacetic Acid
THF Tetrahydrofurane
TMEDA N,N,N',N'-Tetramethylethylenediamine
Tmob 2,4,6-Trimethoxybenzyl
TSA Trypticase Soy Agar
TSB Tryptic Soy Broth
TSTU N,N,N',N'-Tetramethyl-O—(N-succinimidyl)uronium Tetrafluorborate
Tween® 20 Polyethylene Glycol Sorbitan Monolaurate
Tween® 80 Polyethylene Glycol Sorbitan Monooleate
UHPLC Ultra High Performance Liquid Chromatography
UPLC Ultra Performance Liquid Chromatography
UPLC-MS Mass Spectrometry Coupled Ultra Performance Liquid Chromatography
UV Ultraviolet

The invention claimed is:

1. A method of preventing or treating a joint infection in a patient, the method comprising the step of administering a pharmaceutically effective amount of a conjugate or a pharmaceutically acceptable salt thereof or a pharmaceutical composition comprising said conjugate or its pharmaceutically acceptable salt, wherein said conjugate is water-insoluble and comprises a polymeric moiety-Z, which is a hyaluronic acid-based or PEG-based hydrogel, to which a plurality of moieties $-L^2-X^{0D}-L^1-D$ are covalently conjugated, wherein each -D is independently an antibiotic moiety;

each $-L^1-$ is independently of formula (II):

(II)

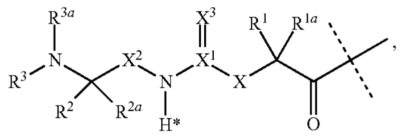

wherein the dashed line indicates the attachment to a nitrogen, hydroxyl or thiol of -D;

—X— is selected from the group consisting of $—C(R^4R^{4a})—$, $—N(R^4)—$, —O—, $—C(R^4R^{4a})—C(R^5R^{5a})—$, $—C(R^5R^{5a})—C(R^4R^{4a})—$, $—C(R^4R^{4a})—N(R^6)—$, $—N(R^6)—C(R^4R^{4a})—$, $—C(R^4R^{4a})—O—$, $—O—C(R^4R^{4a})—$, and $—C(R^7R^{7a})—$;

$X^1$ is selected from the group consisting of C and S (O);

$—X^2—$ is selected from the group consisting of $—C(R^8R^{8a})—$ and $—C(R^8R^{8a})—C(R^9R^{9a})—$;

$=X^3$ is selected from the group consisting of =O, =S, and =N—CN;

$—R^1$, $—R^{1a}$, $—R^2$, $—R^{2a}$, $—R^4$, $—R^{4a}$, $—R^5$, $—R^{5a}$, $—R^6$, $—R^8$, $—R^{8a}$, $—R^9$ and $—R^{9a}$ are independently selected from the group consisting of —H and $C_{1-6}$ alkyl;

$—R^3$ and $—R^{3a}$ are independently selected from the group consisting of —H and $C_{1-6}$ alkyl, provided that in case one of $—R^3$ and $—R^{3a}$ or both are other than —H, they are connected to the nitrogen atom to which they are attached through an $sp^3$-hybridized carbon atom;

$—R^7$ is selected from the group consisting of $—N(R^{10}R^{10a})$ and $—NR^{10}—(C=O)—R^{11}$;

$—R^{7a}$, $—R^{10}$, $—R^{10}$a and $—R^{11}$ are independently of each other selected from the group consisting of —H and $C_{1-6}$ alkyl;

alternatively, one or more of the pairs-$R^1$a/$—R^{4a}$, $—R^1$a/$—R^{5a}$, $—R^1$a/$—R^{7a}$, $—R^{4a}/—R^{5a}$ and $—R^8$a/$—R^{9a}$ form a chemical bond;

alternatively, one or more of the pairs-$R^1/—R^{1a}$, $—R^2/—R^{2a}$, $—R^4/—R^{4a}$, $—R^5/—R^{5a}$, $—R^8/—R^{8a}$ and $—R^9/—R^{9a}$ are joined together with the atom to which they are attached to form a $C_{3-10}$ cycloalkyl or 3- to 10-membered heterocyclyl;

alternatively, one or more of the pairs-$R^1/—R^4$, $—R^1/—R^5$, $—R^1/—R^6$, $—R^1/—R^{7a}$, $—R^4/—R^5$, $—R^4/—R^6$, $—R^8/—R^9$ and $—R^2/—R^3$ are joined together with the atoms to which they are attached to form a ring A;

alternatively, $—R^3/—R^{3a}$ are joined together with the nitrogen atom to which they are attached to form a 3- to 10-membered heterocycle;

A is selected from the group consisting of phenyl, naphthyl, indenyl, indanyl, tetralinyl, $C_{3-10}$ cycloalkyl, 3- to 10-membered heterocyclyl and 8- to 11-membered heterobicyclyl; and wherein $-L^1-$ is substituted with $—X^{0D}-L^2-$ and wherein $-L^1-$ is optionally further substituted, provided that the hydrogen marked with the asterisk in formula (II) is not replaced by $—X^{0D}-L^2-$or a substituent;

each $—X^{0D}—$ is independently absent or a linkage;

each $-L^2-$ is independently absent or a spacer moiety;

the conjugate is a pre-synthesized conjugate; and wherein the method of preventing or treating a joint infection also comprises the step of preventing the formation of a biofilm or eradicating an existing biofilm in said patient.

2. The method of claim 1, wherein the infection is an infection in a body compartment.

3. The method of claim 1, wherein the infection is an infection related to a surgical implant.

4. The method of claim 3, wherein the surgical implant is selected from the group consisting of pins, rods, screws, artificial joints, mesh, clips, sutures, wires, tubes, catheters, pumps, filters, prostheses, plates, fasteners, washers, bolts, seeds, beads, staples, nails, shunts, cuffs, buttons, ports, cements, stents, waxes, wraps, weights, stimulators, anchors, expanders, guidewires, fillers, polymers, film, fixators, drains, lines and cones.

5. The method of claim 3, wherein the surgical implant is an artificial joint.

6. The method of claim 1, wherein administration occurs via intraarticular injection into the infected joint.

7. The method of claim 1, wherein the infected joint is a synovial joint.

8. The method of claim 1, wherein-Z is degradable.

9. The method of claim 1, wherein each -D is independently selected from the group consisting of aminoglycosides, tetracycline antibiotics, amphenicols, pleuromutilins, macrolide antibiotics, lincosamides, steroid antibiotics, antifolate antibiotics, sulfonamides, topoisomerase inhibitors, quinolones, fluoroquinolones, nitroimidazole antibiotics, nitrofuran antibiotics, rifamycins, glycopeptides, penicillins, cephalosporins, monobactams, beta-lactamase inhibitors, polymyxin antibiotics, lipopeptide antibiotics, oxazolidinones, antimicrobial peptides, porphyrins, azole antifungals, polyenes, antiprotozoal drugs, fosfomycin, cycloserine, and bacitracin.

10. The method of claim 1, wherein-D is daptomycin.

11. The method of claim 10, wherein $-L^1-$ is connected via the primary amine of the ornithine side chain.

* * * * *